(12) United States Patent
Mahmud et al.

(10) Patent No.: US 11,072,806 B2
(45) Date of Patent: Jul. 27, 2021

(54) GADUSOL PRODUCTION

(71) Applicant: Oregon State University, Corvallis, OR (US)

(72) Inventors: Taifo Mahmud, Corvallis, OR (US); Alan Bakalinsky, Corvallis, OR (US); Andrew Osborn, Corvallis, OR (US); Garrett Holzwarth, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 16/720,435

(22) Filed: Dec. 19, 2019

(65) Prior Publication Data

US 2020/0199631 A1     Jun. 25, 2020

Related U.S. Application Data

(60) Provisional application No. 62/782,090, filed on Dec. 19, 2018.

(51) Int. Cl.
| | |
|---|---|
| *C12P 7/26* | (2006.01) |
| *C12N 9/88* | (2006.01) |
| *C12N 9/00* | (2006.01) |
| *C12N 9/10* | (2006.01) |
| *C12N 9/02* | (2006.01) |

(52) U.S. Cl.
CPC .............. *C12P 7/26* (2013.01); *C12N 9/0004* (2013.01); *C12N 9/1007* (2013.01); *C12N 9/88* (2013.01); *C12Y 402/03* (2013.01)

(58) Field of Classification Search
None
See application file for complete search history.

(56) References Cited

PUBLICATIONS

Osborn et al., "De novo synthesis of a sunscreen compound in vertebrates", eLIFE, 2015, 4:e05919; pp. 1-15. DOI: 10.7554/eLife.05919.001.*
Holzwarth, G. "Gadusol Production in *Saccharomyces cerevisiae*", M.Sc. thesis, Oregon State University, Feb. 27, 2018.*
Addgene plasmid maps for pXP416—retrieved from https://www.addgene.org/26842/ on Dec. 29, 2020.*
Addgene plasmid maps for pXP420—retrieved fromhttps://www.addgene.org/26844/ on Dec. 29, 2020.*

* cited by examiner

*Primary Examiner* — Suzanne M Noakes
(74) *Attorney, Agent, or Firm* — Schwabe, Williamson & Wyatt, P.C.

(57) ABSTRACT

The present disclosure relates to engineered microorganisms capable of producing gadusol. The engineered microorganisms contain a nucleotide sequence encoding 2-epi-5-valione synthase (EEVS) and a nucleotide sequence encoding methyltransferase-oxidoreductase (MT-Ox). Methods of using the engineered microorganisms to produce gadusol, including the culturing of such microorganisms, are also described.

26 Claims, 39 Drawing Sheets

Specification includes a Sequence Listing.

SEQUENCE LISTING

```
<160> NUMBER OF SEQ ID NOS: 90

<210> SEQ ID NO 1
<211> LENGTH: 1410
<212> TYPE: DNA
<213> ORGANISM: Danio rerio

<400> SEQUENCE: 1
atggagcgac ccggggagac atttacagtg agttcacctg aagaagttcg cctgccatct      60
gttcaccggg acaactcgac gatggagaac cacaacaagc aggagactgt cttcagcctg     120
gtgcaggtga aggggacgtg gaaacgcaaa gcagggcaaa atgccaagca aggaatgaaa     180
ggacgagttt caccggctaa aatttacgaa agcagctcct ctagtggcac tacctggaca     240
gtggtcaccc ccatcacctt cacatatact gttactcaga ccaaaaacct tctttgacccc     300 agcaatgaca ctctgctttt gggccacatc attgacactc agcagcttga ggccgtacgg     360
```

```
tccaacacca aaccccttaaa acgcttcata gtcatggatg aggtagtgta caatatctat        420
ggttctcagg tcaccgaata cctcgaggcc agaaatgtcc tgtaccggat cctgcccctg        480
cccacgacag aggagaacaa gtccatggat atggccctga agatcctgga ggaggtgcac        540
cagtttggga tcgaccggcg cacggagccc attatcgcca ttggagggggg cgtctgcctg       600 gatatcgtgg gtctggcggc gtcgctttac agaagacgca ctccatacat tcgtgttccc        660
accactctac tgtcctacat tgacgccagt gtcggagcca aaacaggtgt caatttcgcc        720
aattgtaaga acaaacttgg cacctacatc gcacctgttg ctgcattcct ggaccggtcg        780
tttatacaga gcattcctcg caggcacata gctaacggtc ttgcagaaat gctgaagatg        840
gctcttatga agcacagagg gctgtttgaa ctcctggaag tgcacggaca gttcctctta        900
gactccaagt tccagtctgc ttcagtccta gagaacgacc gcattgaccc tgcttctgtc        960
tctacacgtg tcgcaataga aaccatgcta gaagagttag ccccaaacct gtgggaggat       1020
gatcttgaca gactggttga ctttgggcac tcataagcc tcaactaga gatgaaagtc         1080 ctaccagctc ttctccacgg tgaagcggtg aatattgata tggcctacat ggtgtatgtg       1140
tcttgtgaaa ttggattgct gacagaggag gagaaattca ggatcatctg ttgcatgatg       1200
ggactggagc tgccggtgtg gcatcaagac ttcacatttg ctttggtgca gaagtctctg       1260
tgtgacagac ttcagcattc tggaggcctc gtgagaatgc ctttaccaac aggcctcgga       1320
agagcagaaa tcttcaatga cactgatgaa ggctctctgt ttagggcgta cgagaagtgg       1380
tgtgatgagc tcagcactgg gtcacctcaa                                        1410

<210> SEQ ID NO 2
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggaacgtc cgggcgaaac ctttaccgtc agctccccgg aagaagtgcg tctgccgtct         60
gttcaccgcg ataactcaac gatggaaaac cataataaac aggaaacggt gttttctctg        120
gttcaagtca agggtacctg gaagcgtaag gcgggccaga acgccaaaca gggtatgaag        180
ggccgcgtta gtccggccaa aatttatgaa agctctagtt cctcaggtac cacgtggacg        240
gtggttaccc cgatcacctt tacgtacacc gtgacgcaga ccaaaaacct gctggacccg        300
tcgaacgaca cgctgctgct gggccatatt atcgataccc agcaactgga agctgtccgc        360
agcaatacga aaccgctgaa gcgtttcatt gtgatggacg aagtcgtgta taatatctac        420
ggttcccaag tcaccgaata tctggaagcg cgcaacgtgc tgtaccgtat tctgccgctg        480
ccgaccacgg aagaaaataa atcaatggat atggctctga agattctgga agaagtgcac        540
cagtttggta tcgaccgtcg caccgaaccg attatcgcga ttggcggtgg cgtttgcctg        600
gatatcgtcg gtctggcagc ctctctgtat cgtcgccgta ccccgtacat tcgtgtgccg        660
accacgctgc tgtcttatat cgacgcaagt gtgggtgcta aaacgggcgt taactttgct        720
aattgtaaaa acaagctggg tacctacatt gcgccggttg cagcttttct ggatcgttcg        780
ttcattcaga gcatcccgcg ccgtcacatc gcaaacggtc tggccgaaat gctgaaaatg        840
gccctgatga agcatcgcgg tctgttcgaa ctgctggaag ttcacggcca gtttctgctg        900
gatagtaaat tccaatcggc aagcgtcctg gaaaacgatc gcattgaccc ggcctctgtc        960
```

```
agtacgcgtg tggcaatcga aaccatgctg gaagaactgg ccccgaatct gtgggaagat    1020
gacctggatc gtctggtgga ctttggtcat ctgatttcgc cgcagctgga aatgaaagtt    1080
ctgccggcac tgctgcacgg cgaagctgtc aacattgata tggcgtatat ggtgtacgtt    1140
tcatgcgaaa tcggtctgct gaccgaagaa gaaaaattcc gcattatctg ctgtatgatg    1200
ggcctggaac tgccggtgtg gcatcaggat tttaccttcg cactggttca aaagtccctg    1260
tgtgaccgcc tgcagcactc aggtggcctg gttcgtatgc cgctgccgac gggtctgggt    1320
cgtgcagaaa tttttaatga taccgacgaa ggtagcctgt ccgcgcgta tgaaaaatgg     1380 tgcgatgaac tgtccaccgg ctcaccgcag                                    1410

<210> SEQ ID NO 3
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggaaagac caggtgaaac tttcaccgtc tcctctccag aagaagtcag attaccttcc      60
gtccacagag ataattctac catggaaaac cacaacaagc aagaaaccgt tttctctttg     120
gtccaagtta agggtacttg gaagcgtaag gctggtcaaa acgctaagca aggtatgaaa    180
ggtagagttt ctccagctaa gatttatgaa tcctcttcct cttccggtac cacctggacc    240
gtcgttactc caattacctt cacttacact gttacccaaa ccaaaaactt gttggatcca    300
tctaacgaca ctttgttgtt gggtcatatc atcgataccc aacaattgga ggctgttaga    360
tctaacacca agcctttgaa gcgtttcatt gtcatggatg aagtcgttta taacatttac    420
ggttctcaag ttaccgaata cttggaagct agaaacgttt tgtacagaat cttgccattg    480
ccaactactg aagagaataa gtctatggat atggccttga gatcttgga gaggtccac     540 caattcggta ttgatagaag aaccgaacct attattgcta ttggtggtgg tgtttgtttg    600
gacatcgttg gtttggctgc ctccttgtac cgtagaagaa ctccatatat tagagttcca    660
actaccttat tgtcttatat tgatgcttcc gtcggtgcta agaccggtgt caactttgct    720
aactgtaaga ataagttagg tacttatatc gctccagtcg ccgccttctt agatagatct    780
tttatccaat ccatcccacg tagacacatt gctaatggtt tagctgaaat gttgaagatg    840
gctttgatga agcatagagg tttatttgaa ttattggaag tccacggtca atttttgttg    900
gattctaagt ttcaatccgc ttctgtttta gaaaacgata gaattgatcc agcttctgtc    960
tccaccagag ttgccattga aactatgtta gaagaattag ctccaaactt gtgggaggac    1020
gacttggacc gtttagtcga cttcggtcac ttaatttctc cacaattgga aatgaaggtt    1080
ttaccagcct tattgcatgg tgaagctgtt aacattgata tggcttacat ggtttacgtc    1140
tcttgtgaaa tcggtttatt gactgaagaa gaaaagtttc gtatcatctg ttgtatgatg    1200
ggtttggaat gcctgtctg gcatcaagat ttcactttcg ctttggttca aaagtcctta    1260
tgtgatagat gcaacactc tggtggtttg gtcagaatgc cattgcctac cggtttgggt    1320
agagccgaaa ttttcaacga tactgacgag ggttctttat tcagagctta tgaaaaatgg    1380
tgtgacgaat tgtctactgg ttctccacaa                                    1410

<210> SEQ ID NO 4
<211> LENGTH: 1410
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
atggaaagac caggtgaaac ttttactgtt tcctccccag aagaagtcag attgccttct      60
gttcacagag acaattctac tatggaaaac cataacaagc aagaaactgt cttctcttta     120
gttcaagtca agggtacctg gaaaagaaag gctggtcaaa acgctaaaca aggtatgaag     180
ggtagagtct ccccagctaa gatttatgaa tcctcttcct cttctggtac tacctggacc     240
gtcgtcactc ctattacctt cacctacact gtcacccaaa ctaagaattt gttagatcca     300
tctaacgata ccttgttgtt aggtcacatt attgatactc aacaattaga agctgtccgt     360
tccaacacta agccattgaa agattcatcg ttatggatg aagttgttta caatatttac     420
ggttcccaag tcactgaata cttggaagct agaaatgttt tgtacagaat tttgcctttg     480
cctaccactg aagaaaataa gtctatggac atggctttaa agattttaga ggaagtccat     540
caattcggta tcgatagaag aactgaacca attattgcta tcggtggtgg tgtctgtttg     600
gatatcgtcg gtttggctgc ttctttgtac agaagaagaa ctccatacat cagagtccca     660
accactttgt tgtcttacat cgacgcttcc gttggtgcta agactggtgt taacttcgct     720
aactgtaaaa acaagttggg tacctacatc gccccagtcg ccgctttctt ggatagatct     780
ttcatccaat ctatcccacg tcgtcatatt gctaacggtt tggccgaaat gttgaagatg     840
gccttgatga acatagagg tttattcgaa ttgttagaag ttcatggtca attcttgttg     900
gattctaagt ccaatccgc ttccgttttg gaaaacgatc gtatcgatcc agcctccgtc     960
tctactagag tcgctatcga aaccatgtta gaagaattgg ccccaaactt atgggaagac    1020
gacttggaca gattagtcga tttcggtcat tgatctctc cacaattgga atgaaggtc     1080
ttgccagcct gttgcacgg tgaagctgtt aacatcgata tggcttacat ggtctacgtt    1140
tcttgtgaaa ttggtttatt aaccgaagaa gaaaaattca gaatcatttg ttgtatgatg    1200
ggtttagaat tgccagtctg gcaccaagac ttcactttcg ccttggttca aaagtctttg    1260
tgtgacagat tacaacactc tggtggtttg gtcagaatgc ctttgcctac tggtttgggt    1320
agagctgaaa ttttcaacga tactgacgaa ggttctttgt ccgtgccta tgaaaagtgg    1380
tgtgatgagt tgtccactgg ttctccacaa                                    1410
```

<210> SEQ ID NO 5
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
atggaacgtc caggtgaaac ttttaccgtc tcttctccag aagaagtcag attaccatcc      60
gttcacagag acaattctac tatggaaaat cacaataagc aagaaaccgt cttttctttg     120
gtccaagtca agggtacttg gaagcgtaaa gccggtcaaa acgctaagca aggtatgaag     180
ggtcgtgttt ctcctgccaa gatttatgaa tcctcctctt cctctggtac tacttggacc     240
gttgtcaccc caattacctt tacctacact gtcacccaaa ctaaaaattt gttagatcca     300
tccaatgaca ccttgttgtt gggtcatatt attgacaccc aacaattgga agccgttaga     360
```

-continued

```
tctaatacta agccattgaa gagattcatt gttatggatg aagtcgtcta caacatctac      420
ggttctcaag tcactgaata cttggaagct agaaacgtct tgtaccgtat cttgccattg      480
ccaactactg aagaaaacaa atccatggat atggccttga agattttgga agaagtccac      540
caatttggta tcgatagaag aaccgaacca atcattgcca ttggtggtgg tgtttgttta      600
gacattgttg gtttggctgc ctccttgtat agaagaagaa ctccatacat tagagtccca      660
actaccttgt tgtcttacat cgatgcttct gttggtgcca agactggtgt taacttcgct      720
aactgcaaga acaagttggg tacctacatc gccctgtcg ccgctttctt ggacagatcc      780
ttcatccaat ctatccctag acgtcatatt gccaacggtt tggctgaaat gttgaagatg      840
gctttgatga agcatagagg tttgttcgag ttgttagaag ttcacggtca attcttatta      900
gattctaagt ccaatctgc ttctgtctta gaaaacgacc gtattgaccc agcttccgtt      960
tctactagag ttgctattga aaccatgttg gaagaattag ccccaaactt gtgggaagat     1020
gatttggaca gattggttga cttcggtcat ttaatctccc cacaattgga aatgaaggtt     1080
ttgccagctt tattgcatgg tgaagccgtc aacatcgaca tggcttacat ggtttacgtc     1140
tcctgtgaaa tcggttttgtt aaccgaagaa gaaaaattca gaatcatctg ctgtatgatg     1200
ggtttggaat tgccagtttg gcaccaagac ttcacttttg ctttggttca aaagtccttg     1260
tgtgatagat tgcaacactc cggtggttta gtcagaatgc ctttaccaac tggtttaggt     1320
cgtgctgaaa tcttcaacga tactgatgaa ggttccttat tcagagccta tgaaaagtgg     1380
tgtgacgaat tatctactgg ttctcctcaa                                      1410
```

<210> SEQ ID NO 6
<211> LENGTH: 1410
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
atggaacgtc caggtgaaac tttcaccgtc tcttcccctg aagaggttag attgccttct       60
gtccacagag acaactctac catggaaaac cataacaagc aagaaaccgt cttctccttg      120
gttcaagtca agggtacttg gaagagaaag gctggtcaaa atgctaaaca aggtatgaag      180
ggtcgtgttt ccccagctaa gatttacgaa tcttcctcct cttctggtac tacctggacc      240
gttgttaccc caatcacctt cacctacact gtcaccccaaa ctaagaattt attggaccca      300
tctaacgaca ctttgttgtt gggtcacatc attgatactc aacaattgga agctgttaga      360
tctaacacta aaccattgaa aagattcatt gttatggatg aggttgttta caacatttac      420
ggttctcaag ttaccgaata cttagaagcc agaaatgttt tgtacagaat tttacctttg      480
ccaaccaccg aagaaaataa gtctatggat atggctttga aaatcttgga agaagtccat      540
caattcggta tcgacagaag aactgaacca atcatcgcta ttggtggtgg tgtttgtttg      600
gacattgtcg gtttggctgc ttctttgtac agaagaagaa ctccatacat cagagtccca      660
accactttgt tgtcctacat tgatgcttct gtcggtgcta agactggtgt taacttcgct      720
aactgtaaga acaagttagg tacttacatt gccctgttg ctgccttctt ggacagatct      780
ttcatccaat ctatcccaag aagacatatc gctaacggtt tagccgaaat gttgaaaatg      840
gctttaatga agcacagagg tttgtttgaa ttgttggaag tccacggtca attttttgtta     900 gactctaagt ccaatctgc ctccgttttta gaaaacgata gaattgaccc agcttctgtt      960
```

```
tccacccgtg ttgctattga accatgttg gaagaattgg ccccaaactt gtgggaagac      1020
gacttggacc gtttggtcga tttcggtcac ttaatctccc cacaattgga aatgaaggtc      1080
ttgccagctt tgttgcatgg tgaagccgtt aacattgata tggcctatat ggtctacgtt      1140
tcttgtgaaa tcggtttgtt gaccgaagag gaaaagttca gaattatctg ttgtatgatg      1200
ggtttggaat tgccagtttg gcatcaagat tttacctttg ctttggttca aaagtctttg      1260
tgtgacagat tgcaacattc tggtggtttg gtcagaatgc ctttgccaac tggtttgggt      1320
agagctgaaa ttttcaacga cactgatgaa ggttctttgt tcagagccta cgaaaaatgg      1380
tgcgatgaat tgtctaccgg ttcccccacaa                                      1410
```

<210> SEQ ID NO 7
<211> LENGTH: 1410
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
atggaaagac ctggtgaaac ttttactgtt tcttctcctg aagaagttag attgccatct       60
gttcatagag acaactctac catggaaaat cataacaagc aagaaaccgt cttctctttg      120
gtccaagtca agggtacctg gaagagaaag gctggtcaaa acgccaagca aggtatgaag      180
ggtagagtct ccccagccaa gatctacgaa tcctcctctt cttccggtac cacctggact      240
gttgtcaccc caattacttt cacttacact gtcactcaaa ctaaaaactt gttggaccca      300
tctaacgata ctttgttatt gggtcacatt attgacaccc aacaattgga agctgtcaga      360
tctaacacca agccattaaa gagattcatt gtcatggatg aagttgttta caacatctac      420
ggttctcaag tcaccgaata cttggaagct agaaatgttt tgtatcgtat tttgccattg      480
ccaactaccg aggaaaacaa gtccatggat atggccttga agattttgga agaagtccat      540
caattcggta ttgatagaag aactgaacca attatcgcca tcggtggtgg tgtctgcttg      600
gatattgttg gtttagctgc ttctttgtat agacgtagaa ctccttacat tagagttcca      660
accactttat tatcctacat cgacgcctcc ggttggtgcca aaactggtgt taacttcgct      720
aactgtaaga caagttggg tacttacatc gctccagttg ctgccttctt ggaccgttct      780
ttcattcaat ctatccctcg tcgtcacatt gccaatggtt tagctgaaat gttgaaaatg      840
gctttgatga acatagagg tttgttcgaa ttattggaag tccacggtca attttttgttg      900 gactctaaat tccaatccgc ttctgtcttg gaaaacgata gaattgaccc agcttccgtt      960
tctaccagag tcgctatcga aaccatgttg gaagaattgg ctccaaactt atgggaagat     1020
gatttggata gattggttga tttcggtcac ttgatttccc cacaattgga aatgaaggtt      1080
ttaccagcct tgttgcacgg tgaagctgtt aatattgata tggcttacat ggtctatgtc      1140
tcttgtgaaa tcggtttgtt gactgaagaa gaaaagttca gaatcatttg ttgtatgatg      1200
ggtttggaat tgccagtctg gcatcaagac ttcacttttcg ctttggttca aaagtcccta      1260
tgtgacagat tgcaacattc cggtggtttg gtcagaatgc cattgccaac cggtttgggt      1320
agagctgaaa ttttcaacga cactgacgaa ggttccttgt tccgtgctta cgaaaagtgg      1380
tgcgatgaat tgtctaccgg ttcccccacaa                                     1410
```

<210> SEQ ID NO 8
<211> LENGTH: 1410
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 8

```
atggaaagac caggtgaaac tttcactgtt tcttctccag aagaagttag attgccatct      60
gttcacagag acaactctac tatggaaaac cacaacaagc aagaaactgt tttctctttg     120
gttcaagtta agggtacttg aagagaaag gctggtcaaa cgctaagca aggtatgaag       180
ggtagagttt ctccagctaa gatctacgaa tcttcttctt cttctggtac tacttggact     240
gttgttactc caatcacttt cacttacact gttactcaaa ctaagaactt gttggaccca     300
tctaacgaca ctttgttgtt gggtcacatc atcgacactc aacaattgga agctgttaga     360
tctaacacta agccattgaa gagattcatc gttatggacg aagttgttta caacatctac     420
ggttctcaag ttactgaata cttggaagct agaaacgttt tgtacagaat cttgccattg     480
ccaactactg aagaaaacaa gtctatggac atggctttga gatcttgga gaagttcac      540
caattcggta tcgacagaag aactgaacca atcatcgcta tcggtggtgg tgtttgtttg     600
gacatcgttg gttggctgc ttctttgtac agaagaagaa ctccatacat cagagttcca     660
actactttgt tgtcttacat cgacgcttct gttggtgcta agactggtgt taacttcgct     720
aactgtaaga caagttggg tacttacatc gctccagttg ctgctttctt ggacagatct     780
ttcatccaat ctatcccaag aagacacatc gctaacggtt tggctgaaat gttgaagatg     840
gctttgatga gcacagagg tttgttcgaa ttgttggaag ttcacggtca attcttgttg     900
gactctaagt ccaatctgc ttctgttttg gaaaacgaca gaatcgaccc agcttctgtt     960
tctactagag ttgctatcga aactatgttg aagaattgg ctccaaactt gtgggaagac    1020
gacttggaca gattggttga cttcggtcac ttgatctctc acaattgga atgaaggtt    1080
ttgccagctt tgttgcacgg tgaagctgtt aacatcgaca tggcttacat ggtttacgtt    1140
tcttgtgaaa tcggtttgtt gactgaagaa gaaaagttca gaatcatctg ttgtatgatg    1200
ggtttggaat tgccagtttg gcaccaagac ttcactttcg ctttggttca aaagtctttg    1260
tgtgacagat tgcaacactc tggtggtttg gttagaatgc cattgccaac tggtttgggt    1320
agagctgaaa tcttcaacga cactgacgaa ggttctttgt tcagagctta cgaaagtgg     1380
tgtgacgaat tgtctactgg ttctccacaa                                     1410
```

<210> SEQ ID NO 9
<211> LENGTH: 1653
<212> TYPE: DNA
<213> ORGANISM: Danio rerio

<400> SEQUENCE: 9

```
atgcagacag caaaagtttc agacactcct gtggagttca tcgttgaaca cctgctgaag      60
gcaaaagaga tcgcagagaa tcatgcaagt attccagtcg aacttcggga taatcttcag     120
aaggctttgg acattgctag tggactagac gaataccttg aacaaatgag cagcaaggag     180
agtgaaccgt tgactgagtt gtataggaaa tcagtttctc atgactggaa taaggtgcat     240
gcggacggaa aaaccttatt taggcttcct gttacatgca tcaccggaca ggtagaaggt     300
caagtattga agatgctggt gcatatgagc aaagcaaaga gggtcttaga gataggaatg     360
ttcacagggt atggggcctt gtcaatggcg gaggccttac cagaaaatgg ccagcttatc     420
gcctgtgagc ttgagcctta cctcaaagac tttgcacagc ctatatttga taaatctcct     480
```

```
catgggaaaa agataactgt gaagactggg cctgctatgg ataccctgaa ggaattggct      540
gccacaggag agcagtttga catggtattt attgacgcgg acaagcagaa ctacatcaac      600
tattataagt tcctcctgga ccataacctt ctgcggatcg atggtgttat atgtgtcgac      660
aacacactgt ttaaaggcag agtttacctc aaggactctg tggatgaaat gggaaaagca      720
ttgcgggatt ttaatcagtt tgtcacagct gatcctcgag tagagcaggt catcatccct      780
ctgagagatg gactcactat aatacgaaga gtgccctata caccttcagcc aaactcacag     840 agtggtacag taacctatga tgaggtgttt agaggagtcc aaggaaagcc agttctggac      900
aggttacgtt tggatgggaa agtggcctat gtgaccgggg ccggtcaggg tattggcagg      960
gctttcgcac atgctctcgg agaggctgga gccaaagtcg ccatcataga catggacaga     1020
ggaaaggctg aggatgtggc gcatgaactg actttaaaag gcatttcaag catggctgta    1080
gtggcagaca ttagcaaacc agcgacgtc cagaagatga ttgacgacat cgttacgaaa      1140
tggggcacac ttcacattgc ttgtaacaat gctggcatca acaaaaactc agcaagtgag    1200
gagaccagtc tagaagaatg ggaccaaacc tttaacgtga acctcagagg cactttcatg    1260
tgctgccagg cggccggtcg tgtcatgctg aagcaaggat acggcaagat aatcaacaca    1320
gcttccatgg ccagtttaat agtgccgcat ccacagaagc agctgtccta taacacatcc    1380
aaagctggag tagtgaaact cactcaaacc ctgggcacag aatggattga ccgaggtgtt    1440
cgagtcaatt gcatctcacc tggtattgtt gacacccctc tcatccattc agagagtctg    1500
gagcctctag ttcagcgctg gctgtcagat atcccagccg gacgactggc tcaagtgaca    1560
gacctccaag ctgcagtggt atacttggca tctgacgcct tgactacat gacagggcat     1620 aacttagtca tagagggtgg tcagagtcta tgg                                 1653
```

<210> SEQ ID NO 10
<211> LENGTH: 1653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
atgcaaacgg caaaagtctc ggacaccccg gttgaattta ttgtggaaca tctgctgaag      60
gctaaggaaa tcgctgaaaa tcacgcttcc attccggtgg aactgcgcga taacctgcag     120
aaagctctgg atatcgcgag cggcctggac gaatatctgg aacaaatgag ctctaaagaa     180
tctgaaccgc tgacggaact gtaccgcaag tcagtctcgc atgattggaa taaagtgcac    240
gcggacggca agaccctgtt tcgtctgccg gtgacctgca ttacgggcca ggtcgaaggt     300
caagtgctga aaatgctggt tcacatgagt aaagcgaagc gtgtcctgga aattggcatg     360
tttaccggct atggtgccct gtccatggca gaagctctgc cggaaaacgg tcagctgatc     420
gcttgtgaac tggaaccgta cctgaaagat tttgcacaac cgattttcga caagagtccg     480
catggcaaaa agatcaccgt gaaaacgggt ccggcaatgg ataccctgaa ggaactggcg     540
gccacgggcg aacagtttga catggttttc attgatgcgg acaagcaaaa ctacatcaac     600
tactacaagt tcctgctgga tcacaacctg ctgcgtattg atggcgtcat ctgcgtggac     660
aatacgctgt tcaaaggtcg cgtgtacctg aaggatagcg ttgacgaaat gggtaaagcc    720
ctgcgtgatt ttaaccagtt cgtgaccgca gaccgcgtg ttgaacaagt cattatcccg     780
ctgcgcgatg gcctgaccat tatccgtcgc gtcccgtata cgccgcagcc gaatagccaa     840
```

| | |
|---|---:|
| tctggtaccg tgacgtacga tgaagttttt cgcggcgtcc agggtaaacc ggttctggat | 900 |
| cgtctgcgcc tggacggcaa agtggcttat gttaccggtg ccgtcaggg tattggtcgt | 960 |
| gcattcgccc atgcactggg cgaagctggt gcgaaagttg ccattatcga tatggaccgt | 1020 |
| ggcaaggccg aagatgtcgc acacgaactg accctgaaag gtattagttc catggccgtg | 1080 |
| gttgcagata tcagcaaacc ggatgacgtg cagaagatga ttgatgacat cgttaccaaa | 1140 |
| tggggcacgc tgcatattgc ttgcaacaat gcgggtatca acaaaaatag tgcgtccgaa | 1200 |
| gaaacctctc tggaagaatg ggatcagacg tttaacgtca atctgcgtgg caccttcatg | 1260 |
| tgctgtcagg cagctggtcg cgttatgctg aaacaaggct atggcaagat tatcaacacc | 1320 |
| gctagcatgg cgtctctgat tgtgccgcac ccgcagaaac aactgtcata caatacgtcg | 1380 |
| aaagccggcg tcgtgaagct gacccagacg ctgggcaccg aatggatcga tcgtggtgtg | 1440 |
| cgcgttaact gtatttcacc gggtatcgtg ataccccgc tgattcattc agaatcgctg | 1500 |
| gaaccgctgg ttcagcgttg gctgtcggat atcccggcag gtcgtctggc acaggtgacg | 1560 |
| gacctgcaag cggccgttgt ctatctggcc agtgatgcat ccgactacat gaccggtcac | 1620 |
| aatctggtta ttgaaggcgg tcagtctctg tgg | 1653 |

<210> SEQ ID NO 11
<211> LENGTH: 1653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

| | |
|---|---:|
| atgcaaaccg ctaaagtttc tgatactcca gtcgaattca tcgttgaaca cttgttgaaa | 60 |
| gctaaagaaa ttgctgaaaa ccacgcctcc atcccagttg aattgcgtga acttgcaa | 120 |
| aaggctttgg acattgcttc tggtttggac gaatacttag aacaaatgtc ttccaaggag | 180 |
| tctgaacctt tgaccgaatt atacagaaaa tccgtctccc atgactggaa caaggttcat | 240 |
| gctgacggta aaactttgtt cagattgcca gttacttgta ttactggtca agttgaaggt | 300 |
| caagtcttga agatgttggt tcacatgtct aaggctaaga gagttttgga aattggtatg | 360 |
| ttcaccggtt acggtgcctt atccatggct gaagccttgc cagagaacgg tcaattaatt | 420 |
| gcctgtgaat tggagccata tttgaaggac tttgctcaac caattttcga caagtctcca | 480 |
| cacggtaaaa aaattactgt taagaccggt ccagctatgg acactttaaa ggaattggcc | 540 |
| gctactggtg aacaattcga catggttttc attgatgccg acaagcaaaa ctacatcaac | 600 |
| tactacaagt tcttgttgga tcacaactta ttgagaatcg atggtgttat ctgtgtcgat | 660 |
| aacaccttgt tcaagggtag agtttacttg aaagactctg tcgatgagat gggtaaggct | 720 |
| ttgagagatt tcaaccaatt cgttactgct gatccacgtg tcgaacaagt cattatccca | 780 |
| ttgagagacg gtttgactat cattagacgt gttccataca ccccacaacc aaactctcaa | 840 |
| tctggtactg tcacctacga tgaagttttc agaggtgttc aaggtaagcc tgtttttggac | 900 |
| agattgcgtt tagatggtaa ggttgcttac gttactggtg ctggtcaagg tattggtcgt | 960 |
| gctttcgctc acgccttggg tgaagccggt gccaaagtcg ctattatcga tatggacaga | 1020 |
| ggtaaggccg aagacgttgc tcacgaattg accttgaaag gtatctcctc catggctgtc | 1080 |
| gtcgccgata tctccaagcc agatgacgtt caaaagatga ttgacgatat tgttactaag | 1140 |
| tggggtacct tgcatatcgc ttgtaataac gctggtatca acaagaactc tgcttccgaa | 1200 |

```
gaaacctctt tggaagaatg ggatcaaact ttcaacgtca atttgagagg tactttcatg   1260
tgttgtcaag ctgccggtag agttatgttg aaacaaggtt acggtaagat tattaatacc   1320
gcttctatgg cttccttgat tgtcccacat ccacaaaaac aattgtctta taatacttcc   1380
aaggctggtg ttgttaagtt gactcaaacc ttaggtactg aatggatcga cagaggtgtt   1440
agagtcaact gtatctctcc aggtattgtc gatacccat tgatccactc tgaatcttta   1500
gaaccattgg tccaaagatg gttatctgac atcccagccg gtagattggc tcaagttact   1560
gatttgcaag ctgctgtcgt ctacttggct tctgatgctt ctgactacat gaccggtcac   1620
aacttagtca tcgaaggtgg tcaatctttg tgg                                1653
```

<210> SEQ ID NO 12
<211> LENGTH: 1653
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
atgcaaaccg ctaaggtttc cgacactcca gttgaattta tcgtcgaaca cttattgaaa     60
gctaaggaaa ttgccgaaaa ccatgcctcc attccagtcg aattgcgtga caacttgcaa    120
aaggctttgg acattgcttc tggtttggac gaatacttgg agcaaatgtc ctctaaggaa    180
tctgaaccat tgaccgaatt gtatcgtaaa tccgtctccc atgattggaa taaggttcac    240
gccgacggta agactttgtt tagattgcca gtcacttgta tcaccggtca agttgaaggt    300
caagttttaa agatgttggt tcacatgtcc aaggctaaga gagtcttgga aattggtatg    360
ttcactggtt atggtgcctt atccatggcc gaagctttgc cagaaaacgg tcaattgatt    420
gcttgcgaat tggaaccata tttgaaggat ttcgctcaac caattttcga taaatctcca    480
cacggtaaga aaattactgt caagactggt cctgctatgg acactttaaa agaattggcc    540
gctactggtg agcaattcga catggttttc atcgatgccg ataaacaaaa ctatattaac    600
tactataaat tcttgttgga ccacaacttg ttgagaattg atggtgtcat ctgtgtcgat    660
aacaccttgt tcaagggtag agtctactta aaggactctg tcgatgaaat gggtaaggct    720
ttaagagact tcaaccaatt cgttaccgct gatccaagag ttgaacaagt cattattcca    780
ttgagagatg gtttgactat tattcgtaga gttccttaca ctccacaacc aaactctcaa    840
tctggtaccg tcacctacga tgaagttttc agaggtgttc aaggtaaacc agtcttggat    900
agattgagat tagatggtaa ggttgcctac gttaccggtg ctggtcaagg tatcggtaga    960
gctttcgccc acgctttggg tgaagctggt gccaaggtcg ctatcatcga tatggataga   1020
ggtaaggcca agatgttgc ccacgaattg accttaaaag gtatctcctc catggctgtc   1080
gtcgctgata tctctaaacc tgacgatgtt caaaaaatga ttgacgacat cgtcaccaag   1140
tggggtactt tgcatattgc ttgtaataac gctggtatta caagaactc tgcttctgaa   1200 gaaacttctt ggaagaatg ggatcaaact ttcaacgtta acttgagagg tactttcatg    1260
tgttgtcaag ctgccggtag agtcatgttg aagcaaggtt acggtaagat tatcaacact   1320
gcctccatgg cctccttgat tgttccacat ccacaaaaac aattgtctta caacacctcc   1380
aaggccggtg ttgtcaagtt gacccaaacc ttgggtactg agtggattga tagaggtgtc   1440
agagtcaact gtatctctcc aggtattgtt gatactcctt tgattcactc cgagtccttg   1500
gaaccattgg ttcaaagatg gttatccgac atcccagccg gtagattggc tcaagttacc   1560
```

```
gatttgcaag ctgctgttgt ttacttggcc tccgatgcct ccgattacat gactggtcat    1620
aacttggtca ttgaaggtgg tcaatccttg tgg                                 1653
```

<210> SEQ ID NO 13
<211> LENGTH: 1653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
atgcaaactg ccaaggtctc cgacacccca gtcgaattca ttgttgaaca cttgttgaag     60
gctaaagaaa tcgctgaaaa tcacgcttct attcctgttg aattaagaga caacttgcaa    120
aaagccttgg acattgcttc tggtttagac gaatacttgg aacaaatgtc ttctaaagaa    180
tccgagccat tgactgaatt gtacagaaag tctgtctccc acgactggaa caaggttcac    240
gctgacggta agaccttgtt ccgtttacct gttacctgta tcaccggtca agtcgaaggt    300
caagttttga aaatgttggt tcatatgtcc aaggctaaga gagtcttgga tcggtatg     360 tttaccggtt acggtgcctt gtctatggcc gaagccttgc cagaaaacgg tcaattgatc    420
gcttgtgaat tggaaccata tttgaaggac ttcgctcaac ctatcttcga caagtcccca    480
cacggtaaga gatcaccgt caagaccggt ccagccatgg atactttgaa gaattggcc     540 gctactggtg aacaattcga tatggttttc atcgatgctg ataaacaaaa ctatatcaat    600
tactacaagt tcttgttgga tcacaacttg ttaagaatcg atggtgttat ctgtgttgat    660
aacaccttgt tcaagggtag agtttacttg aaggactctg tcgacgaaat gggtaaagct    720
ttgagagact ttaaccaatt cgttaccgct gacccaagag ttgaacaagt tatcattcca    780
ttaagagatg gtttgaccat tattcgtaga gttccatata ctcctcaacc aaactctcaa    840
tctggtactg tcacttacga cgaagtcttc agaggtgttc aaggtaagcc tgtcttggac    900
cgtttacgtt tggatggtaa ggtcgcttac gtcaccggtg ctggtcaagg tattggtaga    960
gctttcgctc acgctttggg tgaagctggt gccaaggtcg ctattatcga catggataga   1020
ggtaaggctg aagatgtcgc tcatgaattg actttgaagg gtatctcttc catggctgtt   1080
gttgctgata tttctaagcc agatgacgtt caaaaaatga tcgatgacat cgttactaag   1140
tggggtactt tgcacatcgc ctgtaataac gctggtatta ataaaaactc cgcttctgaa   1200
gagacttctt tggaagaatg ggatcaaacc ttcaacgtta acttaagagg tactttcatg   1260
tgttgtcaag ctgctggtag agtcatgttg aagcaaggtt acggtaagat tattaacacc   1320
gcttccatgg cttctttgat tgttccacac ccacaaaaac aattgtccta caacctcc    1380 aaagctggtg tcgttaaatt gacccaaact ttgggtactg aatggattga tagaggtgtc   1440
cgtgttaact gtatttctcc aggtatcgtc gacaccctt tgattcattc tgagtccttg   1500
gaaccattgg tccaaagatg gttatccgac attccagccg gtagattggc tcaagtcacc   1560
gacttgcaag ccgccgtcgt ctacttggct tccgacgctt ccgactacat gactggtcat   1620
aatttggtca ttgaaggtgg tcaatctttta tgg                               1653
```

<210> SEQ ID NO 14
<211> LENGTH: 1653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
atgcaaactg ctaaagtttc tgatactcct gtcgaattca tcgtcgaaca tttgttaaag      60
gctaaggaaa tcgccgaaaa ccacgcctct atccctgttg aattaagaga taacttgcaa     120
aaggctttgg atattgcttc tggtttggac gaatacttag aacaaatgtc ttctaaggaa     180
tctgaaccat tgaccgaatt gtaccgtaaa tccgtttctc acgactggaa caaagtccat     240
gctgacggta aaaccttgtt tagattgcca gttacctgta tcactggtca agttgaaggt     300
caagtcttaa aaatgttggt tcacatgtct aaggccaagc gtgtcttgga aattggtatg     360
tttactggtt atggtgcttt atctatggct gaagctttgc cagaaaacgg tcaattgatt     420
gcttgtgaat tggaacctta cttgaaggac ttcgctcaac ctatcttcga caagtcccca     480
cacggtaaaa agatcaccgt taagactggt ccagctatgg atactttgaa agaattagct     540
gctactggtg agcaattcga catggttttc atcgatgctg acaaacaaaa ctacatcaac     600
tattacaagt ttttgttgga ccataacttg ttgagaatcg atggtgtcat ttgtgttgat     660
aacaccttat tcaaaggtag agtctactta aaagactctg tcgacgaaat gggtaaggct     720
ttaagagact caaccaattt tgttactgct gacccaagag ttgaacaagt tattatccca     780
ttgagagatg gtttgactat tatccgtaga gttccataca ctccacaacc aaactctcaa     840
tccggtaccg ttacttatga tgaagtcttc cgtggtgtcc aaggtaaacc agtcttggac     900
agattgagat ggatggtaa ggtcgcctat gttaccggtg ctggtcaagg tatcggtaga     960
gctttcgctc acgccttggg tgaggccggt gccaaagttg ctattattga tatggacaga    1020
ggtaaggctg aagacgttgc ccacgaattg accttgaagg gtatttcttc catggccgtc    1080
gttgccgata tttctaagcc agacgacgtt caaaagatga ttgacgatat cgttactaaa    1140
tggggtactt tacacatcgc ttgtaacaat gctggtatta taagaactc tgcttccgag    1200
gaaacctctt tggaagaatg ggatcaaact tttaatgtca atttgagagg taccttcatg    1260
tgttgtcaag ctgctggtag agttatgttg aagcaaggtt acggtaagat tattaacacc    1320
gcttccatgg cttctttgat cgtccctcac ccacaaaagc aattgtctta caacacctcc    1380
aaggccggtg ttgtcaagtt aactcaaact ttaggtactg agtggatcga cagaggtgtc    1440
agagttaact gcatttctcc aggtattgtt gacacccat tgatccattc cgaatccttg    1500
gaaccattag tccaaagatg gttgtccgac attcctgccg gtagattggc tcaagtcact    1560
gacttgcaag ccgctgtcgt ttatttggcc tctgacgctt ccgattatat gaccggtcac    1620
aacttggtca tcgaaggtgg tcaatcttta tgg                                 1653
```

<210> SEQ ID NO 15
<211> LENGTH: 1653
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
atgcaaactg ctaaggtctc cgacactcct gttgaattta tcgttgaaca tttgttgaag      60
gctaaagaaa tcgccgaaaa ccacgcttcc atcccagtcg aattgagaga taatttacaa     120
aaggctttag atattgcttc tggtttggac gaatacttgg aacaaatgtc ttccaaggaa     180
tctgaaccat tgactgagtt gtacagaaag tccgtttctc atgattggaa caaagttcac     240
gctgacggta agaccttgtt ccgtttgcca gttacttgta ttactggtca agttgaaggt     300
```

```
caagtcttga agatgttggt ccacatgtct aaagctaaga gagttttgga aatcggtatg      360
tttaccggtt acggtgcctt gtccatggcc gaagctttgc cagaaaacgg tcaattgatt      420
gcttgtgaat tggaaccata cttaaaggat tttgctcaac caattttga caaatcccct       480 catggtaaga agatcactgt taagactggt ccagctatgg ataccttgaa ggaattggct      540
gctactggtg aacaattcga catggtcttc attgatgccg ataagcaaaa ctacattaac      600
tactacaagt ttttgttgga tcataacttg ttaagaattg atggtgttat ctgtgttgac      660
aacaccttgt tcaaaggtag agtttatttg aaagattccg tcgatgaaat gggtaaggct      720
ttaagagact tcaaccaatt tgtcactgct gacccaagag ttgaacaagt cattatccca      780
ttgcgtgatg gtttgactat catccgtaga gttccttaca ctccacaacc aaactctcaa      840
tctggtactt ttacttacga cgaagtcttc agaggtgttc aaggtaagcc agttttggac      900
agattgagat tggacggtaa ggttgcttac gtcaccggtg ctggtcaagg tattggtaga      960
gctttcgctc acgctttggg tgaagctggt gctaaggttg ctatcatcga catggataga     1020
ggtaaggctg aagatgtcgc tcacgaattg accttgaagg gtatttcttc tatggctgtt     1080
gttgctgata tttctaagcc agacgatgtc caaaagatga ttgatgacat cgtcactaag     1140
tggggtacct tgcatatcgc ctgtaacaac gctggtatca acaagaattc tgcttctgaa     1200
gaaacttctt tggaagaatg ggaccaaact ttcaacgtta acttgcgtgg tactttcatg     1260
tgttgtcaag ctgctggtcg tgtcatgttg aagcaaggtt acggtaagat tattaacact     1320
gcttctatgg cttccttgat cgttcctcac ccacaaaagc aattgtctta caacacttct     1380
aaggctggtg tcgtcaagtt gactcaaacc ttgggtaccg aatggatcga tagaggtgtc     1440
cgtgttaact gcatctcccc aggtatcgtc gataccccat tgattcactc tgagtctttg     1500
gagccattgg ttcaaagatg gttgtctgac attccagccg gtagattagc tcaagttact     1560
gatttgcaag ctgccgtcgt ctacttggct tccgacgcct ctgattacat gactggtcat     1620
aacttggtca ttgaaggtgg tcaatcttta tgg                                  1653
```

<210> SEQ ID NO 16
<211> LENGTH: 1653
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 16

```
atgcaaactg ctaaggtttc tgacactcca gttgaattca tcgttgaaca cttgttgaag       60
gctaaggaaa tcgctgaaaa accacgcttct atcccagttg aattgagaga caacttgcaa     120
aaggctttgg acatcgcttc tggtttggac gaatacttgg aacaaatgtc ttctaaggaa      180
tctgaaccat tgactgaatt gtacagaaag tctgtttctc acgactggaa caaggttcac      240
gctgacggta agactttgtt cagattgcca gttacttgta tcactggtca agttgaaggt      300
caagttttga agatgttggt tcacatgtct aaggctaaga gagttttgga aatcggtatg      360
ttcactggtt acggtgcttt gtctatggct gaagctttgc cagaaaacgg tcaattgatc      420
gcttgtgaat tggaaccata cttgaaggac ttcgctcaac caatcttcga caagtctcca      480
cacggtaaga agatcactgt taagactggt ccagctatgg acactttgaa ggaattggct      540
gctactggtg aacaattcga catggttttc atcgacgctg acaagcaaaa ctacatcaac      600
tactacaagt tcttgttgga ccacaacttg ttgagaatcg acggtgttat ctgtgttgac      660
```

```
aacactttgt tcaagggtag agtttacttg aaggactctg ttgacgaaat gggtaaggct      720
ttgagagact tcaaccaatt cgttactgct gacccaagag ttgaacaagt tatcatccca      780
ttgagagacg gttttgactat catcagaaga gttccataca ctccacaacc aaactctcaa     840
tctggtactg ttacttacga cgaagttttc agaggtgttc aaggtaagcc agttttggac     900
agattgagat tggacggtaa ggttgcttac gttactggtg ctggtcaagg tatcggtaga     960
gctttcgctc acgctttggg tgaagctggt gctaaggttg ctatcatcga catggacaga     1020
ggtaaggctg aagacgttgc tcacgaattg actttgaagg gtatctcttc tatggctgtt     1080
gttgctgaca tctctaagcc agacgacgtt caaaagatga tcgacgacat cgttactaag     1140
tggggtactt tgcacatcgc ttgtaacaac gctggtatca acaagaactc tgcttctgaa     1200
gaaacttctt tggaagaatg ggaccaaact ttcaacgtta acttgagagg tacttctcatg    1260 tgttgtcaag ctgctggtag agttatgttg aagcaaggtt acggtaagat catcaacact     1320
gcttctatgg cttctttgat cgttccacac ccacaaaagc aattgtctta caacacttct     1380
aaggctggtg ttgttaagtt gactcaaact ttgggtactg aatggatcga cagaggtgtt     1440
agagttaact gtatctctcc aggtatcgtt gacactccat tgatccactc tgaatctttg     1500
gaaccattgg ttcaaagatg gttgtctgac atcccagctg gtagattggc tcaagttact     1560
gacttgcaag ctgctgttgt ttacttggct tctgacgctt ctgactacat gactggtcac     1620
aacttggtta tcgaaggtgg tcaatctttg tgg                                   1653

<210> SEQ ID NO 17
<211> LENGTH: 2579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcgggctgg cttaactatg cggcatcaga gcagattgta ctgagagtgc       180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt cgagctcggt acctcgcgaa      420
tgcatctaga tatcggatcc cgggcccgtc gactgcagag gcctgcatgc aagcttggcg      480
taatcatggt catagctgtt tcctgtgtga aattgttatc cgctcacaat tccacacaac     540
atacgagccg gaagcataaa gtgtaaagcc tggggtgcct aatgagtgag ctaactcaca    600
ttaattgcgt tgcgctcact gcccgctttc cagtcgggaa acctgtcgtg ccagctgcat    660
taatgaatcg gccaacgcgc ggggagaggc ggtttgcgta ttgggcgctc ttccgcttcc    720
tcgctcactg actcgctgcg ctcggtcgtt cggctgcggc gagcggtatc agctcactca    780
aaggcggtaa tacggttatc cacagaatca ggggataacg caggaaagaa catgtgagca    840
aaaggccagc aaaaggccag gaaccgtaaa aaggccgcgt tgctggcgtt tttccatagg    900
ctccgccccc ctgacgagca tcacaaaaat cgacgctcaa gtcagaggtg gcgaaacccg    960
acaggactat aaagatacca ggcgtttccc cctggaagct ccctcgtgcg ctctcctgtt    1020
```

```
ccgaccctgc cgcttaccgg atacctgtcc gcctttctcc cttcgggaag cgtggcgctt    1080
tctcatagct cacgctgtag gtatctcagt tcggtgtagg tcgttcgctc caagctgggc    1140
tgtgtgcacg aaccccccgt tcagcccgac cgctgcgcct tatccggtaa ctatcgtctt    1200
gagtccaacc cggtaagaca cgacttatcg ccactggcag cagccactgg taacaggatt    1260
agcagagcga ggtatgtagg cggtgctaca gagttcttga agtggtggcc taactacggc    1320
tacactagaa gaacagtatt tggtatctgc gctctgctga agccagttac cttcggaaaa    1380
agagttggta gctcttgatc cggcaaacaa accaccgctg gtagcggtgg ttttttttgtt    1440 tgcaagcagc agattacgcg cagaaaaaaa ggatctcaag aagatccttt gatcttttct    1500
acggggtctg acgctcagtg gaacgaaaac tcacgttaag ggattttggt catgagatta    1560
tcaaaaagga tcttcaccta gatcctttta aattaaaaat gaagttttaa atcaagccca    1620
atctgaataa tgttacaacc aattaaccaa ttctgattag aaaaactcat cgagcatcaa    1680
atgaaactgc aatttattca tatcaggatt atcaatacca tatttttgaa aaagccgttt    1740
ctgtaatgaa ggagaaaact caccgaggca gttccatagg atggcaagat cctggtatcg    1800
gtctgcgatt ccgactcgtc caacatcaat acaacctatt aatttcccct cgtcaaaaat    1860
aaggttatca agtgagaaat caccatgagt gacgactgaa tccggtgaga atggcaaaag    1920
tttatgcatt tctttccaga cttgttcaac aggccagcca ttacgctcgt catcaaaatc    1980
actcgcatca accaaaccgt tattcattcg tgattgcgcc tgagcgagac gaaatacgcg    2040
atcgctgtta aaaggacaat acaaacagg aatcgaatgc aaccggcgca ggaacactgc    2100
cagcgcatca acaatatttt cacctgaatc aggatattct tctaatacct ggaatgctgt    2160
ttttccgggg atcgcagtgg tgagtaacca tgcatcatca ggagtacgga taaaatgctt    2220
gatggtcgga agaggcataa attccgtcag ccagtttagt ctgaccatct catctgtaac    2280
atcattggca acgctacctt tgccatgttt cagaaacaac tctggcgcat cgggcttccc    2340
atacaagcga tagattgtcg cacctgattg cccgacatta tcgcgagccc atttataccc    2400
atataaatca gcatccatgt tggaatttaa tcgcggcctc gacgtttccc gttgaatatg    2460
gctcataaca ccccttgtat tactgtttat gtaagcagac agttttattg ttcatgatga    2520
tatattttta tcttgtgcaa tgtaacatca gagattttga gacacgggcc agagctgca    2579
```

<210> SEQ ID NO 18
<211> LENGTH: 2887
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
gatctcgatc ccgcgaaatt aatacgactc actataggga gaccacaacg gtttccctct     60
agaaataatt ttgtttaact ttaagaagga gatatacata tgcggggttc tcatcatcat    120
catcatcatg gtatggctag catgactggt ggacagcaaa tgggtcggga tctgtacgac    180
gatgacgata aggatccgag ctcgagatct gcagctggta ccatggaatt cgaagcttga    240
tccggctgct aacaaagccc gaaaggaagc tgagttggct gctgccaccg ctgagcaata    300
actagcataa ccccttgggg cctctaaacg ggtcttgagg ggttttttgc tgaaaggagg    360
aactatatcc ggatctggcg taatagcgaa gaggcccgca ccgatcgccc ttcccaacag    420
ttgcgcagcc tgaatggcga atgggacgcg ccctgtagcg gcgcattaag cgcggcgggt    480
```

-continued

```
gtggtggtta cgcgcagcgt gaccgctaca cttgccagcg ccctagcgcc cgctcctttc      540
gctttcttcc cttcctttct cgccacgttc gccggctttc cccgtcaagc tctaaatcgg      600
gggctccctt tagggttccg atttagtgct ttacggcacc tcgacgccaa aaaacttgat      660
tagggtgatg gttcacgtag tgggccatcg ccctgatgaa cggttttcg cccttttgacg      720 ttggagtcca cgttctttaa tagtggactc ttgttccaaa ctggaacaac actcaacct      780 atctcggtct attcttttga tttataaggg atttttgccga tttcggccta ttggttaaaa    840
aatgagctga tttaacaaaa atttaacgcg aattttaaca aaatattaac gcttacaatt     900
taggtggcac ttttcgggga aatgtgcgcg aacccctat ttgtttattt ttctaaatac      960
attcaaatat gtatccgctc atgagacaat aaccctgata aatgcttcaa taatattgaa   1020
aaaggaagag tatgagtatt caacatttcc gtgtcgccct tattcccttt tttgcggcat  1080
tttgccttcc tgtttttgct cacccagaaa cgctggtgaa agtaaaagat gctgaagatc  1140
agttgggtgc acgagtgggt tacatcgaac tggatctcaa cagcggtaag atccttgaga  1200
gttttcgccc cgaagaacgt tttccaatga tgagcacttt taaagttctg ctatgtggcg  1260
cggtattatc ccgtattgac gccgggcaag agcaactcgg tcgccgcata cactattctc  1320
agaatgactt ggttgagtac tcaccagtca cagaaaagca tcttacggat ggcatgacag  1380
taagagaatt atgcagtgct gccataacca tgagtgataa cactgcggcc aacttacttc  1440
tgacaacgat cggaggaccg aaggagctaa ccgcttttt gcacaacatg ggggatcatg  1500
taactcgcct tgatcgttgg gaaccggagc tgaatgaagc cataccaaac gacgagcgtg  1560
acaccacgat gcctgtagca atggcaacaa cgttgcgcaa actattaact ggcgaactac  1620
ttactctagc ttcccggcaa caattaatag actggatgga ggcggataaa gttgcaggac  1680
cacttctgcg ctcggccctt ccggctggct ggtttattgc tgataaatct ggagccggtg  1740
agcgtgggtc tcgcggtatc attgcagcac tggggccaga tggtaagccc tcccgtatcg  1800
tagttatcta cacgacgggg agtcaggcaa ctatggatga acgaaataga cagatcgctg  1860
agataggtgc ctcactgatt aagcattggt aactgtcaga ccaagtttac tcatatatac  1920
tttagattga tttaaaactt cattttaat ttaaaaggat ctaggtgaag atcctttttg  1980
ataatctcat gaccaaaatc ccttaacgtg agttttcgtt ccactgagcg tcagaccccg  2040
tagaaaagat caaaggatct tcttgagatc ctttttttct gcgcgtaatc tgctgcttgc  2100
aaacaaaaaa accaccgcta ccagcggtgg tttgtttgcc ggatcaagag ctaccaactc  2160
tttttccgaa ggtaactggc ttcagcagag cgcagatacc aaatactgtt cttctagtgt  2220
agccgtagtt aggccaccac ttcaagaact ctgtagcacc gcctacatac ctcgctctgc  2280
taatcctgtt accagtggct gctgccagtg gcgataagtc gtgtcttacc gggttggact  2340
caagacgata gttaccggat aaggcgcagc ggtcgggctg aacggggggt tcgtgcacac  2400
agcccagctt ggagcgaacg acctacaccg aactgagata cctacagcgt gagctatgag  2460
aaagcgccac gcttcccgaa gggagaaagg cggacaggta tccggtaagc ggcagggtcg  2520
gaacaggaga gcgcacgagg gagcttccag ggggaaacgc ctggtatctt tatagtcctg  2580
tcgggtttcg ccacctctga cttgagcgtc gatttttgtg atgctcgtca ggggggcgga  2640
gcctatggaa aaacgccagc aacgcggcct ttttacggtt cctggccttt tgctggcctt  2700
ttgctcacat gttctttcct gcgttatccc ctgattctgt ggataaccgt attaccgcct  2760
ttgagtgagc tgataccgct cgccgcagcc gaacgaccga gcgcagcgag tcagtgagcg  2820
```

| aggaagcgga agagcgccca atacgcaaac cgcctctccc cgcgcgttgg ccgattcatt | 2880 |
| aatgcag | 2887 |

<210> SEQ ID NO 19
<211> LENGTH: 5865
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgccaa gcttgcatgc ctgcaggtcg | 420 |
| actctagagg atccccggga taacttcgta tagcatacat tatacgaagt tataacgaca | 480 |
| ttactatata tataatatag gaagcattta atagaacagc atcgtaatat atgtgtactt | 540 |
| tgcagttatg acgccagatg gcagtagtgg aagatattct ttattgaaaa atagcttgtc | 600 |
| accttacgta caatcttgat ccggagcttt tctttttttg ccgattaaga attaattcgg | 660 |
| tcgaaaaaag aaaaggagag ggccaagagg gagggcattg gtgactattg agcacgtgag | 720 |
| tatacgtgat taagcacaca aaggcagctt ggagtatgtc tgttattaat ttcacaggta | 780 |
| gttctggtcc attggtgaaa gtttgcggct tgcagagcac agaggccgca gaatgtgctc | 840 |
| tagattccga tgctgacttg ctgggtatta tatgtgtgcc caatagaaag agaacaattg | 900 |
| acccggttat tgcaaggaaa atttcaagtc ttgtaaaagc atataaaaat agttcaggca | 960 |
| ctccgaaata cttggttggc gtgtttcgta atcaacctaa ggaggatgtt ttggctctgg | 1020 |
| tcaatgatta cggcattgat atcgtccaac tgcatggaga tgagtcgtgg caagaatacc | 1080 |
| aagagttcct cggtttgcca gttattaaaa gactcgtatt tccaaaagac tgcaacatac | 1140 |
| tactcagtgc agcttcacag aaacctcatt cgtttattcc cttgtttgat tcagaagcag | 1200 |
| gtgggacagg tgaacttttg gattggaact cgatttctga ctgggttgga aggcaagaga | 1260 |
| gccccgaaag cttacatttt atgttagctg gtggactgac gccagaaaat gttggtgatg | 1320 |
| cgcttagatt aaatggcgtt attggtgttg atgtaagcgg aggtgtggag acaaatggtg | 1380 |
| taaaagactc taacaaaata gcaaatttcg tcaaaaatgc taagaaatag gttattactg | 1440 |
| agtagtattt atttaagtat tgtttgtgca cttgcctgat aacttcgtat agcatacatt | 1500 |
| atacgaagtt atcccgggta ccgagctcga attcaacgaa gcatctgtgc ttcattttgt | 1560 |
| agaacaaaaa tgcaacgcga gagcgctaat ttttcaaaca aagaatctga gctgcatttt | 1620 |
| tacagaacag aaatgcaacg cgaaagcgct attttaccaa cgaagaatct gtgcttcatt | 1680 |
| tttgtaaaac aaaaatgcaa cgcgagagcg ctaattttc aaacaaagaa tctgagctgc | 1740 |
| atttttacag aacagaaatg caacgcgaga gcgctatttt accaacaaag aatctatact | 1800 |
| tcttttttgt tctacaaaaa tgcatcccga gagcgctatt tttctaacaa agcatcttag | 1860 |
| attacttttt ttctcctttg tgcgctctat aatgcagtct cttgataact ttttgcactg | 1920 |

```
taggtccgtt aaggttagaa gaaggctact ttggtgtcta ttttctcttc cataaaaaaa    1980
gcctgactcc acttcccgcg tttactgatt actagcgaag ctgcgggtgc atttttttcaa   2040 gataaaggca tccccgatta tattctatac cgatgtggat tgcgcatact tgtgaacag    2100 aaagtgatag cgttgatgat tcttcattgg tcagaaaatt atgaacggtt tcttctattt    2160
tgtctctata tactacgtat aggaaatgtt tacattttcg tattgttttc gattcactct    2220
atgaatagtt cttactacaa ttttttttgtc taaagagtaa tactagagat aaacataaaa   2280
aatgtagagg tcgagtttag atgcaagttc aaggagcgaa aggtggatgg gtaggttata    2340
tagggatata gcacagagat atatagcaaa gagatacttt tgagcaatgt ttgtggaagc    2400
ggtattcgca atattttagt agctcgttac agtccggtgc gttttttggtt ttttgaaagt    2460 gcgtcttcag agcgcttttg gttttcaaaa gcgctctgaa gttcctatac tttctagaga    2520
ataggaactt cggaatagga acttcaaagc gtttccgaaa acgagcgctt ccgaaaatgc    2580
aacgcgagct gcgcacatac agctcactgt tcacgtcgca cctatatctg cgtgttgcct    2640
gtatatatat atacatgaga agaacggcat agtgcgtgtt tatgcttaaa tgcgtactta    2700
tatgcgtcta tttatgtagg atgaaaggta gtctagtacc tcctgtgata ttatcccatt    2760
ccatgcgggg tatcgtatgc ttccttcagc actacccttt agctgttcta tatgctgcca    2820
ctcctcaatt ggattagtct catccttcaa tgctatcatt cctttgata ttggatcata    2880 cgaattcgta atcatggtca tagctgtttc ctgtgtgaaa ttgttatccg ctcacaattc    2940
cacacaacat acgagccgga agcataaagt gtaaagcctg gggtgcctaa tgagtgagct    3000
aactcacatt aattgcgttg cgctcactgc ccgctttcca gtcgggaaac ctgtcgtgcc    3060
agctgcatta atgaatcggc caacgcgcgg ggagaggcgg tttgcgtatt gggcgctctt    3120
ccgcttcctc gctcactgac tcgctgcgct cggtcgttcg gctgcggcga gcggtatcag    3180
ctcactcaaa ggcggtaata cggttatcca cagaatcagg ggataacgca ggaaagaaca    3240
tgtgagcaaa aggccagcaa aaggccagga accgtaaaaa ggccgcgttg ctggcgtttt    3300
tccataggct ccgcccccct gacgagcatc acaaaaatcg acgctcaagt cagaggtggc    3360
gaaacccgac aggactataa agataccagg cgtttccccc tggaagctcc ctcgtgcgct    3420
ctcctgttcc gaccctgccg cttaccggat acctgtccgc ctttctccct cgggaagcg    3480 tggcgctttc tcatagctca cgctgtaggt atctcagttc ggtgtaggtc gttcgctcca    3540
agctgggctg tgtgcacgaa ccccccgttc agcccgaccg ctgcgcctta tccggtaact    3600
atcgtcttga gtccaacccg gtaagacacg acttatcgcc actggcagca gccactggta    3660
acaggattag cagagcgagg tatgtaggcg gtgctacaga gttcttgaag tggtggccta    3720
actacggcta cactagaagg acagtatttg gtatctgcgc tctgctgaag ccagttacct    3780
tcggaaaaag agttggtagc tcttgatccg gcaaacaaac caccgctggt agcggtggtt    3840
tttttgtttg caagcagcag attacgcgca gaaaaaaagg atctcaagaa gatcctttga    3900
tcttttctac ggggtctgac gctcagtgga acgaaaactc acgttaaggg attttggtca    3960
tgagattatc aaaaaggatc ttcacctaga tccttttaaa ttaaaaatga agttttaaat    4020
caatctaaag tatatatgag taaacttggt ctgacagtta ccaatgctta atcagtgagg    4080
cacctatctc agcgatctgt ctatttcgtt catccatagt tgcctgactc ccgtcgtgt    4140 agataactac gatacgggag ggcttaccat ctggccccag tgctgcaatg ataccgcgag    4200
acccacgctc accggctcca gatttatcag caataaacca gccagccgga agggccgagc    4260
gcagaagtgg tcctgcaact ttatccgcct ccatccagtc tattaattgt tgccgggaag    4320
```

```
ctagagtaag tagttcgcca gttaatagtt tgcgcaacgt tgttgccatt gctacaggca    4380
tcgtggtgtc acgctcgtcg tttggtatgg cttcattcag ctccggttcc caacgatcaa    4440
ggcgagttac atgatccccc atgttgtgca aaaagcggt  tagctccttc ggtcctccga    4500
tcgttgtcag aagtaagttg gccgcagtgt tatcactcat ggttatggca gcactgcata    4560
attctcttac tgtcatgcca tccgtaagat gcttttctgt gactggtgag tactcaacca    4620
agtcattctg agaatagtgt atgcggcgac cgagttgctc ttgcccggcg tcaatacggg    4680
ataataccgc gccacatagc agaactttaa aagtgctcat cattggaaaa cgttcttcgg    4740
ggcgaaaact ctcaaggatc ttaccgctgt tgagatccag ttcgatgtaa cccactcgtg    4800
cacccaactg atcttcagca tcttttactt tcaccagcgt ttctgggtga gcaaaaacag    4860
gaaggcaaaa tgccgcaaaa aagggaataa gggcgacacg gaaatgttga atactcatac    4920
tcttcctttt tcaatattac cgcgaatcct tacatcacac ccaatccccc acaagtgatc    4980
ccccacacac catagcttca aaatgttct  actccttttt tactcttcca gattttctcg    5040
gactccgcgc atcgccgtac cacttcaaaa cacccaagca cagcatacta aatttcccct    5100
ctttcttcct ctagggtgtc gttaattacc cgtactaaag gtttggaaaa gaaaaaagag    5160
accgcctcgt ttctttttct tcgtcgaaaa aggcaataaa aattttatc  acgtttcttt    5220
ttcttgaaaa ttttttttt  tgattttttt ctctttcgat gacctcccat tgatatttaa    5280
gttaataaac ggtcttcaat ttctcaagtt tcagtttcat ttttcttgtt ctattacaac    5340
tttttttact tcttgctcat tagaaagaaa gcatagcaat ctaatctaag ttttaattac    5400
aaaactagtg atatctgcgc actcgagtca tgtaattagt tatgtcacgc ttacattcac    5460
gccctccccc cacatccgct ctaaccgaaa aggaaggagt tagacaacct gaagtctagg    5520
tccctatttta ttttttata  gttatgttag tattaagaac gttatttata tttcaaattt    5580
ttctttttttt tctgtacaga cgcgtgtacg catgtaacat tatactgaaa accttgcttg    5640
agaaggtttt gggacgctcg aaggctttaa tttgcggcca atattattga agcatttatc    5700
agggttattg tctcatgagc ggatacatat ttgaatgtat ttagaaaaat aaacaaatag    5760
gggttccgcg cacatttccc cgaaaagtgc cacctgacgt ctaagaaacc attattatca    5820
tgacattaac ctataaaaat aggcgtatca cgaggccctt tcgtc                    5865
```

<210> SEQ ID NO 20
<211> LENGTH: 6036
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgccaa gcttgcatgc ctgcaggtcg    420
actctagagg atccccggga taacttcgta tagcatacat tatacgaagt tatcgtttta    480
```

```
agagcttggt gagcgctagg agtcactgcc aggtatcgtt tgaacacggc attagtcagg    540
gaagtcataa cacagtcctt tcccgcaatt ttcttttttct attactcttg gcctcctcta    600
gtacactcta tattttttta tgcctcggta atgattttca tttttttttt tccacctagc    660
ggatgactct ttttttttct tagcgattgg cattatcaca taatgaatta tacattatat    720
aaagtaatgt gatttcttcg aagaatatac taaaaaatga gcaggcaaga taaacgaagg    780
caaagatgac agagcagaaa gccctagtaa agcgtattac aaatgaaacc aagattcaga    840
ttgcgatctc tttaaagggt ggtcccctag cgatagagca ctcgatcttc ccagaaaaag    900
aggcagaagc agtagcagaa caggccacac aatcgcaagt gattaacgtc cacacaggta    960
tagggtttct ggaccatatg atacatgctc tggccaagca ttccggctgg tcgctaatcg   1020
ttgagtgcat tggtgactta cacatagacg accatcacac cactgaagac tgcgggattg   1080
ctctcggtca agcttttaaa gaggccctag gggccgtgcg tggagtaaaa aggtttggat   1140
caggatttgc gcctttggat gaggcacttt ccagagcggt ggtagatctt tcgaacaggc   1200
cgtacgcagt tgtcgaactt ggtttgcaaa gggagaaagt aggagatctc tcttgcgaga   1260
tgatcccgca ttttcttgaa agctttgcag aggctagcag aattaccctc cacgttgatt   1320
gtctgcgagg caagaatgat catcaccgta gtgagagtgc gttcaaggct cttgcggttg   1380
ccataagaga agccacctcg cccaatggta ccaacgatgt tccctccacc aaaggtgttc   1440
ttatgtagtg acaccgatta tttaaagctg cagcatacga tatatataca tgtgtatata   1500
tgtataccta tgaatgtcag taagtatgta tacgaacagt atgatactga agatgacaag   1560
gtaatgcatc attctatacg tgtcattctg aacgaggcgc gctttccttt tttcttttg    1620 cttttttcttt tttttttctct tgaactcgaa taacttcgta tagcatacat tatacgaagt   1680
tatcccgggt accgagctcg aattcgtatg atccaatatc aaaggaaatg atagcattga   1740
aggatgagac taatccaatt gaggagtggc agcatataga acagctaaag ggtagtgctg   1800
aaggaagcat acgatacccc gcatggaatg ggataatatc acaggaggta ctagactacc   1860
tttcatccta cataaataga cgcatataag tacgcattta agcataaaca cgcactatgc   1920
cgttcttctc atgtatatat atatacaggc aacacgcaga tataggtgcg acgtgaacag   1980
tgagctgtat gtgcgcagct cgcgttgcat tttcggaagc gctcgttttc ggaaacgctt   2040
tgaagttcct attccgaagt tcctattctc tagaaagtat aggaacttca gagcgctttt   2100
gaaaaccaaa agcgctctga agacgcactt tcaaaaaacc aaaaacgcac cggactgtaa   2160
cgagctacta aaatattgcg aataccgctt ccacaaacat tgctcaaaag tatctctttg   2220
ctatatatct ctgtgctata tccctatata acctacccat ccacctttcg ctccttgaac   2280
ttgcatctaa actcgacctc tacattttt atgtttatct ctagtattac tctttagaca   2340
aaaaaattgt agtaagaact attcatagag tgaatcgaaa acaatacgaa aatgtaaaca   2400
tttcctatac gtagtatata gagacaaaat agaagaaacc gttcataatt ttctgaccaa   2460
tgaagaatca tcaacgctat cactttctgt tcacaaagta tgcgcaatcc acatcggtat   2520
agaatataat cggggatgcc tttatcttga aaaaatgcac ccgcagcttc gctagtaatc   2580
agtaaacgcg ggaagtggag tcaggctttt tttatggaag agaaaataga caccaaagta   2640
gccttcttct aaccttaacg gacctacagt gcaaaaagtt atcaagagac tgcattatag   2700
agcgcacaaa ggagaaaaaa agtaatctaa gatgctttgt tagaaaaata gcgctctcgg   2760
gatgcatttt tgtagaacaa aaaagaagta tagattcttt gttggtaaaa tagcgctctc   2820
```

```
gcgttgcatt tctgttctgt aaaaatgcag ctcagattct tgtttgaaa aattagcgct    2880 ctcgcgttgc attttgttt tacaaaaatg aagcacagat tcttcgttgg taaaatagcg    2940
ctttcgcgtt gcatttctgt tctgtaaaaa tgcagctcag attctttgtt tgaaaaatta    3000
gcgctctcgc gttgcatttt tgttctacaa aatgaagcac agatgcttcg ttgaattcgt    3060
aatcatggtc atagctgttt cctgtgtgaa attgttatcc gctcacaatt ccacacaaca    3120
tacgagccgg aagcataaag tgtaaagcct ggggtgccta atgagtgagc taactcacat    3180
taattgcgtt gcgctcactg cccgctttcc agtcgggaaa cctgtcgtgc cagctgcatt    3240
aatgaatcgg ccaacgcgcg gggagaggcg gtttgcgtat tgggcgctct tccgcttcct    3300
cgctcactga ctcgctgcgc tcggtcgttc ggctgcggcg agcggtatca gctcactcaa    3360
aggcggtaat acggttatcc acagaatcag gggataacgc aggaaagaac atgtgagcaa    3420
aaggccagca aaaggccagg aaccgtaaaa aggccgcgtt gctggcgttt ttccataggc    3480
tccgcccccc tgacgagcat cacaaaaatc gacgctcaag tcagaggtgg cgaaacccga    3540
caggactata aagataccag gcgtttcccc ctggaagctc cctcgtgcgc tctcctgttc    3600
cgaccctgcc gcttaccgga tacctgtccg cctttctccc ttcgggaagc gtggcgcttt    3660
ctcatagctc acgctgtagg tatctcagtt cggtgtaggt cgttcgctcc aagctgggct    3720
gtgtgcacga accccccgtt cagcccgacc gctgcgcctt atccggtaac tatcgtcttg    3780
agtccaaccc ggtaagacac gacttatcgc cactggcagc agccactggt aacaggatta    3840
gcagagcgag gtatgtaggc ggtgctacag agttcttgaa gtggtggcct aactacggct    3900
acactagaag gacagtattt ggtatctgcg ctctgctgaa gccagttacc ttcggaaaaa    3960
gagttggtag ctcttgatcc ggcaaacaaa ccaccgctgg tagcggtggt ttttttgttt    4020
gcaagcagca gattacgcgc agaaaaaaag gatctcaaga agatcctttg atcttttcta    4080
cggggtctga cgctcagtgg aacgaaaact cacgttaagg gattttggtc atgagattat    4140
caaaaaggat cttcacctag atcctttaa attaaaaatg aagttttaaa tcaatctaaa    4200
gtatatatga gtaaacttgg tctgacagtt accaatgctt aatcagtgag gcacctatct    4260
cagcgatctg tctatttcgt tcatccatag ttgcctgact ccccgtcgtg tagataacta    4320
cgatacggga gggcttacca tctggcccca gtgctgcaat gataccgcga cccacgctc    4380 caccggctcc agatttatca gcaataaacc agccagccgg aagggccgag cgcagaagtg    4440
gtcctgcaac tttatccgcc tccatccagt ctattaattg ttgccgggaa gctagagtaa    4500
gtagttcgcc agttaatagt ttgcgcaacg ttgttgccat tgctacaggc atcgtggtgt    4560
cacgctcgtc gtttggtatg gcttcattca gctccggttc ccaacgatca aggcgagtta    4620
catgatcccc catgttgtgc aaaaaagcgg ttagctcctt cggtcctccg atcgttgtca    4680
gaagtaagtt ggccgcagtg ttatcactca tggttatggc agcactgcat aattctctta    4740
ctgtcatgcc atccgtaaga tgcttttctg tgactggtga gtactcaacc aagtcattct    4800
gagaatagtg tatgcggcga ccgagttgct cttgcccggc gtcaatacgg gataataccg    4860
cgccacatag cagaacttta aaagtgctca tcattggaaa acgttcttcg ggcgaaaac    4920 tctcaaggat cttaccgctg ttgagatcca gttcgatgta acccactcgt gcacccaact    4980
gatcttcagc atcttttact ttcaccagcg tttctgggtg agcaaaaaca ggaaggcaaa    5040
atgccgcaaa aaagggaata agggcgacac ggaaatgttg aatactcata ctcttccttt    5100
ttcaatatta ccgcgaatcc ttacatcaca cccaatcccc cacaagtgat cccccacaca    5160
ccatagcttc aaaatgtttc tactccttt ttactcttcc agattttctc ggactccgcg    5220
```

```
catcgccgta ccacttcaaa acacccaagc acagcatact aaatttcccc tctttcttcc    5280
tctagggtgt cgttaattac ccgtactaaa ggtttggaaa agaaaaaaga gaccgcctcg    5340 tttcttttc ttcgtcgaaa aaggcaataa aaatttttat cacgtttctt tttcttgaaa     5400 atttttttt ttgatttttt tctctttcga tgacctccca ttgatattta agttaataaa     5460
cggtcttcaa tttctcaagt ttcagtttca tttttcttgt tctattacaa cttttttttac  5520 ttcttgctca ttagaaagaa agcatagcaa tctaatctaa gttttaatta caaaactagt    5580
gatatctgcg cactcgagtc atgtaattag ttatgtcacg cttacattca cgccctcccc    5640
ccacatccgc tctaaccgaa aaggaaggag ttagacaacc tgaagtctag gtccctattt    5700 attttttat agttatgtta gtattaagaa cgttatttat atttcaaatt tttctttttt     5760
ttctgtacag acgcgtgtac gcatgtaaca ttatactgaa aaccttgctt gagaaggttt    5820
tgggacgctc gaaggcttta atttgcggcc aatattattg aagcatttat cagggttatt    5880
gtctcatgag cggatacata tttgaatgta tttagaaaaa taaacaaata ggggttccgc    5940
gcacatttcc ccgaaaagtg ccacctgacg tctaagaaac cattattatc atgacattaa    6000
cctataaaaa taggcgtatc acgaggccct ttcgtc                              6036

<210> SEQ ID NO 21
<211> LENGTH: 470
<212> TYPE: PRT
<213> ORGANISM: Danio rerio

<400> SEQUENCE: 21

Met Glu Arg Pro Gly Glu Thr Phe Thr Val Ser Ser Pro Glu Glu Val
1               5                   10                  15

Arg Leu Pro Ser Val His Arg Asp Asn Ser Thr Met Glu Asn His Asn
            20                  25                  30

Lys Gln Glu Thr Val Phe Ser Leu Val Gln Val Lys Gly Thr Trp Lys
        35                  40                  45

Arg Lys Ala Gly Gln Asn Ala Lys Gln Gly Met Lys Gly Arg Val Ser
    50                  55                  60

Pro Ala Lys Ile Tyr Glu Ser Ser Ser Ser Gly Thr Thr Trp Thr
65                  70                  75                  80

Val Val Thr Pro Ile Thr Phe Thr Tyr Thr Val Thr Gln Thr Lys Asn
                85                  90                  95

Leu Leu Asp Pro Ser Asn Asp Thr Leu Leu Gly His Ile Ile Asp
            100                 105                 110

Thr Gln Gln Leu Glu Ala Val Arg Ser Asn Thr Lys Pro Leu Lys Arg
        115                 120                 125

Phe Ile Val Met Asp Glu Val Val Tyr Asn Ile Tyr Gly Ser Gln Val
    130                 135                 140

Thr Glu Tyr Leu Glu Ala Arg Asn Val Leu Tyr Arg Ile Leu Pro Leu
145                 150                 155                 160

Pro Thr Thr Glu Glu Asn Lys Ser Met Asp Met Ala Leu Lys Ile Leu
                165                 170                 175

Glu Glu Val His Gln Phe Gly Ile Asp Arg Arg Thr Glu Pro Ile Ile
            180                 185                 190

Ala Ile Gly Gly Gly Val Cys Leu Asp Ile Val Gly Leu Ala Ala Ser
        195                 200                 205

Leu Tyr Arg Arg Arg Thr Pro Tyr Ile Arg Val Pro Thr Thr Leu Leu
    210                 215                 220
```

Ser Tyr Ile Asp Ala Ser Val Gly Ala Lys Thr Gly Val Asn Phe Ala
225                 230                 235                 240

Asn Cys Lys Asn Lys Leu Gly Thr Tyr Ile Ala Pro Val Ala Ala Phe
            245                 250                 255

Leu Asp Arg Ser Phe Ile Gln Ser Ile Pro Arg Arg His Ile Ala Asn
        260                 265                 270

Gly Leu Ala Glu Met Leu Lys Met Ala Leu Met Lys His Arg Gly Leu
    275                 280                 285

Phe Glu Leu Leu Glu Val His Gly Gln Phe Leu Leu Asp Ser Lys Phe
290                 295                 300

Gln Ser Ala Ser Val Leu Glu Asn Asp Arg Ile Asp Pro Ala Ser Val
305                 310                 315                 320

Ser Thr Arg Val Ala Ile Glu Thr Met Leu Glu Glu Leu Ala Pro Asn
            325                 330                 335

Leu Trp Glu Asp Asp Leu Asp Arg Leu Val Asp Phe Gly His Leu Ile
        340                 345                 350

Ser Pro Gln Leu Glu Met Lys Val Leu Pro Ala Leu Leu His Gly Glu
    355                 360                 365

Ala Val Asn Ile Asp Met Ala Tyr Met Val Tyr Val Ser Cys Glu Ile
370                 375                 380

Gly Leu Leu Thr Glu Glu Lys Phe Arg Ile Ile Cys Cys Met Met
385                 390                 395                 400

Gly Leu Glu Leu Pro Val Trp His Gln Asp Phe Thr Phe Ala Leu Val
            405                 410                 415

Gln Lys Ser Leu Cys Asp Arg Leu Gln His Ser Gly Gly Leu Val Arg
        420                 425                 430

Met Pro Leu Pro Thr Gly Leu Gly Arg Ala Glu Ile Phe Asn Asp Thr
    435                 440                 445

Asp Glu Gly Ser Leu Phe Arg Ala Tyr Glu Lys Trp Cys Asp Glu Leu
450                 455                 460

Ser Thr Gly Ser Pro Gln
465                 470

<210> SEQ ID NO 22
<211> LENGTH: 551
<212> TYPE: PRT
<213> ORGANISM: Danio rerio

<400> SEQUENCE: 22

Met Gln Thr Ala Lys Val Ser Asp Thr Pro Val Glu Phe Ile Val Glu
1               5                   10                  15

His Leu Leu Lys Ala Lys Glu Ile Ala Glu Asn His Ala Ser Ile Pro
            20                  25                  30

Val Glu Leu Arg Asp Asn Leu Gln Lys Ala Leu Asp Ile Ala Ser Gly
        35                  40                  45

Leu Asp Glu Tyr Leu Glu Gln Met Ser Ser Lys Glu Ser Glu Pro Leu
    50                  55                  60

Thr Glu Leu Tyr Arg Lys Ser Val Ser His Asp Trp Asn Lys Val His
65                  70                  75                  80

Ala Asp Gly Lys Thr Leu Phe Arg Leu Pro Val Thr Cys Ile Thr Gly
                85                  90                  95

Gln Val Glu Gly Gln Val Leu Lys Met Leu Val His Met Ser Lys Ala
            100                 105                 110

Lys Arg Val Leu Glu Ile Gly Met Phe Thr Gly Tyr Gly Ala Leu Ser
        115                 120                 125

```
Met Ala Glu Ala Leu Pro Glu Asn Gly Gln Leu Ile Ala Cys Glu Leu
            130                 135                 140

Glu Pro Tyr Leu Lys Asp Phe Ala Gln Pro Ile Phe Asp Lys Ser Pro
145                 150                 155                 160

His Gly Lys Lys Ile Thr Val Lys Thr Gly Pro Ala Met Asp Thr Leu
                165                 170                 175

Lys Glu Leu Ala Ala Thr Gly Glu Gln Phe Asp Met Val Phe Ile Asp
            180                 185                 190

Ala Asp Lys Gln Asn Tyr Ile Asn Tyr Tyr Lys Phe Leu Leu Asp His
        195                 200                 205

Asn Leu Leu Arg Ile Asp Gly Val Ile Cys Val Asp Asn Thr Leu Phe
210                 215                 220

Lys Gly Arg Val Tyr Leu Lys Asp Ser Val Asp Glu Met Gly Lys Ala
225                 230                 235                 240

Leu Arg Asp Phe Asn Gln Phe Val Thr Ala Asp Pro Arg Val Glu Gln
                245                 250                 255

Val Ile Ile Pro Leu Arg Asp Gly Leu Thr Ile Ile Arg Arg Val Pro
            260                 265                 270

Tyr Thr Pro Gln Pro Asn Ser Gln Ser Gly Thr Val Thr Tyr Asp Glu
        275                 280                 285

Val Phe Arg Gly Val Gln Gly Lys Pro Val Leu Asp Arg Leu Arg Leu
290                 295                 300

Asp Gly Lys Val Ala Tyr Val Thr Gly Ala Gly Gln Gly Ile Gly Arg
305                 310                 315                 320

Ala Phe Ala His Ala Leu Gly Glu Ala Gly Ala Lys Val Ala Ile Ile
                325                 330                 335

Asp Met Asp Arg Gly Lys Ala Glu Asp Val Ala His Glu Leu Thr Leu
            340                 345                 350

Lys Gly Ile Ser Ser Met Ala Val Val Ala Asp Ile Ser Lys Pro Asp
        355                 360                 365

Asp Val Gln Lys Met Ile Asp Asp Ile Val Thr Lys Trp Gly Thr Leu
370                 375                 380

His Ile Ala Cys Asn Asn Ala Gly Ile Asn Lys Asn Ser Ala Ser Glu
385                 390                 395                 400

Glu Thr Ser Leu Glu Glu Trp Asp Gln Thr Phe Asn Val Asn Leu Arg
                405                 410                 415

Gly Thr Phe Met Cys Cys Gln Ala Ala Gly Arg Val Met Leu Lys Gln
            420                 425                 430

Gly Tyr Gly Lys Ile Ile Asn Thr Ala Ser Met Ala Ser Leu Ile Val
        435                 440                 445

Pro His Pro Gln Lys Gln Leu Ser Tyr Asn Thr Ser Lys Ala Gly Val
450                 455                 460

Val Lys Leu Thr Gln Thr Leu Gly Thr Glu Trp Ile Asp Arg Gly Val
465                 470                 475                 480

Arg Val Asn Cys Ile Ser Pro Gly Ile Val Asp Thr Pro Leu Ile His
                485                 490                 495

Ser Glu Ser Leu Glu Pro Leu Val Gln Arg Trp Leu Ser Asp Ile Pro
            500                 505                 510

Ala Gly Arg Leu Ala Gln Val Thr Asp Leu Gln Ala Ala Val Val Tyr
        515                 520                 525

Leu Ala Ser Asp Ala Ser Asp Tyr Met Thr Gly His Asn Leu Val Ile
530                 535                 540
```

Glu Gly Gly Gln Ser Leu Trp
545                 550

<210> SEQ ID NO 23
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tataggaagc atttaataga acagcatcgt aatatatgtg tactttgcag ttatgacgcc    60
gaaattgagg ctactgcgcc                                               80

<210> SEQ ID NO 24
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cctgtgaaca ttctcttcaa caagtttgat tccattgcgg tgaaatggta aaagtcaacc    60
ggcagcgttt tgttcttgga                                               80

<210> SEQ ID NO 25
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gagcatttgc taaatgtgta aaaataatat tgcactatcc tgttgaaaat atctttccag    60
cactgttcac gtcgcaccta                                               80

<210> SEQ ID NO 26
<211> LENGTH: 81
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctatagttaa tcgcatttta tactgatgtt ttaacagggt tcgttaaatt aaacaatatt    60
gctgcattaa tgaatcggcc a                                             81

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctcacccgca cggcagagac                                               20

<210> SEQ ID NO 28
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgccggcggt tgtttgcaag                                              20

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtggctgtgg tttcagggtc ca                                           22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cctgaagtgt tctctgtttg cc                                           22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gctcagattc caccaaatac gg                                           22

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agatccacta gtatggaacg tccgggcgaa ac                                32

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tagccactcg agtcactgcg gtgagccggt                                   30

<210> SEQ ID NO 34
<211> LENGTH: 32
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 34
agatccacta gtatgcaaac ggcaaaagtc tc                                        32

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tagccactcg agtcaccaca gagactgacc g                                         31

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccatctgttc accgggacaa                                                      20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tgctggggtc aagaaggttt                                                      20

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agtagagcag gtcatcatcc ct                                                   22

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ctatgatggc gactttggct c                                                    21

<210> SEQ ID NO 40
<211> LENGTH: 80
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 40
ttcttgctag cgtaagtcat aaaaaatagg aaataatcac atatatacaa gaaattaaat      60
cactgttcac gtcgcaccta                                                 80

<210> SEQ ID NO 41
<211> LENGTH: 81
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
attatacgtc agaattttaa tgaatatata agtctgtaca ctatgctatg cacatatact      60
gctgcattaa tgaatcggcc a                                               81

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aaaactcaca tcgcacgcac                                                 20

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gagctgaaag caattctaaa tcca                                            24

<210> SEQ ID NO 44
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
acccagaaac tactttgttt ttgattgctt ccaagacttt cactaccgct gaaactatca      60
atgcgtaagg agaaaatacc                                                 80

<210> SEQ ID NO 45
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
agatagaacc agtagagtag tcagtaaaca cgttacctct ggtaacagac ttaccgttag      60
```
atgcagctca gattctttgt                                                    80

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggcaagaacc gggatggtaa                                                    20

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgtagttact tggacgctgt tc                                                 22

<210> SEQ ID NO 48
<211> LENGTH: 82
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agcacatttt gttcatagct aagtggatag ggaaacacct acacttaatt gcaagcaaca        60
gggcatgatg tgactgtcgc cc                                                 82

<210> SEQ ID NO 49
<211> LENGTH: 82
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aaaaaatgtt tttatcactt tctataactg catatctttt tttgcatttc gaatgattgc        60
tctgggcaga tgatgtcgag gc                                                 82

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ccaccgccaa attgctatcc                                                    20

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 51 acagtcctttt gtactatccc tttta                                           25

<210> SEQ ID NO 52
<211> LENGTH: 82
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
agccaaatca caaaaaaagc cttatagctt gccctgacaa agaatataca actcgggaaa      60
gggcatgatg tgactgtcgc cc                                              82

<210> SEQ ID NO 53
<211> LENGTH: 82
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
aaacctgaat attttccctt ttcaaaaagt aattctaccc ctagattttg cattgctcct      60
tctgggcaga tgatgtcgag gc                                              82

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
aagtggcttg agctgtggat                                                 20

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggttcttctg ctgcattagg c                                               21

<210> SEQ ID NO 56
<211> LENGTH: 78
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ttcttgctca ttagaaagaa agcatagcaa tctaatctaa gttttaatta caaaactagt      60
atgccttcgc taacccccc                                                  78

<210> SEQ ID NO 57
<211> LENGTH: 80
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gagcggatgt gggggagggg cgtgaatgta agcgtgacat aactaattac atgactcgag    60
ttacacatcg ccatgctggg                                                80

<210> SEQ ID NO 58
<211> LENGTH: 81
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
actatatgtg aaggcatggc tatggcacgg cagacattcc gccagatcat caataggcac    60
cttcattcaa cgtttcccat t                                              81

<210> SEQ ID NO 59
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gttgaacatt cttaggctgg tcgaatcatt tagacacggg catcgtcctc tcgaaaggtg    60
tgatgcatta ccttgtcatc                                                80

<210> SEQ ID NO 60
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
acctttcgag aggacgatgc ccgtgtctaa atgattcgac cagcctaaga atgttcaacc    60
ctgacttcaa ctcaagacgc                                                80

<210> SEQ ID NO 61
<211> LENGTH: 95
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cagcagatgt tccacaataa attcaaccgg ggtgtccgag acttttgccg tttgcatact    60
agtatatttg ttgtaaaaag tagataatta cttcc                               95

<210> SEQ ID NO 62
<211> LENGTH: 86
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 62
acgtctcacg gatcgtatat gccgtagcga caatctaaga actatgcgag gacacgctag    60
actagtatgc aaacggcaaa agtctc                                         86

<210> SEQ ID NO 63
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
aatcactctc catacagggt ttcatacatt tctccacggg acccacagtc gtagatgcgt    60
ctcgagtcac cacagagact gaccg                                          85

<210> SEQ ID NO 64
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gcatccgact acatgaccgg tcacaatctg gttattgaag gcggtcagtc tctgtggtga    60
attgaattga attgaaatcg atagatca                                       88

<210> SEQ ID NO 65
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gcctacggtt cccgaagtat gctgctgatg tctggctata cctatccgtc tacgtgaata    60
ttttgttgca agtgggatga                                                80

<210> SEQ ID NO 66
<211> LENGTH: 81
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tattcacgta gacggatagg tatagccaga catcagcagc atacttcggg aaccgtaggc    60
gaattcgtat gatccaatat c                                              81

<210> SEQ ID NO 67
<211> LENGTH: 82
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67

```
tgccgaactt tccctgtatg aagcgatctg accaatcctt tgccgtagtt tcaacgtatg    60
gaattcaacg aagcatctgt gc                                             82
```

<210> SEQ ID NO 68
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68

```
catacgttga aactacggca aaggattggt cagatcgctt catacaggga aagttcggca    60
aaaggcggta atacggtta                                                 79
```

<210> SEQ ID NO 69
<211> LENGTH: 84
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69

```
gtcacgggtt ctcagcaatt cgagctatta ccgatgatgg ctgaggcgtt agagtaatct    60
gaaaaaggaa gagtatgagt attc                                           84
```

<210> SEQ ID NO 70
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70

```
agattactct aacgcctcag ccatcatcgg taatagctcg aattgctgag aacccgtgac    60
accgcgaatc cttacatcac                                                80
```

<210> SEQ ID NO 71
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71

```
gtgcctattg atgatctggc ggaatgtctg ccgtgccata gccatgcctt cacatatagt    60
cagacaagct gtgaccgtct                                                80
```

<210> SEQ ID NO 72
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72

```
actatatgtg aaggcatggc tatggcacgg cagacattcc gccagatcat caataggcac    60
```

<210> SEQ ID NO 73

```
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
cacctttcga gaggacgatg cccgtgtcta aatgattcga ccagcctaag aatgttcaac    60

<210> SEQ ID NO 74
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tattcacgta gacggatagg tatagccaga catcagcagc atacttcggg aaccgtaggc    60

<210> SEQ ID NO 75
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
catacgttga aactacggca aaggattggt cagatcgctt catacaggga aagttcggca    60

<210> SEQ ID NO 76
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
agattactct aacgcctcag ccatcatcgg taatagctcg aattgctgag aacccgtgac    60

<210> SEQ ID NO 77
<211> LENGTH: 816
<212> TYPE: DNA
<213> ORGANISM: Saccharomyces cerevisiae

<400> SEQUENCE: 77
atgccttcgc taaccccccag atgtatcatt gtcagacacg gtcaaactga atggtccaag    60
tcaggccagt atactggttt gacagatcta ccgttaacgc cctacggtga gggccaaatg   120
ttgaggaccg gtgagagtgt tttccgcaat aatcagtttt tgaatccaga caacatcact   180
tatatcttca cctctccacg tttgcgtgcc aggcaaactg tggatttggt tttgaaacca   240
ttaagcgacg agcaaagagc taagatccgt gtggtggtag acgacgactt gcgagagtgg   300
gagtacggtg actacgaggg aatgctgact cgagaaatca ttgaattgag aaagtcacgc   360
ggtttggaca aggagaggcc atggaatatc tggagagatg ggtgtgagaa cggtgagact   420
actcagcaaa ttgggttgag actttcccgc gctattgcca gaatccagaa cttgcaccgc   480
aagcaccaga gtgagggcag agcatcagac atcatggtct ttgcgcacgg acatgcattg   540
cgttattttg ctgctatttg gtttggactg ggtgtgcaaa agaagtgtga gacgattgaa   600
gaaattcaaa atgtcaaatc ttatgatgac gacacagttc catatgtgaa attggaatct   660
```

| tacagacatt tggtagacaa tccatgtttc ttactggacg ccggtgggat tggtgttttg | 720 |
|---|---|
| tcatacgctc accacaacat tgacgaacct gcattggaat tagcaggtcc atttgtctca | 780 |
| ccaccagagg aggaatccca gcatggcgat gtgtaa | 816 |

<210> SEQ ID NO 78
<211> LENGTH: 1517
<212> TYPE: DNA
<213> ORGANISM: Saccharomyces cerevisiae

<400> SEQUENCE: 78

| atgagtgaag cccccgtcaa attcgaaaaa aataccgtca tatctgtctt tggtgcgtca | 60 |
|---|---|
| ggtgatctgg caaagaagaa gacttttccc gccttatttg ggcttttcag agaaggttac | 120 |
| cttgatccat ctaccaagat cttcggttat gcccggtcca aattgtccat ggaggaggac | 180 |
| ctgaagtccc gtgtcctacc ccacttgaaa aaacctcacg gtgaagccga tgactctaag | 240 |
| gtcgaacagt tcttcaagat ggtcagctac atttcgggaa attacgacac agatgaaggc | 300 |
| ttcgacgaat taagaacgca gatcgagaaa ttcgagaaaa gtgccaacgt cgatgtccca | 360 |
| caccgtctct tctatctggc cttgccgcca gcgttttttt gacggtggcc aagcagatca | 420 |
| agagtcgtgt gtacgcagag aatggcatca cccgtgtaat cgtagagaaa cctttcggcc | 480 |
| acgacctggc ctctgccagg gagctgcaaa aaaacctggg gcccctcttt aaagaagaag | 540 |
| agttgtacag aattgaccat tacttgggta agagttggt caagaatctt ttagtcttga | 600 |
| ggttcggtaa ccagtttttg aatgcctcgt ggaatagaga caacattcaa agcgttcaga | 660 |
| tttcgtttaa agagaggttc ggcaccgaag gccgtggcgg ctatttcgac tctataggca | 720 |
| taatcagaga cgtgatgcag aaccatctgt tacaaatcat gactctcttg actatggaaa | 780 |
| gaccggtgtc ttttgacccg gaatctattc gtgacgaaaa ggttaaggtt ctaaaggccg | 840 |
| tggcccccat cgacacggac gacgtcctct tgggccagta cggtaaatct gaggacgggt | 900 |
| ctaagcccgc ctacgtggat gatgacactg tagacaagga ctctaaatgt gtcacttttg | 960 |
| cagcaatgac tttcaacatc gaaaacgagc gttgggaggg cgtccccatc atgatgcgtg | 1020 |
| ccggtaaggc tttgaatgag tccaaggtgg agatcagact gcagtacaaa gcggtcgcat | 1080 |
| cgggtgtctt caaagacatt ccaaataacg aactggtcat cagagtgcag cccgatgccg | 1140 |
| ctgtgtacct aaagtttaat gctaagaccc ctggtctgtc aaatgctacc caagtcacag | 1200 |
| atctgaatct aacttacgca agcaggtacc aagacttttg gattccagag cttacgagg | 1260 |
| tgttgataag agacgcccta ctgggtgacc attccaactt tgtcagagat gacgaattgg | 1320 |
| atatcagttg gggcatattc accccattac tgaagcacat agagcgtccg gacggtccaa | 1380 |
| caccggaaat ttacccctac ggatcaagag gtccaaaggg attgaaggaa tatatgcaaa | 1440 |
| aacacaagta tgttatgccc gaaaagcacc cttacgcttg gcccgtgact aagccagaag | 1500 |
| atacgaagga taattag | 1517 |

<210> SEQ ID NO 79
<211> LENGTH: 8482
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 79

| actatatgtg aaggcatggc tatggcacgg cagacattcc gccagatcat caataggcac | 60 |
|---|---|

```
cttcattcaa cgtttcccat tgttttttc  tactattgct ttgctgtggg aaaaacttat      120
cgaaagatga cgactttttc ttaattctcg ttttaagagc ttggtgagcg ctaggagtca      180
ctgccaggta tcgtttgaac acggcattag tcagggaagt cataacacag tcctttcccg      240
caattttctt tttctattac tcttggcctc ctctagtaca ctctatattt ttttatgcct      300
cggtaatgat tttcattttt ttttttccac ctagcggatg actcttttt  tttcttagcg      360 attggcatta tcacataatg aattatacat tatataaagt aatgtgattt cttcgaagaa      420
tatactaaaa aatgagcagg caagataaac gaaggcaaag atgacagagc agaaagccct      480
agtaaagcgt attacaaatg aaaccaagat tcagattgcg atctctttaa agggtggtcc      540
cctagcgata gagcactcga tcttcccaga aaaagaggca gaagcagtag cagaacaggc      600
cacacaatcg caagtgatta acgtccacac aggtataggg tttctggacc atatgataca      660
tgctctggcc aagcattccg gctggtcgct aatcgttgag tgcattggtg acttacacat      720
agacgaccat cacaccactg aagactgcgg gattgctctc ggtcaagctt ttaaagaggc      780
cctaggggcc gtgcgtggag taaaaaggtt tggatcagga tttgcgcctt tggatgaggc      840
actttccaga gcggtggtag atctttcgaa caggccgtac gcagttgtcg aacttggttt      900
gcaaagggag aaagtaggag atctctcttg cgagatgatc ccgcattttc ttgaaagctt      960
tgcagaggct agcagaatta ccctccacgt tgattgtctg cgaggcaaga atgatcatca     1020
ccgtagtgag agtgcgttca aggctcttgc ggttgccata agagaagcca cctcgcccaa     1080
tggtaccaac gatgttccct ccaccaaagg tgttcttatg tagtgacacc gattatttaa     1140
agctgcagca tacgatatat atacatgtgt atatatgtat acctatgaat gtcagtaagt     1200
atgtatacga acagtatgat actgaagatg acaaggtaat gcatcacacc tttcgagagg     1260
acgatgcccg tgtctaaatg attcgaccag cctaagaatg ttcaaccctg acttcaactc     1320
aagacgcaca gatattataa catctgcata ataggcattt gcaagaatta ctcgtgagta     1380
aggaaagagt gaggaactat cgcatacctg catttaaaga tgccgatttg ggcgcgaatc     1440 ctttatttg  gcttcaccct catactatta tcagggccag aaaaaggaag tgtttccctc     1500
cttcttgaat tgatgttacc ctcataaagc acgtggcctc ttatcgagaa agaaattacc     1560
gtcgctcgtg atttgtttgc aaaaagaaca aaactgaaaa aacccagaca cgctcgactt     1620
cctgtcttcc tattgattgc agcttccaat ttcgtcacac aacaaggtcc tagcgacggc     1680
tcacaggttt tgtaacaagc aatcgaaggt tctggaatgg cgggaaaggg tttagtacca     1740
catgctatga tgcccactgt gatctccaga gcaaagttcg ttcgatcgta ctgttactct     1800
ctctctttca aacagaattg tccgaatcgt gtgacaacaa cagcctgttc tcacacactc     1860
ttttcttcta accaaggggg tggtttagtt tagtagaacc tcgtgaaact tacatttaca     1920
tatatataaa cttgcataaa ttggtcaatg caagaaatac atatttggtc ttttctaatt     1980
cgtagttttt caagttctta gatgctttct ttttctcttt tttacagatc atcaaggaag     2040
taattatcta cttttttacaa caaatataat gcaaacggca aaagtctcgg acaccccggt     2100
tgaatttatt gtggaacatc tgctgaaggc taaggaaatc gctgaaaatc acgcttccat     2160
tccggtggaa ctgcgcgata acctgcagaa agctctggat atcgcgagcg gcctggacga     2220
atatctggaa caaatgagct ctaaagaatc tgaaccgctg acggaactgt accgcaagtc     2280
agtctcgcat gattggaata agtgcacgc  ggacggcaag accctgtttc gtctgccggt     2340
gacctgcatt acgggccagg tcgaaggtca agtgctgaaa atgctggttc acatgagtaa     2400
```

-continued

```
agcgaagcgt gtcctggaaa ttggcatgtt taccggctat ggtgccctgt ccatggcaga    2460
agctctgccg gaaaacggtc agctgatcgc ttgtgaactg gaaccgtacc tgaaagattt    2520
tgcacaaccg attttcgaca agagtccgca tggcaaaaag atcaccgtga aaacgggtcc    2580
ggcaatggat accctgaagg aactggcggc cacgggcgaa cagtttgaca tggttttcat    2640
tgatgcggac aagcaaaact acatcaacta ctacaagttc ctgctggatc acaacctgct    2700
gcgtattgat ggcgtcatct gcgtggacaa tacgctgttc aaaggtcgcg tgtacctgaa    2760
ggatagcgtt gacgaaatgg gtaaagccct gcgtgatttt aaccagttcg tgaccgcaga    2820
cccgcgtgtt gaacaagtca ttatcccgct gcgcgatggc ctgaccatta tccgtcgcgt    2880
cccgtatacg ccgcagccga atagccaatc tggtaccgtg acgtacgatg aagttttcg    2940 cggcgtccag ggtaaaccgg ttctggatcg tctgcgcctg gacggcaaag tggcttatgt    3000
taccggtgcc ggtcagggta ttggtcgtgc attcgcccat gcactgggcg aagctggtgc    3060
gaaagttgcc attatcgata tggaccgtgg caaggccgaa gatgtcgcac acgaactgac    3120
cctgaaaggt attagttcca tggccgtggt tgcagatatc agcaaaccgg atgacgtgca    3180
gaagatgatt gatgacatcg ttaccaaatg gggcacgctg catattgctt gcaacaatgc    3240
gggtatcaac aaaaatagtg cgtccgaaga aacctctctg gaagaatggg atcagacgtt    3300
taacgtcaat ctgcgtggca ccttcatgtg ctgtcaggca gctggtcgcg ttatgctgaa    3360
acaaggctat ggcaagatta tcaacaccgc tagcatggcg tctctgattg tgccgcaccc    3420
gcagaaacaa ctgtcataca atacgtcgaa agccggcgtc gtgaagctga cccagacgct    3480
gggcaccgaa tggatcgatc gtggtgtgcg cgttaactgt atttcaccgg gtatcgtgga    3540
taccccgctg attcattcag aatcgctgga accgctggtt cagcgttggc tgtcggatat    3600
cccggcaggt cgtctggcac aggtgacgga cctgcaagcg gccgttgtct atctggccag    3660
tgatgcatcc gactacatga ccggtcacaa tctggttatt gaaggcggtc agtctctgtg    3720
gtgaattgaa ttgaattgaa atcgatagat caatttttt cttttctctt tccccatcct    3780
ttacgctaaa ataatagttt attttatttt ttgaatattt tttatttata tacgtatata    3840
tagactatta tttatctttt aatgattatt aagattttta ttaaaaaaaa attcgctcct    3900
cttttaatgc ctttatgcag ttttttttc ccattcgata tttctatgtt cgggttcagc    3960
gtattttaag tttaataact cgaaaattct gcgttcgtta aagctttcga gaaggatatt    4020
atttcgaaat aaaccgtgtt gtgtaagctt gaagcctttt tgcgctgcca atattcttat    4080
ccatctattg tactctttag atccagtata gtgtattctt cctgctccaa gctcatccca    4140
cttgcaacaa atatattcacg tagacggata ggtatagcca gacatcagca gcatacttcg    4200
ggaaccgtag gcgaattcca tacgttgaaa ctacggcaaa ggattggtca gatcgcttca    4260
tacagggaaa gttcggcaaa aggcggtaat acggttatcc acagaatcag gggataacgc    4320
aggaaagaac atgtgagcaa aaggccagca aaaggccagg aaccgtaaaa aggccgcgtt    4380
gctggcgttt ttccataggc tccgccccccc tgacgagcat cacaaaaatc gacgctcaag    4440
tcagaggtgg cgaaacccga caggactata agataccagg cgtttccccc ctggaagctc    4500
cctcgtgcgc tctcctgttc cgaccctgcc gcttaccgga tacctgtccg cctttctccc    4560
ttcgggaagc gtggcgcttt ctcatagctc acgctgtagg tatctcagtt cggtgtaggt    4620
cgttcgctcc aagctgggct gtgtgcacga accccccgtt cagcccgacc gctgcgcctt    4680
atccggtaac tatcgtcttg agtccaaccc ggtaagacac gacttatcgc cactggcagc    4740
agccactggt aacaggatta gcagagcgag gtatgtaggc ggtgctacag agttcttgaa    4800
```

```
gtggtggcct aactacggct acactagaag gacagtattt ggtatctgcg ctctgctgaa    4860
gccagttacc ttcggaaaaa gagttggtag ctccttgatcc ggcaaacaaa ccaccgctgg    4920
tagcggtggt ttttttgttt gcaagcagca gattacgcgc agaaaaaaag gatctcaaga    4980
agatcctttg atcttttcta cggggtctga cgctcagtgg aacgaaaact cacgttaagg    5040
gattttggtc atgagattat caaaaaggat cttcacctag atccttttaa attaaaaatg    5100
aagttttaaa tcaatctaaa gtatatatga gtaaacttgg tctgacagtt accaatgctt    5160
aatcagtgag gcacctatct cagcgatctg tctatttcgt tcatccatag ttgcctgact    5220
ccccgtcgtg tagataacta cgatacggga gggcttacca tctggcccca gtgctgcaat    5280
gataccgcga gacccacgct caccggctcc agatttatca gcaataaacc agccagccgg    5340
aagggccgag cgcagaagtg gtcctgcaac tttatccgcc tccatccagt ctattaattg    5400
ttgccgggaa gctagagtaa gtagttcgcc agttaatagt ttgcgcaacg ttgttgccat    5460
tgctacaggc atcgtggtgt cacgctcgtc gtttggtatg gcttcattca gctccggttc    5520
ccaacgatca aggcgagtta catgatcccc catgttgtgc aaaaaagcgg ttagctcctt    5580
cggtcctccg atcgttgtca gaagtaagtt ggccgcagtg ttatcactca tggttatggc    5640
agcactgcat aattctctta ctgtcatgcc atccgtaaga tgcttttctg tgactggtga    5700
gtactcaacc aagtcattct gagaatagtg tatgcggcga ccgagttgct cttgcccggc    5760
gtcaatacgg gataataccg cgccacatag cagaacttta aaagtgctca tcattggaaa    5820
acgttcttcg gggcgaaaac tctcaaggat cttaccgctg ttgagatcca gttcgatgta    5880
acccactcgt gcacccaact gatcttcagc atcttttact ttcaccagcg tttctgggtg    5940
agcaaaaaca ggaaggcaaa atgccgcaaa aaagggaata agggcgacac ggaaatgttg    6000
aatactcata ctcttccttt ttcagattac tctaacgcct cagccatcat cggtaatagc    6060
tcgaattgct gagaacccgt gacaccgcga atccttacat cacacccaat cccccacaag    6120
tgatccccca cacaccatag cttcaaaatg tttctactcc tttttttactc ttccagattt    6180 tctcggactc cgcgcatcgc cgtaccactt caaaacaccc aagcacagca tactaaattt    6240
cccctctttc ttcctctagg gtgtcgttaa ttacccgtac taaaggtttg gaaaagaaaa    6300
aagagaccgc ctcgtttctt tttcttcgtc gaaaaaggca ataaaatttt ttatcacgtt    6360 tcttttttctt gaaaattttt ttttttgatt ttttttctctt tcgatgacct cccattgata    6420
tttaagttaa taaacggtct tcaattttctc aagtttcagt ttcattttttc ttgttctatt    6480 acaacttttt ttacttcttg ctcattagaa agaaagcata gcaatctaat ctaagtttta    6540
attacaaaac tagtatggaa cgtccgggcg aaacctttac cgtcagctcc ccggaagaag    6600
tgcgtctgcc gtctgttcac cgcgataact caacgatgga aaaccataat aaacaggaaa    6660
cggtgttttc tctggttcaa gtcaagggta cctggaagcg taaggcgggc cagaacgcca    6720
aacagggtat gaagggccgc gttagtccgg ccaaaattta tgaaagctct agttcctcag    6780
gtaccacgtg gacggtggtt accccgatca cctttacgta caccgtgacg cagaccaaaa    6840
acctgctgga cccgtcgaac gacacgctgc tgctgggcca tattatcgat acccagcaac    6900
tggaagctgt ccgcagcaat acgaaaccgc tgaagcgttt cattgtgatg gacgaagtcg    6960
tgtataatat ctacggttcc caagtcaccg aatatctgga agcgcgcaac gtgctgtacc    7020
gtattctgcc gctgccgacc acggaagaaa ataaatcaat ggatatggct ctgaagattc    7080
tggaagaagt gcaccagttt ggtatcgacc gtcgcaccga accgattatc gcgattggcg    7140
```

```
gtggcgtttg cctggatatc gtcggtctgg cagcctctct gtatcgtcgc cgtaccccgt    7200
acattcgtgt gccgaccacg ctgctgtctt atatcgacgc aagtgtgggt gctaaaacgg    7260
gcgttaactt tgctaattgt aaaaacaagc tgggtaccta cattgcgccg gttgcagctt    7320
ttctggatcg ttcgttcatt cagagcatcc cgcgccgtca catcgcaaac ggtctggccg    7380
aaatgctgaa aatggccctg atgaagcatc gcggtctgtt cgaactgctg aagttcacg     7440 gccagtttct gctggatagt aaattccaat cggcaagcgt cctggaaaac gatcgcattg    7500
acccggcctc tgtcagtacg cgtgtggcaa tcgaaaccat gctggaagaa ctggccccga    7560
atctgtggga agatgacctg gatcgtctgg tggactttgg tcatctgatt cgccgcagc    7620 tggaaatgaa agttctgccg gcactgctgc acggcgaagc tgtcaacatt gatatggcgt    7680
atatggtgta cgtttcatgc gaaatcggtc tgctgaccga agaagaaaaa ttccgcatta    7740
tctgctgtat gatgggcctg gaactgccgg tgtggcatca ggattttacc ttcgcactgg    7800
ttcaaaagtc cctgtgtgac cgcctgcagc actcaggtgg cctggttcgt atgccgctgc    7860
cgacgggtct gggtcgtgca gaaatttta atgataccga cgaaggtagc ctgttccgcg     7920
cgtatgaaaa atggtgcgat gaactgtcca ccggctcacc gcagtgactc gagtcatgta    7980
attagttatg tcacgcttac attcacgccc tcccccaca tccgctctaa ccgaaaagga    8040
aggagttaga caacctgaag tctaggtccc tatttatttt tttatagtta tgttagtatt    8100
aagaacgtta tttatatttc aaatttttct tttttttctg tacagacgcg tgtacgcatg    8160
taacattata ctgaaaacct tgcttgagaa ggttttggga cgctcgaagg ctttaatttg    8220
cggccaatat tattgaagca tttatcaggg ttattgtctc atgagcggat acatatttga    8280
atgtatttag aaaaataaac aaataggggt tccgcgcaca tttccccgaa aagtgccacc    8340
tgacgtctaa gaaaccatta ttatcatgac attaacctat aaaaataggc gtatcacgag    8400 gcccttttcgt ctcgcgcgtt tcggtgatga cggtgaaaac ctctgacaca tgcagctccc    8460
ggagacggtc acagcttgtc tg                                              8482

<210> SEQ ID NO 80
<211> LENGTH: 5316
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgccaa gcttgcatgc ctgcaggtcg    420
actctagagg atccccggga taacttcgta tagcatacat tatacgaagt tataacgaca    480
ttactatata tataatatag gaagcattta atagaacagc atcgtaatat atgtgtactt    540
tgcagttatg acgccagatg gcagtagtgg aagatattct ttattgaaaa atagcttgtc    600
accttacgta caatcttgat ccggagcttt tcttttttg ccgattaaga attaattcgg    660
```

-continued

```
tcgaaaaaag aaaaggagag ggccaagagg gagggcattg gtgactattg agcacgtgag       720
tatacgtgat taagcacaca aaggcagctt ggagtatgtc tgttattaat ttcacaggta       780
gttctggtcc attggtgaaa gtttgcggct tgcagagcac agaggccgca gaatgtgctc       840
tagattccga tgctgacttg ctgggtatta tatgtgtgcc aatagaaaag agaacaattg       900
acccggttat tgcaaggaaa atttcaagtc ttgtaaaagc atataaaaat agttcaggca       960
ctccgaaata cttggttggc gtgtttcgta atcaacctaa ggaggatgtt ttggctctgg      1020
tcaatgatta cggcattgat atcgtccaac tgcatggaga tgagtcgtgg caagaatacc      1080
aagagttcct cggtttgcca gttattaaaa gactcgtatt tccaaaagac tgcaacatac      1140
tactcagtgc agcttcacag aaacctcatt cgtttattcc cttgtttgat tcagaagcag      1200
gtgggacagg tgaactttg gattggaact cgatttctga ctgggttgga aggcaagaga      1260
gccccgaaag cttacatttt atgttagctg gtggactgac gccagaaaat gttggtgatg      1320
cgcttagatt aaatggcgtt attggtgttg atgtaagcgg aggtgtggag acaaatggtg      1380
taaaagactc taacaaaata gcaaatttcg tcaaaaatgc taagaaatag gttattactg      1440
agtagtattt atttaagtat tgtttgtgca cttgcctgat aacttcgtat agcatacatt      1500
atacgaagtt atcccgggta ccgagctcga attcgtaatc atggtcatag ctgtttcctg      1560
tgtgaaattg ttatccgctc acaattccac acaacatacg agccggaagc ataaagtgta      1620
aagcctgggg tgcctaatga gtgagctaac tcacattaat tgcgttgcgc tcactgcccg      1680
ctttccagtc gggaaacctg tcgtgccagc tgcattaatg aatcggccaa cgcgcgggga      1740
gaggcggttt gcgtattggg cgctcttccg cttcctcgct cactgactcg ctgcgctcgg      1800
tcgttcggct gcggcgagcg gtatcagctc actcaaaggc ggtaatacgg ttatccacag      1860
aatcagggga taacgcagga aagaacatgt gagcaaaagg ccagcaaaag gccaggaacc      1920
gtaaaaaggc cgcgttgctg gcgtttttcc ataggctccg cccccctgac gagcatcaca      1980
aaaatcgacg ctcaagtcag aggtggcgaa acccgacagg actataaaga taccaggcgt      2040
ttccccctgg aagctccctc gtgcgctctc ctgttccgac cctgccgctt accggatacc      2100
tgtccgcctt tctcccttcg ggaagcgtgg cgctttctca tagctcacgc tgtaggtatc      2160
tcagttcggt gtaggtcgtt cgctccaagc tgggctgtgt gcacgaaccc cccgttcagc      2220
ccgaccgctg cgccttatcc ggtaactatc gtcttgagtc aacccggta agacacgact      2280 tatcgccact ggcagcagcc actggtaaca ggattagcag agcgaggtat gtaggcggtg      2340
ctacagagtt cttgaagtgg tggcctaact acggctacac tagaaggaca gtatttggta      2400
tctgcgctct gctgaagcca gttaccttcg gaaaaagagt tggtagctct tgatccggca      2460
aacaaaccac cgctggtagc ggtggttttt tgtttgcaa gcagcagatt acgcgcagaa      2520
aaaaaggatc tcaagaagat cctttgatct tttctacggg gtctgacgct cagtggaacg      2580
aaaactcacg ttaagggatt ttggtcatga gattatcaaa aaggatcttc acctagatcc      2640 tttaaatta aaaatgaagt tttaaatcaa tctaaagtat atatgagtaa acttggtctg      2700
acagttacca atgcttaatc agtgaggcac ctatctcagc gatctgtcta tttcgttcat      2760
ccatagttgc ctgactcccc gtcgtgtaga taactacgat acgggagggc ttaccatctg      2820
gccccagtgc tgcaatgata ccgcgagacc cacgctcacc ggctccagat ttatcagcaa      2880
taaaccagcc agccggaagg gccgagcgca gaagtggtcc tgcaacttta tccgcctcca      2940
tccagtctat taattgttgc cgggaagcta gagtaagtag ttcgccagtt aatagtttgc      3000
gcaacgttgt tgccattgct acaggcatcg tggtgtcacg ctcgtcgttt ggtatggctt      3060
```

```
cattcagctc cggttcccaa cgatcaaggc gagttacatg atcccccatg ttgtgcaaaa      3120
aagcggttag ctccttcggt cctccgatcg ttgtcagaag taagttggcc gcagtgttat      3180
cactcatggt tatggcagca ctgcataatt ctcttactgt catgccatcc gtaagatgct      3240
tttctgtgac tggtgagtac tcaaccaagt cattctgaga atagtgtatg cggcgaccga      3300
gttgctcttg cccggcgtca atacgggata ataccgcgcc acatagcaga actttaaaag      3360
tgctcatcat tggaaaacgt tcttcggggc gaaaactctc aaggatctta ccgctgttga      3420
gatccagttc gatgtaaccc actcgtgcac ccaactgatc ttcagcatct tttactttca      3480
ccagcgtttc tgggtgagca aaaacaggaa ggcaaaatgc cgcaaaaaag gaataagggg      3540
cgacacggaa atgttgaata ctcatactct tcctttttca atattaccgc gaatccttac      3600
atcacaccca atccccaca agtgatcccc cacacaccat agcttcaaaa tgtttctact      3660 cctttttac tcttccagat tttctcggac tccgcgcatc gccgtaccac ttcaaaacac      3720
ccaagcacag catactaaat ttcccctctt tcttcctcta gggtgtcgtt aattacccgt      3780
actaaaggtt tggaaaagaa aaagagacc gcctcgtttc ttttttcttcg tcgaaaaagg      3840 caataaaaat ttttatcacg tttcttttc ttgaaaattt ttttttttga ttttttctc      3900 tttcgatgac ctcccattga tatttaagtt aataaacggt cttcaatttc tcaagtttca      3960
gtttcatttt tcttgttcta ttacaacttt ttttacttct tgctcattag aaagaaagca      4020
tagcaatcta atctaagttt taattacaaa actagtatgc cttcgctaac ccccagatgt      4080
atcattgtca gacacggtca aactgaatgg tccaagtcag gccagtatac tggtttgaca      4140
gatctaccgt taacgcccta cggtgagggc caaatgttga ggaccggtga gagtgttttc      4200
cgcaataatc agttttttgaa tccagacaac atcacttata tcttcacctc tccacgtttg      4260
cgtgccaggc aaactgtgga tttggttttg aaaccattaa gcgacgagca aagagctaag      4320
atccgtgtgg tggtagacga cgacttgcga gagtgggagt acggtgacta cgagggaatg      4380
ctgactcgag aaatcattga attgagaaag tcacgcggtt tggacaagga gaggccatgg      4440
aatatctgga gagatgggtg tgagaacggt gagactactc agcaaattgg gttgagactt      4500
tcccgcgcta ttgccagaat ccagaacttg caccgcaagc accagagtga gggcagagca      4560
tcagacatca tggtctttgc gcacggacat gcattgcgtt attttgctgc tatttggttt      4620
ggactgggtg tgcaaaagaa gtgtgagacg attgaagaaa ttcaaaatgt caaatcttat      4680
gatgacgaca cagttccata tgtgaaattg gaatcttaca gacatttggt agacaatcca      4740
tgtttcttac tggacgccgg tgggattggt gttttgtcat acgctcacca caacattgac      4800
gaacctgcat tggaattagc aggtccattt gtctcaccac cagaggagga atcccagcat      4860
ggcgatgtgt aactcgagtc atgtaattag ttatgtcacg cttacattca cgccctcccc      4920
ccacatccgc tctaaccgaa aaggaaggag ttagacaacc tgaagtctag gtccctatt      4980 atttttttat agttatgtta gtattaagaa cgttatttat atttcaaatt tttctttttt      5040
ttctgtacag acgcgtgtac gcatgtaaca ttatactgaa aaccttgctt gagaaggttt      5100
tgggacgctc gaaggcttta atttgcggcc aatattattg aagcatttat cagggttatt      5160
gtctcatgag cggatacata tttgaatgta tttagaaaaa taaacaaata ggggttccgc      5220
gcacatttcc ccgaaaagtg ccacctgacg tctaagaaac cattattatc atgacattaa      5280
cctataaaaa taggcgtatc acgaggccct ttcgtc                              5316
```

<210> SEQ ID NO 81

<211> LENGTH: 939
<212> TYPE: DNA
<213> ORGANISM: Saccharomyces cerevisiae

<400> SEQUENCE: 81

```
atgactgctc aacaaggtgt accaataaag ataaccaata aggagattgc tcaagaattc    60
ttggacaaat atgacacgtt tctgttcgat tgtgatggtg tattatggtt aggttctcaa   120
gcattaccat acaccctgga aattctaaac cttttgaagc aattgggcaa acaactgatc   180
ttcgttacga ataactctac caagtcccgt ttagcataca cgaaaaagtt tgcttcgttt   240
ggtattgatg tcaaagaaga acagattttc acctctggtt atgcgtcagc tgtttatatt   300
cgtgactttc tgaaattgca gcctggcaaa gataaggtat gggtatttgg agaaagcggt   360
attggtgaag aattgaaact aatggggtac gaatctctag gaggtgccga ttccagattg   420
gatacgccgt tcgatgcagc taaatcacca ttttggtga acggccttga taggatgtt    480
agttgtgtta ttgctgggtt agacacgaag gtaaattacc accgtttggc tgttacactg   540
cagtatttgc agaaggattc tgttcacttt gttggtacaa atgttgattc tactttcccg   600
caaaagggtt atacatttcc cggtgcaggc tccatgattg aatcattggc attctcatct   660
aataggaggc catcgtactg tggtaagcca aatcaaaata tgctaaacag cattatatcg   720
gcattcaacc tggatagatc aaagtgctgt atggttggtg acagattaaa caccgatatg   780
aaattcggtg ttgaaggtgg gttaggtggc acactactcg ttttgagtgg tattgaaacc   840
gaagagagag ccttgaagat tcgcacgat tatccaagac ctaaatttta cattgataaa    900
cttggtgaca tctacacctt aaccaataat gagttatag                           939
```

<210> SEQ ID NO 82
<211> LENGTH: 9835
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82

```
actatatgtg aaggcatggc tatggcacgg cagacattcc gccagatcat caataggcac    60
cttcattcaa cgtttcccat tgtttttttc tactattgct ttgctgtggg aaaaacttat   120
cgaaagatga cgacttttc ttaattctcg ttttaagagc ttggtgagcg ctaggagtca   180
ctgccaggta tcgtttgaac acggcattag tcagggaagt cataacacag tcctttcccg   240
caatttttctt tttctattac tcttggcctc ctctagtaca ctctatattt ttttatgcct   300
cggtaatgat tttcatttt tttttccac ctagcggatg actcttttt tttcttagcg    360
attggcatta tcacataatg aattatacat tatataaagt aatgtgattt cttcgaagaa   420
tatactaaaa aatgagcagg caagataaac gaaggcaaag atgacagagc agaaagccct   480
agtaaagcgt attacaaatg aaaccaagat tcagattgcg atctctttaa agggtggtcc   540
cctagcgata gagcactcga tcttcccaga aaagaggca gaagcagtag cagaacaggc   600
cacacaatcg caagtgatta acgtccacac aggtataggg tttctggacc atatgataca   660
tgctctggcc aagcattccg gctggtcgct aatcgttgag tgcattggtg acttacacat   720
agacgaccat cacaccactg aagactgcgg gattgctctc ggtcaagctt ttaaagaggc   780
cctaggggcc gtgcgtggag taaaaaggtt tggatcagga tttgcgcctt tggatgaggc   840
actttccaga gcggtggtag atctttcgaa caggccgtac gcagttgtcg aacttggttt   900
```

```
gcaaagggag aaagtaggag atctctcttg cgagatgatc ccgcattttc ttgaaagctt    960
tgcagaggct agcagaatta ccctccacgt tgattgtctg cgaggcaaga atgatcatca   1020
ccgtagtgag agtgcgttca aggctcttgc ggttgccata agagaagcca cctcgcccaa   1080
tggtaccaac gatgttccct ccaccaaagg tgttcttatg tagtgacacc gattatttaa   1140
agctgcagca tacgatatat atacatgtgt atatatgtat acctatgaat gtcagtaagt   1200
atgtatacga acagtatgat actgaagatg acaaggtaat gcatcacacc tttcgagagg   1260
acgatgcccg tgtctaaatg attcgaccag cctaagaatg ttcaaccctg acttcaactc   1320
aagacgcaca gatattataa catctgcata ataggcattt gcaagaatta ctcgtgagta   1380
aggaaagagt gaggaactat cgcatacctg catttaaaga tgccgatttg ggcgcgaatc   1440
ctttattttg gcttcaccct catactatta tcagggccag aaaaaggaag tgtttccctc   1500
cttcttgaat tgatgttacc ctcataaagc acgtggcctc ttatcgagaa agaaattacc   1560
gtcgctcgtg atttgtttgc aaaaagaaca aaactgaaaa acccagaca cgctcgactt    1620 cctgtcttcc tattgattgc agcttccaat ttcgtcacac aacaaggtcc tagcgacggc   1680
tcacaggttt tgtaacaagc aatcgaaggt tctggaatgg cgggaaaggg tttagtacca   1740
catgctatga tgcccactgt gatctccaga gcaaagttcg ttcgatcgta ctgttactct   1800
ctctcttcca aacagaattg tccgaatcgt gtgacaacaa cagcctgttc tcacacactc   1860
ttttcttcta accaaggggg tggtttagtt tagtagaacc tcgtgaaact acatttaca    1920 tatatataaa cttgcataaa ttggtcaatg caagaaatac atatttggtc ttttctaatt   1980
cgtagttttt caagttctta gatgctttct ttttctcttt tttacagatc atcaaggaag   2040
taattatcta cttttacaa caaatataat gcaaacggca aaagtctcgg acaccccggt    2100
tgaatttatt gtggaacatc tgctgaaggc taaggaaatc gctgaaaatc acgcttccat   2160
tccggtggaa ctgcgcgata acctgcagaa agctctggat atcgcgagcg gcctggacga   2220
atatctggaa caaatgagct ctaaagaatc tgaaccgctg acggaactgt accgcaagtc   2280
agtctcgcat gattggaata aagtgcacgc ggacggcaag accctgtttc gtctgccggt   2340
gacctgcatt acgggccagg tcgaaggtca agtgctgaaa atgctggttc acatgagtaa   2400
agcgaagcgt gtcctggaaa ttggcatgtt taccggctat ggtgccctgt ccatggcaga   2460
agctctgccg gaaaacggtc agctgatcgc ttgtgaactg gaaccgtacc tgaaagattt   2520
tgcacaaccg attttcgaca agagtccgca tggcaaaaag atcaccgtga aacgggtcc    2580 ggcaatggat accctgaagg aactggcggc acgggcgaa cagtttgaca tggttttcat    2640
tgatgcggac aagcaaaact acatcaacta ctacaagttc ctgctggatc acaacctgct   2700
gcgtattgat ggcgtcatct gcgtggacaa tacgctgttc aaaggtcgcg tgtacctgaa   2760
ggatagcgtt gacgaaatgg gtaaagccct gcgtgatttt aaccagttcg tgaccgcaga   2820
cccgcgtgtt gaacaagtca ttatcccgct gcgcgatggc ctgaccatta tccgtcgcgt   2880
cccgtatacg ccgcagccga atagccaatc tggtaccgtg acgtacgatg aagttttcg    2940 cggcgtccag ggtaaaccgg ttctggatcg tctgcgcctg gacggcaaag tggcttatgt   3000
taccggtgcc ggtcagggta ttggtcgtgc attcgcccat gcactgggcg aagctggtgc   3060
gaaagttgcc attatcgata tggaccgtgg caaggccgaa gatgtcgcac acgaactgac   3120
cctgaaaggt attagttcca tggccgtggt tgcagatatc agcaaacggg atgacgtgca   3180
gaagatgatt gatgacatcg ttaccaaatg gggcacgctg catattgctt gcaacaatgc   3240
gggtatcaac aaaaatagtg cgtccgaaga aacctctctg gaagaatggg atcagacgtt   3300
```

```
taacgtcaat ctgcgtggca ccttcatgtg ctgtcaggca gctggtcgcg ttatgctgaa    3360
acaaggctat ggcaagatta tcaacaccgc tagcatggcg tctctgattg tgccgcaccc    3420
gcagaaacaa ctgtcataca atacgtcgaa agccggcgtc gtgaagctga cccagacgct    3480
gggcaccgaa tggatcgatc gtggtgtgcg cgttaactgt atttcaccgg gtatcgtgga    3540
taccccgctg attcattcag aatcgctgga accgctggtt cagcgttggc tgtcggatat    3600
cccggcaggt cgtctggcac aggtgacgga cctgcaagcg gccgttgtct atctggccag    3660
tgatgcatcc gactacatga ccggtcacaa tctggttatt gaaggcggtc agtctctgtg    3720
gtgaattgaa ttgaattgaa atcgatagat caattttttt cttttctctt tccccatcct    3780
ttacgctaaa ataatagttt atttttatttt ttgaatattt tttatttata tacgtatata    3840
tagactatta tttatctttt aatgattatt aagattttta ttaaaaaaaa attcgctcct    3900
cttttaatgc ctttatgcag ttttttttttc ccattcgata tttctatgtt cgggttcagc    3960 gtatttttaag tttaataact cgaaaattct gcgttcgtta aagctttcga aaggatatt    4020 atttcgaaat aaaccgtgtt gtgtaagctt gaagcctttt tgcgctgcca atattcttat    4080
ccatctattg tactctttag atccagtata gtgtattctt cctgctccaa gctcatccca    4140
cttgcaacaa atattcacg tagacggata ggtatagcca gacatcagca gcatacttcg    4200
ggaaccgtag gcgaattcaa cgaagcatct gtgcttcatt ttgtagaaca aaatgcaac    4260 gcgagagcgc taatttttca aacaaagaat ctgagctgca tttttacaga acagaaatgc    4320
aacgcgaaag cgctatttta ccaacgaaga atctgtgctt catttttgta aaacaaaaat    4380
gcaacgcgag agcgctaatt tttcaaacaa agaatctgag ctgcattttt acagaacaga    4440
aatgcaacgc gagagcgcta ttttaccaac aaagaatcta tacttctttt ttgttctaca    4500
aaaatgcatc ccgagagcgc tatttttcta acaaagcatc ttagattact ttttttctcc    4560
tttgtgcgct ctataatgca gtctcttgat aacttttttgc actgtaggtc cgttaaggtt    4620
agaagaaggc tactttggtg tctatttttct cttccataaa aaaagcctga ctccacttcc    4680 cgcgttact gattactagc gaagctgcgg gtgcattttt tcaagataaa ggcatccccg    4740
attatattct ataccgatgt ggattgcgca tactttgtga acagaaagtg atagcgttga    4800
tgattcttca ttggtcagaa aattatgaac ggtttcttct attttgtctc tatatactac    4860
gtataggaaa tgtttacatt ttcgtattgt tttcgattca ctctatgaat agttcttact    4920 acaattttttt tgtctaaaga gtaatactag agataaacat aaaaaatgta gaggtcgagt    4980
ttagatgcaa gttcaaggag cgaaaggtgg atgggtaggt tatataggga tatagcacag    5040
agatatatag caaagagata cttttgagca atgtttgtgg aagcggtatt cgcaatattt    5100
tagtagctcg ttcagtccg gtgcgttttt ggttttttga aagtgcgtct tcagagcgct    5160
tttggttttc aaaagcgctc tgaagttcct atactttcta gagaatagga acttcggaat    5220
aggaacttca aagcgtttcc gaaaacgagc gcttccgaaa atgcaacgcg agctgcgcac    5280
atacagctca ctgttcacgt cgcacctata tctgcgtgtt gcctgtatat atatatacat    5340
gagaagaacg gcatagtgcg tgtttatgct taaatgcgta cttatatgcg tctatttatg    5400
taggatgaaa ggtagtctag tacctcctgt gatattatcc cattccatgc ggggtatcgt    5460
atgcttcctt cagcactacc ctttagctgt tctatatgct gccactcctc aattggatta    5520
gtctcatcct tcaatgctat catttccttt gatattggat catacgaatt ccatacgttg    5580
aaactacggc aaaggattgg tcagatcgct tcatacaggg aaagttcggc aaaaggcggt    5640
```

```
aatacggtta tccacagaat caggggataa cgcaggaaag aacatgtgag caaaaggcca    5700
gcaaaaggcc aggaaccgta aaaaggccgc gttgctggcg ttttttccata ggctccgccc   5760 ccctgacgag catcacaaaa atcgacgctc aagtcagagg tggcgaaacc cgacaggact   5820
ataaagatac caggcgtttc ccctggaag ctccctcgtg cgctctcctg ttccgaccct    5880
gccgcttacc ggatacctgt ccgcctttct cccttcggga agcgtggcgc tttctcatag   5940
ctcacgctgt aggtatctca gttcggtgta ggtcgttcgc tccaagctgg gctgtgtgca   6000 cgaaccccc gttcagcccg accgctgcgc cttatccggt aactatcgtc ttgagtccaa    6060
cccggtaaga cacgacttat cgccactggc agcagccact ggtaacagga ttagcagagc   6120
gaggtatgta ggcggtgcta cagagttctt gaagtggtgg cctaactacg gctacactag   6180
aaggacagta tttggtatct gcgctctgct gaagccagtt accttcggaa aaagagttgg   6240
tagctcttga tccggcaaac aaaccaccgc tggtagcggg gtttttttg tttgcaagca    6300 gcagattacg cgcagaaaaa aaggatctca agaagatcct ttgatctttt ctacggggtc   6360
tgacgctcag tggaacgaaa actcacgtta agggattttg gtcatgagat tatcaaaaag   6420
gatcttcacc tagatccttt taaattaaaa atgaagtttt aaatcaatct aaagtatata   6480
tgagtaaact tggtctgaca gttaccaatg cttaatcagt gaggcaccta tctcagcgat   6540
ctgtctattt cgttcatcca tagttgcctg actccccgtc gtgtagataa ctacgatacg   6600
ggagggctta ccatctggcc ccagtgctgc aatgataccg cgagacccac gctcaccggc   6660
tccagattta tcagcaataa accagccagc cggaagggcc gagcgcagaa gtggtcctgc   6720
aactttatcc gcctccatcc agtctattaa ttgttgccgg gaagctagag taagtagttc   6780
gccagttaat agtttgcgca acgttgttgc cattgctaca ggcatcgtgg tgtcacgctc   6840
gtcgtttggt atggcttcat tcagctccgg ttcccaacga tcaaggcgag ttacatgatc   6900
ccccatgttg tgcaaaaaag cggttagctc cttcggtcct ccgatcgttg tcagaagtaa   6960
gttggccgca gtgttatcac tcatggttat ggcagcactg cataattctc ttactgtcat   7020
gccatccgta agatgctttt ctgtgactgg tgagtactca accaagtcat tctgagaata   7080
gtgtatgcgg cgaccgagtt gctcttgccc ggcgtcaata cgggataata ccgcgccaca   7140
tagcagaact ttaaaagtgc tcatcattgg aaaacgttct cggggcgaa aactctcaag    7200 gatcttaccg ctgttgagat ccagttcgat gtaacccact cgtgcaccca actgatcttc   7260
agcatctttt actttcacca cgtttctggg gtgagcaaaa acaggaaggc aaaatgccgc   7320
aaaaaaggga ataagggcga cacggaaatg ttgaatactc atactcttcc ttttcagat   7380 tactctaacg cctcagccat catcggtaat agctcgaatt gctgagaacc cgtgacaccg   7440
cgaatcctta catcacaccc aatcccccac aagtgatccc ccacacacca tagcttcaaa   7500
atgtttctac tcctttttta ctcttccaga ttttctcgga ctccgcgcat cgccgtacca   7560
cttcaaaaca cccaagcaca gcatactaaa tttcccctct ttcttcctct agggtgtcgt   7620
taattacccg tactaaaggt ttggaaaaga aaaagagac cgcctcgttt cttttcttc    7680 gtcgaaaaag gcaataaaaa ttttatcac gtttctttt cttgaaaatt ttttttttg     7740 atttttttct ctttcgatga cctcccattg atatttaagt taataaacgg tcttcaattt   7800
ctcaagtttc agtttcattt tcttgttct attacaactt tttttacttc ttgctcatta    7860
gaaagaaagc atagcaatct aatctaagtt ttaattacaa aactagtatg aacgtccgg    7920 gcgaaaccctt taccgtcagc tccccggaag aagtgcgtct gccgtctgtt caccgcgata   7980
actcaacgat ggaaaaccat aataaacagg aaacggtgtt ttctctggtt caagtcaagg   8040
```

```
gtacctggaa gcgtaaggcg ggccagaacg ccaaacaggg tatgaagggc cgcgttagtc    8100
cggccaaaat ttatgaaagc tctagttcct caggtaccac gtggacggtg gttaccccga    8160
tcacctttac gtacaccgtg acgcagacca aaaacctgct ggaccccgtcg aacgacacgc    8220 tgctgctggg ccatattatc gataccccagc aactggaagc tgtccgcagc aatacgaaac    8280
cgctgaagcg tttcattgtg atggacgaag tcgtgtataa tatctacggt tcccaagtca    8340
ccgaatatct ggaagcgcgc aacgtgctgt accgtattct gccgctgccg accacggaag    8400
aaaataaatc aatggatatg gctctgaaga ttctggaaga agtgcaccag tttggtatcg    8460
accgtcgcac cgaaccgatt atcgcgattg cggtggcgt ttgcctggat atcgtcggtc    8520
tggcagcctc tctgtatcgt cgccgtaccc cgtacattcg tgtgccgacc acgctgctgt    8580
cttatatcga cgcaagtgtg ggtgctaaaa cgggcgttaa ctttgctaat tgtaaaaaca    8640
agctgggtac ctacattgcg ccggttgcag ctttttctgga tcgttcgttc attcagagca    8700
tcccgcgccg tcacatcgca aacggtctgg ccgaaatgct gaaaatggcc ctgatgaagc    8760
atcgcggtct gttcgaactg ctggaagttc acggccagtt tctgctggat agtaaattcc    8820
aatcggcaag cgtcctggaa aacgatcgca ttgacccggc ctctgtcagt acgcgtgtgg    8880
caatcgaaac catgctggaa gaactggccc cgaatctgtg ggaagatgac ctggatcgtc    8940
tggtggactt tggtcatctg atttcgccgc agctggaaat gaaagttctg ccggcactgc    9000
tgcacggcga agctgtcaac attgatatgg cgtatatggt gtacgtttca tgcgaaatcg    9060
gtctgctgac cgaagaagaa aaattccgca ttatctgctg tatgatgggc ctggaactgc    9120
cggtgtggca tcaggatttt accttcgcac tggttcaaaa gtccctgtgt gaccgcctgc    9180
agcactcagg tggcctggtt cgtatgccgc tgccgacggg tctgggtcgt gcagaaattt    9240
ttaatgatac cgacgaaggt agcctgttcc gcgcgtatga aaaatggtgc gatgaactgt    9300
ccaccggctc accgcagtga ctcgagtcat gtaattagtt atgtcacgct tacattcacg    9360 ccctccccc acatccgctc taaccgaaaa ggaaggagtt agacaacctg aagtctaggt    9420
ccctatttat tttttatag ttatgttagt attaagaacg ttatttatat ttcaaatttt    9480 tcttttttt ctgtacagac gcgtgtacgc atgtaacatt atactgaaaa ccttgcttga    9540
gaaggttttg ggacgctcga aggctttaat ttgcggccaa tattattgaa gcatttatca    9600
gggttattgt ctcatgagcg gatacatatt tgaatgtatt tagaaaaata acaaataggg    9660
ggttccgcgc acatttcccc gaaaagtgcc acctgacgtc taagaaacca ttattatcat    9720
gacattaacc tataaaaata ggcgtatcac gaggccctttt cgtctcgcgc gtttcggtga    9780
tgacggtgaa aacctctgac acatgcagct cccggagacg gtcacagctt gtctg         9835
```

<210> SEQ ID NO 83
<211> LENGTH: 1306
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

```
actatatgtg aaggcatggc tatggcacgg cagacattcc gccagatcat caataggcac      60
cttcattcaa cgtttcccat tgttttttc tactattgct ttgctgtggg aaaaacttat     120
cgaaagatga cgacttttc ttaattctcg ttttaagagc ttggtgagcg ctaggagtca     180
ctgccaggta tcgtttgaac acggcattag tcagggaagt cataacacag tcctttcccg     240
```

```
caattttctt tttctattac tcttggcctc ctctagtaca ctctatattt ttttatgcct      300
cggtaatgat tttcattttt tttttccac ctagcggatg actctttttt tttcttagcg       360
attggcatta tcacataatg aattatacat tatataaagt aatgtgattt cttcgaagaa      420
tatactaaaa aatgagcagg caagataaac gaaggcaaag atgacagagc agaaagccct      480
agtaaagcgt attacaaatg aaaccaagat tcagattgcg atctctttaa agggtggtcc      540
cctagcgata gagcactcga tcttcccaga aaaagaggca gaagcagtag cagaacaggc      600
cacacaatcg caagtgatta acgtccacac aggtatagg  tttctggacc atatgataca      660
tgctctggcc aagcattccg gctggtcgct aatcgttgag tgcattggtg acttacacat      720
agacgaccat cacaccactg aagactgcgg gattgctctc ggtcaagctt ttaaagaggc      780
cctaggggcc gtgcgtggag taaaaaggtt tggatcagga tttgcgcctt tggatgaggc      840
actttccaga gcggtggtag atctttcgaa caggccgtac gcagttgtcg aacttggttt      900
gcaaagggag aaagtaggag atctctcttg cgagatgatc ccgcattttc ttgaaagctt      960
tgcagaggct agcagaatta ccctccacgt tgattgtctg cgaggcaaga atgatcatca     1020
ccgtagtgag agtgcgttca aggctcttgc ggttgccata agagaagcca cctcgcccaa     1080
tggtaccaac gatgttccct ccaccaaagg tgttcttatg tagtgacacc gattatttaa     1140
agctgcagca tacgatatat atacatgtgt atatatgtat acctatgaat gtcagtaagt     1200
atgtatacga acagtatgat actgaagatg acaaggtaat gcatcacacc tttcgagagg     1260
acgatgcccg tgtctaaatg attcgaccag cctaagaatg ttcaac                    1306

<210> SEQ ID NO 84
<211> LENGTH: 878
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
acctttcgag aggacgatgc ccgtgtctaa atgattcgac cagcctaaga atgttcaacc       60
ctgacttcaa ctcaagacgc acagatatta taacatctgc ataataggca tttgcaagaa      120
ttactcgtga gtaaggaaag agtgaggaac tatcgcatac ctgcatttaa agatgccgat      180
ttgggcgcga atcctttatt ttggcttcac cctcatacta ttatcagggc cagaaaaagg      240 aagtgttttcc ctccttcttg aattgatgtt accctcataa agcacgtggc ctcttatcga     300
gaaagaaatt accgtcgctc gtgatttgtt tgcaaaaaga acaaaactga aaaaacccag     360
acacgctcga cttcctgtct tcctattgat tgcagcttcc aatttcgtca cacaacaagg      420
tcctagcgac ggctcacagg ttttgtaaca agcaatcgaa ggttctggaa tggcgggaaa     480
gggtttagta ccacatgcta tgatgcccac tgtgatctcc agagcaaagt tcgttcgatc     540
gtactgttac tctctctctt tcaaacagaa ttgtccgaat cgtgtgacaa caacagcctg     600
ttctcacaca ctctttttctt ctaaccaagg gggtggttta gtttagtaga acctcgtgaa     660
acttacattt acatatatat aaacttgcat aaattggtca atgcaagaaa tacatatttg     720
gtcttttcta attcgtagtt tttcaagttc ttagatgctt tcttttttctc tttttttacag    780 atcatcaagg aagtaattat ctactttta caacaaatat aatgcaaacg gcaaagtctc      840 cggacaccc ggttgaattt attgtggaac atctgctg                              878
```

<210> SEQ ID NO 85
<211> LENGTH: 2519
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85

| | | | | | |
|---|---|---|---|---|---|
| agattactct | aacgcctcag | ccatcatcgg | taatagctcg | aattgctgag | aacccgtgac | 60 |
| accgcgaatc | cttacatcac | acccaatccc | ccacaagtga | tccccacac | accatagctt | 120 |
| caaaatgttt | ctactccttt | tttactcttc | cagattttct | cggactccgc | gcatcgccgt | 180 |
| accacttcaa | aacacccaag | cacagcatac | taaatttccc | ctctttcttc | ctctagggtg | 240 |
| tcgttaatta | cccgtactaa | aggtttggaa | aagaaaaaag | agaccgcctc | gtttcttttt | 300 |
| cttcgtcgaa | aaaggcaata | aaaattttta | tcacgtttct | ttttcttgaa | aattttttt | 360 |
| tttgattttt | ttctctttcg | atgacctccc | attgatattt | aagttaataa | acggtcttca | 420 |
| atttctcaag | tttcagtttc | attttctctg | ttctattaca | acttttttta | cttcttgctc | 480 |
| attagaaaga | aagcatagca | atctaatcta | agtttaatt | acaaaactag | tatgggaacgt | 540 |
| ccgggcgaaa | cctttaccgt | cagctccccg | gaagaagtgc | gtctgccgtc | tgttcaccgc | 600 |
| gataactcaa | cgatggaaaa | ccataataaa | caggaaacgg | tgttttctct | ggttcaagtc | 660 |
| aagggtacct | ggaagcgtaa | ggcgggccag | aacgccaaac | agggtatgaa | gggccgcgtt | 720 |
| agtccggcca | aaatttatga | aagctctagt | tcctcaggta | ccacgtggac | ggtggttacc | 780 |
| ccgatcacct | ttacgtacac | cgtgacgcag | accaaaaacc | tgctggaccc | gtcgaacgac | 840 |
| acgctgctgc | tgggccatat | tatcgatacc | cagcaactgg | aagctgtccg | cagcaatacg | 900 |
| aaaccgctga | agcgtttcat | tgtgatggac | gaagtcgtgt | ataatatcta | cggttcccaa | 960 |
| gtcaccgaat | atctggaagc | gcgcaacgtg | ctgtaccgta | ttctgccgct | gccgaccacg | 1020 |
| gaagaaaata | aatcaatgga | tatggctctg | aagattctgg | aagaagtgca | ccagtttggt | 1080 |
| atcgaccgtc | gcaccgaacc | gattatcgcg | attggcggtg | gcgtttgcct | ggatatcgtc | 1140 |
| ggtctggcag | cctctctgta | tcgtcgccgt | accccgtaca | ttcgtgtgcc | gaccacgctg | 1200 |
| ctgtcttata | tcgacgcaag | tgtgggtgct | aaaacgggcg | ttaactttgc | taattgtaaa | 1260 |
| aacaagctgg | gtacctacat | tgcgccggtt | gcagcttttc | tggatcgttc | gttcattcag | 1320 |
| agcatcccgc | gccgtcacat | cgcaaacggt | ctggccgaaa | tgctgaaaat | ggccctgatg | 1380 |
| aagcatcgcg | gtctgttcga | actgctggaa | gttcacggcc | agtttctgct | ggatagtaaa | 1440 |
| ttccaatcgg | caagcgtcct | ggaaaacgat | cgcattgacc | cggcctctgt | cagtacgcgt | 1500 |
| gtggcaatcg | aaaccatgct | ggaagaactg | gccccgaatc | tgtgggaaga | tgacctggat | 1560 |
| cgtctggtgg | actttggtca | tctgatttcg | ccgcagctgg | aaatgaaagt | tctgccggca | 1620 |
| ctgctgcacg | gcgaagctgt | caacattgat | atggcgtata | tggtgtacgt | ttcatgcgaa | 1680 |
| atcggtctgc | tgaccgaaga | agaaaaattc | cgcattatct | gctgtatgat | gggcctggaa | 1740 |
| ctgccggtgt | ggcatcagga | ttttaccttc | gcactggttc | aaaagtccct | gtgtgaccgc | 1800 |
| ctgcagcact | caggtggcct | ggttcgtatg | ccgctgccga | cgggtctggg | tcgtgcagaa | 1860 |
| atttttaatg | ataccgacga | aggtagcctg | ttccgcgcgt | atgaaaaatg | gtgcgatgaa | 1920 |
| ctgtccaccg | gctcaccgca | gtgactcgag | tcatgtaatt | agttatgtca | cgcttacatt | 1980 |
| cacgccctcc | ccccacatcc | gctctaaccg | aaaaggaagg | agttagacaa | cctgaagtct | 2040 |
| aggtccctat | ttattttttt | atagttatgt | tagtattaag | aacgttattt | atatttcaaa | 2100 |

```
ttttctttt ttttctgtac agacgcgtgt acgcatgtaa cattatactg aaaaccttgc    2160
ttgagaaggt tttgggacgc tcgaaggctt taatttgcgg ccaatattat tgaagcattt    2220
atcagggtta ttgtctcatg agcggataca tatttgaatg tatttagaaa aataaacaaa    2280
taggggttcc gcgcacattt ccccgaaaag tgccacctga cgtctaagaa accattatta    2340
tcatgacatt aacctataaa aataggcgta tcacgaggcc ctttcgtctc gcgcgtttcg    2400
gtgatgacgg tgaaaacctc tgacacatgc agctcccgga gacggtcaca gcttgtctga    2460
ctatatgtga aggcatggct atggcacggc agacattccg ccagatcatc aataggcac     2519
```

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cttggattta tggctctttt gg                                              22

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
cttagccttc agcagatgtt cc                                              22

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
agatccacta gtatgagtga aggccccgtc                                      30

<210> SEQ ID NO 89
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
agatccctcg agctaattat ccttcgtatc ttc                                  33

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

```
<400> SEQUENCE: 90

His His His His His His
1               5
```

GADUSOL PRODUCTION

CROSS REFERENCE TO RELATED APPLICATION

This application claims priority to U.S. Patent Application 62/782,090 filed on Dec. 19, 2018, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Nov. 22, 2019, is named 127789-250275_SL.txt and is 125,217 bytes in size.

FIELD

The present disclosure is in the field of molecular biology and is related to engineered microorganisms and the production of gadusol by genetically engineered microorganisms.

BACKGROUND

Exposure to sun is believed to cause many of the skin changes associated with aging and contributes to pre-cancerous and cancerous skin lesions, benign tumors, wrinkling, mottle pigmentations, and other important challenges to human health and well-being.

Despite the wide availability of sun protectant sunscreens and general knowledge of the dangers of too much sun exposure and sun burn, skin cancer rates continue to grow. Each year more and more cases of skin cancer are diagnosed, and every fifty-seven minutes someone dies from melanoma. Unfortunately, consumer's choice in sunscreens remain limited, especially for sunscreens and formulations derived from naturally occurring sun protective compounds.

Gadusol is a natural sunscreen/antioxidant found in marine fish, is derived from 4-deoxygadusol, the precursor of mycosporine-like amino acids produced by cyanobacteria, some Gram-positive bacteria, fungi, macroalgae, and marine invertebrates. These UV-protective compounds appear to be critical for the survival of reef-building corals and other marine organisms exposed to high solar irradiance.

Despite a continued need for better UV protectants and sunscreens, there remains a lack of means for producing sufficient amounts of such compounds. The present disclosure meets those needs.

SUMMARY OF THE DISCLOSURE

Disclosed is a transgenic yeast cell, or population thereof, the transgenic yeast cell including a nucleotide sequence capable of expressing 2-epi-5-valione synthase (EEVS) protein integrated in a genome of the transgenic yeast cell, and a nucleotide sequence capable of expressing methyltransferase/oxidoreductase (MT-Ox) protein integrated in the genome of the transgenic yeast cell.

In embodiments, the yeast cell comprises one or more disrupted transaldolase genes of the transgenic yeast cell, wherein the disruption results in a reduction of transaldolase activity in the transgenic yeast cell as compared to a wild-type yeast cell.

In embodiments, the one or more disrupted transaldolase genes comprises TAL1.

In embodiments, the one or more disrupted transaldolase genes comprises NQM1.

In embodiments, the one or more disrupted transaldolase genes comprises both TAL1 and NQM1.

In embodiments, the yeast cell is engineered to over express ZWF1.

In embodiments, the at least one of the nucleotide sequence capable of expressing EEVS protein and the nucleotide sequence capable of expressing MT-Ox protein are codon optimized for expression in yeast.

In embodiments, the yeast cell comprises a *Saccharomyces cerevisiae* yeast cell.

In embodiments, the nucleotide sequence capable of expressing EEVS protein comprises a yeast promoter operably connected to a nucleic acid sequence encoding a EEVS protein.

In embodiments, the nucleic acid sequence encoding the EEVS protein comprises a nucleic acid sequence that encodes a protein having an amino acid sequence at least 95% identical to SEQ ID NO: 21.

In embodiments, the nucleic acid sequence encoding the EEVS protein comprises a nucleic acid sequence at least 95% identical to any one of SEQ ID NOs 1-8.

In embodiments, the yeast promoter is a yeast TEF1 promoter.

In embodiments, the nucleotide sequence capable of expressing MT-Ox protein comprises a yeast promoter operably connected to a nucleic acid sequence encoding a MT-Ox protein.

In embodiments, the nucleic acid sequence encoding the MT-Ox protein comprises a nucleic acid sequence that encodes a protein having an amino acid sequence at least 95% identical to SEQ ID NO: 22.

In embodiments, the nucleic acid sequence encoding the MT-Ox protein comprises a nucleic acid sequence at least 95% identical to any one of SEQ ID NOs: 9-16.

In embodiments, the yeast promoter is a yeast PGK1 promoter.

In embodiments, the nucleotide sequence capable of expressing EEVS and the nucleotide sequence capable of expressing MT-Ox are integrated into the yeast genome at chromosome 15 at the his3Δ1 locus.

In embodiments, the nucleotide sequence capable of expressing EEVS and the nucleotide sequence capable of expressing MT-Ox are stably integrated.

In embodiments, the nucleotide sequence capable of expressing EEVS and the nucleotide sequence capable of expressing MT-Ox are stably integrated for at least 20 generations.

Disclosed is a bioreactor comprising a population of transgenic yeast cells.

Disclosed is a method for the production of the gadusol, the method comprising culturing a transgenic yeast cell in growth media.

In embodiments, at least a portion of the gadusol in secreted into the growth media.

In embodiments, the method further comprises isolating gadusol.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 26 was made with PyMOL using the coordinates of ValA, an EEVS from *Streptomyces hygroscopicus* subsp. *jinggangensis* 500821.

DETAILED DESCRIPTION OF DISCLOSED EMBODIMENTS

Figure 1:
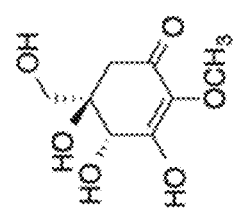
FIG. 1 is the structure of gadusol.
Figure 2:
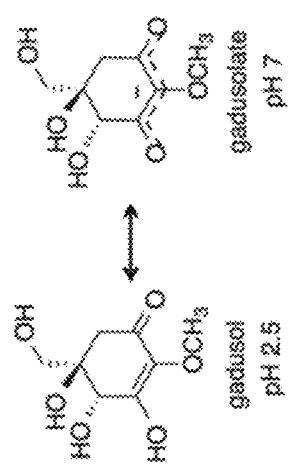
FIG. 2 is a graph showing the pH-dependent tautomers of gadusol.
Figure 3:
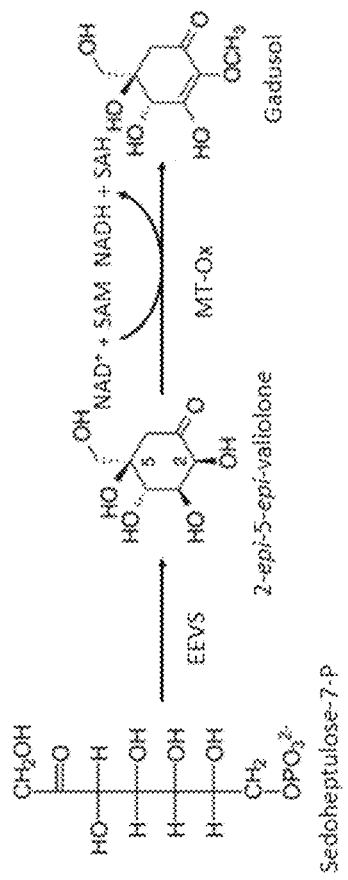
FIG. 3 is a scheme showing the biosynthesis of gadusol from SH7P catalyzed by an EEVS protein (SEQ ID NO. 21) produced using the nucleotide sequence of SEQ ID NO. 1 (LOC100003999) and an MT-Ox protein (SEQ ID NO. 22, encoded by SEQ ID NO. 9, accession no. zgc:113054.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999. In addition, the materials, methods, and examples are illustrative only and not intended to be limiting.

By "bioreactor" is meant a vessel comprising a liquid medium in which biological reactions are carried out by microorganisms, or the enzymes they produce, contained within the vessel itself. The term "bioreactor" is used throughout the specification to describe any vessel or container wherein the biological production and/or isolation of gadusol is carried out in a controlled fashion. The main objective in the design of a bioreactor is to generate an optimal environment for the desired biological process to take place on a large and economic scale. Bioreactors can be made from an inert material such as stainless steel or glass. An exemplary bioreactor may comprise a vertical Pyrex (glass) column that is adapted with at least two inlets for medium and air at the bottom of the column and at least one outlet port at the top of the column to accommodate expunged medium and/or air. See, for example, Hamdy, et al., Biomass., 21, 189-206 (1990).

As used herein, "disrupted gene" refers to an insertion, substitution, or deletion either in a gene of interest or in the vicinity of the gene, i.e., upstream (5') or downstream (3') of the gene, which results in the reduction of the biological activity or the loss of substantially all of the biological activity associated with the gene's product. For example, a disrupted TAL1 gene would be unable to express a protein having substantial TAL1 activity. A gene can be disrupted by any one of a number of methods known to the art, for example, by site-directed mutagenesis or homologous recombination.

"Expression" refers to the transcription and translation of an endogenous gene or a transgene in a host cell. For example, in the case of antisense constructs, expression may refer to the transcription of the antisense DNA only. In addition, expression refers to the transcription and stable accumulation of sense (mRNA) or functional RNA. Expression may also refer to the production of protein.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

A "mutation" refers to an insertion, deletion or substitution of one or more nucleotide bases of a nucleic acid sequence, so that the nucleic acid sequence differs from the wild-type sequence. For example, a 'point' mutation refers to an alteration in the sequence of a nucleotide at a single base position from the wild type sequence.

The term "nucleic acid molecule" refers to a polymer of DNA or RNA that can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene (Batzer et al., 1991; Ohtsuka et al., 1985; Rossolini et al., 1999).

"Operably linked" when used with respect to nucleic acid, means joined as part of the same nucleic acid molecule, suitably positioned and oriented for transcription to be initiated from the promoter. DNA operably linked to a promoter is under transcriptional initiation regulation of the promoter. Coding sequences can be operably-linked to regulatory sequences in sense or antisense orientation.

"Overexpression" refers to the level of expression in transgenic cells or organisms that exceeds levels of expression in corresponding normal or untransformed cells or organisms.

"Promoter" refers to a nucleotide sequence, usually upstream (5') to its coding sequence, which controls the expression of the coding sequence by providing the recognition for RNA polymerase and other factors required for proper transcription. An "inducible promoter" is a regulated promoter that can be turned on in a cell by an external stimulus, such as a chemical, light, hormone, stress, or a pathogen.

The terms "protein," "peptide" and "polypeptide" are used interchangeably herein.

As used herein, a "transgenic", "transformed", or "recombinant" cell refers to a genetically modified or genetically altered cell, the genome of which comprises a recombinant DNA molecule or sequence ("transgene"). For example, a "transgenic cell" can be a cell transformed with a "vector." A "transgenic", "transformed", or "recombinant" cell thus refers to a host cell such as yeast cell into which a heterologous nucleic acid molecule has been introduced. The nucleic acid molecule can be stably integrated into the genome by methods generally known in the art (e.g., disclosed in Sambrook and Russell, 2001). For example, "transformed," "transformant," and "transgenic" cells have been through the transformation process and contain a foreign or exogenous gene. The term "untransformed" refers to cells that have not been through the transformation process.

The term "transformation" refers to the transfer of a nucleic acid fragment into the genome of a host cell, or the transfer into a host cell of a nucleic acid fragment that is maintained extrachromosomally. A "transgene" refers to a gene that has been introduced into the genome by transformation. Transgenes may include, for example, genes that are heterologous or endogenous to the genes of a particular cell to be transformed. Additionally, transgenes may comprise native genes inserted into a non-native organism, or chimeric genes. The term "endogenous gene" refers to a native gene in its natural location in the genome of an organism. Such genes can be hyperactivated in some cases by the introduction of an exogenous strong promoter into operable association with the gene of interest. A "foreign" or an "exogenous" gene refers to a gene not normally found in the host cell but that is introduced by gene transfer.

"Vector" is defined to include, inter alia, any plasmid, cosmid, phage or other construct in double or single stranded linear or circular form that may or may not be self transmissible or mobilizable, and that can transform prokaryotic or eukaryotic host either by integration into the cellular genome or exist extrachromosomally, e.g., autonomous replicating plasmid with an origin of replication. A vector can comprise a construct such as an expression cassette having a DNA sequence capable of directing expression of a particular nucleotide sequence in an appropriate host cell, comprising a promoter operably linked to the nucleotide sequence of interest that also is operably linked to termination signals. An expression cassette also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus.

The term "wild type" refers to an untransformed cell, i.e., one where the genome has not been altered by the presence of the recombinant DNA molecule or sequence or by other means of mutagenesis. A "corresponding" untransformed cell is a typical control cell, i.e., one that has been subjected to transformation conditions, but has not been exposed to exogenous DNA.

In addition, a "wild type" gene refers to a gene, e.g., a recombinant gene, with its original or native DNA sequence, in contrast to a "mutant" gene.

Introduction

Gadusol (FIG. 1) was first identified in the early 1980's by workers at the National Environmental Research Council, Institute of Marine Biochemistry based in Scotland. The team was investigating the composition of roe in fish off the coast of Aberdeen. Gadusol was initially found in the roe of *Gadus morhua* where its UV-absorbent properties were identified (Grant 1980). Subsequently, it was observed in the roe of several additional fish species (*Melanogrammus aeglefinus, Limanda platessa, Hippoglossoides platessa, Platichthys flesus, Pleuronectes platessa*, and *Microstomus kitt*) and in sea urchin eggs (Plack et al. 1981; Chioccara et al. 1986). Plack et al. (1981) reported 4.3±0.30 (mg/g dry wt.) in the roe and between 0.10 to 0.01 mg/g dry wt. gadusol in the tissue of *G. morhua*. The higher levels observed in ovaries suggested that gadusol played a protective role in fish roe. Similar levels were reported for the other fish species studied (Plack et al. 1981).

Figure 37:
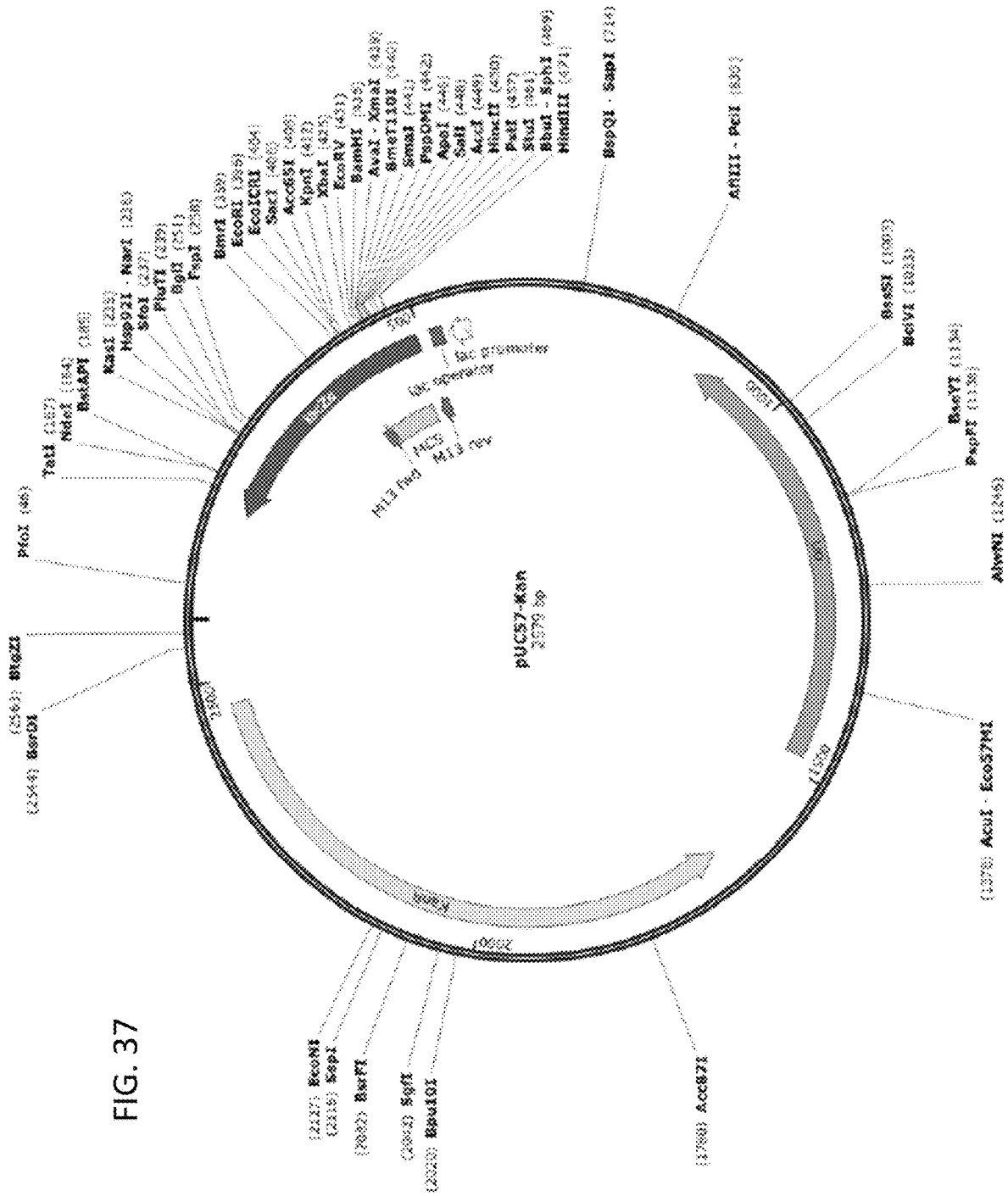
FIG. 37 illustrates an exemplary pUC57-Kan cloning vector.
Figure 38:
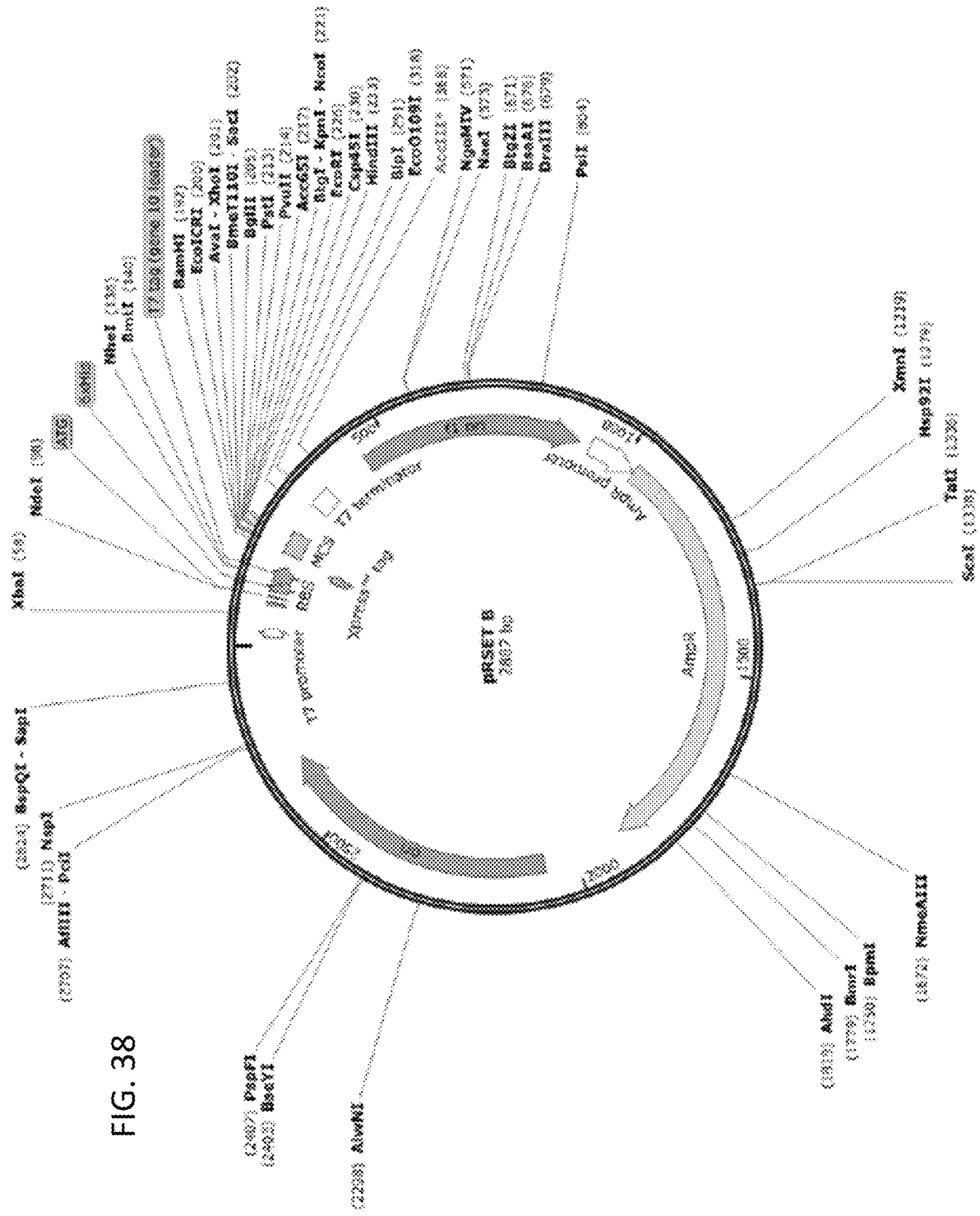
FIG. 38 illustrates an exemplary pRSETB *E. coli* expression vector.
Figure 39:
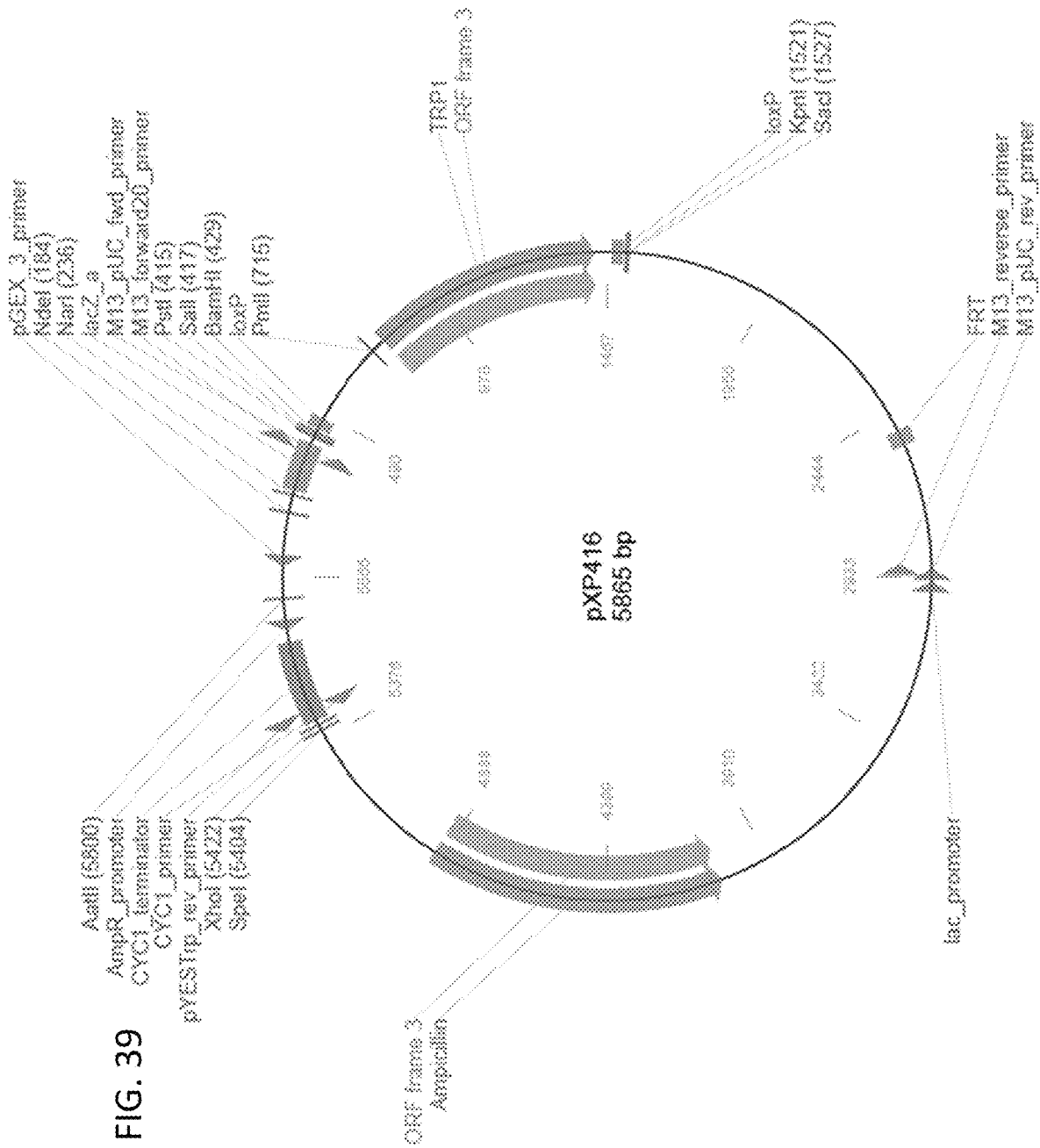
FIG. 39 illustrates an exemplary pXP416 yeast expression vector.

The zebrafish (*Danio rerio*) EEVS-like gene having the sequence shown in SEQ ID NO. 1 was codon-optimized to provide SEQ ID NO. 2 for heterologous expression in *Escherichia coli* and synthesized commercially. Incubation of the recombinant protein with SHIP gave a product, which was confirmed by TLC, GC-MS, ESI-MS and 1H NMR to be 2-epi-5-epi-valiolone (EEV) (FIG. 37) revealing the EEVS activity of recombinant protein encoded by SEQ ID NO. 2. The best characterized bacterial EEVS is ValA from the validamycin pathway in *Streptomyces hygroscopicus* subsp. *jinggangensis* 500819, and the crystal structure of ValA (PDB entry 4P53), allowed identification of a fingerprint set of 14 active site residues with characteristic variations that could differentiate the various SHIP cyclases. Further supporting the assignment of SEQ ID NO. 1 and SEQ ID NO. 2 as encoding an EEVS, sequence comparisons show that all animal EEVS-like proteins are highly similar to each other (60 to 72% identity) and also match the sequence of ValA at all 14 fingerprint sites. Accordingly, the present disclosure provides the first biochemical evidence for EEVS activity in animals and also provides codon-optimized EEVS encoding sequences.

Figure 35:
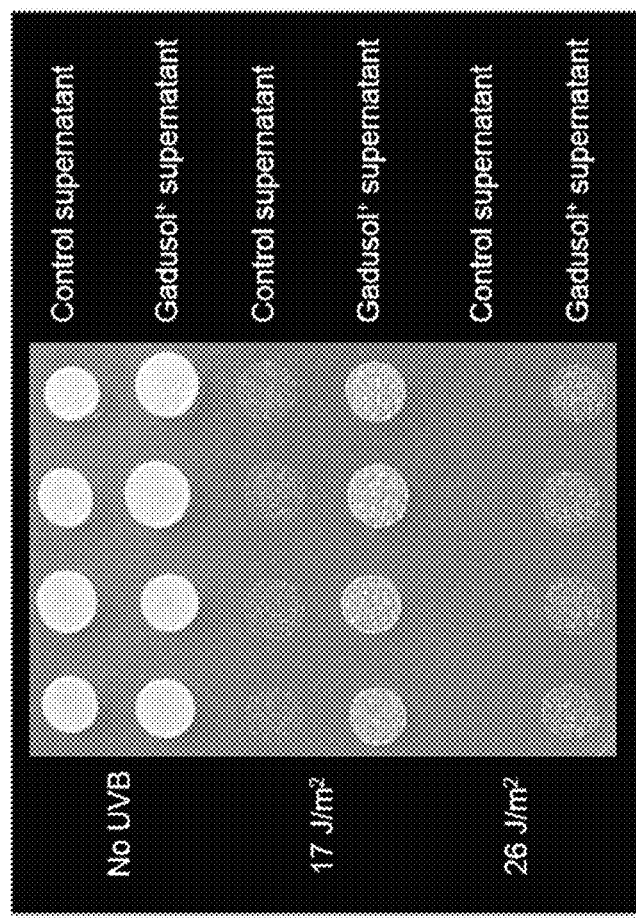
FIG. 35 illustrates results that gadusol suppresses the UVB sensitivity of a rad1Δ yeast mutant.
Figure 36:
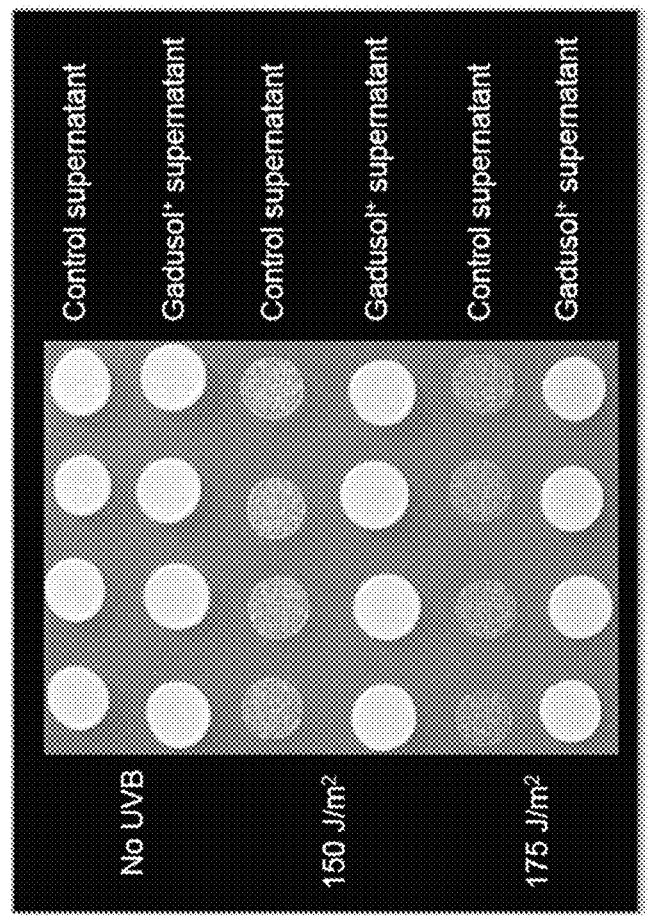
FIG. 36 illustrates results that gadusol increases UVB tolerance of a wild-type (RAD1) strain.

MT-Ox gene sequence shown in SEQ ID NO: 9 (zgc:113054) is predicted to encode a protein that contains two possible domains: the N-terminal domain is similar to SAM-dependent methyltransferases and the C-terminal domain is similar to $NAD^+$-dependent oxidoreductases. The MT-Ox gene is a bifunctional protein involved in modifying EEV to yield a reduced and methylated product (FIG. 37). By way of example, recombinant zgc:113054 protein was incubated with EEV in the presence of S-adenosylmethionine (SAM) and $NAD^+$. Following incubation, a product with λmax of 294 nm (pH 7) and 270 (pH 2.5) was detected (FIG. 27-30) ($A_{294}$ max absorbance). Further analysis of the product by (−)-ESI-MS (m/z 203 $[M-H]^-$) and $^1$H NMR confirmed its identity as gadusol. It is postulated that the conversion of EEV to gadusol by zgc:113054 protein takes place via oxidation of the C-2 or C-3 OH, followed by enolization and methylation of the resulting C-2 OH. In zebrafish, both LOC100003999 and zgc:113054 genes are expressed during embryonic development. qRT-PCR analysis of mRNA isolated from zebrafish embryos at 12, 24, 48, 72, 96, and 120 hpf showed maximal expression at 72 hpf (FIGS. 31-32). To demonstrate de novo synthesis of gadusol in zebrafish, the embryos were collected at 72 hpf, lyophilized and extracted with methanol, and the extract was analyzed by HPLC and ESI-MS (FIG. 33).

Gadusol or 3,5,6-trihydroxy-5-hydroxymethyl-2-methoxycyclohex-2-en-1-one is a cyclohexanone tautomer. Gadusol shifts between enol and enolate forms as a function of pH as shown in FIG. 2. The enol (gadusol) form dominates at lower pH and has a $\lambda_{max}$ of 269 nm, while at neutral and basic pH the enolate (gadusolate) form dominates with $\lambda_{max}$ of 296 nm (Plack et al. 1981). Gadusolate is the more effective sunscreen with an extinction coefficient of 21,800 $M^{-1}$ $cm^{-1}$ compared to 12,400 $M^{-1}$ $cm^{-1}$ for gadusol (Arbeloa et al. 2011). The gadusolate form absorbs light in the UV-B region (290-315 nm). Estimating how much UV-B light penetrates the Earth's atmosphere is difficult because many factors affect UV absorbance. Two major factors include solar angle and the presence of UV-absorbent compounds. The combination of these factors makes it difficult to estimate a typical UV-B dose or how far UV light penetrates into bodies of water (Booth and Morrow 1997). Gadusolate is more photostable than gadusol. Arbeloa et al. (2011) investigated the photodecomposition of gadusol and gadusolate by monitoring the change in gadusol concentration as a function of UV-light absorbed at their respective absorbance maxima. They found that gadusolate, the form that predominates at physiological pH, has a quantum yield of photodecomposition 260 times greater than gadusol indicating that gadusolate can absorb a larger quantity of light before breaking down (Arbeloa et al. 2011). Throughout this disclosure the term "gadusol" will be used generically to refer to both tautomers, unless a distinction is needed for clarity.

Gadusol is synthesized from sedoheptulose 7-phosphate (SH7P), a pentose phosphate pathway (PPP) intermediate. As shown in FIG. 3, 2-epi-5-epi-valiolone synthase (EEVS) initially cyclizes SH7P to 2-epi-5-epi-valiolone (EEV). A bifunctional methyltransferase-oxidase (MT-Ox) then catalyzes the S-adenosyl methionine (SAM)-dependent methylation and $NAD^+$-dependent oxidation of EEV to gadusol (FIG. 3).

While chemical data for gadusol suggest a role as a sunscreen and antioxidant, in vivo studies are less clear. Gadusol's high molar absorptivity in the UV-B range first led to suggestions for a role as a sunscreen (Plack et al. 1981). Sunscreens like gadusol protect tissues by absorbing UV light before it can damage cells. UV-B causes damage through at least two known mechanisms. It induces pyrimidine dimer formation in DNA, leading to mutations and can also generate free radicals which lead to oxidation of lipids and proteins (Sinha and Hader 2002). The photostability of the gadusolate tautomer found at physiological pH supports a sunscreen role (Arbeloa et al. 2011). However, gadusol is found in relatively low concentrations in fish tissues except in the roe (Plack et al. 1981). In order for a sunscreen to be effective, it must be sufficiently concentrated to prevent UV irradiation from penetrating the periphery of the cell and reaching molecular targets. Sunscreens like gadusol, which are soluble in the cytosol, must reach a high-intracellular concentration to provide such protection (Garcia-Pichel 1994; Gao and Garcia-Pichel 2011). While gadusol has also been shown to exhibit antioxidant activity in vitro, it is unknown to what extent it contributes to such activity in vivo where NADPH and GSH play prominent roles. Gadusol may also have protective and tuning roles in animal vision, as it has been found in the lenses of the eyes of several marine animals. In addition to protecting sensitive tissues from UV-B-damage (Dunlap et al. 1989), gadusol also helps tune the UV vision of mantis shrimp by absorbing light in the 296-nm range, preventing activation of receptors that absorb light at that wavelength (Bok et al. 2014).

While it would be possible to harvest gadusol from naturally occurring sources, this would not be economical for producing the quantities of gadusol needed for commercially relevant sunscreen products. To overcome this and other problems, the inventors have developed methods and compositions that allow for the high efficiency production of gadusol in microorganism host cells, such as yeast. Expressing the biosynthetic genes for gadusol in microorganisms, such as yeast, provides an opportunity to leverage in-depth knowledge of yeast biochemistry to generate a sustainable process. Yeast possesses a robust pentose phosphate pathway, and by removing the transaldolase enzyme, which normally metabolizes SH7P, and adding EEVS and MT-Ox facilitated an effective shunt pathway from SH7P to gadusol. The mutant was cultured in YNB+2% glucose supplemented with leucine and lysine at 30° C. for 2 days. Analysis of the culture broth by HPLC, ESI-MS, and UV spectrophotometry revealed the presence of gadusol (FIG. 33). In 20 ml cultures (n=3), the recombinant yeast culture produced approximately 20 mg/I of gadusol after 5 days (FIG. 34). The results not only demonstrate the ability of the engineered yeast to produce and secrete gadusol but also present a new avenue for large-scale production of the compound for possible clinical uses. Large-scale production allows for the use of gadusol in pharmaceuticals, formulations, cosmetics or dietary formulations and products. By way of example, formulations may include pills/capsules, creams, lotions, or the like. In embodiments, the present disclosure provides for a synthetic gadusol having UV-protective activity. By way of example, a yeast rad1Δ mutant, which is sensitive to UVB, was suspended at approximately $10^7$ cells/ml in the concentrated supernatant from the engineered gadusol-producing yeast strain or from an otherwise isogenic control strain that did not produce gadusol. Cells were then irradiated with UVB and spotted in 3 μl aliquots (n=4) onto YEPD plates which were incubated at 30° C. for 24 h. The gadusol-containing supernatant suppressed the UVB-sensitivity of the rad1Δ mutant (FIG. 35), confirming the UVB-protective activity of the synthetic gadusol. Analogous experiments with a wild-type strain (RAD1) at higher doses of UVB showed comparable results (FIG. 36), consistent with UVB protective activity.

Figure 4:
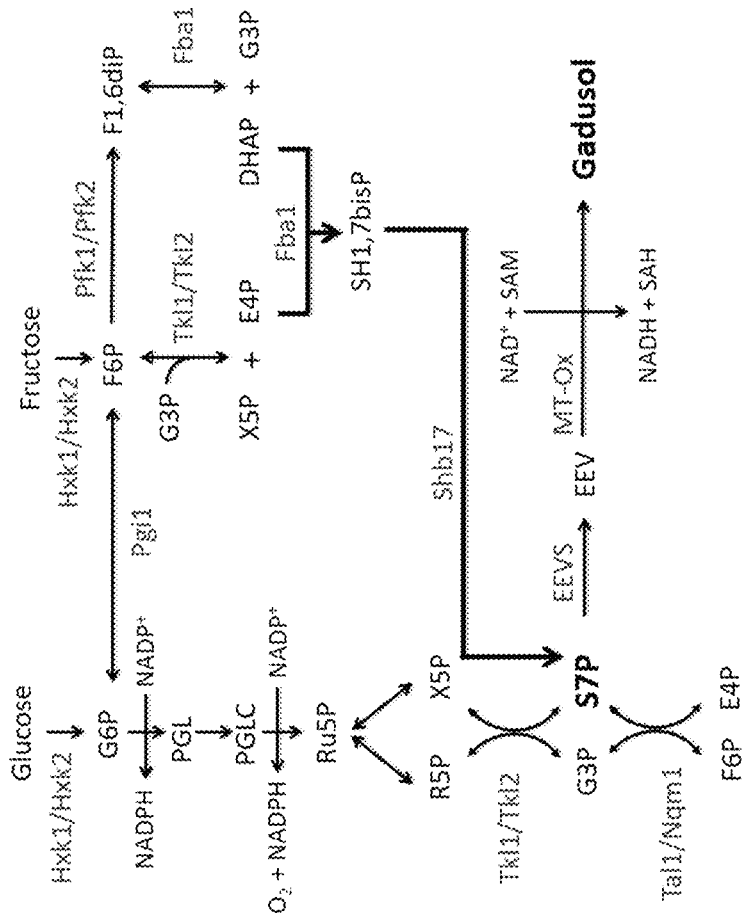
FIG. 4 is schematic showing pathways related to gadusol biosynthesis. Enzymes are labeled in blue and intermediates are labeled in black. Abbreviations: DHAP, dihydroxyacetone phosphate; E4P, erythrose 4-P; EEVS, 2-epi-5-epi-valiolone synthase; F1,6diP, fructose 1,6-diphosphate; F6P, fructose 6-phosphate; Fba1, Fructose bisphosphate aldolase; G3P, glyceraldehyde 3-phosphate; G6P, glucose 6-phosphate; Hxk1/2, hexokinase; MT-Ox, methyl transferase oxidase; Pfk1/2, phosphofructokinase; Pgi1, phosphoglucoisomerase; PGL, phosphogluconolactone; PGLC, phosphogluconate; Ru5P, ribulose 5-phosphate; RSP, ribose 5-phosphate; Shb17, sedoheptulose 1,7-bisphosphatase; SH7P, sedoheptulose 7-phosphate; and SH1,7bisphosphate, sedoheptulose 1,7-P Tal1/Nqm1, transaldolase; Tkl1/Tkl2, transketolase; and XSP, xylulose 5-phosphate. Gadusol and its precursor SH7P are shown in bold.

Sedoheptulose 7-phosphate (SH7P) is the natural precursor of gadusol and is a central intermediate in the pentose phosphate pathway, but is also derived from glycolytic intermediates (FIG. 4). In yeast, most glucose is metabolized by glycolysis, however, it has been estimated that about 20% is metabolized by the oxidative pentose phosphate pathway to generate reducing equivalents (NADPH) and pentoses to meet biosynthetic needs, depending on growth conditions and genotype (Van Winden et al. 2005; Cadière et al. 2011). NADPH is primarily consumed in the biosynthesis of fatty acids, sulfur-containing amino acids, and deoxynucleotides (Stincone et al. 2015). NADPH is also produced to help counteract oxidative stress by serving as a cofactor in the glutathione reductase-dependent regeneration of glutathione from glutathione disulfide (Stincone et al. 2015). The pentose phosphate pathway is largely regulated by altering flux through the rate-limiting step, glucose-6-phosphate dehydrogenase (ZWF1), at both protein and transcriptional levels (Stincone et al. 2015).

Figure 5:
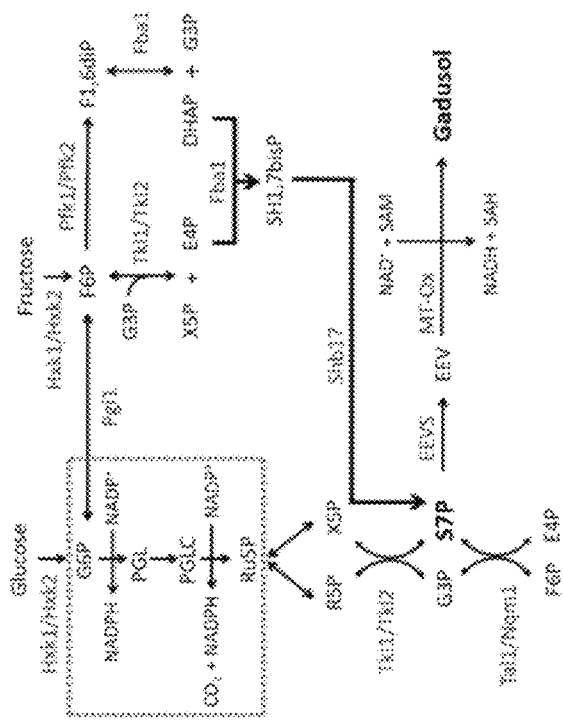
FIG. 5 is schematic showing the oxidative phase of the PPP (red dashed box) in relation to gadusol biosynthesis.

The oxidative phase of the pentose phosphate pathway (PPP) is composed of three steps that generate two NADPH, a $CO_2$ and the SH7P precursor, ribulose 5-phosphate. For emphasis, the oxidative phase of the pentose phosphate pathway originally shown in FIG. 4 is in indicated by a red dashed box in FIG. 5. The pathway begins with an irreversible step that oxidizes glucose 6-phosphate (G6P) to phosphogluconolactone (PGL) while reducing $NADP^+$ to NADPH. PGL is then oxidized to phosphogluconate, yielding another NADPH, $CO_2$ and ribulose 5-phosphate (Ru5P).

Figure 6:
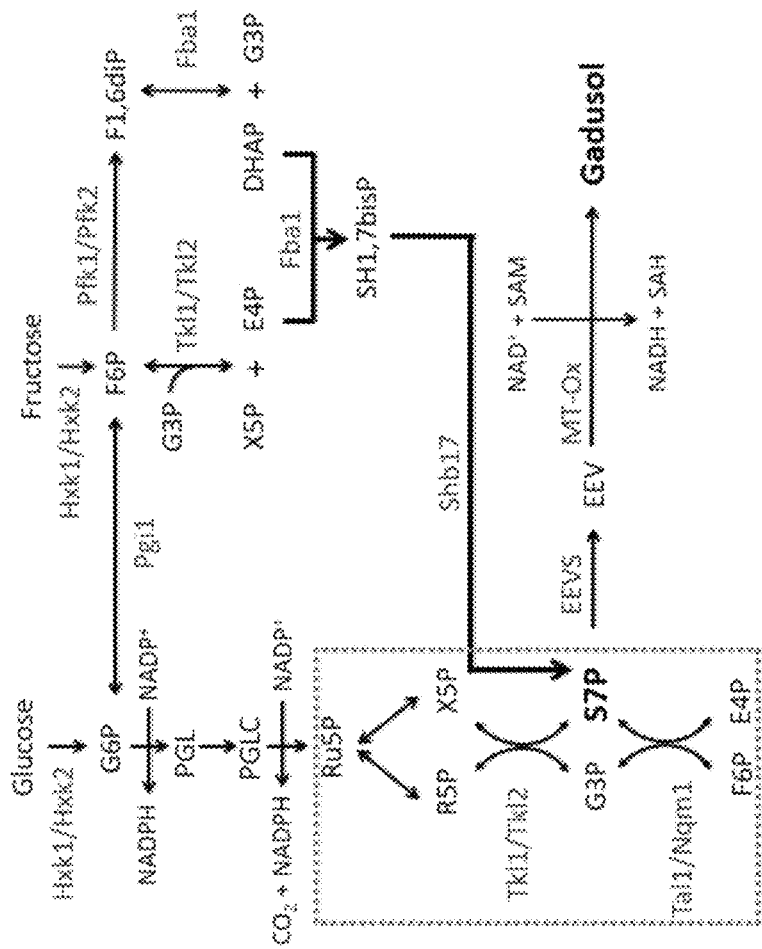
FIG. 6 is schematic showing the non-oxidative phase of the PPP (red dashed box) in relation to gadusol biosynthesis.

The non-oxidative phase of the pentose phosphate pathway shuffles carbons between intermediates to generate a variety of phosphosugars, including SH7P, the precursor for gadusol. The non-oxidative phase of the pentose phosphate pathway originally shown in FIG. 4 is indicated by the red dashed box in FIG. 6. The transketolase step encoded by TKL1 and TKL2 reversibly generates SH7P and glyceraldehyde 3-phosphate (G3P) from the PPP intermediates ribose 5-phosphate (R5P) and xylulose 5-phosphate (X5P) (Schaaff et al. 1990). The SH7P precursor, sedoheptulose 1,7-bisphosphate (SH1,7bisP) can also be generated through an alternative activity of fructose bisphosphate aldolase (Fba1) acting on the PPP intermediate erythrose 4-phosphate (E4P) and the glycolytic intermediate dihydroxyacetone phosphate (DHAP) (Clasquin et al. 2011). SH1,7bisP can then be dephosphorylated to yield SH7P by the phosphatase Shb17. Transaldolase reversibly converts SH7P and glyceraldehyde 3-phosphate into fructose 6-phosphate and E4P. Two yeast-transaldolase paralogs exist, TAL1 and NQM1. Tal1 is the active transaldolase in cells grown on glucose. tal1Δ mutants lack transaldolase activity when incubated on glucose because NQM1 is not expressed when cells grow on fermentable substrates (Huang et al. 2008; Michel et al. 2015). tal1Δ mutants also accumulate SH7P, as noted in a report of a >30-fold increase relative to a wild-type strain grown on glucose (Schaaff et al. 1990). tal1Δ mutants have also been observed to be more sensitive to oxidative stress (Ng et al. 2008). Accumulation of SH7P and other pentose phosphates could inhibit flux through the oxidative portion of the pentose phosphate pathway, depriving cells of the NADPH needed to regenerate glutathione.

Figure 7:
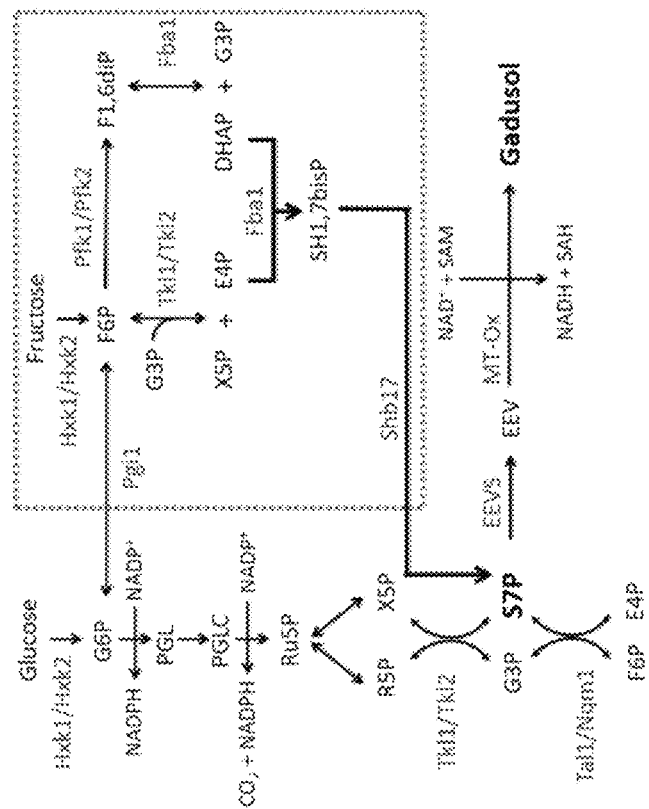
FIG. 7 is schematic showing S7P biosynthesis (red dashed box) from glycolytic intermediates in relation to gadusol.
Figure 8:
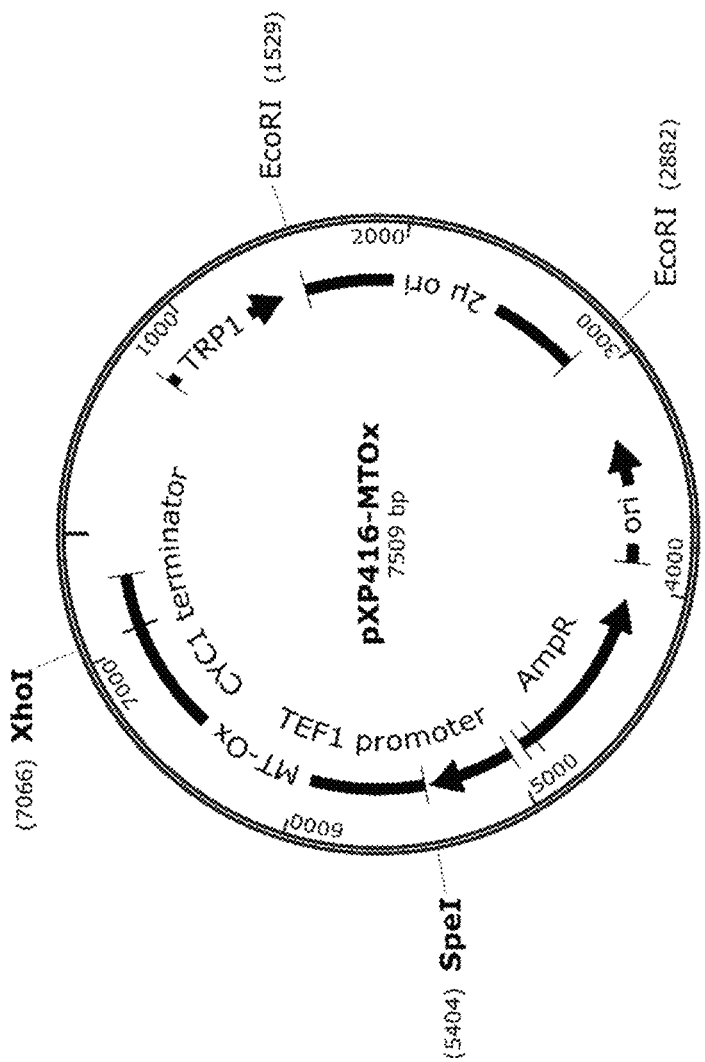
FIG. 8 is a map of plasmid pXP416-MTOx.
Figure 9:
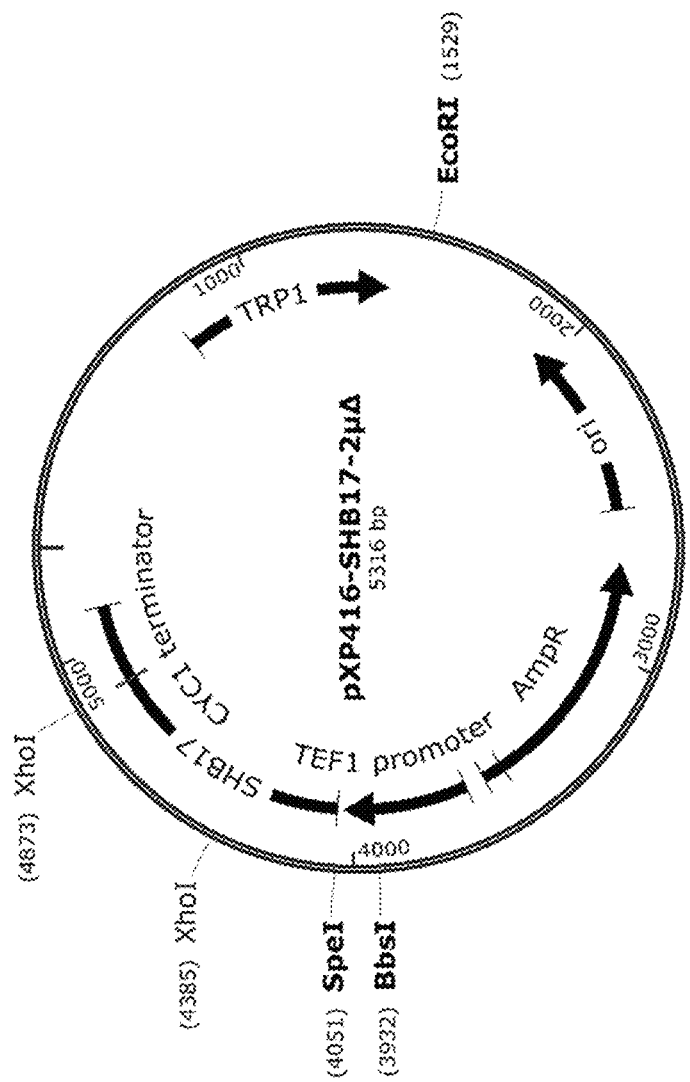
FIG. 9 is a map of plasmid pXP416-SHB17-2μΔ.
Figure 10:
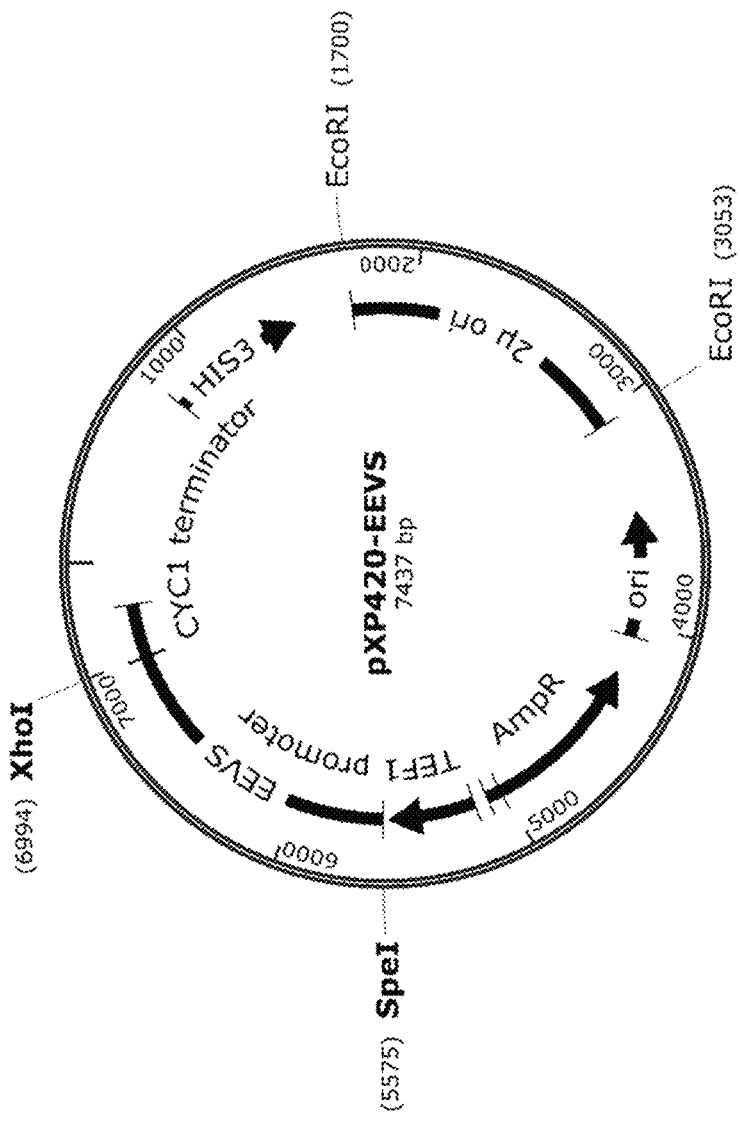
FIG. 10 is a map of plasmid pXP420-EEVS.

An alternative SH7P biosynthetic pathway was recently described based on a previously unknown activity of Fba1 described above, and a newly-discovered phosphatase, Shb17 (Clasquin et al. 2011). This pathway originally shown in FIG. 4 is indicated by the red dashed box in FIG. 7. Previously, Fba1 was only thought to catalyze the conversion of fructose 1,6-diphosphate to dihydroxyacetone-phosphate (DHAP) and glyceraldehyde 3-phosphate. Recently, an additional activity was discovered, the reversible conversion of E4P and DHAP into sedoheptulose 1,7-diphosphate. This previously unrecognized activity was confirmed through labeling experiments where $^{13}C$-labeled DHAP and 4EP led to the production of doubly-labeled sedoheptulose 1,7-diphosphate (SH1,7bisP) (Clasquin et al. 2011). Shb17, a bisphosphatase, dephosphorylates SH1,7bisP to sedepheptulose 7-phosphate. Clasquin et al. (2011) hypothesized that this shunt pathway provided carbon from glycolysis to produce ribose 5-phosphate when NADPH was not required. The authors found that supplementing the growth medium with lipids and aromatic amino acids that presumably reduced demand for NADPH, led to a two-fold increase in flux through Shb17 (Clasquin et al. 2011).

The combined deletion of TAL1 and PGI1 was reported to increase accumulation of SH7P 4-fold, relative to a tal1 mutant (Schaaff et al. 1990). Phosphoglucoisomerase (PGI1) catalyzes the isomerization of glucose 6-phosphate to fructose 6-phosphate. One characteristic of pgi1Δ mutants is an inability to grow on glucose as sole carbon source (Aguilera 1987; Schaaff et al. 1990). Schaaff et al. (1990) isolated pgi1Δ mutants on growth medium containing 2% fructose and 0.1% glucose. pgi1Δ mutants must rely on the SH7P shunt or Tal1 activity to generate ribose 5-phosphate for growth because they cannot generate glucose 6-phosphate from fructose. tal1 pgi1 double mutants are forced to route carbon exclusively through the SHB17-shunt pathway to meet the cell's need for ribose 5-phosphate. Because pgi1 mutants are also unable to generate NADPH via the oxidative portion of the pentose phosphate pathway, they oxidize more acetaldehyde via an $NADP^+$-dependent cytosolic aldehyde dehydrogenase (ALD6) and/or oxidize more isocitrate via $NADP^+$-dependent cytosolic isocitrate dehydrogenase (IDP2) (Grabowska and Chelstowska 2003; Minard and McAlister-Henn 2005). Although pgi1Δ mutants cannot grow on glucose, a small amount (0.1%) is required for growth on fructose (Aguilera 1987). This requirement may arise from the role of glucose as a signaling molecule needed to induce expression of ribosomal protein genes (Pernambuco et al. 1996).

Description of Several Embodiments

The present disclosure provides genetically engineered microorganisms and methods for the production of gadusol, for example using the 2-epi-5-valione synthase (EEVS) and methyltransferase-oxidoreductase (MT-Ox) encoding nucleotide sequences of EEVS and MTOx proteins that are used by the microorganisms in the production of gadusol. Gadusol produced by the engineered microorganisms and methods disclosed herein is useful as a UV protectant, and thus the present disclosure contributes significantly to the improvement of human health and well-being. The engineered microorganisms present a new avenue for large-scale production of a UV protectant for possible commercial and clinical uses. Large-scale production allows for the use of gadusol in pharmaceuticals, formulations, cosmetics, or dietary formulations and products. By way of example, formulations may include pills/capsules, creams, lotions, or the like.

Disclosed is a transgenic yeast cell (or population thereof) that includes a nucleotide sequence capable of expressing EEVS integrated in a genome of the transgenic yeast cell and a nucleotide sequence capable of expressing MT-Ox integrated in the genome of the transgenic yeast cell. During the development of the disclosed genetically engineered microorganisms and methods, the inventors discovered that integration of the EEVS and MT-Ox genes into the genome of a yeast cell had the effect of increasing the production on gadusol over yeast strains where the two genes were carried on one or more plasmids, for example as integrated into yeast chromosome 15 at the his3Δ1 locus. Furthermore, such integration increased the stability of gadusol production from the yeast. For example, a yeast cell containing a linearized and modified construct with EEVS under the control of the yeast TEF1 promoter and CYC1 terminator, MT-Ox under the control of the yeast PGK1 promoter and terminator was found to stably produce 64 mg/L vs 30 mg/L of gadusol. It was also found that integration resulted in yeast cells without significant loss of stability over time, for example, in tests no reduction in gadusol yields was noticed in cultures stored for weeks or months at storage conditions of 4° C. or over longer periods at −70° C. Additional advantages were also observed. For example, in a synthetic YNB-based medium, it had a doubling time of 1.7 hr vs 3.5 hr. In addition, this stable integration required no selection to maintain the genes, for example, one of the early plasmid expression systems tested required a medium lacking histidine and tryptophan. Absent such a selection requirement the yeast cells can be grown in a rich, histidine- and tryptophan-containing medium such as YEPD that will result in a much higher cell titer, and more gadusol. Gadusol production was found to be much more stable. That is, the ability to produce gadusol was lost within a few generations of growth by cells containing the plasmid-based expression system, whereas with the integrated genes, loss of gadusol production was only observed to drop after about 32 generations. By way of example, the yeast *Saccharomyces cerevisiae* may be engineered to include EEVS and MT-Ox sequences that are codon optimized for expression in yeast.

The yeast may be further engineered such that the EEVS and MT-Ox encoding sequences are under the control of at least one yeast promoter. In embodiments, the yeast cell comprises a *Saccharomyces cerevisiae* yeast cell. In embodiments, the nucleotide sequence capable of expressing EEVS comprises a yeast promoter operably connected to a nucleic acid sequence encoding a EEVS protein. In embodiments, the nucleic acid sequence encoding the EEVS protein comprises a nucleic acid sequence that encodes a protein having an amino acid sequence at least 95% identical to SEQ ID NO: 21, such as at least 95%, 96%, 97%, 98% 99% or even 100% identical. In embodiments, the nucleic acid sequence encoding the EEVS protein comprises a nucleic acid sequence at least 95% identical to any one of SEQ ID NOs 1-8, such as at least 95%, 96%, 97%, 98% 99% or even 100% identical. In embodiments, the yeast promoter is a yeast TEF1 promoter. In embodiments, nucleotide sequence capable of expressing MT-Ox protein comprises a yeast promoter operably connected to a nucleic acid sequence encoding a MT-Ox protein. In embodiments, the nucleic acid sequence encoding the MT-Ox protein comprises a nucleic acid sequence that encodes a protein having an amino acid sequence at least 95% identical to SEQ ID NO: 22, such as at least 95%, 96%, 97%, 98% 99% or even 100% identical. In embodiments, the nucleic acid sequence encoding the MT-Ox protein comprises a nucleic acid sequence at least 95% identical to any one of any one of SEQ ID NOs: 9-16, such as at least 95%, 96%, 97%, 98% 99% or even 100% identical. In embodiments, the yeast promoter is a yeast PGK1 promoter. In embodiments, the nucleotide sequence capable of expressing EEVS and the nucleotide sequence capable of expressing MT-Ox are integrated into the genome of the yeast at chromosome 15 at the his3Δ1 locus. In embodiments, the nucleotide sequence capable of expressing EEVS and the nucleotide sequence capable of expressing MT-Ox are stably integrated. In embodiments, the nucleotide sequence capable of expressing EEVS and the nucleotide sequence capable of expressing MT-Ox are stably integrated for at least 20 generations, such as at least 20, 21, 22, 23, 24, 25, 26, 27, 28, 29 or 30 or more. In embodiments, at least one of the nucleotide sequence capable of expressing EEVS and the nucleotide sequence capable of expressing MT-Ox are codon optimized for expression in yeast.

In embodiments, the yeast cell includes one or more disrupted transaldolase genes of the transgenic yeast cell, wherein the disruption results in a reduction of transaldolase activity in the transgenic yeast cell as compared to a wild-type yeast cell. In embodiments, the one or more disrupted transaldolase genes comprises TAL1. In embodiments, the one or more disrupted transaldolase genes comprises NQM1. In embodiments, the one or more disrupted transaldolase genes comprises both TAL1 and NQM1.

The inventors further discovered that over expression of ZWF1 further increased the gadusol production. In embodiments, the transgenic yeast cell is engineered to over express ZWF1. This strain carries an overexpressed yeast gene called ZWF1 that encodes glucose 6-P dehydrogenase. This enzyme catalyzes the first step in the oxidative phase of the pentose phosphate pathway (PPP). This step is also believed to be rate-limiting for the PPP (Ralser et al., 2007; Stincone et al., 2015). Because the PPP generates the gadusol precursor sedoheptulose 7-P (S7P), it was thought that overexpression of ZWF1 would lead to more gadusol by increasing the pool of S7P. In fact, in tests it produced 37 mg/L gadusol vs 22 mg/L for which was isogenic except for the overexpressed ZWF1 gene.

A method for producing gadusol, the method comprising culturing transgenic yeast cell disclosed herein, for example in growth media. In embodiments, at least a portion of the gadusol is secreted into the growth media, for example, were it can be collected. The growth media may be a Yeast Nitrogen Base (YNB) that supports the growth of an engineered strain of yeast. Alternatively, the growth media may support the growth of an engineered bacterial strain. Generally, the method includes culturing a recombinant microorganism harboring functional EEVS and MT-OX genes at a sufficient temperature under sufficient conditions and for a sufficient period of time to allow for the production of gadusol. By way of example, the culturing temperature may be approximately 30° C. Preferably, the temperature is adjusted to match the optimal temperature for the type of microorganism being used, such a yeast strain.

In some embodiments, a starter culture may be used. For example, an engineered microorganism may be cultured for approximately 24-48 hours in YNB. The YNB may include approximately 2% glucose and necessary essential amino acids or nucleic acid bases that the strain itself cannot make. The starter culture may be used to inoculate a larger volume of the same or similar medium that is then cultured at an appropriate temperature for a period of time sufficient for maximum production of gadusol. By way of example, the engineered microorganism may be cultured up to 5 days. After the microorganism is cultured the gadusol containing broth may be subject to centrifugation (≥1,000×g) to provide a cell pellet and a cell-free broth that contains the produced gadusol. The cell-free broth may be extracted and the produced gadusol may be substantially purified from the cell-free broth. By way of example, extracting the cell-free broth may be accomplished with an equal volume of n-butanol. The resulting butanol phase may be recovered using a separatory funnel and the n-butanol removed by rotoevaporation to provide for a gadusol containing residue. The residue may be dissolved in methanol or distilled water or other polar solvent and subjected to various standard chromatographic steps to remove unwanted impurities and provide for substantially pure gadusol. In some embodiments, methods for producing gadusol are carried out in an engineered yeast strain configured for producing gadusol. The engineered yeast may secrete the produced gadusol.

The nucleic acid sequences disclosed herein and/or used for the production of gadusol and the construction of such nucleic acid sequences and/or expression vectors that may be employed in conjunction with the present disclosure will be known to those of skill of the art in light of the present disclosure (see, e.g., Sambrook and Russell, 2001). The expression sequences of the disclosure may contain one or a plurality of restriction sites allowing for placement of the polynucleotide encoding functional EEVS and MT-OX genes under the regulation of a regulatory sequence. The expression cassette may also contain a termination signal operably linked to the polynucleotide as well as regulatory sequences required for proper translation of the polynucleotide. The expression cassette containing the polynucleotide of the disclosure may be chimeric, meaning that at least one of its components is heterologous with respect to at least one of the other components. Expression of the polynucleotide in the expression cassette may be under the control of a constitutive promoter, inducible promoter, regulated promoter, viral promoter or synthetic promoter. The expression cassette may include, in the 5'-3' direction of transcription, a transcriptional and translational initiation region, the polynucleotide of the disclosure and a transcriptional and translational termination region functional in vivo and/or in vitro. The termination region may be native with the transcriptional initiation region, may be native with the polynucleotide, or may be derived from another source. The regulatory sequences may be located upstream (5 non-coding sequences), within (intron), or downstream (3 non-coding sequences) of a coding sequence, and influence the transcription, RNA processing or stability, and/or translation of the associated coding sequence. Regulatory sequences may include, but are not limited to, enhancers, promoters, repressor binding sites, translation leader sequences, introns, and polyadenylation signal sequences. They may include natural and synthetic sequences as well as sequences that may be a combination of synthetic and natural sequences.

Propagation of yeast cells in culture has become a regular procedure in recent years, and the yeast cells of the present disclosure may be grown using conventional techniques. Yeast strains of the disclosure may be cultured in any appropriate medium known to the art for the particular strain (see, for example, Adams et al., 1998). For example, *S. cerevisiae* strains may be grown at 30° C. in complete yeast extract/peptone/dextrose (YPD) medium supplemented with 2% glucose. Alternatively, the minimal selective medium with 2% glucose supplemented with auxotrophic requirements can be used.

A transgenic yeast cell of the disclosure may contain a selective marker, thus requiring selective conditions for culture, e.g., conditions that require the expression of a plasmid encoded gene for growth. Most selective markers currently in use are genes coding for enzymes of amino acid or purine biosynthesis. This makes it necessary to use synthetic minimal media deficient in the corresponding amino acid or purine base. However, some genes conferring antibiotic resistance may be used as well (e.g. genes conferring resistance to cycloheximide or to the amino-glycoside G418). Yeast cells transformed with vectors containing antibiotic resistance genes may be grown in complex media containing the corresponding antibiotic whereby faster growth rates and higher cell densities can be reached. Yeast cells transformed with DNA integrating into the chromosomes do not require selective growth conditions. These transformed cells are sufficiently stable to allow growth without selective pressure. For the above reason, these cells are advantageously grown in complex media.

Further disclosed is a bioreactor comprising a population of the transgenic yeast cell disclosed herein. Any one of a number of bioreactors known to the art can be used with the transgenic yeast cell of the disclosure for the production of gadusol. In some embodiments, methods for producing gadusol are carried out in an engineered bacterial or yeast strain configured for producing gadusol. The engineered bacteria or yeast may secrete the produced gadusol. In some embodiments, the methods for producing gadusol are carried out in a microorganism that lacks, or is engineered to lack, a functional TAL1 gene.

EXAMPLES

Example 1

Materials and Methods
Media and Growth Conditions

Cells were grown in 2X YEPD (2% yeast extract, 4% peptone, and 4% glucose) for transformations, and in minimal medium (M) (Bacto yeast nitrogen base [YNB] without amino acids) (6.7 g/L)+2% glucose supplemented with histidine (20 µg/ml), leucine (30 µg/ml), lysine (30 µg/ml), tryptophan (20 µg/ml), or uracil (10 µg/ml) as needed. pgi1 mutants were grown in YNB+2% fructose+0.1% glucose with supplements as needed. "YNB+NADPH nutr." is YNB+2% glucose supplemented with 20 µg/ml ergosterol from a 2 mg/ml ergosterol stock dissolved in 1:1 (vol/vol) EtOH:Tween 80, lysine (30 µg/ml), tryptophan (20 µg/ml), histidine (20 µg/ml), phenylalanine (50 µg/ml), and tyrosine (30 µg/ml). Stocks of all antibiotics were stored at −20° C. Ampicillin was prepared as an aqueous sterile-filtered 1000× stock (100 mg/ml). G-418 was prepared as an aqueous sterile-filtered 500× stock (100 mg/ml). Hygromycin B was prepared as an aqueous sterile-filtered 500× stock (150 mg/ml). The stocks were filtered through a sterile 0.45-µm filter. Agar-based media were sterilized by autoclaving. Liquid cultures were grown at 30° C. and 200 rpm; plates were incubated statically at 30° C.

For growth and gadusol experiments, isolated colonies from selective media were used to inoculate 2 ml cultures. The 2 ml cultures were grown for either 16 or 48 h at 30° C. and 200 RPM. Cells were harvested by centrifugation, washed with sterile water, and counted using hemocytometer. Cells were inoculated into 75 ml of media that was then split into three 25 ml cultures in 125-ml Erlenmeyer flasks to yield an initial cell density=$10^5$ cell/ml. Cultures were incubated at 30° C. and 200 RPM. Cultures were sampled periodically to measure growth ($A_{600}$) and gadusol ($A_{296}$).

Transformations

Yeast was transformed using the lithium acetate method (Gietz and Woods 2001). Briefly, the strain to be transformed was grown overnight at 30° C. and 200 RPM in 1 ml of 2XYEPD in an incubator shaker. The overnight culture was used to inoculate 25 ml of 2XYEPD at a concentration of $5 \times 10^6$ cells/ml. The 25 ml 2XYEPD culture was kept at 30° C. and 200 RPM until at least two cell doublings had occurred. Cells were then harvested by centrifugation at 1,200 g and washed twice with sterile water. An aliquot of $2 \times 10^8$ cells was then transferred to a 1.5 ml Eppendorf tube and centrifuged at 16,000 RPM in a microcentrifuge. Supernatant was removed from the tube without disturbing cells. The following chemicals and DNAs were then added in this specific order: 240 µl 50% (w/v) polyethylene glycol 3500, 36 µl lithium acetate, 50 µl 2.0 mg/ml single-stranded carrier DNA, and 34 µl of plasmid or PCR amplicon DNA. The transformation mixture was then mixed by pipetting and incubated at 42° C. for 40 minutes. Cells were pelleted to remove the transformation mixture and then washed with 1 ml of sterile water before plating on selective media.

*E. coli* strains were transformed according to suppliers' directions for chemically competent TOP10 cells (Invitrogen) and NEB-2β cells (New England Biolabs). Suppliers' directions briefly stated that 50 µl aliquots of the cells were to be removed from −70° C. storage and thawed on ice for 10 minutes. A 1-5 µl aliquot of DNA was added to the thawed cells followed by a 30-minute incubation on ice. After the incubation, the DNA-treated cells were heat shocked for 30 sec at 42° C. followed by a second 5 min incubation on ice. Cells were resuspended in 950 µl of SOC medium before aliquots were plated on selective media and grown at 37° C.

Strain Construction

*E. coli* strains (Table 1) maintained on LB+amp at 37° C. Liquid cultures were grown at 37° C. and shaken at 200 RPM.

TABLE 1

| Strain | Genotype | Origin |
| --- | --- | --- |
| BL21 | B F⁻ ompT gal dcm lon hsdS$_B$(r$_B^-$m$_B^-$) [malB⁺]$_{K-12}$(λ$^S$) | Stratagene Inc., CA |
| DH5α | F⁻endA1 glnV44 thi-1 recA1 relA1 gyrA96 deoR nupG purB20 φ80dlacZΔM15 Δ(lacZYA-argF)U169, hsdR17(r$_K^-$m$_K^+$), λ⁻ | ThermoFisher Scientific Inc., Waltham, MA |
| NEB-5α | DH5α derivative | New England Biolabs Inc., Ipswich, MA |
| NEB-10β | DH10B derivative, F− mcrA Δ(mrr-hsdRMS-mcrBC) Φ80lacZΔM15 ΔlacX74 recA1 endA1 araD139 Δ(araleu) 7697 galU galK rpsL nupG λ− | New England Biolabs Inc., Ipswich, MA |
| TOP10 | F− mcrA Δ(mrr-hsdRMS-mcrBC) Φ80lacZΔM15 Δ lacX74 recA1 araD139 Δ(araleu)7697 galU galK rpsL (StrR) endA1 nupG | ThermoFisher Scientific Inc., Waltham, MA |

Yeast strains (Table 2) were constructed as described below.

TABLE 2

| Strain | Genotype | Origin |
| --- | --- | --- |
| BY4742 | MATα his3Δ1 leu2Δ0 lys2Δ0 ura3Δ0 | ATC 204508, Manassas, VA |
| BY4742 tal1Δ | MATα tal1Δ::KanMX4 his3Δ1 leu2Δ0 lys2Δ0 ura3Δ0 | Thermo Fisher Scientific Inc., Waltham, MA |
| BY4742 trp1Δ | MATα his3Δ1 leu2Δ0 lys2Δ0 ura3Δ0 trp1Δ::URA3 | This study |
| G0 | MATα his3Δ1 leu2Δ0 lys2Δ0 ura3Δ0 trp1Δ::URA3/pXP416-MTOx, pXP420-EEVS | This study |
| G1 | MATα tal1Δ::KanMX4 his3Δ1 leu2Δ0 lys2Δ0 ura3Δ0 trp1Δ::URA3/pXP416-MTOx, pXP420-EEVS | This study |
| G2 | MATα tal1Δ::KanMX4 nqm1Δ::LEU2 his3Δ1 leu2Δ0 lys2Δ0 ura3Δ0 trp1Δ::URA3/pXP416-MT-Ox, pXP420-EEVS | This study |
| G2C | MATα tal1Δ::KanMX4 nqm1Δ::LEU2 his3Δ1 leu2Δ0 lys2Δ0 ura3Δ0 trp1Δ::URA3/pXP416, pXP420 | This study |
| G3 | MATα tal1Δ::KanMX4 nqm1Δ::LEU2 his3Δ1::pGH420-EEVS-MTOx-2µΔ leu2Δ0 lys2Δ0 ura3Δ0 trp1Δ::URA3 | This study |
| G4 | MATα tal1Δ::KanMX4 nqm1Δ::LEU2 pgi1Δ::TRP1 his3Δ1::pGH420-EEVS-MTOx-2µΔ leu2Δ0 lys2Δ0 ura3Δ0 trp1Δ::URA3 | This study |
| G5 | MATα tal1Δ::KanMX4 pgi1Δ::TRP1 his3Δ1::pGH420-EEVS-MTOx-2µΔ leu2Δ0 lys2Δ0 ura3Δ0 trp1Δ::URA3 | This study |
| G6 | MATα tal1Δ::KanMX4 nqm1Δ::Leu2 shb17Δ::HphMX his3Δ1 leu2Δ0 lys2Δ0 ura3Δ0 trp1Δ::URA3/pXP416-MTOx, pXP420-EEVS | This study |

TABLE 2-continued

| Strain | Genotype | Origin |
| --- | --- | --- |
| G7 | MATα tal1Δ::KanMX4 nqm1Δ::Leu2 his3Δ1::pGH420-EEVS-MTOx-2μΔ leu2Δ0 lys2Δ0 ura3Δ0 trp1Δ::URA3/pXP416-SHB17 | This study |
| G8 | MATα tal1Δ::KanMX4 nqm1Δ::Leu2 his3Δ1::pGH420-EEVS-MTOx-2μΔ TEF1 TEF1::pXP416-SHB17-2μΔ leu2Δ0 lys2Δ0 ura3Δ0 trp1Δ::URA3 | This study |
| G9 | MATα tal1Δ::KanMX4 his3Δ1 leu2Δ0 lys2Δ0 ura3Δ0 pho13Δ::HphMX trp1Δ::URA3/pXP416-MT-Ox, pXP420-EEVS | This study |
| G10 | MATα tal1Δ::KanMX4 his3Δ1 leu2Δ0 lys2Δ0 ura3Δ0 trp1Δ::URA3/pXP416-MT-Ox, pXP420-EEVS, pXP422-ZWF1 | This study |

G0 (BY4742 trp1/pXP416-MTOx, pXP420-EEVS)

TRP1 in BY4742 was deleted by replacement with a 1.8 Kb PCR amplicon encoding URA3. The URA3 amplicon was generated using the TRP1DisURA3UP/LO primers (SEQ ID NO. 23 and 24) according to standard methods (Baudin et al. 1993; Gietz and Woods 2001). Transformants were selected on M+his+trp+leu+lys. The deletion of TRP1 was confirmed by diagnostic PCR, using the TRP1DisUP/LO primers (SEQ ID NO. 27 and 28) to generate a unique PCR amplicon of the URA3 gene inserted at the TRP1 locus (1.9 Kb). The BY4742 trp1Δ strain was co-transformed with both pXP416-MTOx (SEQ ID NO. 10 from the original provisional to which a stop codon has now been added) and pXP420-EEVS (SEQ ID NO. 2 from the original provisional to which a stop codon has now been added) using the lithium acetate method (Gietz and Woods 2001). Transformants were selected and maintained on M+leu+lys.

G1 (BY4742 tal1Δ trp1Δ/pXP416-MTOx, pXP420-EEVS)

TRP1 in BY4742 tal1Δ::KanMX4 was deleted by replacement with a 1.8 Kb PCR amplicon encoding URA3. The URA3 amplicon was generated using the TRP1DisURA3UP/LO primers according to standard methods (Baudin et al. 1993; Gietz and Woods 2001). Transformants were selected on M+his+trp+leu+lys+G418. Deletion of TRP1 was confirmed by diagnostic PCR using the TRP1DisUP/LO primers (SEQ ID NO. 27 and 28) to generate a unique PCR amplicon of the URA3 gene inserted at the TRP1 locus (1.9 Kb). The BY4742 tal1Δ trp1Δ strain was co-transformed with both pXP416-MTOx (SEQ ID NO. 10) and pXP420-EEVS (SEQ ID NO. 2) using the lithium acetate method (Gietz and Woods 2001). Transformants were selected and maintained on M+leu+lys.

G2 (BY4742 tal1Δ nqm1Δ trp1Δ/pXP416-MTOx, pXP420-EEVS)

NQM1 in BY4742 tal1Δ::KanMX4 was deleted by replacement with a 3.1 Kb PCR amplicon encoding LEU2. The LEU2 amplicon was generated using the NQM1DisLEU2UP/LO primers (SEQ ID NO. 40 and 41) according to standard methods (Baudin et al. 1993; Gietz and Woods 2001). Transformants were selected on M+his+trp+lys. Deletion of NQM1 was confirmed by diagnostic PCR using NQM1UP/LO primers (SEQ ID NO. 42 and 43) to generate a unique 4.2 Kb PCR amplicon. The BY4742 tal1Δ trp1Δ nqm1Δ strain was co-transformed with both pXP416-MTOx (SEQ ID NO. 10) and pXP420-EEVS (SEQ ID NO. 2) using the lithium acetate method (Gietz and Woods 2001). Transformants were selected and maintained on M+leu+lys.

G2C (BY4742 tal1Δ nqm1Δ trp1Δ/pXP416, pXP420)

The BY4742 tal1Δ trp1Δ nqm1Δ strain was co-transformed with both pXP416 and pXP420 using the lithium acetate method (Gietz and Woods 2001). Transformants were selected and maintained on M+leu+lys.

G3 (tal1Δ nqm1Δ trp1Δ his3Δ::pGH420-EEVS-MTOx-2μΔ)

BY4742 tal1Δ::KanMX4 trp1Δ nqm1Δ was transformed with NdeI-linearized pGH420-EEVS-MTOx-2μΔ (SEQ ID NO. 79) to direct integration to the his3Δ locus according to standard methods (Gietz and Woods 2001). Transformants were selected on M+lys+trp. Integration of pGH420-EEVS-MTOx-2μΔ (SEQ ID NO. 79) at the his3Δ locus was confirmed by diagnostic PCR targeting the junction between HIS3 and the MTOx gene (SEQ ID NO. 10) to generate a 2.3 Kb amplicon using HIS3MTOx-F/R primers (SEQ ID NO. 86 and 87).

G4 (BY4742 tal1Δ nqm1Δ trp1Δ pgi1Δ his3Δ::pGH420-EEVS-MTOx)

PGI1 in BY4742 tal1Δ::KanMX4 trp1Δ nqm1Δ his3Δ::pGH420-EEVS-MTOx-2μ was deleted by replacement with a 1.9 Kb PCR amplicon encoding TRP1. The TRP1 amplicon was generated using the PGI1DisTRP1UP/LO primers (SEQ ID NO. 44 and 45) according to standard protocols (Baudin et al. 1993; Gietz and Woods 2001). Transformants were selected and maintained on YNB+2% fructose+0.1% glucose+lys. Deletion of PGI1 was confirmed by diagnostic PCR using PGI1DisUP/LO primers (SEQ ID NO. 46 and 47) to generate a unique 3.2 Kb PCR amplicon.

G5 (BY4742 tal1Δ trp1Δ pgi1Δhis3Δ::pGH420-EEVS-MTOx)

PGI1 in BY4742 tal1Δ::KanMX4 trp1Δ was deleted by replacement with a 1.9 Kb PCR amplicon encoding TRP1. The TRP1 amplicon was generated using the PGI1DisTRP1UP/LO primers according to standard protocols (Baudin et al. 1993; Gietz and Woods 2001). Transformants were selected and maintained on YNB+2% fructose+0.1% glucose+his+leu+lys. Deletion of PGI1 was confirmed by diagnostic PCR using PGI1DisUP/LO primers (SEQ ID NO. 44 and 45) to generate a unique 3.2 Kb PCR amplicon. BY4742 tal1Δ::KanMX4 trp1Δ pgi1Δ was transformed with NdeI-linearized pGH420-EEVS-MTOx-2μΔ (SEQ ID NO. 79) to direct integration to the his3Δ locus according to standard methods (Baudin et al. 1993). Transformants were selected on YNB+2% fructose+0.1% glucose+leu+lys. Integration of pGH420-EEVS-MTOx-2μΔ (SEQ ID NO. 79) at the his3Δ locus was confirmed by diagnostic PCR targeting the junction between the HIS3 marker and the MTOx gene (SEQ ID NO. 10) using HIS3MTOx-F/R primers (SEQ ID NO. 86 and 87) to generate a 2.3 Kb amplicon.

G6 (BY4742 tal1Δ trp1Δ nqm1Δ shb17Δ/pXP416-MTOx, pXP420-EEVS)

SHB17 in BY4742 tal1Δ trp1Δ nqm1Δ was deleted by replacement with a 1.6 Kb PCR amplicon encoding HphMX. HphMX was generated using SHB17disHphUP/LO primers (SEQ ID NO. 48 and 49) according to standard protocols (Baudin et al. 1993; Gietz and Woods 2001). Transformants were selected and maintained on YEPD+hygromycin B. Deletion of SHB17 (SEQ ID NO. 77) was confirmed by diagnostic PCR using SHB17DisUP/LO (SEQ ID NO. 50 and 51) to generate a unique 2 Kb PCR amplicon. BY4742 tal1Δ trp1Δ nqm1Δ shb17Δ was co-transformed with both pXP416-MTOx (SEQ ID NO. 10—MTOx only, not pXP416) and pXP420-EEVS (SEQ ID NO. 2—EEVS only, not pXP420) according to the lithium-acetate method. Transformants were selected and maintained on M+lys.

G7 (BY4742 tal1Δ trp1Δ nqm1Δ his3Δ::pGH420-EEVS-MTOx-2μΔ/pXP416-SHB17)

BY4742 tal1Δ trp1Δ nqm1Δ his3Δ::pGH420-EEVS-MTOx-2μΔ was transformed with pXP416-SHB17 (SEQ ID NO. 77—SHB17 only, not pXP416) according to the lithium-acetate method (Gietz and Woods 2001). Transformants were selected and maintained on M+lys.

G8 (BY4742 tal1Δ trp1Δ nqm1Δ his3Δ::pGH420-EEVS-MTOx TEF1::pXP416-SHB17-2μΔ)

BY4742 tal1Δ trp1Δ nqm1Δ his3Δ::pGH420-EEVS-MTOx was transformed with BbsI-linearized pXP416-SHB17-2μΔ (SEQ ID NO. 80) to direct integration to the TEF1 locus according to the lithium-acetate method (Gietz and Woods 2001). The 2μ yeast replicative origin was removed (−2 μΔ) to ensure construct integration. Transformants were selected and maintained on M+lys media. Integration of pXP416-SHB17-2μΔ (SEQ ID NO. 80) at the TEF1 locus could not be verified by PCR. However, growth on the selection medium indicates integration of at least the TRP1 gene with the genome.

G9 (BY4742 tal1Δ trp1Δ pho13Δ/pXP416-MTOx, pXP420-EEVS)

PHO13 (SEQ ID NO. 81) in BY4742 tal1Δ trp1Δ was deleted by replacement with a 1.6 Kb PCR amplicon encoding HphMX. The HphMX amplicon was generated using the PHO13HphUP/LO primers according to standard methods (Baudin et al. 1993; Gietz and Woods 2001). Transformants were selected on YEPD+hygromycin B. Deletion of PH013 (SEQ ID NO. 81) was confirmed by diagnostic PCR using PHO13UP/LO primers (SEQ ID NO. 54 and 55) to generate a unique 2.4 Kb PCR amplicon. The BY4742 tal1Δ trp1Δ pho13Δ strain was co-transformed with both pXP416-MTOx (SEQ ID NO. 10—MTOx only) and pXP420-EEVS (SEQ ID NO. 2—EEVS only) using the lithium acetate method (Gietz and Woods 2001). Transformants were selected and maintained on M+leu+lys.

G10 (BY4742 tal1Δ trp1Δ/pXP416-MTOx, pXP420-EEVS, pXP422-ZWF1)

BY4742 tal1Δ trp1Δ was transformed with pXP420-EEVS (SEQ ID NO. 2—EEVS only), pXP416-MTOx (SEQ ID NO. 10—MTOx only), and pXP422-ZWF1 (SEQ ID NO. 78—ZWF1 only) according to the lithium-acetate method (Gietz and Woods 2001). Transformants were selected and maintained on M+lys.

DNA Primers

DNA primers needed to construct yeast strains and plasmids are listed in Table 3.

TABLE 3

| Primer Name | SEQ ID NO: | Sequence (5'→3') | Notes |
| --- | --- | --- | --- |
| TRP1DisURA3UP | SEQ ID NO. 23 | TATAGGAAGCATTTAATAGAACAGCATCGTAATATATGTGTACTTTGCAGTTATGACGCCGAAATTGAGGCTACTGCGCC | TRP1-annealing sequence underlined |
| TRP1DisURA3LO | SEQ ID NO. 24 | CCTGTGAACATTCTCTTCAACAAGTTTGATTCCATTGCGGTGAAATGGTAAAAGTCAACCGGCAGCGTTTTGTTCTTGGA | TRP1-annealing sequence underlined |
| TRP1DisUP | SEQ ID NO. 27 | CTCACCCGCACGGCAGAGAC | — |
| TRP1DisLO | SEQ ID NO. 28 | TGCCGGCGGTTGTTTGCAAG | — |
| NQM1DisLEU2UP | SEQ ID NO. 40 | TTCTTGCTAGCGTAAGTCATAAAAAATAGGAAATAATCACATATATACAAGAAATTAAATCACTGTTCACGTCGCACCTA | LEU2-annealing sequence underlined |
| NQM1DisLEU2LO | SEQ ID NO. 41 | ATTATACGTCAGAATTTTAATGAATATATAAGTCTGTACACTATGCTATGCACATATACTGCTGCATTAATGAATCGGCCA | LEU2-annealing sequence underlined |
| NQM1DisUP | SEQ ID NO. 42 | AAAACTCACATCGCACGCAC | — |
| NQM1DisLO | SEQ ID NO. 43 | GAGCTGAAAGCAATTCTAAATCCA | — |
| PGI1DisTRP1UP | SEQ ID NO. 44 | ACCCAGAAACTACTTTGTTTTTGATTGCTTCCAAGACTTTCACTACCGCTGAAACTATCAATGCGTAAGGAGAAAATACC | TRP1-annealing sequence underlined |

TABLE 3-continued

| Primer Name | SEQ ID NO: | Sequence (5'→3') | Notes |
|---|---|---|---|
| PGI1DisTRP1LO | SEQ ID NO. 45 | AGATAGAACCAGTAGAGTAGTCAGT AAACACGTTACCTCTGGTAACAGAC TTACCGTTAG<u>ATGCAGCTCAGATTC TTTGT</u> | TRP1-annealing sequence underlined |
| PGI1DisUP | SEQ ID NO. 46 | GGCAAGAACCGGGATGGTAA | — |
| PGI1DisLO | SEQ ID NO. 47 | TGTAGTTACTTGGACGCTGTTC | — |
| SHB17DisHphUP | SEQ ID NO. 48 | AGCACATTTTGTTCATAGCTAAGTG GATAGGGAAACACCTACACTTAATT GCAAGCAACA<u>GGGCATGATGTGACT GTCGCCC</u> | HphMX-annealing sequence underlined |
| SHB17DisHphLO | SEQ ID NO. 49 | AAAAAATGTTTTTATCACTTTCTAT AACTGCATATCTTTTTTTGCATTTC GAATGATT<u>GCTCTGGGCAGATGATG TCGAGGC</u> | HphMX-annealing sequence underlined |
| SHB17DisUP | SEQ ID NO. 50 | CCACCGCCAAAATTGCTATCC | — |
| SHB17DisLO | SEQ ID NO. 51 | ACAGTCCTTTGTACTATCCCTTTTA | — |
| PHO13HphUP | SEQ ID NO. 52 | AGCCAAATCACAAAAAAAGCCTTAT AGCTTGCCCTGACAAAGAATATACA ACTCGGGAAG<u>GGGCATGATGTGACT GTCGCCC</u> | HphMX-annealing sequence underlined |
| PHO13HphLO | SEQ ID NO. 53 | AAACCTGAATATTTTTCCTTTTCAA AAAGTAATTCTACCCCTAGATTTTG CATTGCTCCT<u>TCTGGGCAGATGATG TCGAGGC</u> | HphMX-annealing sequence underlined |
| PHO13Up | SEQ ID NO. 54 | AAGTGGCTTGAGCTGTGGAT | — |
| PHO13LO | SEQ ID NO. 55 | GGTTCTTCTGCTGCATTAGGC | — |
| MTOXUP | SEQ ID NO. 34 | AGATCC<u>ACTAGT</u>ATGCAAACGGCAA AAGTCTC | SpeI site underlined |
| MTOXLO | SEQ ID NO. 35 | TAGCCA<u>CTCGAG</u>TCACCACAGAGAC TGACCG | XhoI site underlined |
| PTEF1-Spe1-SHB17 | SEQ ID NO. 56 | <u>TTCTTGCTCATTAGAAAGAAAGCAT AGCAATCTAATCTAAGTTTTAATTA CAAAA</u>CTAGTATGCCTTCGCTAACC CCC | pXP416-annealing sequence underlined |
| TCYC1-XhoI-SHB17 | SEQ ID NO. 57 | <u>GAGCGGATGTGGGGGGAGGGCGTGA ATGTAAGCGTGACATAACTAATTAC ATG</u>ACTCGAGTTACACATCGCCATG CTGGG | pXP416-annealing sequence underlined |
| DEEVSUP | SEQ ID NO. 32 | AGATCC<u>ACTAGT</u>ATGGAACGTCCGG GCGAAAC | SpeI site underlined |
| DEEVSLO | SEQ ID NO. 33 | TAGCCA<u>CTCGAG</u>TCACTGCGGTGAG CCGGT | XhoI site underlined |
| A-HIS3-F | SEQ ID NO. 58 | ACTATATGTGAAGGCATGGCTATGG CACGGCAGACATTCCGCCAGATCAT CAATAGGCACcttcattcaacgttt cccatt | Paired with B-HIS3-R |
| B-HIS3-R | SEQ ID NO. 59 | GTTGAACATTCTTAGGCTGGTCGAA TCATTTAGACACGGGCATCGTCCTC TCGAAAGGTgtgatgcattaccttg tcatc | Paired with A-HIS3-F |

TABLE 3-continued

| Primer Name | SEQ ID NO: | Sequence (5'→3') | Notes |
| --- | --- | --- | --- |
| B-PPGK1-FII | SEQ ID NO. 60 | ACCTTTCGAGAGGACGATGCCCGTGTCTAAATGATTCGACCAGCCTAAGAATGTTCAACcctgacttcaactcaagacgc | Paired with MT-P$_{PGK1}$-RII |
| MT-P$_{PGK1}$-RII | SEQ ID NO. 61 | CAGCAGATGTTCCACAATAAATTCAACCGGGGTGTCCGAGACTTTTGCCGTTTGCATactagtatatttgttgtaaaaagtagataattacttcc | Paired with B-PPGK1-FII |
| MTOx-F | SEQ ID NO. 62 | ACGTCTCACGGATCGTATATGCCGTAGCGACAATCTAAGAACTATGCGAGGACACGCTAGactagtatgcaaacggcaaaagtctc | Paired with MTOx-R |
| MTOx-R | SEQ ID NO. 63 | AATCACTCTCCATACAGGGTTTCATACATTTCTCCACGGGACCCACAGTCGTAGATGCGTctcgagtcaccacagagactgaccg | Paired with MTOx-F |
| Ox-T$_{PGK1}$-FII | SEQ ID NO. 64 | GCATCCGACTACATGACCGGTCACAATCTGGTTATTGAAGGCGGTCAGTCTCTGTGGTGAattgaattgaattgaaatcgatagatca | Paired with C-T$_{PGK1}$-RII |
| C-T$_{PGK1}$-RII | SEQ ID NO. 65 | GCCTACGGTTCCCGAAGTATGCTGCTGATGTCTGGCTATACCTATCCGTCTACGTGAATAtttttgttgcaagtgggatga | Paired with OX-T$_{PGK1}$-FII |
| C-2µ-F | SEQ ID NO. 66 | TATTCACGTAGACGGATAGGTATAGCCAGACATCAGCAGCATACTTCGGGAACCGTAGGCgaattcgtatgatccaatatc | Paired with D-2µ-R |
| D-2µ-R | SEQ ID NO. 67 | TGCCGAACTTTCCCTGTATGAAGCGATCTGACCAATCCTTTGCCGTAGTTTCAACGTATGgaattcaacgaagcatctgtgc | Paired with C-2µ-F |
| D-ORI-F | SEQ ID NO. 68 | CATACGTTGAAACTACGGCAAAGGATTGGTCAGATCGCTTCATACAGGGAAGTTCGGCAaaaggcggtaatacggtta | Paired with E-AMP-R |
| E-AMP-R | SEQ ID NO. 69 | GTCACGGGTTCTCAGCAATTCGAGCTATTACCGATGATGGCTGAGGCGTTAGAGTAATCTgaaaaaggaagagtatgagtattc | Paired with D-ORI-F |
| E-PTEF1-F | SEQ ID NO. 70 | AGATTACTCTAACGCCTCAGCCATCATCGGTAATAGCTCGAATTGCTGAGAACCCGTGACaccgcgaatccttacatcac | Paired with A-TCYC1-RII |
| A-TCYC1-RII | SEQ ID NO. 71 | GTGCCTATTGATGATCTGGCGGAATGTCTGCCGTGCCATAGCCATGCCTTCACATATAGTcagacaagctgtgaccgtct | Paired with E-PTEF1-F |
| HIS3MTOx-F | SEQ ID NO. 86 | CTTGGATTTATGGCTCTTTTGG | Confirmation of pGH420-EEVS-MTOx-2µΔ integration |
| HIS3MTOx-R | SEQ ID NO. 87 | CTTAGCCTTCAGCAGATGTTCC | Confirmation of pGH420-EEVS-MTOx-2µΔ integration |
| ZWF1SpeIUP | SEQ ID NO. 88 | AGATCCACTAGTATGAGTGAAGGCCCCGTC | SpeI restriction site underlined |

TABLE 3-continued

| Primer Name | SEQ ID NO: | Sequence (5'→3') | Notes |
|---|---|---|---|
| ZWF1XhoILO | SEQ ID NO. 89 | AGATCCCTCGAGCTAATTATCCTTC GTATCTTC | XhoI restriction site underlined |

Construction of Plasmids

Plasmids (Table 4) were constructed as described below. Plasmid maps are shown in FIG. 8-12.

TABLE 4

| Plasmid | Feature | E. coli carrier | Source/reference |
|---|---|---|---|
| pRSETB-EEVS | EEVS (EcoRV) | BL-21 | (Osborn et al. 2015) |
| pRSETB-MTOX | MTOx (EcoRV) | BL-21 | (Osborn et al. 2015) |
| pXP416 | TRP1; TEF1 promoter | DH5α | (Fang et al. 2011) |
| pXP416-MTOx | MT-Ox (SpeI + XhoI) | NEB-10β | (Osborn et al. 2015) |
| pXP416-SHB17 | SHB17 | TOP10 | |
| pXP416-SHB17-2μΔ | SHB17, and missing 2μ ORI | TOP10 | |
| pXP420 | HIS3; TEF1 promoter | DH5α | (Fang et al. 2011) |
| pXP420-EEVS | EEVS (SpeI + XhoI) | TOP10 | (Osborn et al. 2015) |
| pGH420-EEVS-MTOx | EEVS, MT-Ox | TOP10 | |
| pGH420-EEVS-MTOx-2μΔ | EEVS, MT-Ox, and missing 2μ ORI | TOP10 | |
| pXP422 | LEU2; TEF1 promoter | TOP10 | (Fang et al. 2011) |
| pXP422-ZWF1 | ZWF1 | NEB-5α | | pXP416-MTOx (SEQ ID NO. 10—MTOx only)

pXP416 plasmid was extracted and purified from a 1-ml culture of DH5a/pXP416 E. coli grown in LB+amp. An aliquot of pXP416 was digested with SpeI- and XhoI-restriction enzymes yielding a 5.8 Kb fragment. SpeI-, XhoI-digested plasmid was gel purified using a Qiagen gel-purification kit. The MTOx cDNA (SEQ ID NO. 10—MTOx only) was amplified by PCR from pRSETB-MTOx (SEQ ID NO. 10—MTOx only) yielding a 1.7 Kb amplicon. The MTOXUP/MTOXLO primers (SEQ ID NO. 34 and 35) used for amplification attached a SpeI site to the 5'-end and a XhoI site to the 3'-end of the cDNA. The MTOx PCR amplicon (SEQ ID NO. 10—MTOx with added 5' SpeI site 3' XhoI site) flanked by SpeI and XhoI sites was digested with SpeI and XhoI and gel purified using a gel-purification kit (Qiagen). The purified SpeI-XhoI-digested MTOx cDNA (SEQ ID NO. 10) was ligated into SpeI-XhoI-digested pXP416 using New England Biolab's T4 DNA ligase kit. The ligation mixture was used to transform competent TOP10 E. coli (Invitrogen). Transformants were selected and maintained on LB+amp plates. Construction of pXP420-MTOx (SEQ ID NO. 10—MTOx only) (FIG. 8) was confirmed by digesting purified plasmid DNA with SpeI and XhoI to yield 5.8 and 1.7 Kb fragments.

pXP416-SHB17

SHB17 (SEQ ID NO. 77) was cloned into pXP416 by homologous recombination to avoid disrupting the SHB17 ORF by cutting with XhoI. SHB17 was amplified using PTEF1-SpeI-SHB17/TCYC1-XhoI-SHB17 primers (SEQ ID NO. 56 and 57) that contained 60-bp of sequence homologous to both ends of SpeI-XhoI-linearized pXP416. BY4742 tal1Δ trp1Δ was transformed with SHB17 amplicon (SEQ ID NO. 77) and SpeI-XhoI linearized pXP416 plasmid according to standard methods (Gietz and Woods 2001). Transformants were selected and maintained on M+his+leu+lys. The plasmid was rescued from a yeast transformant by extracting DNA according to a genomic DNA extraction protocol and used to transform competent TOP10 E. coli (Schwartz and Sherlock 2016). Plasmid DNA was extracted and purified from E. coli transformants using a plasmid miniprep kit (Qiagen). Construction of pXP416-SHB17 (SEQ ID NO. 77—SHB17 only) was verified by digestion with BbsI and analysis by gel electrophoresis which yielded 2.8 and 3.8 Kb fragments as expected.

pXP416-SHB17-2μΔ

The yeast origin of replication (2 μA) sequence was removed from pXP416-SHB17 (SEQ ID NO. 77—SHB17 only) by digestion with EcoRI. Five nanograms of EcoRI-digested pXP416-SHB17 DNA (SEQ ID NO. 77—SHB17 only) were added to a T4 ligase-mediated ligation reaction after which competent TOP10 E. coli was transformed with 5 μl of the reaction mixture. Transformants were selected on LB+Amp. Construction of pXP416-SHB17-2μΔ (SEQ ID NO. 77—SHB17 only) (FIG. 9) was confirmed by digestion with BbsI and analyzed by gel electrophoresis which indicated a 5.3 Kb fragment.

pXP420-EEVS pXP420 plasmid was extracted and purified from a 1-ml culture of DH5a/pXP420 E. coli grown in LB+amp. An aliquot of pXP420 was digested with SpeI- and XhoI-restriction enzymes yielding a 6.0 Kb fragment. SpeI-, XhoI-digested plasmid was gel purified using a Qiagen gel-purification kit. The EEVS cDNA (SEQ ID NO. 2) was amplified by PCR from pRSETB-EEVS (SEQ ID NO. 2—EEVS only) yielding a 1.4 Kb amplicon. The DEEVSUP/DEEVSLO primers (SEQ ID NO. 32 and 33) used for amplification attached a SpeI site to the 5'-end and a XhoI site to the 3'-end of the cDNA. The EEVS PCR amplicon (SEQ ID NO. 2—EEVS with added 5'SpeI and 3'XhoI sites) bordered by SpeI and XhoI sites was digested with SpeI and XhoI and gel purified using a Qiagen gel-purification kit. The purified SpeI-XhoI digested EEVS cDNA (SEQ ID NO. 2—EEVS with added 5'SpeI and 3'XhoI sites) was ligated into SpeI-XhoI digested pXP420 using New England Biolab's T4 DNA ligase kit. The ligation mixture was then used to transform competent TOP10 E. coli from Invitrogen. Transformants were selected and maintained on LB+amp plates. Construction of pXP420-EEVS (SEQ ID NO. 2—EEVS only) (FIG. 10) was confirmed by digesting purified plasmid DNA with SpeI and XhoI to yield 6.0 and 1.4 Kb fragments.

pGH420-EEVS-MTOx

A plasmid expressing both EEVS (SEQ ID NO. 2—EEVS only) and MTOx (SEQ ID NO. 10—MTOx only) was constructed using in vivo ligation. BY4742 tal1Δ trp1Δ nqm1Δ was co-transformed with seven PCR amplicons as described in Example 2. Yeast transformants were selected on M+trp+lys. Plasmid DNA was purified from a yeast transformant and used to transform *E. coli*. Transformants were selected on LB+amp and verified as described in the Example 2.

pGH420-EEVS-MTOx-2µΔ

Figure 11:
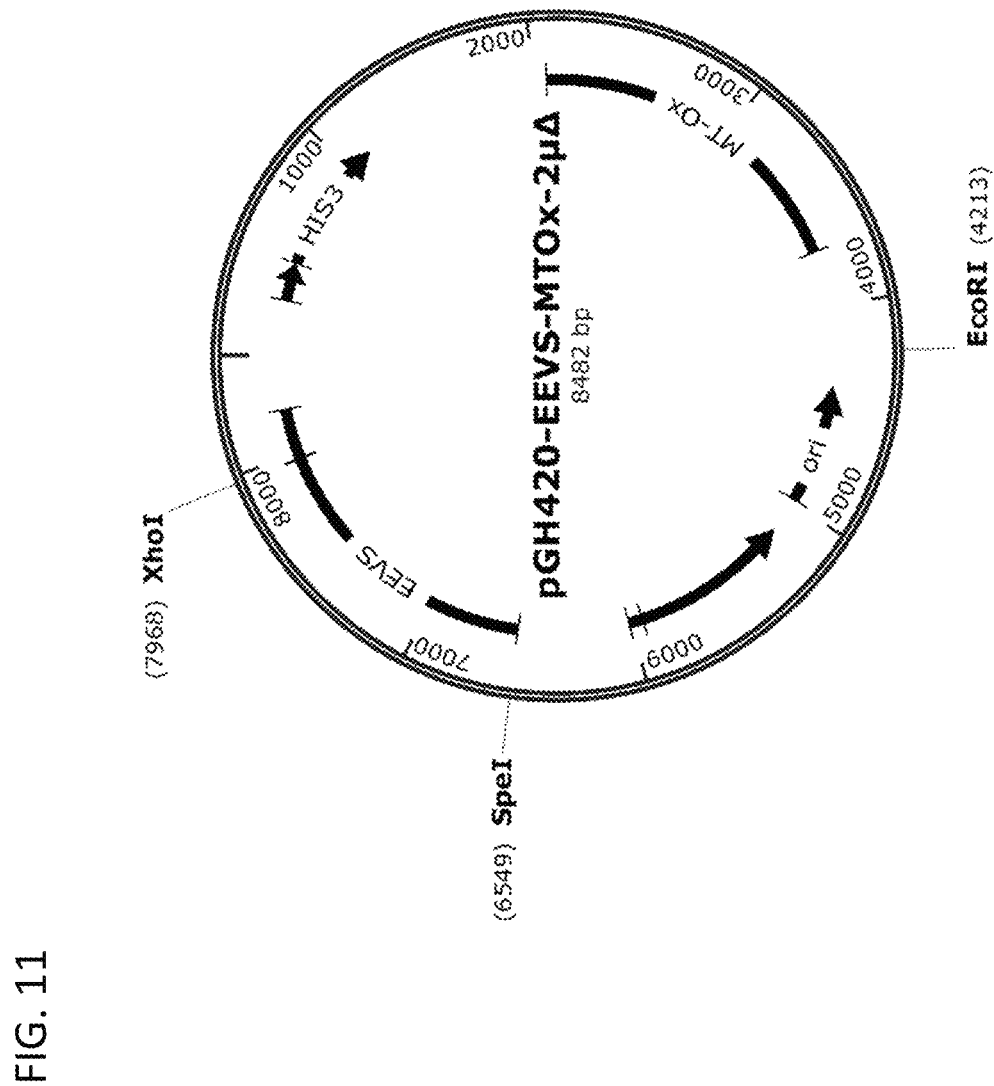
FIG. 11 is a map of plasmid pGH420-EEVS-MTOx-2μΔ.
Figure 12:
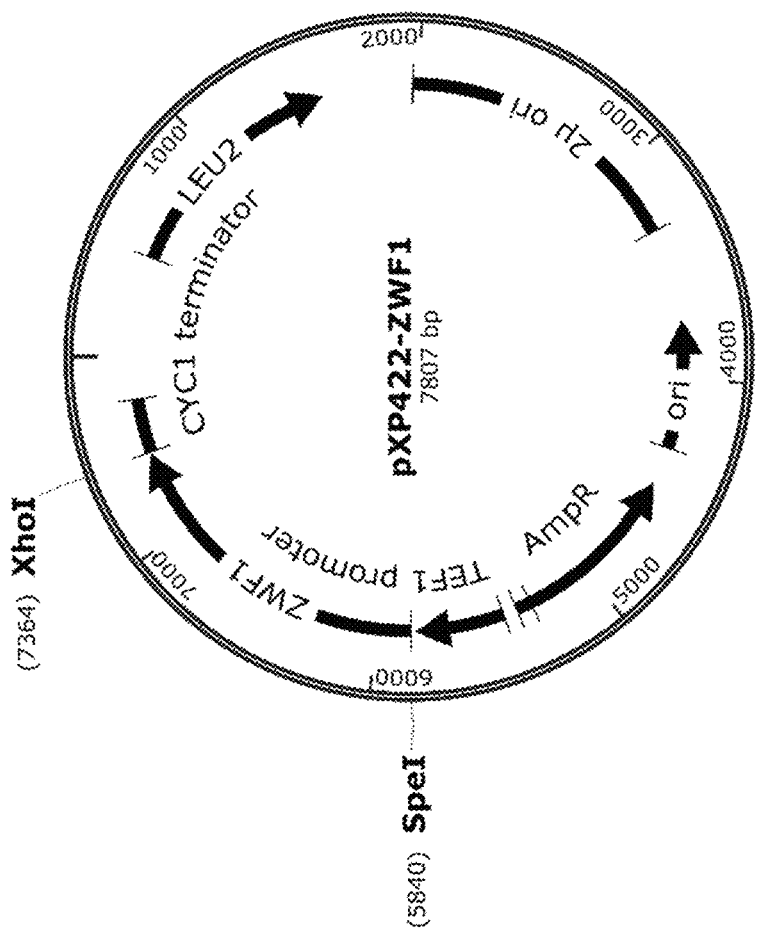
FIG. 12 is a map of plasmid pXP422-ZWF1.

To facilitate stable integration of the pGH420-EEVS-MTOx plasmid (SEQ ID NOs. 2 and 10—EEVS and MTOx only) into the yeast genome the yeast origin of replication (2µ) was first digested with EcoRI restriction enzyme for 30 min at 37° C. EcoRI-digested pGH420-EEVS-MTOx (SEQ ID NOs. 2 and 10—EEVS and MTOx only) was then heated to 65° C. for 20 min to inactivate enzyme. Digested plasmid was diluted 20-fold in a T4 DNA ligase reaction to circularize the construct without the 2µ sequence (FIG. 11). Competent TOP10 *E. coli* was transformed with 5 µl of the ligation mixture. Transformants were selected and maintained on LB+amp plates. Construction of pGH420-EEVS-MTOx-2µΔ (SEQ ID NOs. 2 and 10—EEVS and MTOx only) was confirmed by digestion with EcoRI which yielded an 8.5 Kb fragment by gel electrophoresis.

pXP422-ZWF1 (SEQ ID No. 78)

pXP422 plasmid was extracted and purified from a 1-ml culture of TOP10/pXP420 *E. coli* grown in LB+amp. An aliquot of pXP422 was digested with SpeI- and XhoI-restriction enzymes yielding a 6.3 Kb fragment. SpeI-, XhoI-digested plasmid was gel purified using a Qiagen gel-purification kit. The ZWF1 gene (SEQ ID NO. 78) was amplified by PCR from BY4742 yielding a 1.5 Kb amplicon. The ZWF1SpeIUP/ZWF1XhoILO primers (SEQ ID NOs. 88 and 89) used for amplification attached a SpeI site to the 5'-end and a XhoI site to the 3'-end of the gene. The ZWF1 PCR amplicon (SEQ ID NO. 78 with added 5' XhoI and 3' SpeI sites) bordered by SpeI and XhoI sites was digested with SpeI and XhoI and gel purified using a Qiagen gel-purification kit. The purified SpeI-XhoI digested ZWF1 gene (SEQ ID NO. 78 with added 5' XhoI and 3' Spa sites) was ligated into SpeI-XhoI digested pXP422 using New England Biolab's T4 DNA ligase kit. The ligation mixture was then used to transform competent TOP10 *E. coli* from Invitrogen. Transformants were selected and maintained on LB+amp plates. Construction of pXP422-ZWF1 (SEQ ID NO. 78—ZWF1 only) (FIG. 12) was confirmed by digesting purified plasmid DNA with SpeI and XhoI to yield 6.3 and 1.5 Kb fragments. The DNA sequence for ZWF1 (SEQ ID NO. 78—ZWF1 only) can be found in below.

Measurements of Biomass and Gadusol

Figure 25:
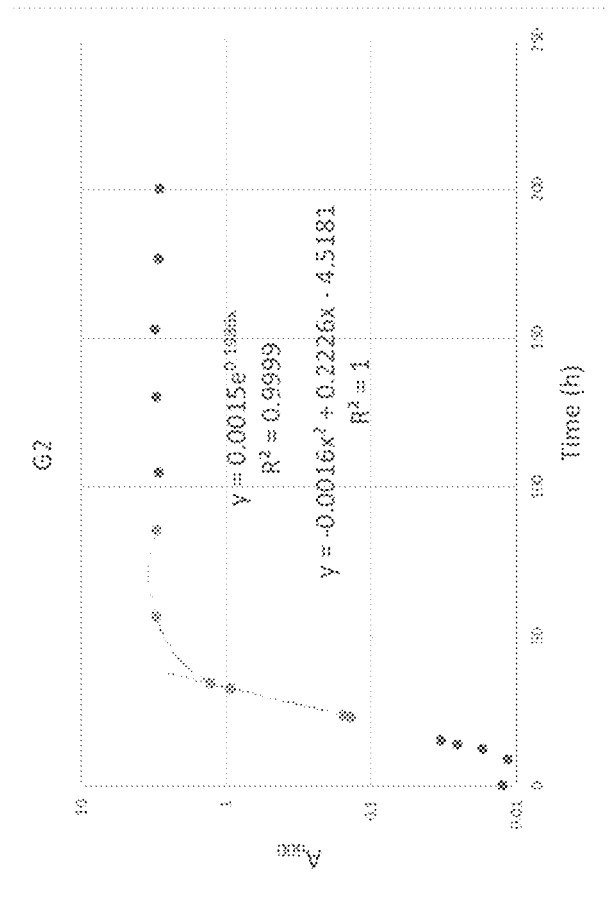
FIG. 25 is a graph of determining exit from log phase for G2.
Figure 26:
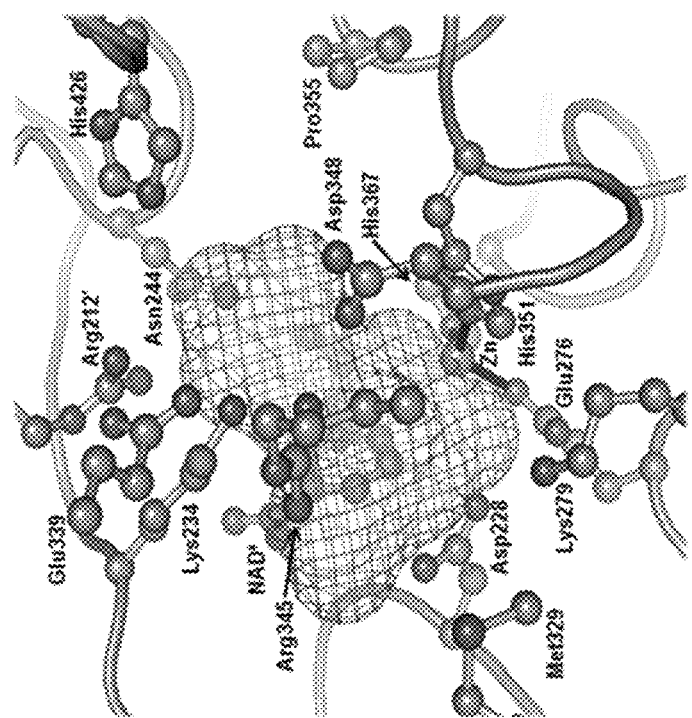
FIG. 26 illustrates a model for the active site geometry of EEVS. Shown are the 14 active site residues conserved in all EEVS enzymes, the $NAD^+$, and the $Zn^{2+}$ atom, along with a mesh that delineates the pocket suitable for binding a SHIP substrate. Residue numbers identifying the active site residues are from the EEVS.
Figure 27:
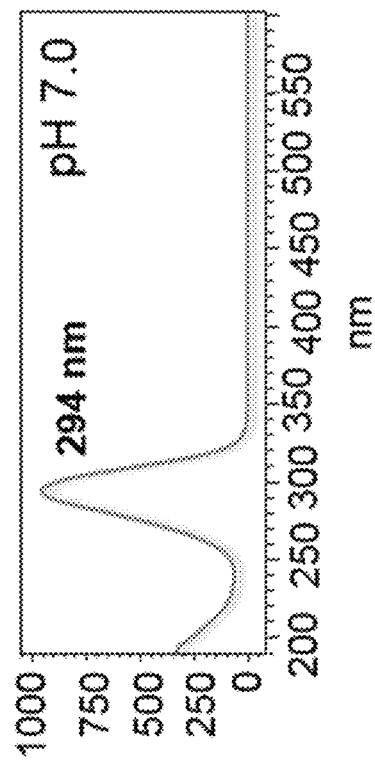
FIGS. 27-28 illustrate UV absorptions of gadusol at pH7.0 and 2.5.
Figure 28:
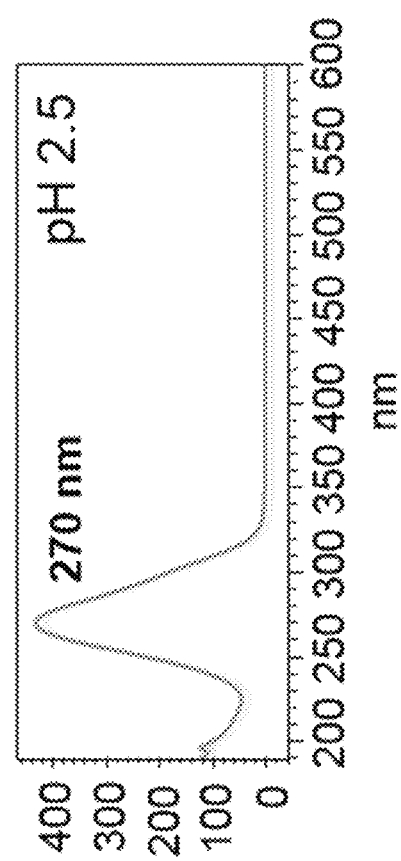
Figure 29:
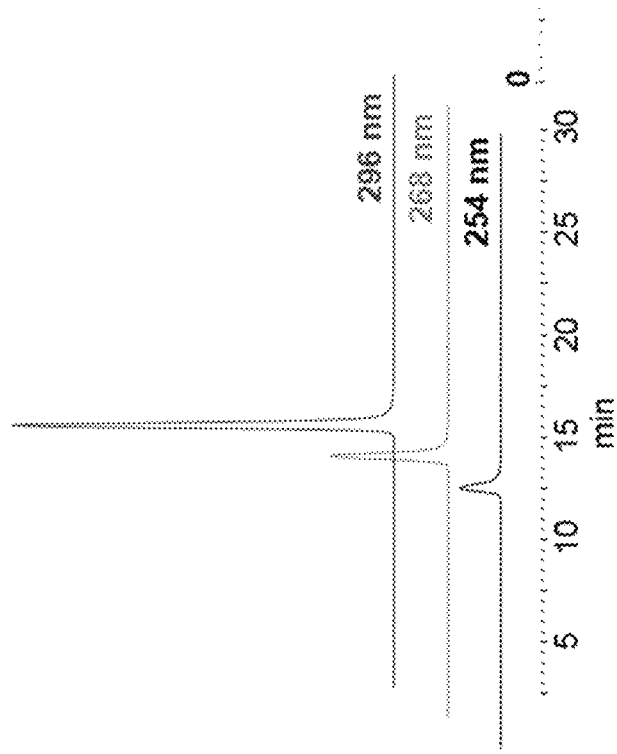
FIGS. 29-30 illustrate high-performance liquidchromatography (HPLC) traces of gadusol at pH 7.0 and 2.5.
Figure 30:
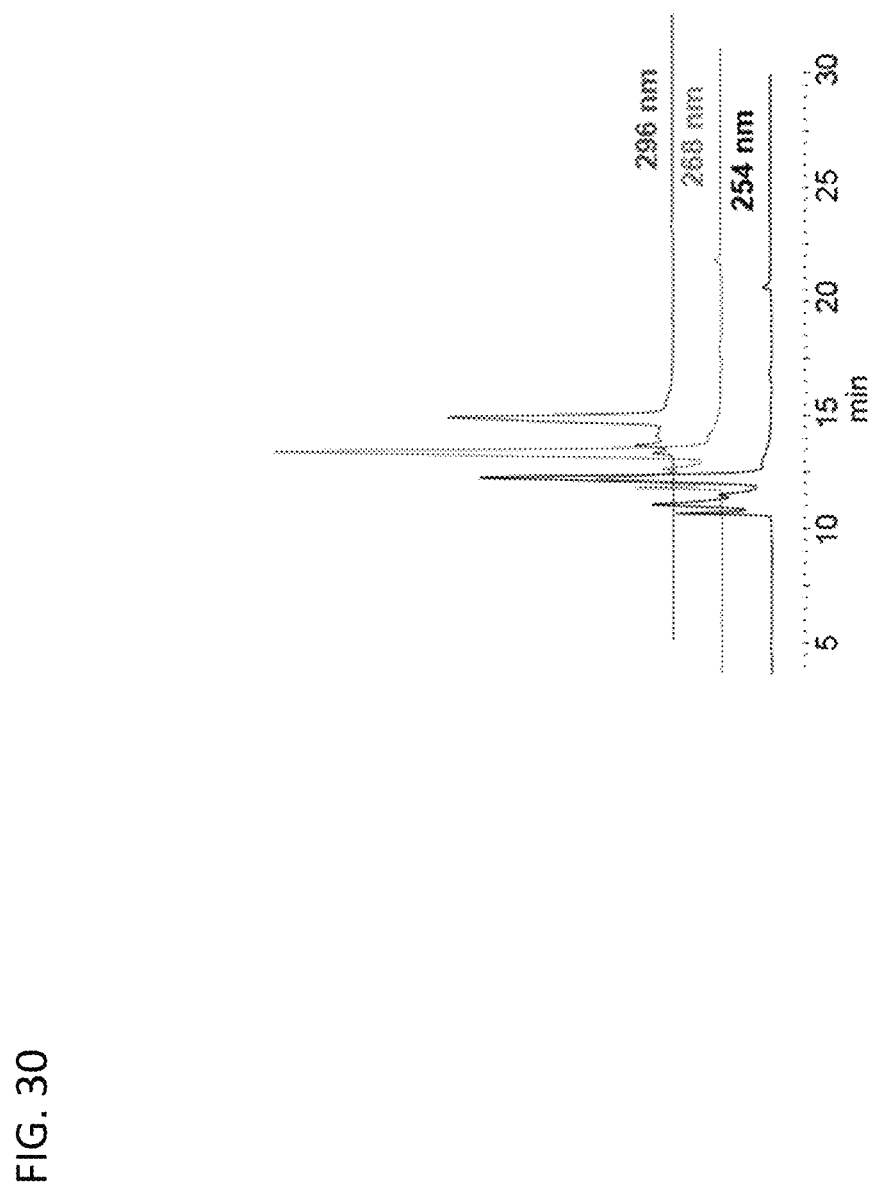
Figure 31:
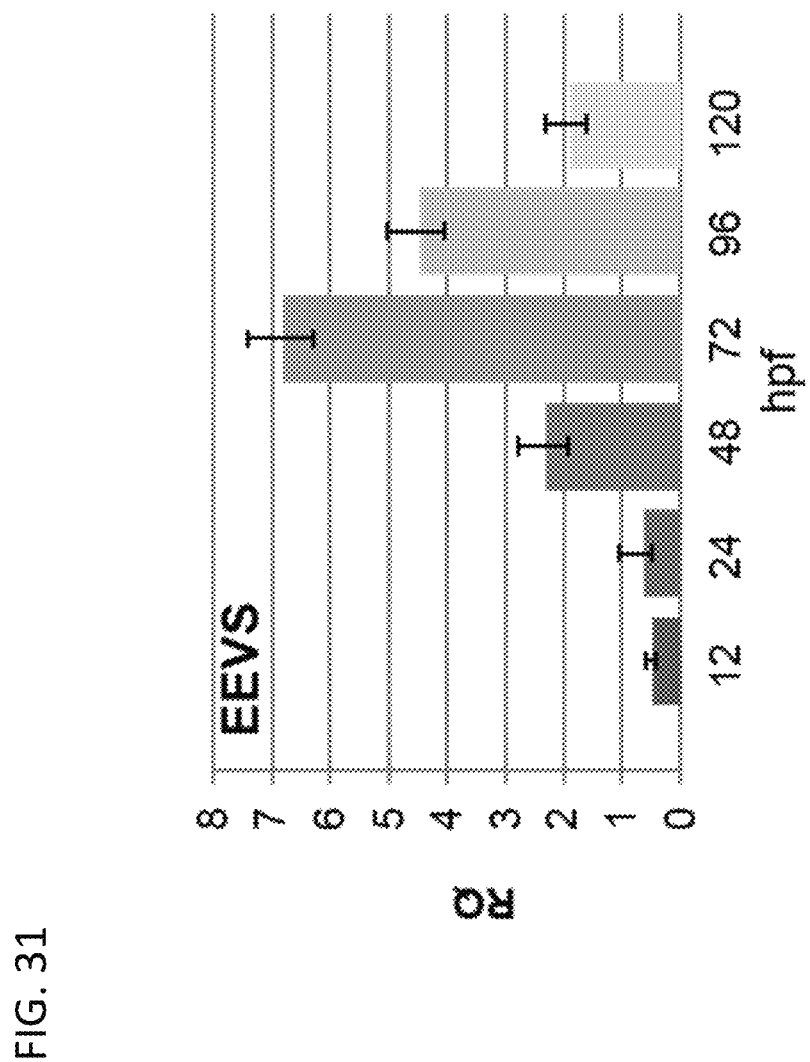
FIGS. 31-32 illustrate transcription patterns of EEVS and MT-Ox encoding genes during zebrafish embryonic development using qRT-PCR analysis of mRNA isolated from zebrafish embryos at 12, 24, 48, 72, 96, and 120 hours post fertilization (hpf).
Figure 32:
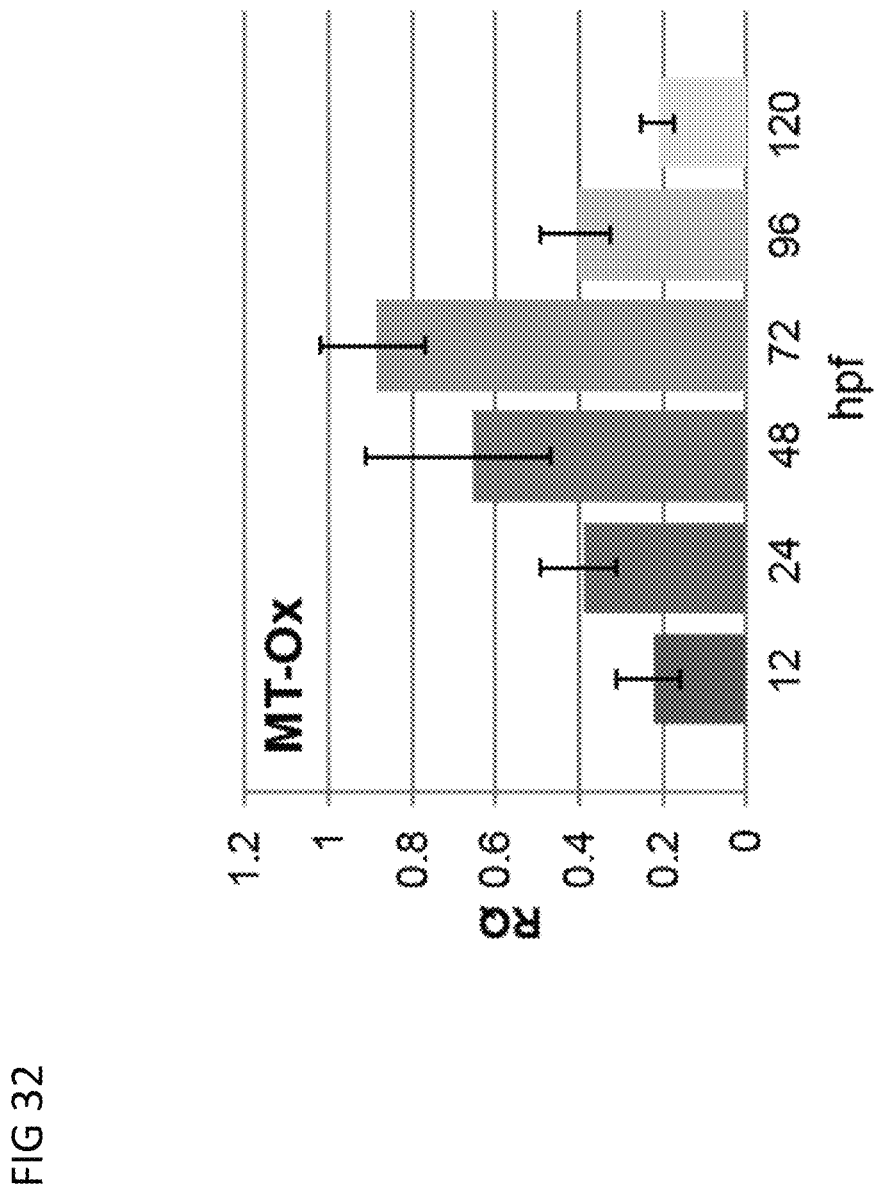
Figure 33:
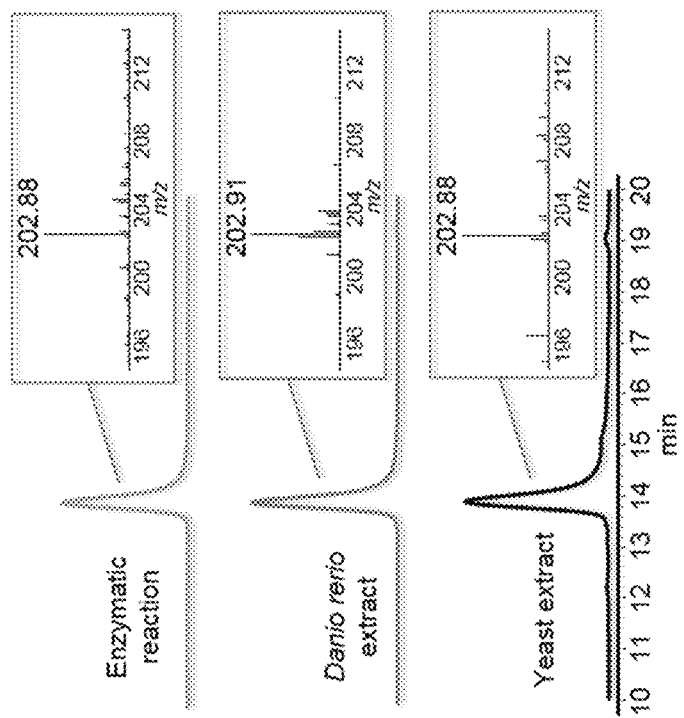
FIG. 33 illustrates results of a comparative HPLC analysis of gadusol from recombinant enzymatic reaction, *Danio rerio* (zebrafish) extract, and yeast extract.
Figure 34:
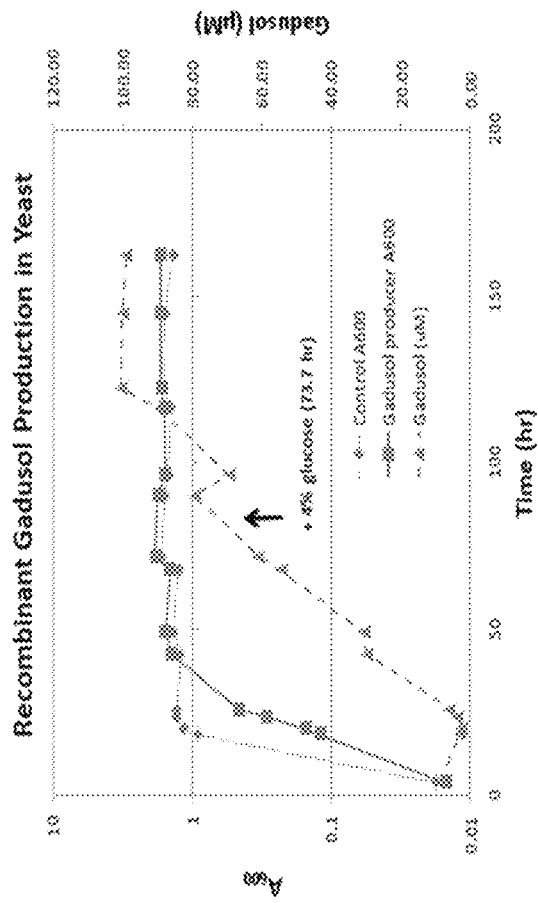
FIG. 34 illustrates a time course of gadusol production in an engineered yeast comprising SEQ ID NO. 2 (EEVS) and SEQ ID NO. 10 (MT-Ox) genes. Yeast growth was monitored as $A_{600}$ values (control, dotted line; gadusol producer, solid line). Gadusol concentration in the supernatant was monitored as A296 values in 50 mM phosphate buffer, pH 7.0 (dashed line) corrected for non-gadusol background absorbance in the control supernatant, normalized to $A_{600}$ value. Gadusol was quantified based on an extinction coefficient of 21,800 $M^{-1}$ $cm^{-1}$ in 50 mM phosphate buffer, pH 7.

Yeast biomass was monitored spectrophotometrically at $A_{600}$ using a UV-visible spectrophotometer (Shimadzu UV-1601). Cultures were diluted with distilled water such that the measured values did not exceed 0.3 because previous measurements had shown this to be the limit of linearity for this spectrophotometer. Actual $A_{600}$ values were calculated by multiplying by the dilution factor. Exit from log phase was determined to estimate when gadusol production was relative to growth. Exit from log phase was estimated by finding the intersection of an exponential growth trend line fitted to cultures in log phase and a polynomial trend line fitted to cultures exiting log phase (Microsoft Excel, Redmond, Wash.). An example featuring strain G2 may be found in FIG. 25.

To measure extracellular gadusol from a culture, yeast cells were spun down and a sample of culture supernatant was diluted to 50 mM phosphate, pH 7. The absorbance of the supernatant was measured at 296 nm using distilled water as a blank. Gadusol concentrations were calculated according to Beer's law using gadusol's extinction coefficient, 21,800 $M^{-1}$ $cm^{-1}$ at pH 7 in 50 mM phosphate. This value was determined previously for a gadusol sample of undefined purity (Plack et al. 1981). The formula below accounts for background absorbance at 296 nm due to non-gadusol components in the fermentation. The average $A_{296}/A_{600}$ ratio (0.0537) of a control strain (G2C) grown in triplicate for three days at 30° C. and 200 RPM, was subtracted from the $A_{296}/A_{600}$ ratio of a sample to correct for background $A_{296}$ absorbance. The difference in ratios was then multiplied by the sample's $A_{600}$, giving absorbance from gadusol which was then divided by gadusol's extinction coefficient (21,800 $M^{-1}$ $cm^{-1}$) to determine molarity.

$$\text{Gadusol (M)} = \frac{\left[\left(\frac{A_{296}}{A_{600}}\right)_{Gad} - 0.0537\right] \times (A_{600})_{Gad}}{21{,}800 \text{ M}^{-1}\text{cm}^{-1}}$$

$(A_{296})_{Gad}$=The $A_{296}$ of a yeast culture supernatant as described in the preceding section.

$(A_{600})_{Gad}$=The $A_{600}$ of a yeast culture as described in the preceding section.

Statistical Analysis

Statistical significance ($p<0.05$) of differences was determined using Student's two-tailed, paired t test (Microsoft Excel, Redmond, Wash.).

Results and Discussion

The gadusol biosynthetic pathway in vertebrates was recently shown to originate from the pentose phosphate pathway intermediate SHIP and to require two enzymes: EEVS and bifunctional MT-Ox (Osborn et al. 2015). cDNAs encoding the two genes from zebrafish (*Danio rerio*) were expressed in *E. coli* and were shown to mediate the in vitro conversion of S7P to EEV, and the SAM- and $NAD^+$-dependent conversion of EEV to gadusol, respectively. In order to explore the possibility of producing gadusol in yeast, the cDNAs were sub-cloned into the yeast expression vectors pXP420 and pXP416 to yield pXP420-EEVS (SEQ ID NO. 2—EEVS only) and pXP416-MTOx (SEQ ID NO. 10—MTOx only), respectively. Both vectors contained the same strong constitutive *S. cerevisiae* promoter, TEF1, but different selectable markers. Table 5 lists a set of gadusol-producing strains that were constructed and provides characteristics related to growth and gadusol yields. Although the strains have been numbered, no relationship is necessarily implied based on the numerical designation. Strains and interventions that increased gadusol yields are presented earlier in the table and reflect their position in the text, while the remaining strains and interventions follow.

TABLE 5

| Strain | Conditions | Doubling time (h)[1] | End of log phase (h) | Gadusol made (%) after exiting log phase | Time to reach maximal gadusol (h) | Biomass ($A_{600}$) at maximal gadusol[1] | Maximal gadusol (mg/L)[1] | Feature |
|---|---|---|---|---|---|---|---|---|
| G0 | YNB + 2% glu + leu + lys | $2.0 \pm 0.1^a$ | 17 | 96 | 110 | $1.30 \pm 0.3^a$ | $11.9 \pm 0.1^a$ | TAL1 NQM1/pXP416-MTOx, pXP420-EEVS |
| G1 | YNB + 2% glu + leu + lys | $3.6 \pm 0.4^b$ | 26 | 87 | 110 | $1.42 \pm 0.04^a$ | $22.4 \pm 0.5^e$ | tal1Δ NQM1/pXP416-MTOx, pXP420-EEVS |
| G10 | YNB + 2% glu + lys | $3.0 \pm 1.4^{abcd}$ | 39 | 93 | 207 | $3.31 \pm 0.47^{bcfg}$ | $36.7 \pm 1.5^f$ | tal1Δ NQM1/pXP422-ZWF1, pXP416-MTOx, pXP420-EEVS |
| G2 | YNB + 2% glu + lys | $3.5 \pm 0.1^b$ | 33 | 93 | 130 | $3.07 \pm 0.08^b$ | $30.1 \pm 0.2^c$ | tal1Δ nqm1Δ/pXP416-MTOx, pXP420-EEVS |
| G3 | YNB + 2% glu + lys + trp | $1.7 \pm 0.0^c$ | 15 | 98 | 169 | $3.54 \pm 0.42^c$ | $64.1 \pm 7.5^c$ | tal1Δ nqm1Δ his3Δ1::pGH420-EEVS-MTOx-2μΔ |
| G3 | 2xlys + 2Xtrp | $2.1 \pm 0.7^{acd}$ | 24 | 86 | 155 | $5.53 \pm 0.20^d$ | $65.7 \pm 1.4^{ce}$ | tal1Δ nqm1Δ his3Δ1::pGH420-EEVS-MTOx-2μΔ |
| G3 | 2xtrp | $2.5 \pm 0.1^d$ | 27 | 85 | 155 | $5.00\pm0.13^{eh}$ | $66.5\pm 6.3^{def}$ | tal1Δ nqm1Δ his3Δ1::pGH420-EEVS-MTOx-2μΔ |
| G3 | 2xlys | $2.3 \pm 0.0^d$ | 23 | 88 | 131 | $3.50 \pm 0.29^{bcf}$ | $63.3 \pm 3.9^{def}$ | tal1Δ nqm1Δ his3Δ1::pGH420-EEVS-MTOx-2μΔ |
| G3 | YNB + 2% glu + leu + lys | $3.6 \pm 0.2^b$ | 35 | 95 | 186 | $1.56 \pm 0.05$ | $13.7 \pm 0.4^h$ | tal1Δ NQM1 pho13Δ/pXP416-MTOx, pXP420-EEVS |
| G6 | YNB + 2% glu + lys | $5.9 \pm 0.6^f$ | 60 | 74 | 156 | $2.91 \pm 0.06^b$ | $17.9 \pm 0.8^h$ | tal1Δ nqm1 shb17Δ/pXP416-MTOx, pXP420-EEVS |
| G7 | YNB + 2% glu + lys | $4.4 \pm 0.1^g$ | 48 | 84 | 106 | $4.76 \pm 0.15^b$ | $28.4 \pm 3.5^c$ | tal1Δ nqm1Δ his3Δ1::pGH420-EEVS-MTOx-2μΔ/pXP416-SHB17 |
| G8 | YNB + 2% glu + lys | $2.0 \pm 0.0$ | 17 | 98 | 208 | $3.44 \pm 0.22^{bcf}$ | $60.6 \pm 2.5^{cfg}$ | tal1Δ nqm1Δ his3Δ1::pGH420-EEVS-MTOx-2μΔ/pXP416-SHB17 integrant |
| G3 | NADPH nutr. | $2.6 \pm 0.1^{ad}$ | 32 | 85 | 230 | $3.67 \pm 0.14^{ef}$ | $67.8 \pm 2.2^{cef}$ | tal1Δ nqm1Δ his3Δ1::pGH420-EEVS-MTOx-2μΔ |
| G4 | YNB + 2% fru + 0.1% glu + lys | $8.6 \pm 0.4^e$ | 47 | 83 | 264 | $2.56 \pm 0.06^g$ | $53.0 \pm 4.7^g$ | tal1Δ nqm1Δ pgi1Δ his3Δ1::pGH420-EEVS-MTOx-2μΔ |
| G5 | YNB + 2% fru + 0.1% glu + leu + lys | $4.2 \pm 0.5^b$ | 39 | 90 | 302 | $0.93 \pm 0.21$ | $15.1 \pm 3.0$ | tal1Δ NQM1Δ pgi1Δ his3Δ1::pGH420-EEVS-MTOx-2μΔ |

EEVS (SEQ ID NO. 2) and MTOx (SEQ ID NO. 10) Expression is Sufficient for Gadusol Synthesis in *S. cerevisiae*

Figure 13:
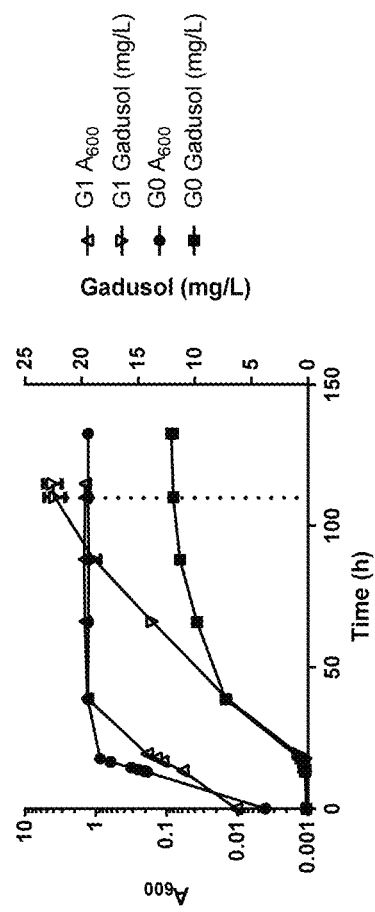
FIG. 13 is a graph showing growth and gadusol production by G0 (TAL1) and G1 (tal1Δ). Maximal measurements for gadusol and biomass were taken at 110 hours as indicated by the dashed line. Error bars are standard deviations.

A trp1Δ derivative of the laboratory haploid BY4742 was co-transformed with both plasmids to generate strain G0 that was found to produce 12 mg/L of gadusol after 110 h (FIG. 13). Comparing G0 to a standard haploid laboratory strain, S288c leu2Δ/pGP564 grown in YNB+2% glucose, pH 4.8 ($t_d$=2.0 vs 2.0 h), shows that expression of EEVS and MTOx is not particularly costly for yeast (Ding et al. 2015). To determine whether deletion of the major yeast transaldolase gene TAL1 would increase yields by eliminating an important S7P-consuming reaction, strain G1 was constructed that lacked Tal1 activity but still expressed EEVS (SEQ ID NO. 2) and MTOx (SEQ ID NO. 10). G1 (tal1Δ) was found to produce 22 mg/L after the same 110 h (FIG. 13). While G1 produced almost twice as much gadusol as G0, it grew more slowly than G1 ($t_d$=3.6 vs 2 h), but reached about the same final cell titer ($A_{600}$=1.4 vs 1.3). The increase in doubling time between G0 and G1 could be explained by the loss of Tal1 activity, which would lead to decreased throughput in the PPP and availability of intermediates needed for producing biomass (E4P, and R5P).

Overexpression of ZWF1 Increases Gadusol Production

Figure 14:
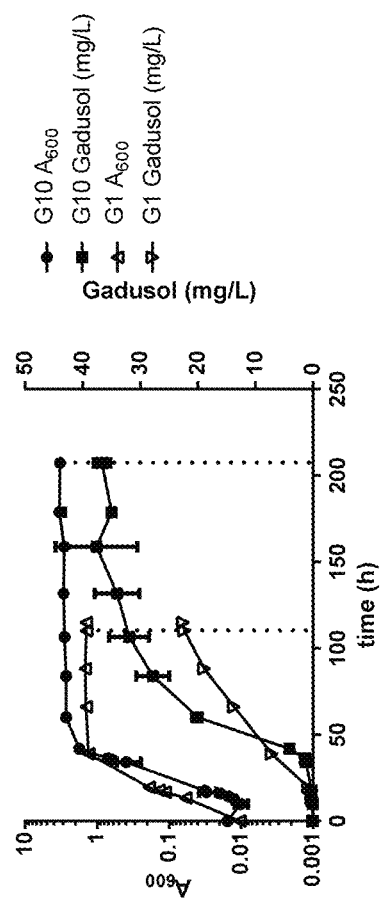
FIG. 14 is a graph showing growth and gadusol production by G1 (tal1Δ) and G10 (tal1Δ/pXP422-ZWF1). Maximal gadusol and biomass measurements for G10 and G1 were taken at 207 and 110 hours, respectively (dashed lines). Error bars are standard deviations.
Figure 15:
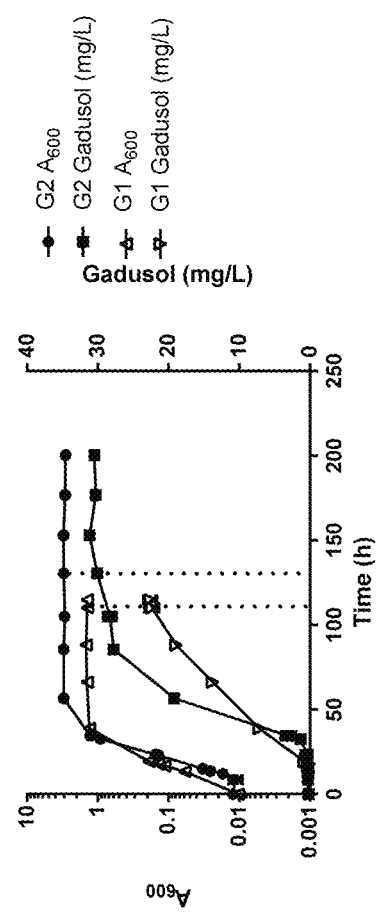
FIG. 15 is a graph showing growth and gadusol production by G1 (tal1Δ NQM1) and G2 (tal1Δ nqm1Δ). Maximal gadusol and biomass measurements for G1 and G2 were taken at 110 and 130 hours, respectively (dashed lines). Error bars are standard deviations.

ZWF1 (SEQ ID NO. 78) encodes glucose 6-P dehydrogenase which catalyzes the first step in the oxidative phase of the PPP (Stincone et al. 2015). A ZWF1-overexpressing mutant (G10) was constructed in the G1 background (tal1Δ) because it is thought to be the rate-limiting step in the PPP (Raiser et al. 2007; Stincone et al. 2015). Overexpression of ZWF1 was therefore expected to divert more glucose 6-P from glycolysis to the PPP to form more S7P, the gadusol precursor. FIG. 14 compares growth and gadusol yield for the G1 (tal1Δ) and G10 (tal1Δ/pXP422-ZWF1) strains to allow assessment of the contribution of ZWF1 (SEQ ID NO. 78) overexpression.

The G10 strain produced 37 mg/L of gadusol compared to 22 mg/L for G1, a 68% increase (FIG. 14). However, G10 required 207 h to reach this higher concentration. It is not clear if gadusol production by G1 would have continued to increase after the final measurement was taken for this strain at 110 h. G10 grew faster than G1 ($t_d$=2.6 vs 3.6 h) and produced 2.4 times more cells ($A_{600}$=3.3 vs 1.4). This latter observation indicates greater carbon assimilation by the ZWF1-overexpressing G10 strain, consistent with a more active PPP.

Elimination of a Second Transaldolase Gene NQM1 Increases Gadusol Yield

NQM1 encodes a paralogue of TAL1 (Huang et al. 2008). While the encoded enzyme is not active during fermentative growth on glucose, it is heavily transcribed during respiratory growth on glycerol (21, 31). Deletion of NQM1 was expected to eliminate all known transaldolase activity and therefore increase gadusol yields. To this end, the G2 strain (tal1Δ nqm1Δ) was constructed and compared to G1 (tal1Δ).

The G2 strain produced 30 vs 22 mg/L of gadusol or 36% more than G1, but required 130 h to reach this level. While the two strains grew at about the same rate ($t_d$~3.5 h), G2 produced twice as much biomass as G1 ($A_{600}$=3.1 vs 1.4). It is likely that decreased throughput in the PPP blocked by a lack of transaldolase activity elevated levels of ribose 5-P which in turn fueled greater carbon assimilation. G2 produced more than twice the gadusol made by G1 during stationary phase.

Figure 16:
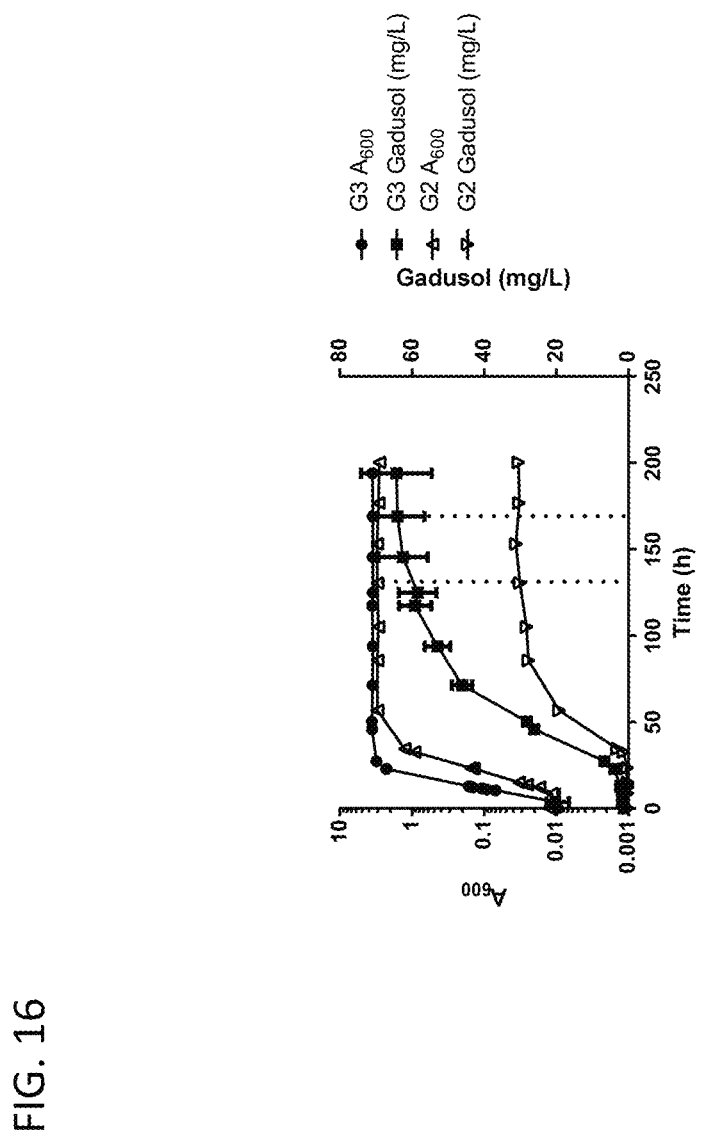
FIG. 16 is a graph showing growth and gadusol production by G2 (tal1Δ nqm1Δ) and G3 (tal1Δ nqm1Δ his3Δ1::pGH420-EEVS-MTOx). Maximal gadusol and biomass measurements for G2 and G3 were taken at 130 and 169 hours, respectively (dashed lines). Error bars are standard deviations.

Chromosomal Integration of a Plasmid Carrying EEVS (SEQ ID NO. 2) and MTOx (SEQ ID NO. 10) Leads to Increased Gadusol Production The limited number of genetic markers available in the G2 strain necessitated redesigning the gadusol expression system. In order to eliminate the need for two plasmids (and two genetic markers), both EEVS (SEQ ID NO. 2) and MTOx (SEQ ID NO. 10) genes were cloned into a single plasmid by in vivo ligation to generate pGH420-EEVS-MTOx (SEQ ID NO. 2 and 10—EEVS and MTOx only). The plasmid was then converted into an integrative construct by excision of the 2µ yeast origin of replication. The pGH420-EEVS-MTOx-2µΔ construct (SEQ ID NO. 79) was digested with NdeI and used to transform a tal1Δ nqm1Δ yeast mutant. Prior digestion with NdeI was meant to facilitate integration of the construct at the NdeI site in the his3Δ1 locus. The resultant strain was designated G3 (FIG. 16).

The G3 strain produced 64 vs 30 mg/L of gadusol or 113% more than G2, but required 169 h to reach this concentration. In contrast, G2 reached 30 mg/L by 130 h. G3 grew much faster than G2 ($t_d$=1.6 vs 3.5 h), but did not produce significantly more biomass, ($A_{600}$=3.5 vs 3.1). The observation that G3 grew more than two times faster than G2 and that the only difference between the strains was the integrated construct vs two high copy plasmids suggests that the plasmids caused growth inhibition. Inclusion of constitutive glycolytic promoters on plasmids has been reported to reduce yeast growth rates by 12-15% (Görgens et al. 2001). In this particular case, the authors speculated that multiple copies of plasmid-borne constitutive promoters could attenuate the transcriptional machinery by titrating a limited number of transcription factors and RNA polymerases which would normally exist in excess.

Supplementation with the Growth-Limiting Nutrients Tryptophan and Lysine has No Effect on Gadusol Yield Supplementing growth medium with the nutrients lysine (Lys) and tryptophan (Trp) was tested as a means to increase gadusol production. Supplementation had no significant effect on gadusol production by G3 (64 vs 63-67 mg/L).

The culture treated with 2XLys+2XTrp (FIG. 17), where the concentration of lysine and tryptophan were doubled, did not grow significantly faster than the 2XTrp or 2XLys treatments (2.1 vs 2.5 vs 2.3 h). The 2XTrp+2XLys treatment resulted in the largest increase in biomass followed by 2XTrp then 2XLys ($A_{600}$=5.5>5.0>3.5).

Figure 17:
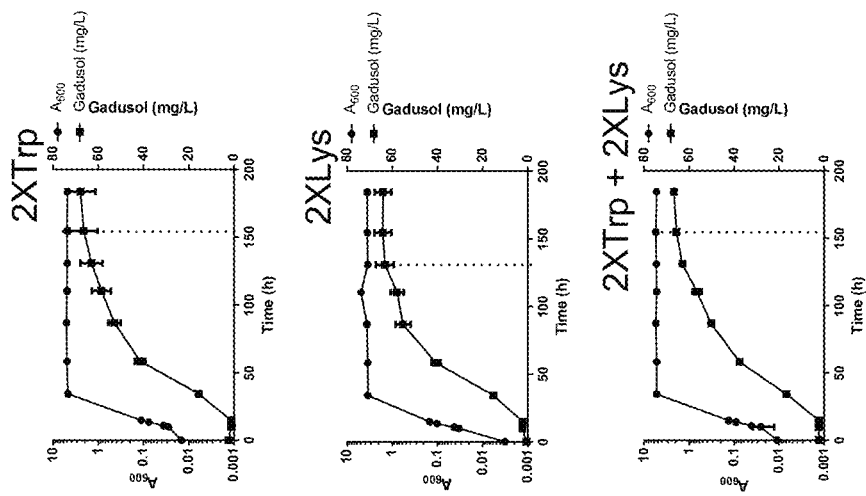
FIG. 17 is a graph showing growth and gadusol production by G3 (tal1Δ nqm1Δ his3Δ1::pGH420-EEVS-MTOx) in YNB+2% glucose supplemented with 2XTrp+2XLys, 2XTrp, and 2XLys. Maximal gadusol and biomass measurements for the 2XTrp+2XLys and 2XTrp treatments were taken at 154 h (dashed line). Maximal gadusol and biomass measurements for the 2XLys treatments were taken at 131 hours (dashed line). Error bars are standard deviations.

Doubling the concentration of lysine alone had no effect on peak $A_{600}$ (3.5 vs 3.5) or gadusol levels, however it was found to reduce the time to reach final gadusol by 38 h compared to the standard YNB+2% glucose+lys+trp medium (FIG. 17). Doubling the tryptophan concentration significantly increased biomass, indicating that tryptophan was a limiting nutrient for growth but not gadusol production (FIG. 17). When lysine was doubled in conjunction with tryptophan, biomass increased even further suggesting that lysine was the next nutrient to become growth limiting (FIG. 17). Despite increases in biomass, gadusol levels did not increase significantly. It is unclear why gadusol production did not increase with biomass in the supplemented cultures. If accumulated intracellular metabolites inhibited gadusol yield then production should have scaled proportionally with biomass, which was not observed. Alternatively, inhibition by gadusol or another extracellular metabolite could have led to production that did not scale proportionately or that stopped at a certain threshold.

Deletion of PHO13 Decreases Gadusol Production

Figure 18:
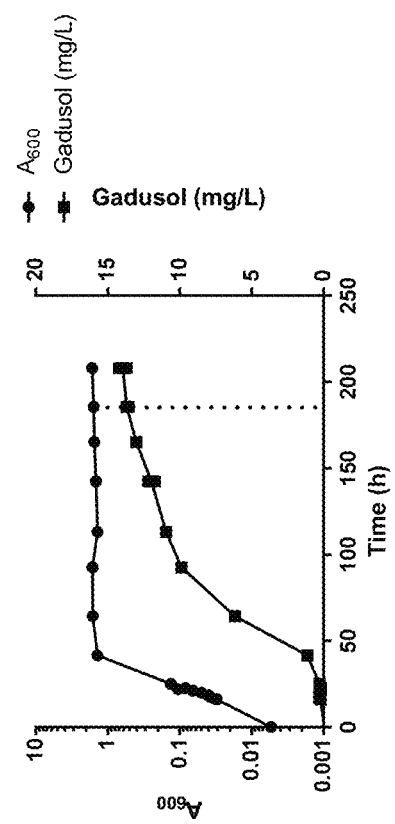
FIG. 18 is a graph showing growth and gadusol production by G9 (tal1Δ pho13Δ). Maximal gadusol and biomass measurements for G9 were taken at 186 hours (dashed line). Error bars are standard deviations.

PHO13 (SEQ ID NO. 81) encodes a phosphatase whose deletion was found to upregulate the second and third steps of the PPP, 6-phosphogluconolactonase (SOL3) and 6-phosphogluconate dehydrogenase (GND1) (Kim et al. 2015). pho13Δ's upregulation of the PPP was originally identified during a screen for mutants with enhanced xylose fermentation rates (Ni et al. 2007). It was thought that a pho13Δ mutation would enhance gadusol yield by increasing expression of two enzymes that provide precursors for S7P biosynthesis. A pho13Δ mutant in the tal1Δ, gadusol-producing background was designated G9 (FIG. 18).

G9 produced 36% less gadusol (14 vs 22 mg/L) than G1, but required 185.6 h to reach this concentration. In contrast, G1 reached 22 mg/L by 110 h. G9 and G1 reached comparable cell densities ($A_{600}$=1.6 vs 1.4). G9 grew at the same rate as G1 ($t_d$=3.6 h). It is unclear why pho13Δ lead to a substantial decrease in gadusol yield. Increased expression of the two steps after glucose 6-P dehydrogenase was expected to cause accumulation of PPP intermediates. However, if such accumulation occurred it did not result in improved gadusol yield and hindered production.

The SHB17 Shunt is a Key Source of S7P for Gadusol Biosynthesis

Sedoheptulose 7-P can be generated from the PPP and glycolytic intermediates erythrose 4-P and DHAP by a two-step pathway. Erythrose 4-P and DHAP combine to form sedoheptulose 1,7-P via an additional activity of Fba1 (Clasquin et al. 2011). Sedoheptulose 1,7-P is then dephosphorylated by the phosphatase Shb17 to generate S7P. SHB17 (SEQ ID NO. 77) was deleted to determine if the SHB17 (SEQ ID NO. 77) shunt is a significant source of S7P.

Figure 19:
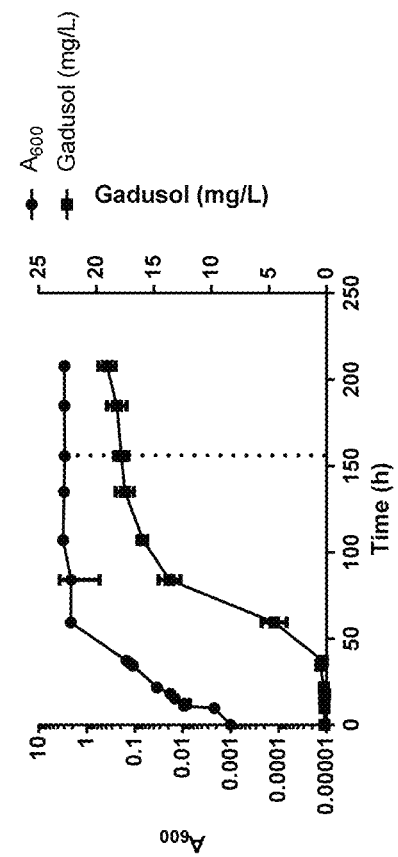
FIG. 19 is a graph showing growth and gadusol production by G6 (tal1Δ shb17Δ). Maximal gadusol and biomass measurements for G6 were taken at 156 hours (dashed line). Error bars are standard deviations.

As shown in FIG. 19, G6 (tal1Δ nqm1Δ shb17d) produced 40% less gadusol than G2 (18 mg/L vs 30 mg/L). The G6 strain showed increased biomass production ($A_{600}$=2.9 vs 1.4) but grew more slowly ($t_d$=5.9 vs 3.6 h) than G2. These results show that SHB17 (SEQ ID NO. 77) has a role in generating SHIP precursor for gadusol production however the increase in biomass was unexpected. Clasquin et al. (2011) speculated that Shb17 provided a route to generate ribose 5-P precursors without generating NADPH. Based on that hypothesis deletion of SHB17 (SEQ ID NO. 77) should have decreased rather than increased biomass.

Overexpression of SHB17 (SEQ ID NO. 77) does not Increase Gadusol Yield

Figure 20:
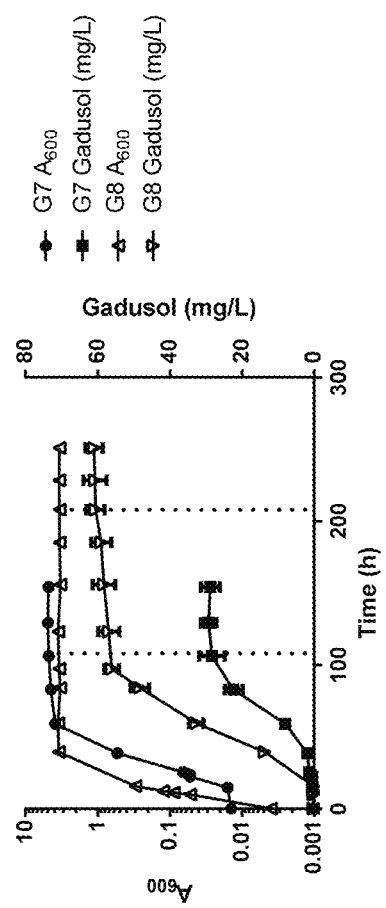
FIG. 20 is a graph showing growth and gadusol production by G7 (tal1Δ nqm1Δ his3Δ1::pGH420-EEVS-MTOx/pXP416-SHB17) and G8 (tal1Δ nqm1Δ his3Δ1::pGH420-EEVS-MTOx pXP416-SHB17 integrant). Maximal gadusol and biomass measurements for G7 and G8 were taken at 208 and 106 hours, respectively (dashed lines). Error bars are standard deviations.

Because deletion of SHB17 (SEQ ID NO. 77) reduced gadusol yield, it was reasoned that overexpression of SHB17 (SEQ ID NO. 77) would lead to an increase. SHB17 (SEQ ID NO. 77) was overexpressed in the transaldolase mutant strain G3 (tal1Δ nqm1Δ) and designated G7. Contrary to expectations, overexpression of SHB17 (SEQ ID NO. 77) decreased gadusol production as shown in FIG. 20. G7 produced much less gadusol than G3 (18 vs 64 mg/L). Overexpression of SHB17 (SEQ ID NO. 77) increased biomass ($A_{600}$=4.8 vs 3.5) and slowed growth ($t_d$=4.4 vs 1.7 h) compared to G3. These results indicate that overexpression of SHB17 (SEQ ID NO. 77) led to more biomass but reduced gadusol production. Based on these results, it is possible that overexpression of SHB17 (SEQ ID NO. 77) may have titrated transcription proteins as described earlier or that accumulation of EEV in the gadusol biosynthesis pathway inhibited production.

It is unclear why overexpression of SHB17 (SEQ ID NO. 77) failed to increase gadusol yield. Based on the improvement in gadusol production observed when the gadusol construct was integrated it was decided to integrate the SHB17 construct to determine if eliminating plasmid burden would improve yield. The resultant strain was designated G8.

As shown in FIG. 20, the G8 strain did not produce more gadusol than G3 (61 vs 64 mg/L). However, it made twice as much gadusol as the G7 strain, which relied on a high-copy plasmid to overexpress SHB17 (SEQ ID NO. 77). G8 reached a similar biomass ($A_{600}$=3.4 vs 3.5) to G3 but grew significantly more slowly ($t_d$=2.0 vs 1.7 h). The restoration of 95% of the gadusol yield by integrating the SHB17 construct suggests that use of high-copy plasmids inhibits gadusol yield. It was speculated that the similar gadusol yields between G8 and G3 were caused by inhibition at a step after S7P, either the 2-epi-5-epi valiolone synthase or methyl transferase-oxidoreductase steps in gadusol biosynthesis.

Supplementation with Nutrients to Increase Activity of Shb17 does not Increase Gadusol Yield Previous work has shown that growing yeast in YNB+2% glucose medium with nutrients that require NADPH for biosynthesis increased production of ribose 5-P via the SHB17 (SEQ ID NO. 77) shunt while repressing the PPP reactions that generate NADPH (Clasquin et al. 2011). Supplementing the growth medium for G3 was rationalized to increase gadusol yield by forcing more glycolytic intermediates to enter the PPP via the SHB17 (SEQ ID NO. 77) shunt and increase the amount of available S7P. Supplementation was expected to reduce the requirement for NADPH while maintaining the need for ribose 5-P. Biosynthetic requirements for ribose 5-P were expected to draw intermediates from the SHB17 (SEQ ID NO. 77) shunt towards S7P, providing a source of precursor for gadusol biosynthesis.

Figure 21:
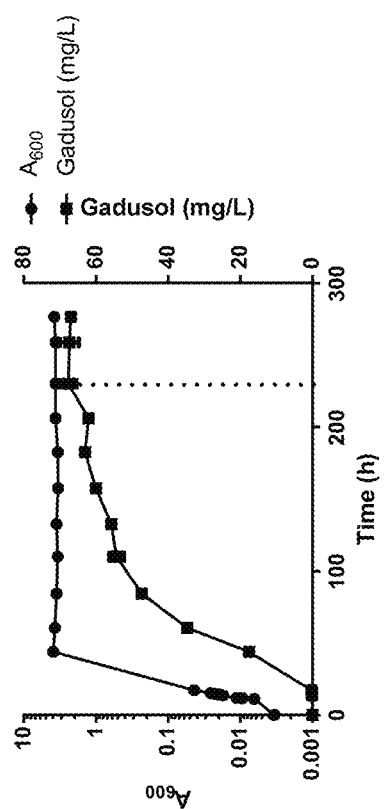
FIG. 21 is a graph showing growth and gadusol production by G3 (tal1Δ nqm1Δ his3Δ1::pGH420-EEVS-MTOx) in YNB+NADPH nutr. Maximal gadusol and biomass measurements for G3 grown in YNB+NADPH nutr. were taken at 230 hours (dashed line). Error bars are standard deviations.

As shown in FIG. 21, the YNB+NADPH nutr. did not increase gadusol production (68 mg/L vs 64 mg/L) or change biomass ($A_{600}$=3.8 vs 3.5) of G3. The YNB+NADPH nutr. medium made G3 grow slower than normal ($t_d$=2.57 vs 1.65 h). The supplementation also increased the time to reach maximal gadusol levels by 61 h (FIG. 21). It is possible that increased availability of S7P may have been insufficient to increase gadusol yield if production was inhibited at one of the steps after S7P formation.

Eliminating Phosphoglucoisomerase Activity in Transaldolase Mutants does not Increase Gadusol Yield.

Deletion of PGI1 was rationalized to increase gadusol yields in the transaldolase mutant background based on a report showing a tal1Δ pgi1Δ mutant accumulating up to 4-fold more S7P than a tal1Δ strain (Schaaff et al. 1990). PGI1 encodes a phosphoglucoisomerase that converts glucose 6-P to fructose 6-P. Phosphoglucoisomerase-transaldolase double mutants (pgi1Δ tal1Δ) are unable to grow on glucose as the sole carbon source because glycolysis is interrupted after glucose 6-P formation (Aguilera 1986). These mutants must rely on the SHB17 (SEQ ID NO. 77) shunt to generate S7P and ribose 5-P. PGI1 mutants in both the tal1Δ nqm1Δ (G4) and tal1Δ (G5) backgrounds were generated. Gadusol production was evaluated in YNB+2% fructose+0.1% glucose medium supplemented with lysine for G4 and both lysine and tryptophan for G5.

Figure 22:
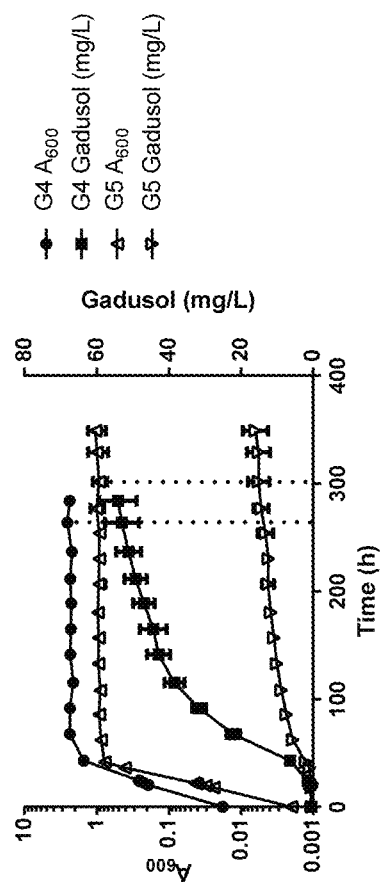
FIG. 22 is a graph showing growth and gadusol production by G4 (tal1Δ nqm1Δ pgi1Δ) and G5 (tal1Δ pgi1Δ). Maximal gadusol and biomass measurements for G4 and G5 were taken at 264 and 302 hours, respectively (dashed lines). Error bars are standard deviations.
Figure 23:
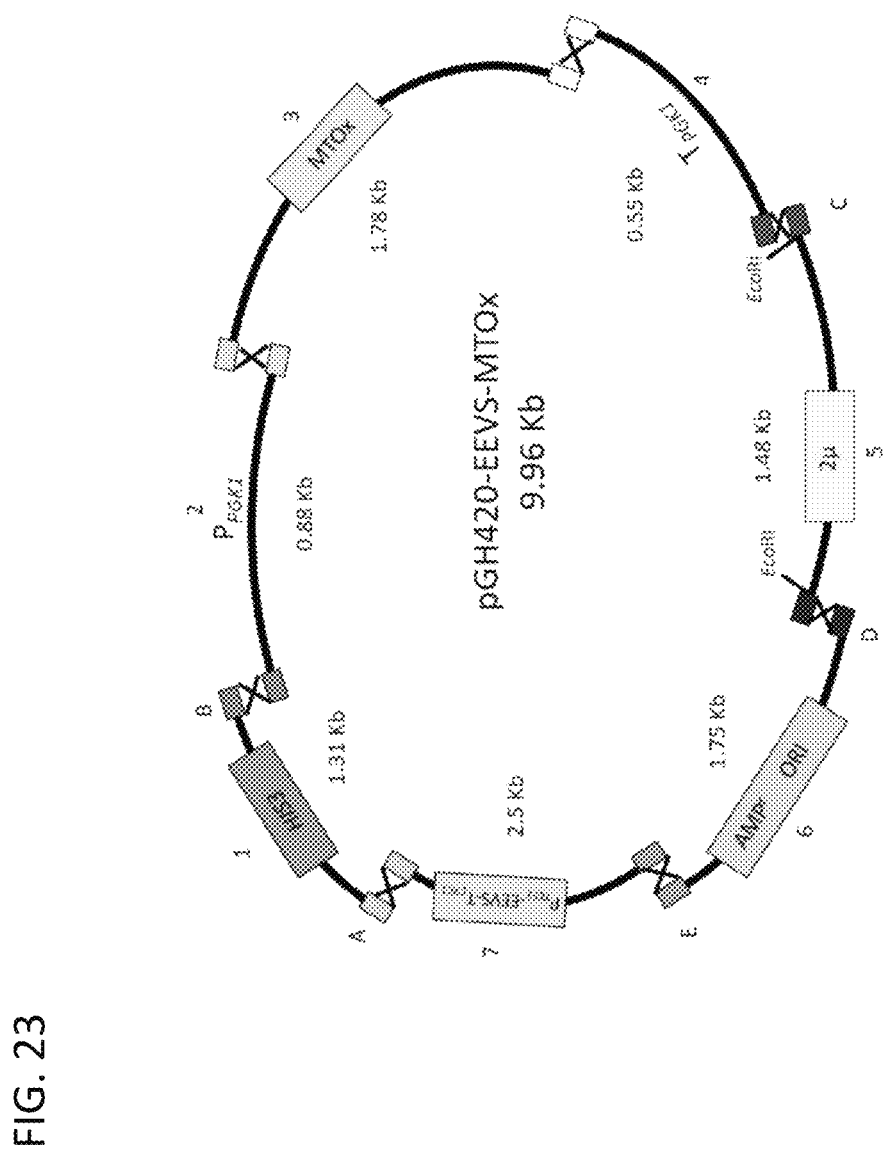
FIG. 23 is scheme for constructing pGH420-EEVS-MTOx by in vivo ligation.

As shown in FIG. 22, eliminating phosphoglucoisomerase activity significantly reduced gadusol production in both G4 and G5. G4 produced much more gadusol than G5 (53 vs 15 mg/L) and reached a higher biomass ($A_{600}$=2.6 vs 0.9). However, G4 grew more slowly than G5 ($t_d$=8.6 vs 4.2 h). The higher gadusol yield by G4 compared to G5 was consistent with observations by Michel et al. (2015) who showed that expression of the second transaldolase Nqm1 increased under glucose-restricted conditions (<0.5%) in tal1Δ mutants. G4 and G5 were grown on medium containing 2% fructose and 0.1% glucose, which may have caused upregulation of NQM1 and concomitant loss of S7P by transaldolase activity in the G5 strain. The absence of transaldolase activity in G4 may have also decreased throughput in the PPP, resulting in elevated levels of ribose 5-P that could have translated to greater biomass relative to G5. It is difficult to disentangle the effect of pgi1Δ on growth from its effect on gadusol production. G4 produced significantly less gadusol than G3 (53 vs 64 mg/L) and grew much more slowly ($t_d$=8.6 vs 1.7 h). G4 also reached a lower biomass than G3 ($A_{600}$=2.6 vs 3.5). It is possible that in addition to the growth defects caused by pgi1Δ, both G4 and G5 would encounter the same problem that prevented SHB17 overexpression from increasing gadusol yield. Both interventions were intended to make S7P rate limiting for production of ribose 5-P and presumably biomass. However, gadusol yield either decreased or was unaffected, suggesting that the step limiting production comes after S7P.

Promoter Titration May Inhibit Gadusol Production

Simultaneous integration of the gadusol biosynthesis genes into yeast chromosome XV and promoter swapping led to a doubling in gadsuol yield from 30 to 64 mg/L. Although the integrated construct used a different promoter for MTOx (Ppm), this change is unlikely to explain the increase in gadusol yield because $P_{PGK1}$ possess roughly half of the activity of $P_{TEF1}$ as estimated using a GFP assay (Sun et al. 2012). Promoters on high-copy plasmids can deplete transcription factors, and RNA polymerase activity leading to competition for transcription machinery that is normally in excess. Because constitutive promoters typically derive from genes encoding essential functions (e.g., translation or glycolysis), promoter titration can lead to growth defects (Görgens et al. 2001). Integration of EEVS (SEQ ID NO. 2) and MTOx (SEQ ID NO. 10) decreased the doubling time of G3 compared to G2 ($t_d$=1.7 vs 3.5 h). Integrating EEVS (SEQ ID NO. 2) and MTOx (SEQ ID NO. 10) would leave limited copies of the promoters in each cell, reducing competition for transcription factors. Using the same promoter ($P_{TEF1}$) to express both EEVS (SEQ ID NO. 2) and MTOx (SEQ ID NO. 10) in G2 could have led to reduced expression of these genes in addition to growth defects. Determining expression levels for EEVS (SEQ ID NO. 2) and MTOx (SEQ ID NO. 10) in the G2 and G3 strains would help determine if gene expression increased after integration or if gadusol yield improved because of changes in growth from plasmid integration.

Observations from the SHB17 (SEQ ID NO. 77) overexpression experiments support a role for promoter titration in gadusol production. Introduction of the high-copy plasmid pXP416-SHB17 ($P_{TEF1}$) (SEQ ID NO. 77—SHB17 only) into the G3 strain led to a sharp decrease in gadusol production (64 vs 28 mg/L). Integration of a construct derived from pXP416-SHB17 (SEQ ID NO. 77—SHB17 only) resulted in the near complete restoration of gadusol production in strain G8 (60 vs 64 mg/L). This difference suggests that high-copy plasmids have an inhibitory effect on gadusol production that should be recognized when testing further interventions. Measuring gadusol production and expression of EEVS (SEQ ID NO. 2) and MTOx (SEQ ID NO. 10) in G3 derivative strains carrying empty $P_{TEF1}$-expression vector or integrated $P_{TEF1}$-expression vector would help support this conclusion.

Conclusion

This study demonstrated that rational genetic interventions were able to increase gadusol yields approximately 5-fold. Deleting both transaldolase genes (TAL1 and NQM1) resulted in a 2.5-fold increase in gadusol yield compared to the tal1Δ mutant. Overexpressing the glucose 6-P dehydrogenase gene (ZWF1) (SEQ ID NO. 78) in a tal1Δ strain caused a 64% increase in gadusol yield. Integrating the gadusol genes and switching the promoter for MTOx (SEQ ID NO. 10) doubled gadsuol production relative to a tal1Δ nqm1Δ strain expressing the gadusol genes from free plasmids. In most of the strains studied, 83-98% of gadusol was made after exiting log phase.

Example 2

Construction of pGH420-EEVS-MTOx (SEQ ID NO. 82)
A plasmid expressing both EEVS (SEQ ID NO. 2) and MTOx (SEQ ID NO. 10) was constructed using in vivo ligation as described, according to the scheme outlined in FIG. 1 (Kuijpers et al, 2013). The essential elements in the construct were synthesized via PCR as seven individual amplicons sharing terminal homology that directed ligation and recombination in a unique order. The seven amplicons are numbered, and the terminal sequence regions are lettered in FIG. 1. For example, sequence A (SEQ ID NO. 72) mediates ligation between amplicons 1 (SEQ ID NO. 83) and 7 (SEQ NO. 85) and sequence B (SEQ ID NO. 73) mediates ligation between amplicons 1 (SEQ ID NO. 83) and 2 (SEQ NO. 84). The plasmid was designed to place the yeast origin of replication (2μ and selectable marker (HIS3) on non-contiguous amplicons because previous work demonstrated that such a separation reduced the number of false positive transformants (Kuijpers et al. 2013).

PCR primers designed to amplify DNA sequences containing the HIS3 marker, PGK1 promoter, MTOx ORF (SEQ NO. 10), PGK1 terminator, 2μ yeast ORI, E. coli AMP$^r$-ORI sequence, and the EEVS (SEQ NO. 2) expression cassette are listed in Table 3. Primers containing 5'-60-bp barcode sequences were designed using the sequences described in Table 7. The barcode sequences lacked homology to the yeast genome, limiting the risk of chromosomal recombination. In the case of MTOx (SEQ NO. 10) (3) a portion of the ORF sequence was used to target recombination. Specifically, the downstream end of fragment 2 contained 60-bp of homology to the 5'-region of the MTOx ORF (SEQ NO. 10) while the upstream region of fragment 4 contained 60-bp of homology to 3'-region of the MTOx ORF (SEQ NO. 10).

TABLE 7

| Barcode sequence | | Sequence 5'-3' |
|---|---|---|
| A | SEQ ID NO. 72 | ACTATATGTGAAGGCATGGCTATGGC ACGGCAGACATTCCGCCAGATCATCA ATAGGCAC |
| B | SEQ ID NO. 73 | CACCTTTCGAGAGGACGATGCCCGTG TCTAAATGATTCGACCAGCCTAAGAA TGTTCAAC |
| C | SEQ ID NO. 74 (This is a portion of SEQ ID NO. 66) | TATTCACGTAGACGGATAGGTATAGC CAGACATCAGCAGCATACTTCGGGAA CCGTAGGC |
| D | SEQ ID NO. 75 | CATACGTTGAAACTACGGCAAAGGAT TGGTCAGATCGCTTCATACAGGGAAA GTTCGGCA |
| E | SEQ ID NO. 76 | AGATTACTCTAACGCCTCAGCCATCA TCGGTAATAGCTCGAATTGCTGAGAA CCCGTGAC |

Figure 24:
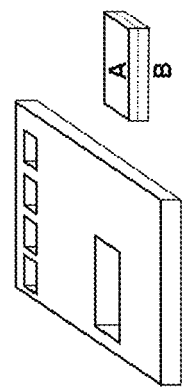
FIG. 24 is schematic diagram showing gel dissection for DNA purification

The PCR conditions used to amplify the components of the plasmid construct were modified from the manufacturer's instructions for the polymerase (Thermofisher Phusion Hot Start II). Primer concentrations were lowered from 500 to 200 nM and polymerase concentration was raised from 0.02 to 0.03 U/μl. Amplicons were gel-purified using a Qiagen gel purification kit. To improve DNA extraction, after a PCR amplicon was excised from a horizontal gel, the slice was cut into a top layer (A) and a bottom layer (B) (FIG. 24). The bottom layer (b) typically contained most of the DNA and was processed according to the manufacturer's instructions while the top layer (A) was disposed of. Approximately 200 fmol each of the purified 2μ and HISS amplicons and 100 fmol each of the purified MTOx ORF (SEQ NO. 10), EEVS (SEQ NO. 2) cassette, E. coli AMP$^r$-ORI, PGK1 promoter, and terminator amplicons were used to transform BY4742 tal1Δ trp1Δ nqm1Δ using the lithium-acetate method (Gietz and Woods 2001). Transformants were selected and maintained on M+lys+trp plates. Transformants were screened for gadusol production in 1 ml YNB+2% glucose+lys+trp screwcap-tube cultures shaken at 200 RPM and 30° C. for 72-h. A gadusol-producing strain was then screened for the E. coli AMP$^r$-ORI sequence using the primers F-ORI-F/H-AMP-R to generate a 1.8 Kb PCR amplicon. The pGH420-EEVS-MTOx plasmid (SEQ NO. 2 and 10—EEVS and MTOx only) was extracted using Zymoprep yeast plasmid miniprep II kit (Zymoresearch). A 5 μl aliquot of yeast plasmid DNA was used to transform competent TOP10 E. coli cells (Invitrogen). Transformants were selected and maintained on LB+amp plates. Then a transformant was selected for culturing and plasmid DNA purification using a Qiaquick plasmid miniprep kit. Plasmid construction was confirmed by EcoRI digestion and analysis by agarose gel electrophoresis, yielding 8.5 and 1.5 Kb fragments.

References Cited in Examples 1 and 2 and Specifically Incorporated Herein by

REFERENCE

Aguilera A (1987) Mutations suppressing the effects of a deletion of the Phosphoglucose isomerase gene PGI1 in *Saccharomyces cerevisiae*. Curr Genet 11:429-434. doi: 10.1007/BF00384603

Aguilera A (1986) Deletion of the phosphoglucose isomerase structural gene makes growth and sporulation glucose dependent in *Saccharomyces cerevisiae*. Mol Gen Genet 204:310-316

Arbeloa E M, Bertolotti S G, Churio M S (2011) Photophysics and reductive quenching reactivity of gadusol in solution. Photochem Photobiol Sci 10:133-42. doi: 10.1039/c0pp00250j Arbeloa E M, Uez M J, Bertolotti S G, Churio M S (2010) Antioxidant activity of gadusol and occurrence in fish roes from Argentine Sea. Food Chem 119:586-591. doi: 10.1016/j.foodchem.2009.06.061

Baudin A, Ozier-kalogeropoulos O, Denouel A, et al (1993) A simple and efficient method for direct gene deletion in *Saccharomyces cerevisiae*. Nucleic Acids Res 21:3329-3330. doi: 10.1093/nar/21.14.3329

Bok M J, Porter M L, Place A R, Cronin T W (2014) Biological Sunscreens Tune Polychromatic Ultraviolet Vision in Mantis Shrimp. Curr Biol 24:1636-1642. doi: 10.1016/j.cub.2014.05.071

Booth C, Morrow J (1997) The penetration of U V into natural waters. Photochem Photobiol 65:355-358

Cadière A, Ortiz-Julien A, Camarasa C, Dequin S (2011) Evolutionary engineered *Saccharomyces cerevisiae* wine yeast strains with increased in vivo flux through the pentose phosphate pathway. Metab Eng 13:263-271. doi: 10.1016/j.ymben.2011.01.008

Chioccara F, Zeuli L, Novellino E (1986) Occurrence of mycosporine related compounds in sea urchin eggs. Comp Biochem Physiol 85:459-461. doi: 10.1016/0305-0491(86)90027-1

Clasquin M F, Melamud E, Singer A, et al (2011) Riboneogenesis in yeast. Cell 145:969-980. doi: 10.1016/j.cell.2011.05.022

Ding J, Holzwarth G, Bradford C S, et al (2015) PEP3 overexpression shortens lag phase but does not alter growth rate in Saccharomyces cerevisiae exposed to acetic acid stress. Appl Microb Cell Physiol 99:8667-8680. doi: 10.1007/s00253-015-6708-9

Dunlap W C, Williams D M, Chalker B E, Banaszak A T (1989) Biochemical protoadaption in vision: UV absorbing pigments in fish eye tissue. Comp Biochem Physiol 93B:601-607

Fang F, Salmon K, Shen M W Y, et al (2011) A vector set for systematic metabolic engineering in Saccharomyces cerevisiae. Yeast 3:123-136. doi: 10.1002/yea Gao Q, Garcia-Pichel F (2011) Microbial ultraviolet sunscreens. Nat Rev Microbiol 9:791-802. doi: 10.1038/nrmicro2649

Garcia-Pichel F (1998) Solar ultraviolet and the evolutionary history of cyanobacteria. In: Origins of Life and Evolution of the Biosphere. pp 321-347

Garcia-Pichel F (1994) A model for internal self-shading in planktonic organisms and its implications for the usefulness of ultraviolet sunscreens. Limnol Oceanogr 39:1704-1717. doi: 10.4319/10.1994.39.7.1704

Gietz R D, Woods R (2001) Genetic transformation of yeast. Biotechniques 30:816-831

Görgens J F, Van Zyl W H, Knoetze J H, Hahn-Hagerdal B (2001) The metabolic burden of the PGK1 and ADH2 promoter systems for heterologous xylanase production by Saccharomyces cerevisiae in defined medium. Biotechnol Bioeng 73:238-245. doi: 10.1002/bit.1056

Grabowska D, Chelstowska A (2003) The ALD6 gene product is indispensable for providing NADPH in yeast cells lacking glucose-6-phosphate dehydrogenase activity. J Biol Chem 278:13984-8. doi: 10.1074/jbc.M210076200

Grant P T (1980) Gadusol, a metabolite from fish eggs. Tetrahedron Lett 21:4043-4044

Huang H, Rong H, Li X, et al (2008) The crystal structure and identification of NQM1/YGR043C, a transaldolase from Saccharomyces cerevisiae. Proteins Struct Funct Bioinforma 73:1076-1081. doi: 10.1002/prot.22237

Kim S R, Xu H, Lesmana A, et al (2015) Deletion of PHO13, Encoding Haloacid Dehalogenase Type IIA Phosphatase, Results in Upregulation of the Pentose Phosphate Pathway in Saccharomyces cerevisiae. Appl Environ Microbiol 81:1601-1609. doi: 10.1128/AEM.03474-14

Kuijpers N G A, Solis-escalante D, Bosman L, et al (2013) A versatile, efficient strategy for assembly of multifragment expression vectors in Saccharomyces cerevisiae using 60 bp synthetic recombination sequences. Microb Cell Fact 12:1-13

Michel S, Keller M A, Wamelink MMC, Raiser M (2015) A haploproficient interaction of the transaldolase paralogue NQM1 with the transcription factor VHR1 affects stationary phase survival and oxidative stress resistance. BMC Genet 16:13. doi: 10.1186/s12863-015-0171-6

Minard K I, McAlister-Henn L (2005) Sources of NADPH in yeast vary with carbon source. J Biol Chem 280:39890-39896. doi: 10.1074/jbc.M509461200

Ng C H, Tan S X, Perrone G G, et al (2008) Adaptation to hydrogen peroxide in Saccharomyces cerevisiae: The role of NADPH-generating systems and the SKN7 transcription factor. Free Radic Biol Med 44:1131-1145. doi: 10.1016/j.freeradbiomed.2007.12.008

Ni H, Laplaza J M, Jeffries T W (2007) Transposon mutagenesis to improve the growth of recombinant Saccharomyces cerevisiae on D-xylose. Appl Environ Microbiol 73:2061-2066. doi: 10.1128/AEM.02564-06

Osborn A R, Almabruk K H, Holzwarth G, et al (2015) De novo synthesis of a sunscreen compound in vertebrates. Elife 4:1-15. doi: 10.7554/eLife.05919

Pernambuco M B, Winderickx J, Crauwels M, et al (1996) Glucose-triggered signaling in Saccharomyces cerevisiae: different requirements for sugar phosphorylation between cells grown on non-fermentable carbon sources. Microbiology 142:1775-1782. doi: 10.1099/13500872-142-7-1775

Plack P A, Fraser N W, Grant P T, et al (1981) Gadusol, an enolic derivative of cyclohexane-1,3-dione present in the roes of cod and other marine fish. Biochem J 199:741-747

Raiser M, Wamelink M M, Kowald A, et al (2007) Dynamic rerouting of the carbohydrate flux is key to counteracting oxidative stress. J Biol 6:10. doi: 10.1186/jbiol61

Ro D K, Paradise E M, Ouellet M, et al (2006) Production of the antimalarial drug precursor artemisinic acid in engineered yeast. Nature 440:940-943. doi: 10.1038/nature04640

Schaaff I, Hohmann S, Zimmermann F K (1990) Molecular analysis of the structural gene for yeast transaldolase. Eur J Biochem 188:597-603. doi: 10.1111/j.1432-1033.1990.tb15440.x Schwartz K, Sherlock G (2016) Preparation of yeast DNA sequencing libraries. Cold Spring Harb Protoc 2016:871-876. doi: 10.1101/pdb.prot088930

Sinha R P, Hader D-P (2002) UV-induced DNA damage and repair: a review. Photochem Photobiol Sci 1:225-236. doi: 10.1039/b201230h Stincone A, Prigione A, Cramer T, et al (2015) The return of metabolism: Biochemistry and physiology of the pentose phosphate pathway. Biol Rev 90:927-963. doi: 10.1111/brv.12140

Sun J, Shao Z, Zhao H, et al (2012) Cloning and Characterization of a Panel of Constitutive Promoters for Applications in Pathway Engineering in Saccharomyces cerevisiae. 109:2082-2092. doi: 10.1002/bit.24481

Thodey K, Galanie S, Smolke C D (2014) A microbial biomanufacturing platform for natural and semisynthetic opioids. Nat Chem Biol 1-10. doi: 10.1038/nchembio.1613

Van Winden W A, Van Dam J C, Ras C, et al (2005) Metabolic-flux analysis of Saccharomyces cerevisiae CEN.PK113-7D based on mass isotopomer measurements of 13C-labeled primary metabolites. FEMS Yeast Res 5:559-568. doi: 10.1016/j.femsyr.2004.10.007

Example 3

EEVS and MT-Ox

The inventors made the discovery that gadusol is synthesized de novo in zebrafish (Danio rerio) from a pentose phosphate pathway intermediate, sedoheptulose 7-phosphate, by a 2-epi-5-epi-valiolone synthase (EEVS) and a methyltransferase-oxidoreductase (MT-Ox). The EEVS and MT-Ox genes are clustered with a suite of conserved transcription factor genes. Homologous gene clusters have been identified in the genomes of some other fish, amphibians, reptiles, and birds. Mammals do not have the EEVS and MT-Ox genes, but do have a homologous transcription factor gene cluster in their genomes. It has been postulated that these ancient genes were lost during the evolution of mammals circa 220 million years ago. The applicant's discovery revealed the molecular basis for gadusol formation in fish and other vertebrates.

Construction of LOC100003999 and ZGC:113054 Gene Expression Vectors

The LOC100003999 gene was codon optimized for *Escherichia coli* and synthesized commercially (GeneScript USA Inc.). The optimized gene was cloned into EcoRV site of pUC57-Kan vector. The plasmid was digested with BglII and EcoRI and ligated into BamHI and EcoRI site of pRSET-B (Invitrogen) for the expression of N-terminal hexa-histidine-tagged protein ("hexa-histidine" disclosed as SEQ ID NO: 90). The zgc:113054 gene was also codon optimized for *E. coli* and commercially synthesized (GeneScript USA Inc.). The optimized gene was cloned into EcoRV site of pUC57-amp vector. The plasmid was digested with BglII and EcoRI and ligated into BamHI and EcoRI site of pRSET-B (Invitrogen) for the expression of N-terminal hexa-histidine-tagged protein ("hexa-histidine" disclosed as SEQ ID NO: 90).

Expression of VALA, LOC100003999 AND ZGC: 113054 Genes in *Escherichia coli* pRSETB-valA, pRSETB-LOC100003999 and pRSETB-zgc:113054 plasmids were individually used to transform *E. coli* BL21 GOLD (DE3) pLysS. Transformants were grown overnight at 37° C. on LB agar plate containing ampicillin (100 μg/mL) and chloramphenicol (25 μg/mL). A single colony was inoculated into LB medium (2 mL) containing the above antibiotics and cultured at 37° C. for 8 h. The seed culture (1 mL) was transferred into LB medium (100 mL) in a 500 mL flask and grown at 30° C. until OD600 reached 0.6. Then, the temperature was reduced to 18° C. After 1 h adaptation, isopropyl-D-1-thiogalactopyranoside (IPTG) (0.1 mM) was added to induce the N-terminal hexa-histidine-tagged proteins ("hexa-histidine" disclosed as SEQ ID NO: 90). After further growth for 16 h, the cells were harvested by centrifugation (5000 rpm, 10 min, 4° C.), washed twice with cold water and stored at −80° C. until used.

Purification of Recombinant VALA, LOC100003999 AND ZGC:113054

Cell pellets from a 400 ml culture of *E. coli* BL21 GOLD (DE3) pLysS containing pRSETB-valA, pRSETB-LOC100003999 or pRSETB-zgc:113054 plasmids was resuspended in 20 ml of B buffer (40 mM Tris-HCl, 300 mM NaCl, 10 mM imidazole, pH 7.5). Cells were disrupted by sonication for 1 min (4 times, 2 min interval) at 13 watts on ice (Probe sonicator, Misonix). Twenty mL of lysate was divided into 2 mL tubes and centrifuged (14,500 rpm, 20 min, 4° C.). Soluble fractions were collected and transferred into a 50 ml tube. Ni-NTA (QIAGEN) resin (5 mL) was applied into 10 ml volume empty column and the Ni-NTA resin was equilibrated with B buffer (50 ml, 10 CV). About 20 mL of supernatant from cell lysate was applied to the column (flow rate; 0.8 ml/min). The column was then washed with 100 ml (20 CV) of W buffer (40 mM Tris-HCl, 300 mM NaCl, 20 mM imidazole, pH 7.5) at 0.8 ml/min. The hexa-histidine-tagged proteins ("hexa-histidine" disclosed as SEQ ID NO: 90) were eluted by imidazole addition using a gradient mixer containing 100 ml of W buffer and 100 ml of E buffer (40 mM Tris-HCl, 300 mM NaCl, 300 mM imidazole, pH 7.5). The fractions (150 drops or about 5 mL) were collected and checked by SDS-PAGE (Coomassie Blue staining). Fractions containing pure proteins were combined (25 ml) and dialyzed against 2 L of D buffer (10 mM Tris-HCl, pH 7.5) 3 times (every 3 h). Dialyzed protein solution was concentrated by ultrafiltration (MWCO 10 K) to 200 μM and flash frozen in liquid N2 prior to storage at −80° C.

LOC100003999 assay condition

Each reaction mixture (25 μL) contained Tris-HCl buffer (20 mM, pH 7.5), NAD$^+$ (1 mM), CoCl$_2$ or ZnSO$_4$ (0.1 mM), sedoheptulose 7-phosphate (4 mM), and enzymes (0.12 mM). The mixture was incubated at 30° C. for 2 h. ValA (instead of LOC100003999) was used as a positive control. No enzyme (buffer only) was used as a negative control.

Coupled LOC100003999 AND ZGC:113054 assay condition

Each reaction mixture (50 μL) contained potassium phosphate buffer (10 mM, pH 7.4), NAD$^+$ (2 mM), CoCl$_2$ (0.2 mM), sedoheptulose 7-phosphate (4 mM), and LOC100003999 cell-free extracts (20 μL) was incubated at 30° C. After 6 h, S-adenosylmethionine (5 mM) and zgc: 113054 cell-free extracts (30 μL) were added. The mixture was incubated at 30° C. for another 6 h. ValA was used (instead of LOC100003999) as a positive control. Extract of *E. coli* harboring pRSET B empty vector was used as a negative control.

ZGC:113054 Assay Using [6,6-$^2$H$_2$]-EEV as Substrate

A reaction mixture (25 μL) containing potassium phosphate buffer (10 mM, pH 7.4), NAD$^+$ (2 mM), CoCl$_2$ (0.2 mM), S-adenosylmethionine (5 mM), [6,6-$^2$H$_2$]-EEV (4 mM), and zgc:113054 cell-free extract (20 μL) was incubated at 30° C. for 2 h. An extract of *E. coli* harboring pRSET B empty vector was used as a negative control.

TLC Analysis of EEV AND Gadusol

Analytical thin-layer chromatography (TLC) was performed using silica gel plates (60 Å) with a fluorescent indicator (254 nm), which were visualized with a UV lamp and ceric ammonium molybdate (CAM) or 5% FeCl$_3$ in MeOH—H$_2$O (1:1) solutions.

GC-MS Analysis of EEV

The enzymatic reaction mixtures were lyophilized and the products were extracted with MeOH. The MeOH extract was then dried and Tri-Sil HTP (Thermo Scientific) (100 μL) was added and left stand for 20 min. The solvent was removed in a flow of Argon gas and the silylated products were extracted with hexanes (100 μL) and injected into the GC-MS (Hewlett Packard 5890 SERIES II Gas chromatograph).

Enzymatic Synthesis, Purification, and Analysis of Gadusol

Fifty eppendorf tubes containing reaction mixtures (100 μL each), which consist of potassium phosphate buffer (10 mM, pH 7.4), SH7P (5 mM), NAD$^+$ (2 mM), CoCl$_2$ (0.2 mM), and LOC100003999 cell-free extract (40 μL) was incubated at 30° C. After 6 h, S-adenosylmethionine (5.5 mM) and zgc:113054 cell-free extracts (30 μL) were added. The reaction mixtures were incubated at 30° C. for another 6 h. The reaction mixtures were quenched with 2 volumes of MeOH, held at −20° C. for 20 min, then centrifuged at 14,500 rpm for 20 min. The supernatants were pooled and dried under vacuum. The residual water was frozen and lyophilized. The crude sample was dissolved in water (1 mL) and subjected to Sephadex LH-20 column chromatography using phosphate buffer (2.5 mM, pH 7) as an eluent. Fractions containing the product as judged by MS were combined and lyophilized. Furthermore, the product was purified by HPLC [Shimadzu LC-20AD, C18 column (YMC), 250×10 mm, 4 µm, flow rate 1 mL/min]. Solvent system: MeOH—phosphate buffer (5 mM, pH 7), gradient 1%-100% of MeOH (0-40 min). Peak at 12.74 min was collected and dried to give gadusol (0.4 mg). 1H NMR (700 MHz, $D_2O$, cryo-probe): δ 4.10 (s, 1H, H-4), 3.71 (d, J=12 Hz, H-7a), 3.56 (d, J=12 Hz, H-7β), 3.49 (s, 3H, $OCH_3$), 2.68 (d, J=17 Hz, H-6a), 2.38 (d, J=17 Hz, H-6β). HR-MS (ESI-TOF) m/z 205.0709 (calculated for $C_8H_{13}O_6$ [M+H]+: 205.0707).

Zebrafish Lines and Embryos

Adult wild type 5D zebrafish were housed at the Sinnhuber Aquatic Research Laboratory on a recirculating system maintained at 28±1° C. with a 14 h light/10 h dark schedule. Embryos were collected from group spawns of adult zebrafish as described previously and all experiments were conducted with fertilized embryos. Embryos were staged and collected by hand for all experiments. Embryos were reared in media consisting of 15 mM NaCl, 0.5 mM KCl, 1 mM $MgSO_4$, 0.15 mM $KH_2PO_4$, 0.05 mM $Na_2HPO_4$ and 0.7 mM $NaHCO_3$.

Polymerase Chain Reaction (PCR)

All PCR reactions were performed according to manufacturer's specifications.

Cycling conditions: 96° C. for 3 minutes, 95° C. for 1 minute, 65° C. for 1 minute, and 72° C. for 1 minute per kB DNA; 35 cycles were used followed by 10 minutes at 72° C. All PCR products were characterized on an agarose gel. If needed, the PCR product was excised from the gel and purified using the E.Z.N.A. Gel Extraction Kit from Omega Bio-tek.

Quantitative PCR of Zebrafish Samples qPCR was performed on an Applied Biosystems StepOnePlus machine. The super mix PerfeCTa® SYBR® Green FastMix®, ROX™ by Quanta biosciences was used. cDNA (100 ng) from time points at 6, 12, 24, 48, 72, 96, and 120 hpf were used. Super mix (18 µL) were added to bring the final volume to 20 µL. PCR conditions suggested by the supplier were used. For total RNA isolation, 30 embryos were homogenized in RNAzol (Molecular Research Center); RNA was purified according to the manufacturer's protocol. RNA was quantified by A260/280 ratios measured using a SynergyMx microplate reader (Biotek) and analyzed with the Gen5 Take3 module. One µg of RNA was used for cDNA synthesis. Superscript III First-Strand Synthesis (Invitrogen) and oligo d(T) primers were used to synthesize cDNA from the total RNA.

Isolation of Gadusol from Zebrafish

Embryos were collected and euthanized at 72 hpf by induced hypoxia through rapid chilling on ice for 30 minutes. Embryo media was removed until about 5 mL were left and frozen at −80° C. Embryos were lyophilized overnight. The freeze-dried embryos were then ground with a pestle and mortar under liquid nitrogen. The powder was collected and placed in a pre-weighed glass vial. The mortar was washed with MeOH—$H_2O$ (80:20) and the solvent was added to the powder. The solvent was evaporated and powder was weighed. The embryo powder was extracted twice with MeOH—$H_2O$ (80:20). The two extracts were combined, dried, and weighed. The extract was suspended in MeOH—$H_2O$ (80:20) (1 mL) and extracted twice with hexane. The aqueous layer was recovered, dried, and weighed. The extract was suspended in MeOH for analysis by mass spectrometry. The extract was dissolved in phosphate buffer pH 7.0 for identification by HPLC (Shimadzu SPD-20A system, YMC ODS-A column (4.6 id×250 mm), MeOH—5 mM phosphate buffer (1% MeOH for 20 min followed by a gradient from 1 to 95% MeOH in 20 min), flow rate 0.3 mL/min, 296 nm. The isolated gadusol was analyzed by MS (ThermoFinnigan LCQ Advantage system) and NMR [in $D_2O$; Bruker Unity 300 (300.15 MHz) spectrometer].

Yeast Strains, Media and Growth Conditions

The yeast strains used are listed in Table 8. For cases in which the yeast strain was newly generated to carry out the work described in this disclosure, the source is listed an "N/A".

TABLE 8

Yeast strains used

| Strain | Genotype | Source |
| --- | --- | --- |
| S288c | MATα SUC gal mal mel flo1 flo8-1 hap bio1 bio6 | ATCC 204508, Manassas, VA |
| BY4742 tal1Δ | MATα his3Δ1 leu2Δ0 lys2Δ0 ura3Δ0 tal1Δ::KanMX4 | Thermo Fisher Scientific Inc., Waltham, MA |
| BY4742 tal1Δtrp1Δ | MATα his3Δ1 leu2Δ0 lys2Δ0 ura3Δ0 tal1Δ trp1Δ::URA3 | N/A |
| BY4742 tal1Δtrp1Δrad1Δ | MATα his3Δ1 leu2Δ0 lys2Δ0 ura3Δ0 tal1Δ trp1Δ::URA3 rad1Δ::LEU2 | N/A |
| BY4742 tal1Δtrp1Δ/ pXP416 pXP420 | MATα his3Δ1 leu2Δ0 lys2Δ0 ura3Δ0 tal1Δ trp1Δ::URA3/ pXP416 pXP420 | N/A |
| BY4742 tal1Δ trp1Δ/pXP416-MTOX pXP420-EEVS | MATα his3Δ1 leu2Δ0 lys2Δ0 ura3Δ0 tal1Δ trp1Δ::URA3/pXP416-EEVS pXP420-MTOX | N/A |
| BY4742 tal1Δtrp1Δrad1Δ/ pXP416 pXP420 | MATα his3Δ1 leu2Δ0 lys2Δ0 ura3Δ0 tal1Δ trp1Δ::URA3 rad1Δ::LEU2/pXP416 pXP420 | N/A |

The TRP1 gene was replaced in BY4742 tal1Δ::KanMX4 with a wild-type URA3 allele from S288c by standard methods. The deletion was confirmed by PCR using primer pairs TRP1DisUP/TRP1DisLO and URA3DisUP/TRP1DisLO. The BY4742 tal1Δ::KanMX4 trp1Δ::URA3 strain was then co-transformed5 with pXP416 and pXP420 to generate an empty vector control strain, and with pXP420-EEVS and pXP416-MT-Ox to generate a gadusol-producing strain. The EEVS and MT-Ox genes introduced into yeast were codon-optimized for expression in *E. coli*.

The RAD1 gene was replaced in BY4742 tal1Δ::KanMX4 trp1Δ::URA3 with a wild-type LEU2 allele from S288c by standard methods. The deletion was confirmed by PCR using primer pairs RAD1UP/RAD1LO. The resultant BY4742 tal1Δ::KanMX4 trp1Δ::URA3 rad1Δ::LEU2 strain was then co-transformed with pXP416 and pXP420. Cells were pre-grown in YEPD (1% yeast extract, 2% peptone, and 2% glucose) for transformations, and in YNB (Bacto yeast nitrogen base without amino acids)+2% glucose supplemented with 30 μg/ml leucine and 30 μg/ml lysine to select for transformants and to produce gadusol. Liquid media were sterilized by filtration using a 0.45 μm filter and agar-based media were sterilized by autoclaving. Liquid cultures were grown at 30° C. for 48 h and 200 rpm; plates were incubated at 30° C.

Yeast Overexpression Plasmid Construction

Plasmids are listed in Table 11. Primers used for PCR are listed in Table 12. PCR amplicons with SpeI and XhoI terminal restriction sites were generated for the EEVS gene and MT-Ox gene using pRSETB-EEVS and pRSETB-MTOx as templates, respectively. The EEVS and MT-Ox amplicons were then digested with SpeI and XhoI and ligated into SpeI- and XhoI-digested pXP420 and pXP416, respectively, and introduced into competent E. coli (Top 10; Invitrogen) by transformation. E. coli transformants were selected on LB plates supplemented with ampicillin (100 μg/ml). Transformants were then screened by digesting plasmid DNA with SpeI and XhoI restriction enzymes and analyzing fragments by agarose gel electrophoresis.

Identification of Gadusol Production in S. cerevisiae

S. cerevisiae cell pellets from 5 mL cultures were extracted with MeOH and the supernatant was extracted with nBuOH. Extracts were concentrated and analyzed by HPLC (Shimadzu SPD-20A system, YMC ODS-A column (4.6 id×250 mm), MeOH—5 mM phosphate buffer (1% MeOH for 20 min followed by a gradient from 1 to 95% MeOH in 20 min), flow rate 0.3 mL/min, 296 nm.

Irradiation Protocol

A rad1Δ mutant (MATα his3Δ1 leu2Δ0 lys2Δ0 trp1Δ::URA3 ura3Δ0 rad1Δ::LEU2 tal1Δ::KanMX4/pXP416, pXP420) or wild-type RAD1 strain (S288c, MATα SUC2 gal2 malt mel flo1 flo8-1 hap1 ho bio1 bio6) was grown at 30° C. and 200 rpm in YNB+2% glucose+30 μg/mL leu+30 mg/mL lys. Cells were harvested after 24 h by centrifugation, washed twice in the 9-fold concentrated supernatant of either the gadusol-producing strain BY4742 tal1Δ trp1 A/pXP416-MTOx, pXP420-EEVS or of the control strain BY4742 tal1Δ trp1Δ/pXP416, pXP420, and suspended in the respective supernatants at $10^7$ cells/mL. Cells (375 μL) were irradiated with UVB (302 nm) at the indicated doses in wells of a 24-well microtiter plate shaken at 900 rpm. Three μL aliquots of cells were then spotted onto a YEPD plate which was incubated 24 h at 30° C. prior to being photographed. The supernatants of the gadusol-producing and control strains were obtained by centrifugation following 5 days of growth in YNB+2% glucose+30 mg/mL leucine+30 mg/mL lysine at 30° C. and 200 rpm. Supernatants were freeze-dried, dissolved in a volume of distilled water 1/10 of the initial culture volume, and stored at 4° C. until use. Just prior to suspension of cells, the concentrated supernatant was adjusted to 50 mM phosphate, pH 7.0 resulting in a final 9-fold concentrate.

Sugar Phosphate Cyclases

Table 9 lists Sugar Phosphate Cyclases, including EEVS proteins.

TABLE 9

Sugar Phosphate Cyclases

| Family | Protein | Accession No. | Organism |
| --- | --- | --- | --- |
| Bacterial EEVS | AcbC | AEV84575.1 | Actinoplanes sp. SE50/110 |
| | EEVS | WP_005152974.1 | Amycolatopsis azurea DSM 43854 |
| | EEVS | WP_020673085 | Amycolatopsis nigrescens |
| | EEVS | WP_006999601.1 | Candidatus Burkholderia kirkii |
| | EEVS | CCD36718 | Candidatus Burkholderia kirkii UZHbot1 |
| | Cja_3250 | ACE84801.1 | Cellvibrio japonicus Ueda107 |
| | CLD_3207 | ACA45465.1 | Clostridium botulinum B1 str. Okra |
| | Cpap_0968 | EGD46588.1 | Clostridium papyrosolvens DSM 2782 |
| | D187_002969 | EPX59479.1 | Cystobacter fuscus DSM 2262 |
| | AcbC | CBL44970.1 | gamma proteobacterium HdN1 |
| | EEVS | WP_007320675.1 | Gordania araii NBRC 100433 |
| | MESS4_430082 | CCV12436.1 | Mesorhizobium sp. STM 4661 |
| | EEVS | WP_020731587.1 | Mycobacterium marinum |
| | AroB_1 | ACC39042.1 | Mycobacterium marinum M |
| | EEVS | WP_020727917.1 | Mycobacterium marinum MB2 |
| | MMEU_4200 | EPQ72818.1 | Mycobacterium marinum str. Europe |
| | EEVS | WP_019045670 | Nocardia asteroides |
| | NS07 CONTIG 00143-0015 | GAF31941.1 | Nocardia seriolae N-2927 |
| | PrlA | ABL74380.1 | Nonomuraea spiralis |
| | EEVS | WP_023102627.1 | Pseudomonas aeruginosa |
| | PflA506_4591 | AFJ55097.1 | Pseudomonas fluorescens A506 |
| | EEVS | WP_019817993.1 | Pseudomonas sp. CFT9 |
| | UUC_15323 | EIL99898.1 | Rhodanobacter denitrificans |
| | EEVS | WP_008438647.1 | Rhodanobacter thiooxydans |
| | UUA_15933 | EIL97123.1 | Rhodanobacter thiooxydans LCS2 |
| | EEVS | WP_020113256.1 | Rhodococcus 114MFTsu3.1 |
| | EEVS | WP_019667777.1 | Rhodococcus 29MFTsu3.1 |
| | EEVS | WP_021331771 | Rhodococcus erythropolis |
| | O5Y_25890 | AGT94995.1 | Rhodococcus erythropolis CCM2595 |
| | N601_00990 | EQM35423.1 | Rhodococcus erythropolis DN1 |
| | RER_54360 | BAH36144.1 | Rhodococcus erythropolis PR4 |
| | EEVS | WP_021345782 | Rhodococcus sp. P27 |
| | EEVS | YP_007039401.1 | Saccharothrix espanaensis DSM 44229 |
| | Staur_1386 | ADO69190.1 | Stigmatella aurantiaca DW4/3-1 |

TABLE 9-continued

Sugar Phosphate Cyclases

| Family | Protein | Accession No. | Organism |
|---|---|---|---|
| | EEVS | WP_010359798.1 | *Streptomyces acidiscabies* 84-104 |
| | SalQ | ABV57470.1 | *Streptomyces albus* |
| | EEVS | WP_006603459.1 | *Streptomyces auratus* |
| | SU9_09459 | EJJ07289.1 | *Streptomyces auratus* AGR0001 |
| | EEVS | WP_005477027.1 | *Streptomyces bottropensis* ATCC 25435 |
| | EEVS | WP_010034415.1 | *Streptomyces chartreusis* |
| | SSCG_00526 | EDY47498.1 | *Streptomyces clavuligerus* ATCC 27064 |
| | SMCF_997 | EHN79464.1 | *Streptomyces coelicoflavus* ZG0656 |
| | GacC | CAL64849.1 | *Streptomyces glaucescens* GLA.O |
| | VldA | ABC67267.1 | *Streptomyces hygroscopicus* subsp. *limoneus* |
| | EEVS | AAZ91667.1 | *Streptomyces hygroscopicus* subsp. *yingchengensis* |
| | EEVS | WP_009076280.1 | *Streptomyces* sp. AA4 |
| | EEVS | WP_018894817.1 | *Streptomyces* sp. CNY228 |
| | EEVS | AGZ94062.1 | *Streptomyces* sp. MMG1533 |
| | EEVS | WP_010644135.1 | *Streptomyces* sp. S4 |
| | EEVS | WP_007385523.1 | *Streptomyces sviceus* |
| | SSEG_08792 | EDY55324.2 | *Streptomyces sviceus* ATCC 29083 |
| | AciPR4_1231 | ADV82056 | *Terriglobus saanensis* SP1PR4 |
| Animal EEVS | LOC101799904 | XP_005011275.1 | *Anas platyrhynchos* |
| | LOC100554413 | XP_003217873.2 | *Anolis carolinensis* |
| | LOC103021483 | XP_007241787.1 | *Astyanax mexicanus* |
| | UY3_08628 | EMP34204.1 | *Chelonia mydas* |
| | LOC101935311 | XP_005282175.1 | *Chrysemys picta bellii* |
| | A306_01079 | EMC89871.1 | *Columba livia* |
| | LOC100003999 | XP_001343422.1 | *Danio rerio* |
| | DLA_It04010 | CBN80976.1 | *Dicentrarchus labrax* |
| | LOC102050204 | XP_005432702.1 | *Falco cherrug* |
| | LOC101920037 | XP_005230087.1 | *Falco peregrinus* |
| | LOC101811082 | XP_005053423.1 | *Ficedula albicollis* |
| | ENSGMOG00000007414.1 | ENSGMOG00000007414 | *Gadus morhua* |
| | LOC427594 | XP_425167.2 | *Gallus gallus* |
| | ENSGACG00000011871 | ENSGACP00000015700 | *Gasterosteus aculeatus* |
| | LOC102035384 | XP_005420282.1 | *Geospiza fortis* |
| | LOC102309185 | XP_005947633.1 | *Haplochromis burtoni* |
| | LOC102684922 | XP_006630707.1 | *Lepisosteus oculatus* |
| | LOC101474077 | XP_004567457.1 | *Maylandia zebra* |
| | LOC100539368 | XP_003210235.1 | *Meleagris gallopavo* |
| | LOC101868264 | XP_005149534.1 | *Melopsittacus undulatus* |
| | LOC102782305 | XP_006784803.1 | *Neolamprologus brichardi* |
| | GSONMT00065608001 | CDQ61676.1 | *Oncorhynchus mykiss* |
| | LOC100690451 | XP_003442831.1 | *Oreochromis niloticus* |
| | LOC101163482 | XP_004068647.1 | *Oryzias latipes* |
| | LOC102457108 | XP_006120116.1 | *Pelodiscus sinensis* |
| | LOC103129387 | XP_007540516.1 | *Poecilia formosa* |
| | LOC102106679 | XP_005522289.1 | *Pseudopodoces humilis* |
| | LOC102205679 | XP_005726665.1 | *Pundamilia nyererei* |
| | LOC100223651 | XP_002188776.1 | *Taeniopygia guttata* |
| | LOC100492806 | XP_002940521.1 | *Xenopus* (*Silurana*) *tropicalis* |
| | LOC102222998 | XP_005815791.1 | *Xiphophorus maculatus* |
| Stramenopile EEVS | CYME_CMP183C | XP_005537849 | *Cyanidioschyzon merolae* strain 10D |
| | Esi_0086_0074 | CBJ27882 | *Ectocarpus siliculosus* |
| | THAOC_37874 | EJK43661 | *Thalassiosira oceanica* |
| | PHATRDRAFT87_72 | XP_002177202 | *Phaeodactylum tricornutum* |
| | HAPSDRAFT_21539 | XP002287560 | *Thalassiosira pseudonana* |
| | CHC_T00009338001 | XP005713525 | *Chondrus crispus* |
| | Gasu_30570 | XP_005706140 | *Galdieria sulphuraria* |
| EVS | Amir_2000 | ACU35948.1 | *Actinosynnema mirum* DSM 43827 |
| | Staur_3140 | ADO70932.1 | *Stigmatella aurantiaca* DW4/3-1 |
| | DHQS | WP_002620792.1 | *Cystobacter fuscus* |
| | DHQS | WP_02806414.1 | *Solirubrobacter soli* |
| | DHQS | WP_015800837.1 | *Actinosynnema mirum* |
| | DHQS | WP_014443330.1 | *Actinoplanes missouriensis* |
| | DHQS | WP_019435820 | *Streptomyces* sp. AA0539 |
| | KF386858.1 | AGZ15443 | *Streptomyces* sp. MK498-98F14 |
| | DHQS | WP_02550010 | *Streptomyces scabrisporus* |
| Archaeal DHQS | WP_013776014 | WP_013776014.1 | *Acidianus hospitalis* |
| | WP_015231795 | WP_015231795.1 | *Caldisphaera lagunensis* |
| | DHQS | WP_012185860.1 | *Caldivirga maquilingensis* |
| | CM19_06260 | EZQ06961.1 | *Candidatus acidianus copahuensis* |
| | DHQS | WP_011998054.1 | *Ignicoccus hospitalis* |
| | DHQS | WP_013304180.1 | *Ignisphaera aggregans* |
| | DHQS | WP_013737014.1 | *Metallosphaera cuprina* |
| | DHQS | WP_012021802.1 | *Metallosphaera sedula* |
| | DHQS | WP_009075654.1 | *Metallosphaera yellowstonensis* |
| | DHQS | WP_011901560.1 | *Pyrobaculum arsenaticum* |

TABLE 9-continued

Sugar Phosphate Cyclases

| Family | Protein | Accession No. | Organism |
|---|---|---|---|
| | DHQS | WP_011849579.1 | *Pyrobaculum calidifontis* |
| | ASUL_02139 | EWG07805.1 | *Sulfolobales archaeon* AZ1 |
| | DHQS | WP_012711772.1 | *Sulfolobus islandicus* |
| | DHQS | WP_009990597.1 | *Sulfolobus solfataricus* |
| | DHQS | WP_010980356.1 | *Sulfolobus tokodaii* |
| | DHQS | WP_014127627.1 | *Thermoproteus tenax* |
| | DHQS | WP_013335353.1 | *Vulcanisaeta distributa* |
| | DHQS | WP_013604797.1 | *Vulcanisaeta moutnovskia* |
| Bacterial | DHQS | WP_018087611 | *Streptomyces* sp. FxanaC1 |
| and fungal | Amir_5253**** | ACU39074.1 | *Actinosynnema mirum* DSM 43827 |
| DHQS | Ava_4386 | ABA23984.1 | *Anabaena variabilis* ATCC 29413 |
| | An1DQS | 1DQS_A | *Aspergillus nidulans* |
| | BsDHQS | AAA20860.1 | *Bacillus subtilis* |
| | DHQS | CDH47441 | *Candidatus Contendobacter odensis* |
| | EcDHQS | AAA58186.1 | *Escherichia coli* str. K-12 |
| | Hp3CLH | 3CLH_A | *Helicobacter pylori* |
| | DHQS | WP_020681978 | *Marinobacterium rhizophilum* |
| | DHQS | WP_009725480 | *Methylophaga lonarensis* |
| | DHQS | WP_008290485 | *Methylophaga thiooxydans* |
| | MtDHQS | CAB06200.1 | *Mycobacterium tuberculosis* H37Rv |
| | Npun_5729 | ACC84029.1 | *Nostoc punctiforme* PCC 73102 (ATCC 29133) |
| | DHQS | WP_023970131 | *Pseudomonas chlororaphis* |
| | DHQS | WP_015479237 | *Pseudomonas denitrificans* |
| | PKB_5345 | CDF86657 | *Pseudomonas knackmussii* B13 |
| | DHQS | WP_016712492 | *Pseudomonas monteilii* |
| | AU05_25215 | EZH77367 | *Pseudomonas pseudoalcaligenes* AD6 |
| | Sa1XAG | 1XAG_A | *Staphylococcus aureus* |
| | Staur_4041**** | ADO71827.1 | *Stigmatella aurantiaca* DW4/3-1 |
| | P354_02295 | EXU86293 | *Streptomyces albulus* |
| | DHQS | WP_0066074643 | *Streptomyces auratus* |
| | DHQS | WP_014157372 | *Streptomyces flavogriseus* |
| | DHQS | WP_004942390 | *Streptomyces mobaraensis* |
| | DHQS | WP_005319844 | *Streptomyces pristinaespiralis* ATCC_25486 |
| | DHQS | WP_019884829 | *Streptomyces purpureus* |
| | DHQS | WP_003984693 | *Streptomyces rimosus* |
| | DHQS | WP_026249565 | *Streptomyces* sp. ATexAB-D23 |
| | DHQS | WP_026359219 | *Streptomyces* sp. DvalAA-83 |
| | DHQS | WP_016467710 | *Streptomyces* sp. HPH0547 |
| | DHQS | WP_018087611 | *Streptomyces* sp. FxanaC1 |
| | DHQS | WP_018539828 | *Streptomyces* sp. MspMP-M5 |
| | DHQS | WP_014044818 | *Streptomyces* sp. SirexAA-E |
| | Tt1UJN | 1UJN_A | *Thermus thermophilus* HB8 |
| | DHQS | WP_012639562 | *Thioalkalivibrio sulfidophilus* |
| | DHQS | WP_026186219 | *Thioalkalivibrio thiocyanodenitrzficans* |
| Plant and | DHQS | 3ZOK_A | *Actinidia chinensis* |
| algal | AT5G66120 | NP_56029 | *Arabidopsis thaliana* |
| DHQS | LOC100834750 | XP_003578532 | *Brachypodium distachyon* |
| | CARUB_v10026413mg | XP_006280477 | *Capsella rubella* |
| | CISIN_1g013271mg | KDO171284 | *Citrus sinensis* |
| | COCSUDRAFT_35806 | XP_005649993 | *Coccomyxa subellipsoidea* C-169 |
| | EUGRSUZ_J02467 | KCW53191 | *Eucalyptus grandis* |
| | EUTSA_v10004219mg | XP_00639797 | *Eutrema salsugineum* |
| | L484_026650 | EXC35326 | *Morus notabilis* |
| | LOC102714768 | XP_006661484 | *Oryza brachyantha* |
| | Os09g0539100 | NP_001063802 | *Oryza sativa Japonica* |
| | EF678425.1 | ABR18182 | *Picea sitchensis* |
| | LOC101782627 | XP_004957492 | *Setaria italica* |
| | LOC 102598775 | XP_006340763 | *Solanum tuberosum* |
| | BT043106.1 | ACF88111 | *Zea mays* |
| DDGS | PDE_00008 | WP_018334610.1 | *Actinomycetospora chiangmaiensis* |
| | Amir_4259 | ACU38114.1 | *Actinosynnema mirum* DSM 43827 |
| | Ava_3858 | ABA23463.1 | *Anabaena variabilis* ATCC 29413 |
| | DDGS | BAO51913.1 | *Aphanothece halophytica* |
| | ACLA_055850 | EAW13537.1 | *Aspergillus clavatus* NRRL 1 |
| | ANIA_06403.2 | CBF69538.1 | *Aspergillus nidulans* FGSC A4 |
| | BAUCODRAFT_80557 | EMC91075.1 | *Baudoinia compniacensis* UAMH 10762 |
| | BBA_00472 | EJP70842.1 | *Beauveria bassiana* ARSEF 2860 |
| | COCC4DRAFT_167163 | ENI05767.1 | *Bipolaris maydis* ATCC 48331 |
| | COCHEDRAFT_1194844 | EMD91152.1 | *Bipolaris maydis* C5 |
| | COCMIDRAFT_8170 | EUC42205.1 | *Bipolaris oryzae* ATCC 44560 |
| | COCSADRAFT_38955 | EMD62170.1 | *Bipolaris sorokiniana* ND90Pr |
| | COCV1DRAFT_15921 | EUN27206.1 | *Bipolaris victoriae* FI3 |
| | BC1G_03060 | XP_001558028.1 | *Botryotinia fuckeliana* B05.10 |
| | BcDW1_9470 | EMR81915.1 | *Botryotinia fuckeliana* BcDW1 |
| | BofuT4_P133930.1 | CCD53839.1 | *Botryotinia fuckeliana* T4 |
| | DDGS | AFZ02505 | *Calothrix* sp. PCC 6303 |

TABLE 9-continued

Sugar Phosphate Cyclases

| Family | Protein | Accession No. | Organism |
|---|---|---|---|
| | DDGS | WP_019490229.1 | *Calothrix* sp. PCC 7103 |
| | DDGS 1 | WP_019490229.1 | *Calothrix* sp. PCC 7103 |
| | DDGS 2 | WP_019491244.1 | *Calothrix* sp. PCC 7103 |
| | A1O1_01840 | EXJ93448.1 | *Capronia coronata* CBS 617.96 |
| | DDGS | WP_015160001.1 | *Chamaesiphon minutus* |
| | Cha6605_2820 | AFY93856.1 | *Chamaesiphon minutus* PCC 6605 |
| | DDGS | WP_016876765.1 | *Chlorogloeopsis* |
| | Chro_0778 | AFY86324.1 | *Chroococcidiopsis thermalis* PCC 7203 |
| | G647_03988 | ETI24619.1 | *Cladophialophora carrionii* CBS 160.54 |
| | A1O5_01012 | EXJ76504.1 | *Cladophialophora psammophila* CBS 110553 |
| | A1O7_04691 | EXJ60538.1 | *Cladophialophora yegresii* CBS 114405 |
| | CPUR_02718 | CCE29027.1 | *Claviceps purpurea* 20.1 |
| | CFIO01_11686 | EXF78170.1 | *Colletotrichum fioriniae* PJ7 |
| | CGLO_11575 | EQB49116.1 | *Colletotrichum gloeosporioides* Cg-14 |
| | CGGC5_4437 | XP_007274966.1 | *Colletotrichum gloeosporioides* Nara gc5 |
| | GLRG_05915 | EFQ30771.1 | *Colletotrichum graminicola* M1.001 |
| | Cob_10738 | ENH80676.1 | *Colletotrichum orbiculare* MAFF 240422 |
| | W97_04284 | EON65049.1 | *Coniosporium apollinis* CBS 100218 |
| | CCM_06613 | EGX90194.1 | *Cordyceps militaris* CM01 |
| | Cri9333_2379 | AFZ13246.1 | *Crinalium epipsammum* PCC 9333 |
| | DDGS | YP_002380202.1 | *Cyanothece* sp. PCC 7424 |
| | Cylst_1339 | AFZ23628.1 | *Cylindrospermum stagnale* PCC 7417 |
| | HMPREF1541_10826 | ETN43961.1 | *Cyphellophora europaea* CBS 101466 |
| | DACRYDRAFT_108509 | EJU01177.1 | *Dacryopinax* sp. DJM-731 SSI |
| | DDGS | WP_015229181 | *Dactylococcopsis sauna* |
| | DOTSEDRAFT_74971 | EME40344.1 | *Dothistroma septosporum* NZE10 |
| | EPUS_06787 | ERF68371.1 | *Endocarpon pusillum* Z07020 |
| | HMPREF1120_03313 | EHY55163.1 | *Exophiala dermatitidis* NIH/UT8656 |
| | DDGS | WP_016867391.1 | *Fischerella muscicola* |
| | FFUJ_02302 | CCT65366.1 | *Fusarium fujikuroi* IMI 58289 |
| | FGSG_07578.1 | ESU13851.1 | *Fusarium graminearum* PH-1 |
| | FOPG_14554 | EXL69517.1 | *Fusarium oxysporum* f. sp. *conglutinans* race 2 54008 |
| | FOC1_g10007978 | ENH63840.1 | *Fusarium oxysporum* f. sp. *cubense* race 1 |
| | FOC4_g10004309 | EMT72824.1 | *Fusarium oxysporum* f. sp. *cubense* race 4 |
| | FOWG_01820 | EWZ97333.1 | *Fusarium oxysporum* f. sp. *lycopersici* MN25 |
| | FOMG_05909 | EXK43277.1 | *Fusarium oxysporum* f. sp. *melonis* 26406 |
| | FOVG_03599 | EXA51127.1 | *Fusarium oxysporum* f. sp. *pisi* HDV247 |
| | FOCG_01565 | EXL63199.1 | *Fusarium oxysporum* f. sp. *radicis-lycopersici* 26381 |
| | FOQG_12197 | EXK83496.1 | *Fusarium oxysporum* f. sp. *raphani* 54005 |
| | FOTG_14331 | EXM17492.1 | *Fusarium oxysporum* f. sp. *vasinfectum* 25433 |
| | FOZG_06058 | EWZ45846.1 | *Fusarium oxysporum* Fo47 |
| | FOXB_11899 | EGU77611.1 | *Fusarium oxysporum* Fo5176 |
| | FOYG_03768 | EWY99830.1 | *Fusarium oxysporum* FOSC 3-a |
| | FPSE_08031 | EKJ71763.1 | *Fusarium pseudograminearum* CS3096 |
| | FVEG_12691 | EWG54478.1 | *Fusarium verticillioides* 7600 |
| | M7I_2461 | EHL01576.1 | *Glarea lozoyensis* 74030 |
| | GLAREA_08216 | EPE24364.1 | *Glarea lozoyensis* ATCC 20868 |
| | GLOTRDRAFT_39501 | XP_007864776.1 | *Gloeophyllum trabeum* ATCC 11539 |
| | DDGS | WP_023072000 | *Leptolyngbya* sp. Heron Island J |
| | DDGS | WP_006516570 | *Leptolyngbya* sp. PCC 7375 |
| | LEMA_P063060.1 | CBX90180.1 | *Leptosphaeria maculans* JN3 |
| | DDGS | WP_023068561.1 | *Lyngbya aestuarii* |
| | L8106_16364 | EAW37588.1 | *Lyngbya* sp. PCC 8106 |
| | MPH_07850 | EKG14950.1 | *Macrophomina phaseolina* MS6 |
| | MGG_00016 | EHA49547.1 | *Magnaporthe oryzae* 70-15 |
| | OOU_Y34scaffold01060g1 | ELQ32736.1 | *Magnaporthe oryzae* Y34 |
| | MBM_04236 | EKD17735.1 | *Marssonina brunnea* f. sp. *multigermtubi* MB_m1 |
| | MELLADRAFT_46120 | XP_007418557.1 | *Melampsora larici-populina* 98AG31 |
| | MAC_00588 | EFY93350.1 | *Metarhizium acridum* CQMa 102 |
| | FVEG_12691 | WP_017655453.1 | *Microchaete* sp. PCC 7126 |
| | DDGS | WP_002794106.1 | *Microcystis aeruginosa* |
| | C789_465 | ELS49746.1 | *Microcystis aeruginosa* DIANCHI905 |
| | IPF_3031 | CAO90104.1 | *Microcystis aeruginosa* PCC 7806 |
| | acbC | CCI02410.1 | *Microcystis aeruginosa* PCC 9443 |
| | acbC | CCH99802.1 | *Microcystis aeruginosa* PCC 9717 |
| | acbC | CCI19960.1 | *Microcystis aeruginosa* PCC 9807 |
| | MICAG_2780005 | CCI25385.1 | *Microcystis aeruginosa* PCC 9808 |
| | E5Q_03910 | GAA97234.1 | *Mixia osmundae* IAM 14324 |
| | DDGS | WP_014813469.1 | *Mycobacterium chubuense* |
| | DDGS | AFM14977.1 | *Mycobacterium chubuense* NBB4 |
| | NECHADRAFT_48307 | XP_003043726.1 | *Nectria haematococca* mpVI 77-13-4 |
| | UCRNP2_5834 | EOD47414.1 | *Neofusicoccum parvum* UCRNP2 |
| | N9414_08103 | EAW44170.1 | *Nodularia spumigena* CCY9414 |
| | DDGS | WP_006197691.1 | *Nodularia spumigena* |

TABLE 9-continued

Sugar Phosphate Cyclases

| Family | Protein | Accession No. | Organism |
|---|---|---|---|
| | Npun_R5600 | ACC83905.1 | *Nostoc punctiforme* PCC 73102 |
| | Nos7524_3370 | AFY49165.1 | *Nostoc* sp. PCC 7524 |
| | OCS_06803 | EQK97484.1 | *Ophiocordyceps sinensis* CO18 |
| | Osc7112_3782 | AFZ08125.1 | *Oscillatoria nigro-viridis* PCC 7112 |
| | PDE_00008 | EPS25077.1 | *Penicillium oxalicum* 114-2 |
| | PFICI_12759 | ETS75815.1 | *Pestalotiopsis fici* W106-1 |
| | DDGS | WP_019504239 | *Pleurocapsa* sp. PCC 7319 |
| | MYCFIDRAFT_33875 | XP007931255.1 | *Pseudocercospora fijiensis* CIRAD86 |
| | DDGS | WP_010243321.1 | *Pseudonocardia* sp. P1 |
| | PaG_02576 | ETS62823 | *Pseudozyma aphidis* DSM 70725 |
| | PFL1_03740 | EPQ28940.1 | *Pseudozyma flocculosa* PF-1 |
| | PTT_06860 | EFQ95201.1 | *Pyrenophora teres* f. *teres* 0-1 |
| | PTRG_02787 | EDU45310.1 | *Pyrenophora tritici-repentis* Pt-1C-BFP |
| | PCON_03344 | CCX16645 | *Pyronema omphalodes* CBS 100304 |
| | DDGS | WP_020111281.1 | *Rhodococcus* sp. 114MFTsu3.1 |
| | DDGS | WP_019663384.1 | *Rhodococcus* sp. 29MFTsu3.1 |
| | DDGS | WP_008719709.1 | *Rhodococcus* sp. AW25M09 |
| | DDGS | YP_007053294.1 | *Rivularia* sp. PCC 7116 |
| | DDGS | WP_022606420 | *Rubidibacter lacunae* |
| | SBOR_4234 | ESZ95378.1 | *Sclerotinia borealis* F-4157 |
| | SS1G_08336 | EDN92473.1 | *Sclerotinia sclerotiorum* 1980 UF-70 |
| | DDGS | WP_017743132.1 | *Scytonema hofmanni* |
| | SETTUDRAFT_100700 | EOA81028.1 | *Setosphaeria turcica* Et28A |
| | SEPMUDRAFT_151827 | EMF08929.1 | *Sphaerulina musiva* SO2202 |
| | sr12669 | CBQ71813.1 | *Sporisorium reilianum* SRZ2 |
| | DDGS | YP_007132170.1 | *Stanieria cyanosphaera* PCC 7437 |
| | STEHIDRAFT_146260 | EIM88185.1 | *Stereum hirsutum* FP-91666 SS1 |
| | UCRPA7_3232 | EOO01292.1 | *Togninia minima* UCRPA7 |
| | UHOR_02376 | CCF53523.1 | *Ustilago hordei* |
| | VDBG_08620 | EEY22510.1 | *Verticillium alfalfae* VaMs.102 |
| | VDAG_08289 | EGY17125.1 | *Verticillium dahliae* VdLs.17 |
| | DDGS | WP_006509782 | *Xenococcus* sp. PCC 7305 |
| | MYCGRDRAFT_76728 | XP_003848682.1 | *Zymoseptoria tritici* IPO323 |
| DHQS-like | Npun_5231*** | ACC83559.1 | *Nostoc punctiforme* PCC 73102 (ATCC 29133) |
| | Npun_1267*** | ACC79988.1 | *Nostoc punctiforme* PCC 73102 (ATCC 29133) |
| aDHQS | Amir_3296***** | ACU37202.1 | *Actinosynnema mirum* DSM 43827 |
| | Asm47 | AAC14006.1 | *Actinosynnema pretiosum* subsp. *auranticum* |
| | GdmO | AAO06928.1 | *Streptomyces hygroscopicus* |
| | MitP | AAD28456.1 | *Streptomyces lavendulae* |
| | RifG | AAC01717.1 | *Amycolatopsis mediterranei* S699 |
| DOIS | TbmA | CAE22471.1 | *Streptoalloteichus tenebrarius* |
| | KanA | BAD20759.1 | *Streptomyces kanamyceticus* |
| | RbmA | CAG34037.1 | *Streptomyces ribosidificus* |
| | NemA | BAD95820.1 | *Streptomyces fradiae* |
| | GntB | AAR98548.1 | *Micromonospora echinospora* |
| | BtrC | BAA83344.1 | *Bacillus circulans* |

MT-OX Proteins

Table 10 provides examples of MT-Ox proteins and lists a gene symbol, accession number, and source organism for each protein.

TABLE 3

MT-Ox proteins

| Family | Gene symbol | Accession No. | Organism |
|---|---|---|---|
| MT-Ox | LOC102560707 | XP_006270840.1 | *Alligator mississippiensis* |
| | LOC101799721 | XP_005011274 | *Anas platyrhynchos* |
| | LOC100554218 | XP_008103594 | *Anolis carolinensis* |
| | LOC103021811 | XP_007241788.1 2 | *Astyanax mexicanus* |
| | LOC101935589 | XP_005282176.1 | *Chrysemys picta bellii* |
| | LOC102090989 | XP_005514955.1 | *Columba livia* |
| | zgc:113054 | NP_001013468.1 | *Danio rerio* |
| | DLA_It04000 | CBN80975.1 | *Dicentrarchus labrax* |
| | LOC102050380 | XP_005432703 | *Falco cherrug* |
| | LOC101919857 | XP_005230086 | *Falco peregrinus* |
| | LOC101811274 | XP_005053424 | *Ficedula albicollis* |
| | ENSGMOG00000007404 | ENSGMOP00000007916 | *Gadus morhua* |
| | LOC427595 | XP_425168.3 | *Gallus gallus* |
| | ENSGACG00000011845 | ENSGACP00000015696 | *Gasterosteus aculeatus* |
| | LOC102035220 | XP_005420281.1 | *Geospiza fortis* |

TABLE 3-continued

MT-Ox proteins

| Family | Gene symbol | Accession No. | Organism |
|---|---|---|---|
| | LOC102308870 | XP_005943916 | *Haplochromis burtoni* |
| | LOC102695979 | XP_006630675.1 | *Lepisosteus oculatus* |
| | LOC101474366 | XP_004567458.1 | *Maylandia zebra* |
| | LOC100539521 | XP_003210236 | *Meleagris gallopavo* |
| | LOC101868426 | XP_005149535 | *Melopsittacus undulatus* |
| | LOC102782600 | XP_006784804.1 | *Neolamprologus brichardi* |
| | GSONMT00065609001 | CDQ61677.1 | *Oncorhynchus mykiss* |
| | LOC100697673 | XP_005450406.1 | *Oreochromis niloticus* |
| | LOC101163242 | XP_004068646.1 | *Oryzias latipes* |
| | LOC102457357 | XP_006120117.1 | *Pelodiscus sinensis* |
| | LOC103129385 | XP_007540514.1 | *Poecilia formosa* |
| | LOC102106494 | XP_005522288 | *Pseudopodoces humilis* |
| | LOC102205957 | XP_005726666.1 | *Pundamilia nyererei* |
| | LOC100220728 | XP_002188799 | *Taeniopygia guttata* |
| | MGC147226 | NP_001072630 | *Xenopus (Silttrana) tropicalis* |
| | LOC102222561 | XP_005814009.1 | *Xiphophorus maculatus* |
| | LOC102064640 | XP_005491459 | *Zonotrichia albicollis* |

Primers

Table 11 lists primers useful in making or using the various embodiments of the disclosure disclosed herein. The function for each primer is also disclosed.

TABLE 11

Primers used

| SEQ ID NO. | Primer | Sequence (5'→3')$^a$ | Function |
|---|---|---|---|
| 23 | TRP1DisURA3UP | TATAGGAAGCATTTAATAGAACAGCATCGTA ATATATGTGTACTTTGAGTTATGACGCCGAA ATTGAGGCTACTGCGCC | TRP1 deletion |
| 24 | TRP1DisURA3LO | CCTGTGAACATTCTCTTCAACAAGTTTGATT CCATTGCGGTGAAATGGTAAAAGTCAACCGG CAGCGTTTTGTTCTTGGA | TRP1 deletion |
| 25 | RAD1DisLEU2UP | GAGCATTTGCTAAATGTGTAAAAATAATATT GCACTATCCTGTTGAAAATATCTTTCCAGCA CTGTTCACGTCGCACCTA | RAD1 deletion |
| 26 | RAD1DisLEU2LO | CTATAGTTAATCGCATTTTATACTGATGTTT TAACAGGGTTCGTTAAATTAAACAATATTGC TGCATTAATGAATCGGCCA | RAD1 deletion |
| 27 | TRP1DisUP | CTCACCCGCACGGCAGAGAC | Confirmation |
| 28 | TRP1DisLO | TGCCGGCGGTTGTTTGCAAG | Confirmation |
| 29 | URA3DisUp | GTGGCTGTGGTTTCAGGGTCCA | Confirmation |
| 30 | RAD1UP | CCTGAAGTGTTCTCTGTTTGCC | Confirmation |
| 31 | RAD1LO | GCTCAGATTCCACCAAATACGG | Confirmation |
| 32 | DEEVSUP | AGATCC<u>ACTAGT</u>ATGGAACGTCCGGGCGAAAC | EEVS cloning |
| 33 | DEEVSLO | TAGCCA<u>CTCGAG</u>TCACTGCGGTGAGCCGGT | EEVS cloning |
| 34 | MTOXUP | AGATCC<u>ACTAGT</u>ATGCAAACGGCAAAAGTCTC | MTOX cloning |
| 35 | MTOXLO | TAGCCA<u>CTCGAG</u>TCACCACAGAGACTGACCG | MTOX cloning |
| 36 | DEEVS-q-F | CCATCTGTTCACCGGGACAA | qPCR EEVS |
| 37 | DEEVS-q-R | TGCTGGGGTCAAGAAGGTTT | qPCR EEVS |

TABLE 11-continued

Primers used

| SEQ ID NO. | Primer | Sequence (5'→3')[a] | Function |
|---|---|---|---|
| 38 | MTOX-q-F | AGTAGAGCAGGTCATCATCCCT | qPCR MTOX |
| 39 | MTOX-q-R | CTATGATGGCGACTTTGGCTC | qPCR MTOX |

[a]SpeI and XhoI restriction sites are underlined

Plasmids

Table 12 lists plasmids that may be useful in making or using the various embodiments of the disclosure disclosed herein. The source of each plasmid is listed. For cases in which the plasmid was newly generated to carry out the work described in this disclosure, the source is listed an "N/A."

TABLE 12

| Plasmids used | | |
|---|---|---|
| Plasmid | Insert | Source/reference |
| pUC57-EEVS | EEVS (EcoRV) | GeneScript USA Inc. |
| pUC57-MTOX | MT-Ox (EcoRV ) | GeneScript USA Inc. |
| pRSETB-EEVS | EEVS (Bg/II) | This study |
| pRSETB-MTOX | MT-Ox (Bg/II) | This study |
| pXP416 | none | Fang et al. 2011[1]; Addgene, Cambridge, MA |
| pXP416-MTOX | MT-OX (SpeI/XhoI) | This study |
| pXP20 | none | Fang et al. 2011[1]; Addgene, Cambridge, MA |
| pXP420-EEVS | EEVS (SpeI/XhoI) | This study |

Sequences

DNA sequences of EEVS and MT-Ox genes, and vectors pUC57-Kan, pRSET-B, pXP416, pXP420.

*Danio rerio* EEVS cDNA (accession no. LOC100003999)

SEQ ID NO. 1 atggagcgacccggggagacatttacagtgagttcacctgaagaagttcg cctgccatctgttcaccgggacaactcgacgatggagaaccacaacaagc aggagactgtcttcagcctggtgcaggtgaaggggacgtggaaacgcaaa gcagggcaaaatgccaagcaaggaatgaaaggacgagtttcaccggctaa aatttacgaaagcagctcctctagtggcactacctggacagtggtcaccc ccatcaccttcacatatactgttactcagaccaaaaaccttcttgacccc agcaatgacactctgcttttgggccacatcattgacactcagcagcttga ggccgtacggtccaacaccaaacccttaaaacgcttcatagtcatggatg aggtagtgtacaatatctatggttctcaggtcaccgaatacctcgaggcc agaaatgtcctgtaccggatcctgcccctgcccacgacagaggagaacaa gtccatggatatggccctgaagatcctggaggaggtgcaccagtttggga tcgaccggcgcacggagcccattatcgccattggagggggcgtctgcctg gatatcgtgggtctggcggcgtcgctttacagaagacgcactccatacat -continued tcgtgttcccaccactctactgtcctacattgacgccagtgtcggagcca aaacaggtgtcaatttcgccaattgtaagaacaaacttggcacctacatc gcacctgttgctgcattcctggaccggtcgtttatacagagcattcctcg caggcacatagctaacggtcttgcagaaatgctgaagatggctcttatga agcacagagggctgtttgaactcctggaagtgcacggacagttcctctta gactccaagttccagtctgcttcagtcctagagaacgaccgcattgaccc tgcttctgtctctacacgtgtcgcaatagaaaccatgctagaagagttag ccccaaacctgtgggaggatgatcttgacagactggttgactttgggcac ctcataagccctcaactagagatgaaagtcctaccagctcttctccacgg tgaagcggtgaatattgatatggcctacatggtgtatgtgtcttgtgaaa ttggattgctgacagaggaggagaaattcaggatcatctgttgcatgatg ggactggagctgccggtgtggcatcaagacttcacatttgctttggtgca gaagtctctgtgtgacagacttcagcattctggaggcctcgtgagaatgc ctttaccaacaggcctcggaagagcagaaatcttcaatgacactgatgaa ggctctctgtttagggcgtacgagaagtggtgtgatgagctcagcactgg gtcacctcaa EEVS optimized for *E. coli*

SEQ ID NO. 2

ATGGAACGTCCGGGCGAAACCTTTACCGTCAGCTCCCCGGAAGAAGTGCG

TCTGCCGTCTGTTCACCGCGATAACTCAACGATGGAAAACCATAATAAAC

AGGAAACGGTGTTTTCTCTGGTTCAAGTCAAGGGTACCTGGAAGCGTAAG

GCGGGCCAGAACGCCAAACAGGGTATGAAGGGCCGCGTTAGTCCGGCCAA

AATTTATGAAAGCTCTAGTTCCTCAGGTACCACGTGGACGGTGGTTACCC

CGATCACCTTTACGTACACCGTGACGCAGACCAAAAACCTGCTGGACCCG

TCGAACGACACGCTGCTGCTGGGCCATATTATCGATACCCAGCAACTGGA

AGCTGTCCGCAGCAATACGAAACCGCTGAAGCGTTTCATTGTGATGGACG

AAGTCGTGTATAATATCTACGGTTCCCAAGTCACCGAATATCTGGAAGCG

CGCAACGTGCTGTACCGTATTCTGCCGCTGCCGACCACGGAAGAAAATAA

ATCAATGGATATGGCTCTGAAGATTCTGGAAGAAGTGCACCAGTTTGGTA

TCGACCGTCGCACCGAACCGATTATCGCGATTGGCGGTGGCGTTTGCCTG

GATATCGTCGGTCTGGCAGCCTCTCTGTATCGTCGCCGTACCCCGTACAT

TCGTGTGCCGACCACGCTGCTGTCTTATATCGACGCAAGTGTGGGTGCTA

AAACGGGCGTTAACTTTGCTAATTGTAAAAACAAGCTGGGTACCTACATT

GCGCCGGTTGCAGCTTTTCTGGATCGTTCGTTCATTCAGAGCATCCCGCG

CCGTCACATCGCAAACGGTCTGGCCGAAATGCTGAAAATGGCCCTGATGA

AGCATCGCGGTCTGTTCGAACTGCTGGAAGTTCACGGCCAGTTTCTGCTG

GATAGTAAATTCCAATCGGCAAGCGTCCTGGAAAACGATCGCATTGACCC

GGCCTCTGTCAGTACGCGTGTGGCAATCGAAACCATGCTGGAAGAACTGG

CCCCGAATCTGTGGGAAGATGACCTGGATCGTCTGGTGGACTTTGGTCAT

CTGATTTCGCCGCAGCTGGAAATGAAAGTTCTGCCGGCACTGCTGCACGG

CGAAGCTGTCAACATTGATATGGCGTATATGGTGTACGTTTCATGCGAAA

TCGGTCTGCTGACCGAAGAAGAAAAATTCCGCATTATCTGCTGTATGATG

GGCCTGGAACTGCCGGTGTGGCATCAGGATTTTACCTTCGCACTGGTTCA

AAAGTCCCTGTGTGACCGCCTGCAGCACTCAGGTGGCCTGGTTCGTATGC

CGCTGCCGACGGGTCTGGGTCGTGCAGAAATTTTTAATGATACCGACGAA

GGTAGCCTGTTCCGCGCGTATGAAAAATGGTGCGATGAACTGTCCACCGG

CTCACCGCAG

*S. cerevisiae*-optimized EEVS sequence #1

SEQ ID NO. 3

ATGGAAAGACCAGGTGAAACTTTCACCGTCTCCTCTCCAGAAGAAGTCAG

ATTACCTTCCGTCCACAGAGATAATTCTACCATGGAAAACCACAACAAGC

AAGAAACCGTTTTCTCTTTGGTCCAAGTTAAGGGTACTTGGAAGCGTAAG

GCTGGTCAAAACGCTAAGCAAGGTATGAAAGGTAGAGTTTCTCCAGCTAA

GATTTATGAATCCTCTTCCTCTTCCGGTACCACCTGGACCGTCGTTACTC

CAATTACCTTCACTTACACTGTTACCCAAACCAAAAACTTGTTGGATCCA

TCTAACGACACTTTGTTGTTGGGTCATATCATCGATACCCAACAATTGGA

GGCTGTTAGATCTAACACCAAGCCTTTGAAGCGTTTCATTGTCATGGATG

AAGTCGTTTATAACATTTACGGTTCTCAAGTTACCGAATACTTGGAAGCT

AGAAACGTTTTGTACAGAATCTTGCCATTGCCAACTACTGAAGAGAATAA

GTCTATGGATATGGCCTTGAAGATCTTGGAAGAGGTCCACCAATTCGGTA

TTGATAGAAGAACCGAACCTATTATTGCTATTGGTGGTGGTGTTTGTTTG

GACATCGTTGGTTTGGCTGCCTCCTTGTACCGTAGAAGAACTCCATATAT

TAGAGTTCCAACTACCTTATTGTCTTATATTGATGCTTCCGTCGGTGCTA

AGACCGGTGTCAACTTTGCTAACTGTAAGAATAAGTTAGGTACTTATATC

GCTCCAGTCGCCGCCTTCTTAGATAGATCTTTTATCCAATCCATCCCACG

TAGACACATTGCTAATGGTTTAGCTGAAATGTTGAAGATGGCTTTGATGA

AGCATAGAGGTTTATTTGAATTATTGGAAGTCCACGGTCAATTTTTGTTG

GATTCTAAGTTTCAATCCGCTTCTGTTTTAGAAAACGATAGAATTGATCC

AGCTTCTGTCTCCACCAGAGTTGCCATTGAAACTATGTTAGAAGAATTAG

CTCCAAACTTGTGGGAGGACGACTTGGACCGTTTAGTCGACTTCGGTCAC

TTAATTTCTCCACAATTGGAAATGAAGGTTTTACCAGCCTTATTGCATGG

TGAAGCTGTTAACATTGATATGGCTTACATGGTTTACGTCTCTTGTGAAA

TCGGTTTATTGACTGAAGAAGAAAAGTTTCGTATCATCTGTTGTATGATG

GGTTTGGAATTGCCTGTCTGGCATCAAGATTTCACTTTCGCTTTGGTTCA

AAAGTCCTTATGTGATAGATTGCAACACTCTGGTGGTTTGGTCAGAATGC

CATTGCCTACCGGTTTGGGTAGAGCCGAAATTTTCAACGATACTGACGAG

GGTTCTTTATTCAGAGCTTATGAAAATGGTGTGACGAATTGTCTACTGG

TTCTCCACAA

*S. cerevisiae*-optimized EEVS sequence #2

SEQ ID NO. 4

ATGGAAAGACCAGGTGAAACTTTTACTGTTTCCTCCCCAGAAGAAGTCAG

ATTGCCTTCTGTTCACAGAGACAATTCTACTATGGAAAACCATAACAAGC

AAGAAACTGTCTTCTCTTTAGTTCAAGTCAAGGGTACCTGGAAAAGAAAG

GCTGGTCAAAACGCTAAACAAGGTATGAAGGGTAGAGTCTCCCCAGCTAA

GATTTATGAATCCTCTTCCTCTTCTGGTACTACCTGGACCGTCGTCACTC

CTATTACCTTCACCTACACTGTCACCCAAACTAAGAATTTGTTAGATCCA

TCTAACGATACCTTGTTGTTAGGTCACATTATTGATACTCAACAATTAGA

AGCTGTCCGTTCCAACACTAAGCCATTGAAAAGATTCATCGTTATGGATG

AAGTTGTTTACAATATTTACGGTTCCCAAGTCACTGAATACTTGGAAGCT

AGAAATGTTTTGTACAGAATTTTGCCTTTGCCTACCACTGAAGAAAATAA

GTCTATGGACATGGCTTTAAAGATTTTAGAGGAAGTCCATCAATTCGGTA

TCGATAGAAGAACTGAACCAATTATTGCTATCGGTGGTGGTGTCTGTTTG

GATATCGTCGGTTTGGCTGCTTCTTTGTACAGAAGAAGAACTCCATACAT

CAGAGTCCCAACCACTTTGTTGTCTTACATCGACGCTTCCGTTGGTGCTA

AGACTGGTGTTAACTTCGCTAACTGTAAAAACAAGTTGGGTACCTACATC

GCCCCAGTCGCCGCTTTCTTGGATAGATCTTTCATCCAATCTATCCCACG

TCGTCATATTGCTAACGGTTTGGCCGAAATGTTGAAGATGGCCTTGATGA

AACATAGAGGTTTATTCGAATTGTTAGAAGTTCATGGTCAATTCTTGTTG

GATTCTAAGTTCCAATCCGCTTCCGTTTTGGAAAACGATCGTATCGATCC

AGCCTCCGTCTCTACTAGAGTCGCTATCGAAACCATGTTAGAAGAATTGG

CCCCAAACTTATGGGAAGACGACTTGGACAGATTAGTCGATTTCGGTCAT

TTGATCTCTCCACAATTGGAAATGAAGGTCTTGCCAGCCTTGTTGCACGG

TGAAGCTGTTAACATCGATATGGCTTACATGGTCTACGTTTCTTGTGAAA

TTGGTTTATTAACCGAAGAAGAAAAATTCAGAATCATTTGTTGTATGATG

GGTTTAGAATTGCCAGTCTGGCACCAAGACTTCACTTTCGCCTTGGTTCA

AAAGTCTTTGTGTGACAGATTACAACACTCTGGTGGTTTGGTCAGAATGC

CTTTGCCTACTGGTTTGGGTAGAGCTGAAATTTTCAACGATACTGACGAA

GGTTCTTTGTTCCGTGCCTATGAAAAGTGGTGTGATGAGTTGTCCACTGG

TTCTCCACAA

*S. cerevisiae*-optimized EEVS sequence #3

SEQ ID NO. 5

ATGGAACGTCCAGGTGAAACTTTTACCGTCTCTTCTCCAGAAGAAGTCAG

ATTACCATCCGTTCACAGAGACAATTCTACTATGGAAAATCACAATAAGC

AAGAAACCGTCTTTTCTTTGGTCCAAGTCAAGGGTACTTGGAAGCGTAAA

GCCGGTCAAAACGCTAAGCAAGGTATGAAGGGTCGTGTTTCTCCTGCCAA

GATTTATGAATCCTCCTCTTCCTCTGGTACTACTTGGACCGTTGTCACCC

CAATTACCTTTACCTACACTGTCACCCAAACTAAAAATTTGTTAGATCCA

TCCAATGACACCTTGTTGTTGGGTCATATTATTGACACCCAACAATTGGA

AGCCGTTAGATCTAATACTAAGCCATTGAAGAGATTCATTGTTATGGATG

AAGTCGTCTACAACATCTACGGTTCTCAAGTCACTGAATACTTGGAAGCT

AGAAACGTCTTGTACCGTATCTTGCCATTGCCAACTACTGAAGAAAACAA

ATCCATGGATATGGCCTTGAAGATTTTGGAAGAAGTCCACCAATTTGGTA

TCGATAGAAGAACCGAACCAATCATTGCCATTGGTGGTGGTGTTTGTTTA

GACATTGTTGGTTTGGCTGCCTCCTTGTATAGAAGAAGAACTCCATACAT

TAGAGTCCCAACTACCTTGTTGTCTTACATCGATGCTTCTGTTGGTGCCA

AGACTGGTGTTAACTTCGCTAACTGCAAGAACAAGTTGGGTACCTACATC

GCCCCTGTCGCCGCTTTCTTGGACAGATCCTTCATCCAATCTATCCCTAG

ACGTCATATTGCCAACGGTTTGGCTGAAATGTTGAAGATGGCTTTGATGA

AGCATAGAGGTTTGTTCGAGTTGTTAGAAGTTCACGGTCAATTCTTATTA

GATTCTAAGTTCCAATCTGCTTCTGTCTTAGAAAACGACCGTATTGACCC

AGCTTCCGTTTCTACTAGAGTTGCTATTGAAACCATGTTGGAAGAATTAG

CCCCAAACTTGTGGGAAGATGATTTGGACAGATTGGTTGACTTCGGTCAT

TTAATCTCCCCACAATTGGAAATGAAGGTTTTGCCAGCTTTATTGCATGG

TGAAGCCGTCAACATCGACATGGCTTACATGGTTTACGTCTCCTGTGAAA

TCGGTTTGTTAACCGAAGAAGAAAAATTCAGAATCATCTGCTGTATGATG

GGTTTGGAATTGCCAGTTTGGCACCAAGACTTCACTTTTGCTTTGGTTCA

AAAGTCCTTGTGTGATAGATTGCAACACTCCGGTGGTTTAGTCAGAATGC

CTTTACCAACTGGTTTAGGTCGTGCTGAAATCTTCAACGATACTGATGAA

GGTTCCTTATTCAGAGCCTATGAAAAGTGGTGTGACGAATTATCTACTGG

TTCTCCTCAA

*S. cerevisiae*-optimized EEVS sequence #4

SEQ ID NO. 6

ATGGAACGTCCAGGTGAAACTTTCACCGTCTCTTCCCCTGAAGAGGTTAG
ATTGCCTTCTGTCCACAGAGACAACTCTACCATGGAAAACCATAACAAGC
AAGAAACCGTCTTCTCCTTGGTTCAAGTCAAGGGTACTTGGAAGAGAAAG
GCTGGTCAAAATGCTAAACAAGGTATGAAGGGTCGTGTTTCCCCAGCTAA
GATTTACGAATCTTCCTCCTCTTCTGGTACTACCTGGACCGTTGTTACCC
CAATCACCTTCACCTACACTGTCACCCAAACTAAGAATTTATTGGACCCA
TCTAACGACACTTTGTTGTTGGGTCACATCATTGATACTCAACAATTGGA
AGCTGTTAGATCTAACACTAAACCATTGAAAAGATTCATTGTTATGGATG
AGGTTGTTTACAACATTTACGGTTCTCAAGTTACCGAATACTTAGAAGCC
AGAAATGTTTTGTACAGAATTTTACCTTTGCCAACCACCGAAGAAAATAA
GTCTATGGATATGGCTTTGAAAATCTTGGAAGAAGTCCATCAATTCGGTA
TCGACAGAAGAACTGAACCAATCATCGCTATTGGTGGTGGTGTTTGTTTG
GACATTGTCGGTTTGGCTGCTTCTTTGTACAGAAGAAGAACTCCATACAT
CAGAGTCCCAACCACTTTGTTGTCCTACATTGATGCTTCTGTCGGTGCTA
AGACTGGTGTTAACTTTGCTAACTGTAAGAACAAGTTAGGTACTTACATT
GCCCCTGTTGCTGCCTTCTTGGACAGATCTTTCATCCAATCTATCCCAAG

-continued

AAGACATATCGCTAACGGTTTAGCCGAAATGTTGAAAATGGCTTTAATGA
AGCACAGAGGTTTGTTTGAATTGTTGGAAGTCCACGGTCAATTTTTGTTA
GACTCTAAGTTCCAATCTGCCTCCGTTTTAGAAAACGATAGAATTGACCC
AGCTTCTGTTTCCACCCGTGTTGCTATTGAGACCATGTTGGAAGAATTGG
CCCCAAACTTGTGGGAAGACGACTTGGACCGTTTGGTCGATTTCGGTCAC
TTAATCTCCCCACAATTGGAAATGAAGGTCTTGCCAGCTTTGTTGCATGG
TGAAGCCGTTAACATTGATATGGCCTATATGGTCTACGTTTCTTGTGAAA
TCGGTTTGTTGACCGAAGAGGAAAAGTTCAGAATTATCTGTTGTATGATG
GGTTTGGAATTGCCAGTTTGGCATCAAGATTTTACCTTTGCTTTGGTTCA
AAAGTCTTTGTGTGACAGATTGCAACATTCTGGTGGTTTGGTCAGAATGC
CTTTGCCAACTGGTTTGGGTAGAGCTGAAATTTTCAACGACACTGATGAA
GGTTCTTTGTTCAGAGCCTACGAAAAATGGTGCGATGAATTGTCTACCGG
TTCCCCACAA

*S. cerevisiae*-optimized EEVS sequence #5

SEQ ID NO. 7

ATGGAAAGACCTGGTGAAACTTTTACTGTTTCTTCTCCTGAAGAAGTTAG
ATTGCCATCTGTTCATAGAGACAACTCTACCATGGAAAATCATAACAAGC
AAGAAACCGTCTTCTCTTTGGTCCAAGTCAAGGGTACCTGGAAGAGAAAG
GCTGGTCAAAACGCCAAGCAAGGTATGAAGGGTAGAGTCTCCCCAGCCAA
GATCTACGAATCCTCCTCTTCTTCCGGTACCACCTGGACTGTTGTCACCC
CAATTACTTTCACTTACACTGTCACTCAAACTAAAAACTTGTTGGACCCA
TCTAACGATACTTTGTTATTGGGTCACATTATTGACACCCAACAATTGGA
AGCTGTCAGATCTAACACCAAGCCATTAAAGAGATTCATTGTCATGGATG
AAGTTGTTTACAACATCTACGGTTCTCAAGTCACCGAATACTTGGAAGCT
AGAAATGTTTTGTATCGTATTTTGCCATTGCCAACTACCGAGGAAAACAA
GTCCATGGATATGGCCTTGAAGATTTTGGAAGAAGTCCATCAATTCGGTA
TTGATAGAAGAACTGAACCAATTATCGCCATCGGTGGTGGTGTCTGCTTG
GATATTGTTGGTTTAGCTGCTTCTTTGTATAGACGTAGAACTCCTTACAT
TAGAGTTCCAACCACTTTATTATCCTACATCGACGCCTCCGTTGGTGCCA
AAACTGGTGTTAACTTCGCTAACTGTAAGAACAAGTTGGGTACTTACATC
GCTCCAGTTGCTGCCTTCTTGGACCGTTCTTTCATTCAATCTATCCCTCG
TCGTCACATTGCCAATGGTTTAGCTGAAATGTTGAAAATGGCTTTGATGA
AACATAGAGGTTTGTTCGAATTATTGGAAGTCCACGGTCAATTTTTGTTG
GACTCTAAATTCCAATCCGCTTCTGTCTTGGAAAACGATAGAATTGACCC
AGCTTCCGTTTCTACCAGAGTCGCTATCGAAACCATGTTGGAAGAATTGG
CTCCAAACTTATGGGAAGATGATTTGGATAGATTGGTTGATTTCGGTCAC
TTGATTTCCCCACAATTGGAAATGAAGGTTTTACCAGCCTTGTTGCACGG
TGAAGCTGTTAATATTGATATGGCTTACATGGTCTATGTCTCTTGTGAAA
TCGGTTTGTTGACTGAAGAAGAAAAGTTCAGAATCATTTGTTGTATGATG
GGTTTGGAATTGCCAGTCTGGCATCAAGACTTCACTTTCGCTTTGGTTCA
AAAGTCCTTATGTGACAGATTGCAACATTCCGGTGGTTTGGTCAGAATGC
CATTGCCAACCGGTTTGGGTAGAGCTGAAATTTTCAACGACACTGACGAA

GGTTCCTTGTTCCGTGCTTACGAAAAGTGGTGCGATGAATTGTCTACCGG

TTCCCCACAA

*S. cerevisiae*-optimized EEVS sequence #6

SEQ ID NO. 8

ATGGAAAGACCAGGTGAAACTTTCACTGTTTCTTCTCCAGAAGAAGTTAG

ATTGCCATCTGTTCACAGAGACAACTCTACTATGGAAAACCACAACAAGC

AAGAAACTGTTTTCTCTTTGGTTCAAGTTAAGGGTACTTGGAAGAGAAAG

GCTGGTCAAAACGCTAAGCAAGGTATGAAGGGTAGAGTTTCTCCAGCTAA

GATCTACGAATCTTCTTCTTCTTCTGGTACTACTTGGACTGTTGTTACTC

CAATCACTTTCACTTACACTGTTACTCAAACTAAGAACTTGTTGGACCCA

TCTAACGACACTTTGTTGTTGGGTCACATCATCGACACTCAACAATTGGA

AGCTGTTAGATCTAACACTAAGCCATTGAAGAGATTCATCGTTATGGACG

AAGTTGTTTACAACATCTACGGTTCTCAAGTTACTGAATACTTGGAAGCT

AGAAACGTTTTGTACAGAATCTTGCCATTGCCAACTACTGAAGAAAACAA

GTCTATGGACATGGCTTTGAAGATCTTGGAAGAAGTTCACCAATTCGGTA

TCGACAGAAGAACTGAACCAATCATCGCTATCGGTGGTGGTGTTTGTTTG

GACATCGTTGGTTTGGCTGCTTCTTTGTACAAGAAGAACTCCATACAT

CAGAGTTCCAACTACTTTGTTGTCTTACATCGACGCTTCTGTTGGTGCTA

AGACTGGTGTTAACTTCGCTAACTGTAAGAACAAGTTGGGTACTTACATC

GCTCCAGTTGCTGCTTTCTTGGACAGATCTTTCATCCAATCTATCCCAAG

AAGACACATCGCTAACGGTTTGGCTGAAATGTTGAAGATGGCTTTGATGA

AGCACAGAGGTTTGTTCGAATTGTTGGAAGTTCACGGTCAATTCTTGTTG

GACTCTAAGTTCCAATCTGCTTCTGTTTTGGAAAACGACAGAATCGACCC

AGCTTCTGTTTCTACTAGAGTTGCTATCGAAACTATGTTGGAAGAATTGG

CTCCAAACTTGTGGGAAGACGACTTGGACAGATTGGTTGACTTCGGTCAC

TTGATCTCTCCACAATTGGAAATGAAGGTTTTGCCAGCTTTGTTGCACGG

TGAAGCTGTTAACATCGACATGGCTTACATGGTTTACGTTTCTTGTGAAA

TCGGTTTGTTGACTGAAGAAGAAAAGTTCAGAATCATCTGTTGTATGATG

GGTTTGGAATTGCCAGTTTGGCACCAAGACTTCACTTTCGCTTTGGTTCA

AAAGTCTTTGTGTGACAGATTGCAACACTCTGGTGGTTTGGTTAGAATGC

CATTGCCAACTGGTTTGGGTAGAGCTGAAATCTTCAACGACACTGACGAA

GGTTCTTTGTTCAGAGCTTACGAAAAGTGGTGTGACGAATTGTCTACTGG

TTCTCCACAA

MT-OX cDNA from *Danio rerio* (accession no.
zgc: 113054)

SEQ ID NO. 9 atgcagacagcaaaagtttcagacactcctgtggagttcatcgttgaaca cctgctgaaggcaaaagagatcgcagagaatcatgcaagtattccagtcg aacttcgggataatcttcagaaggctttggacattgctagtggactagac gaatacctttgaacaaatgagcagcaaggagagtgaaccgttgactgagtt gtataggaaatcagtttctcatgactggaataaggtgcatgcggacggaa aaaccttatttaggcttcctgttacatgcatcaccggacaggtagaaggt caagtattgaagatgctggtgcatatgagcaaagcaaagagggtcttaga gataggaatgttcacagggtatggggccttgtcaatggcggaggccttac cagaaaatggccagcttatcgcctgtgagcttgagccttacctcaaagac tttgcacagcctatatttgataaatctcctcatgggaaaaagataactgt gaagactgggcctgctatggataccctgaaggaattggctgccacaggag agcagtttgacatggtatttattgacgcggacaagcagaactacatcaac tattataagttcctcctggaccataaccttctgcgcgatcgatggtgttat atgtgtcgacaacacactgtttaaaggcagagtttacctcaaggactctg tggatgaaatgggaaaagcattgcggattttaatcagtttgtcacagct gatcctcgagtagagcaggtcatcatccctctgagagatggactcactat aatacgaagagtgccctatacacctcagccaaactcacagagtggtacag taacctatgatgaggtgtttagaggagtccaaggaaagccagttctggac aggttacgtttggatgggaaagtggcctatgtgaccggggccggtcaggg tattggcagggctttcgcacatgctctcggagaggctggagccaaagtcg ccatcatagacatggacagaggaaaggctgaggatgtggcgcatgaactg actttaaaaggcatttcaagcatggctgtagtggcagacattagcaaacc agacgacgtccagaagatgattgacgacatcgttacgaaatggggcacac ttcacattgcttgtaacaatgctggcatcaacaaaaactcagcaagtgag gagaccagtctagaagaatgggaccaaacctttaacgtgaacctcagagg cactttcatgtgctgccaggcggccggtcgtgtcatgctgaagcaaggat acggcaagataatcaacacagcttccatggccagtttaatagtgccgcat ccacagaagcagctgtcctataacacatccaaagctggagtagtgaaact cactcaaaccctgggcacagaatggattgaccgaggtgttcgagtcaatt gcatctcacctggtattgttgacacccctctcatccattcagagagtctg gagcctctagttcagcgctggctgtcagatatcccagccggacgactggc tcaagtgacagacctccaagctgcagtggtatacttggcatctgacgcct ctgactacatgacagggcataacttagtcatagagggtggtcagagtcta tgg Optimized MT-Ox for *E. coli*

SEQ ID NO. 10

ATGCAAACGGCAAAAGTCTCGGACACCCCGGTTGAATTTATTGTGGAACA

TCTGCTGAAGGCTAAGGAAATCGCTGAAAATCACGCTTCCATTCCGGTGG

AACTGCGCGATAACCTGCAGAAAGCTCTGGATATCGCGAGCGGCCTGGAC

GAATATCTGGAACAAATGAGCTCTAAAGAATCTGAACCGCTGACGGAACT

GTACCGCAAGTCAGTCTCGCATGATTGGAATAAAGTGCACGCGGACGGCA

AGACCCTGTTTCGTCTGCCGGTGACCTGCATTACGGGCCAGGTCGAAGGT

CAAGTGCTGAAAATGCTGGTTCACATGAGTAAAGCGAAGCGTGTCCTGGA

AATTGGCATGTTTACCGGCTATGGTGCCCTGTCCATGGCAGAAGCTCTGC

CGGAAAACGGTCAGCTGATCGCTTGTGAACTGGAACCGTACCTGAAAGAT

TTTGCACAACCGATTTTCGACAAGAGTCCGCATGGCAAAAAGATCACCGT

GAAAACGGGTCCGGCAATGGATACCCTGAAGGAACTGGCGGCCACGGGCG

AACAGTTTGACATGGTTTTCATTGATGCGGACAAGCAAAACTACATCAAC

-continued

TACTACAAGTTCCTGCTGGATCACAACCTGCTGCGTATTGATGGCGTCAT
CTGCGTGGACAATACGCTGTTCAAAGGTCGCGTGTACCTGAAGGATAGCG
TTGACGAAATGGGTAAAGCCCTGCGTGATTTTAACCAGTTCGTGACCGCA
GACCCGCGTGTTGAACAAGTCATTATCCCGCTGCGCGATGGCCTGACCAT
TATCCGTCGCGTCCCGTATACGCCGCAGCCGAATAGCCAATCTGGTACCG
TGACGTACGATGAAGTTTTTCGCGGCGTCCAGGGTAAACCGGTTCTGGAT
CGTCTGCGCCTGGACGGCAAAGTGGCTTATGTTACCGGTGCCGGTCAGGG
TATTGGTCGTGCATTCGCCCATGCACTGGGCGAAGCTGGTGCGAAAGTTG
CCATTATCGATATGGACCGTGGCAAGGCCGAAGATGTCGCACACGAACTG
ACCCTGAAAGGTATTAGTTCCATGGCCGTGGTTGCAGATATCAGCAAACC
GGATGACGTGCAGAAGATGATTGATGACATCGTTACCAAATGGGGCACGC
TGCATATTGCTTGCAACAATGCGGGTATCAACAAAAATAGTGCGTCCGAA
GAAACCTCTCTGGAAGAATGGGATCAGACGTTTAACGTCAATCTGCGTGG
CACCTTCATGTGCTGTCAGGCAGCTGGTCGCGTTATGCTGAAACAAGGCT
ATGGCAAGATTATCAACACCGCTAGCATGGCGTCTCTGATTGTGCCGCAC
CCGCAGAAACAACTGTCATACAATACGTCGAAAGCCGGCGTCGTGAAGCT
GACCCAGACGCTGGGCACCGAATGGATCGATCGTGGTGTGCGCGTTAACT
GTATTTCACCGGGTATCGTGGATACCCCGCTGATTCATTCAGAATCGCTG
GAACCGCTGGTTCAGCGTTGGCTGTCGGATATCCCGGCAGGTCGTCTGGC
ACAGGTGACGGACCTGCAAGCGGCCGTTGTCTATCTGGCCAGTGATGCAT
CCGACTACATGACCGGTCACAATCTGGTTATTGAAGGCGGTCAGTCTCTG
TGG

*S. cerevisiae*-optimized MT-Ox sequence #1

SEQ ID NO. 11

ATGCAAACCGCTAAAGTTTCTGATACTCCAGTCGAATTCATCGTTGAACA
CTTGTTGAAAGCTAAAGAAATTGCTGAAAACCACGCCTCCATCCCAGTTG
AATTGCGTGACAACTTGCAAAAGGCTTTGGACATTGCTTCTGGTTTGGAC
GAATACTTAGAACAAATGTCTTCCAAGGAGTCTGAACCTTTGACCGAATT
ATACAGAAAATCCGTCTCCCATGACTGGAACAAGGTTCATGCTGACGGTA
AAACTTTGTTCAGATTGCCAGTTACTTGTATTACTGGTCAAGTTGAAGGT
CAAGTCTTGAAGATGTTGGTTCACATGTCTAAGGCTAAGAGAGTTTTGGA
AATTGGTATGTTCACCGGTTACGGTGCCTTATCCATGGCTGAAGCCTTGC
CAGAGAACGGTCAATTAATTGCCTGTGAATTGGAGCCATATTTGAAGGAC
TTTGCTCAACCAATTTTCGACAAGTCTCCACACGGTAAAAAAATTACTGT
TAAGACCGGTCCAGCTATGGACACTTTAAAGGAATTGGCCGCTACTGGTG
AACAATTCGACATGGTTTTCATTGATGCCGACAAGCAAAACTACATCAAC
TACTACAAGTTCTTGTTGGATCACAACTTATTGAGAATCGATGGTGTTAT

CTGTGTCGATAACACCTTGTTCAAGGGTAGAGTTTACTTGAAAGACTCTG

TCGATGAGATGGGTAAGGCTTTGAGAGATTTCAACCAATTCGTTACTGCT
GATCCACGTGTCGAACAAGTCATTATCCCATTGAGAGACGGTTTGACTAT
CATTAGACGTGTTCCATACACCCCACAACCAAACTCTCAATCTGGTACTG
TCACCTACGATGAAGTTTTCAGAGGTGTTCAAGGTAAGCCTGTTTTGGAC
AGATTGCGTTTAGATGGTAAGGTTGCTTACGTTACTGGTGCTGGTCAAGG
TATTGGTCGTGCTTTCGCTCACGCCTTGGGTGAAGCCGGTGCCAAAGTCG
CTATTATCGATATGGACAGAGGTAAGGCCGAAGACGTTGCTCACGAATTG
ACCTTGAAAGGTATCTCCTCCATGGCTGTCGTCGCCGATATCTCCAAGCC
AGATGACGTTCAAAAGATGATTGACGATATTGTTACTAAGTGGGGTACCT
TGCATATCGCTTGTAATAACGCTGGTATCAACAAGAACTCTGCTTCCGAA
GAAACCTCTTTGGAAGAATGGGATCAAACTTTCAACGTCAATTTGAGAGG
TACTTTCATGTGTTGTCAAGCTGCCGGTAGAGTTATGTTGAAACAAGGTT
ACGGTAAGATTATTAATACCGCTTCTATGGCTTCCTTGATTGTCCCACAT
CCACAAAAACAATTGTCTTATAATACTTCCAAGGCTGGTGTTGTTAAGTT
GACTCAAACCTTAGGTACTGAATGGATCGACAGAGGTGTTAGAGTCAACT

GTATCTCTCCAGGTATTGTCGATACCCCATTGATCCACTCTGAATCTTTA

GAACCATTGGTCCAAAGATGGTTATCTGACATCCCAGCCGGTAGATTGGC
TCAAGTTACTGATTTGCAAGCTGCTGTCGTCTACTTGGCTTCTGATGCTT
CTGACTACATGACCGGTCACAACTTAGTCATCGAAGGTGGTCAATCTTTG
TGG

*S. cerevisiae*-optimized MT-Ox sequence #2

SEQ ID NO. 12

ATGCAAACCGCTAAGGTTTCCGACACTCCAGTTGAATTTATCGTCGAACA

CTTATTGAAAGCTAAGGAAATTGCCGAAAACCATGCCTCCATTCCAGTCG

AATTGCGTGACAACTTGCAAAAGGCTTTGGACATTGCTTCTGGTTTGGAC

GAATACTTGGAGCAAATGTCCTCTAAGGAATCTGAACCATTGACCGAATT

GTATCGTAAATCCGTCTCCCATGATTGGAATAAGGTTCACGCCGACGGTA

AGACTTTGTTTAGATTGCCAGTCACTTGTATCACCGGTCAAGTTGAAGGT

CAAGTTTTAAAGATGTTGGTTCACATGTCCAAGGCTAAGAGAGTCTTGGA

AATTGGTATGTTCACTGGTTATGGTGCCTTATCCATGGCCGAAGCTTTGC

CAGAAAACGGTCAATTGATTGCTTGCGAATTGGAACCATATTTGAAGGAT

TTCGCTCAACCAATTTTCGATAAATCTCCACACGGTAAGAAAATTACTGT

CAAGACTGGTCCTGCTATGGACACTTTAAAAGAATTGGCCGCTACTGGTG

AGCAATTCGACATGGTTTTCATCGATGCCGATAAACAAAACTATATTAAC

TACTATAAATTCTTGTTGGACCACAACTTGTTGAGAATTGATGGTGTCAT

CTGTGTCGATAACACCTTGTTCAAGGGTAGAGTCTACTTAAAGGACTCTG

TCGATGAAATGGGTAAGGCTTTAAGAGACTTCAACCAATTCGTTACCGCT

GATCCAAGAGTTGAACAAGTCATTATTCCATTGAGAGATGGTTTGACTAT

TATTCGTAGAGTTCCTTACACTCCACAACCAAACTCTCAATCTGGTACCG

TCACCTACGATGAAGTTTTCAGAGGTGTTCAAGGTAAACCAGTCTTGGAT

AGATTGAGATTAGATGGTAAGGTTGCCTACGTTACCGGTGCTGGTCAAGG

TATCGGTAGAGCTTTCGCCCACGCTTTGGGTGAAGCTGGTGCCAAGGTCG

CTATCATCGATATGGATAGAGGTAAGGCCGAAGATGTTGCCCACGAATTG

ACCTTAAAAGGTATCTCCTCCATGGCTGTCGTCGCTGATATCTCTAAACC

TGACGATGTTCAAAAAATGATTGACGACATCGTCACCAAGTGGGGTACTT

-continued

TGCATATTGCTTGTAATAACGCTGGTATTAACAAGAACTCTGCTTCTGAA
GAAACTTCTTTGGAAGAATGGGATCAAACTTTCAACGTTAACTTGAGAGG
TACTTTCATGTGTTGTCAAGCTGCCGGTAGAGTCATGTTGAAGCAAGGTT
ACGGTAAGATTATCAACACTGCCTCCATGGCCTCCTTGATTGTTCCACAT
CCACAAAAACAATTGTCTTACAACACCTCCAAGGCCGGTGTTGTCAAGTT
GACCCAAACCTTGGGTACTGAGTGGATTGATAGAGGTGTCAGAGTCAACT
GTATCTCTCCAGGTATTGTTGATACTCCTTTGATTCACTCCGAGTCCTTG
GAACCATTGGTTCAAAGATGGTTATCCGACATCCCAGCTGGTAGATTGGC
TCAAGTTACCGATTTGCAAGCTGCTGTTGTTTACTTGGCCTCCGATGCCT
CCGATTACATGACTGGTCATAACTTGGTCATTGAAGGTGGTCAATCCTTG
TGG

*S. cerevisiae*-optimized MT-Ox sequence #3
SEQ ID NO. 13
ATGCAAACTGCCAAGGTCTCCGACACCCCAGTCGAATTCATTGTTGAACA
CTTGTTGAAGGCTAAAGAAATCGCTGAAAATCACGCTTCTATTCCTGTTG
AATTAAGAGACAACTTGCAAAAAGCCTTGGACATTGCTTCTGGTTTAGAC
GAATACTTGGAACAAATGTCTTCTAAAGAATCCGAGCCATTGACTGAATT
GTACAGAAAGTCTGTCTCCCACGACTGGAACAAGGTTCACGCTGACGGTA
AGACCTTGTTCCGTTTACCTGTTACCTGTATCACCGGTCAAGTCGAAGGT
CAAGTTTTGAAAATGTTGGTTCATATGTCCAAGGCTAAGAGAGTCTTGGA
GATCGGTATGTTTACCGGTTACGGTGCCTTGTCTATGGCCGAAGCCTTGC

CAGAAAACGGTCAATTGATCGCTTGTGAATTGGAACCATATTTGAAGGAC

TTCGCTCAACCTATCTTCGACAAGTCCCCACACGGTAAGAAGATCACCGT
CAAGACCGGTCCAGCCATGGATACTTTGAAAGAATTGGCCGCTACTGGTG
AACAATTCGATATGGTTTTCATCGATGCTGATAAACAAAACTATATCAAT
TACTACAAGTTCTTGTTGGATCACAACTTGTTAAGAATCGATGGTGTTAT
CTGTGTTGATAACACCTTGTTCAAGGGTAGAGTTTACTTGAAGGACTCTG
TCGACGAAATGGGTAAAGCTTTGAGAGACTTTAACCAATTCGTTACCGCT

GACCCAAGAGTTGAACAAGTTATCATTCCATTAAGAGATGGTTTGACCAT

TATTCGTAGAGTTCCATATACTCCTCAACCAAACTCTCAATCTGGTACTG
TCACTTACGACGAAGTCTTCAGAGGTGTTCAAGGTAAGCCTGTCTTGGAC
CGTTTACGTTTGGATGGTAAGGTCGCTTACGTCACCGGTGCTGGTCAAGG
TATTGGTAGAGCTTTCGCTCACGCTTTGGGTGAAGCTGGTGCCAAGGTCG
CTATTATCGACATGGATAGAGGTAAGGCTGAAGATGTCGCTCATGAATTG
ACTTTGAAGGGTATCTCTTCCATGGCTGTTGTTGCTGATATTTCTAAGCC
AGATGACGTTCAAAAAATGATCGATGACATCGTTACTAAGTGGGGTACTT
TGCACATCGCCTGTAATAACGCTGGTATTAATAAAAACTCCGCTTCTGAA
GAGACTTCTTTGGAAGAATGGGATCAAACCTTCAACGTTAACTTAAGAGG
TACTTTCATGTGTTGTCAAGCTGCTGGTAGAGTCATGTTGAAGCAAGGTT
ACGGTAAGATTATTAACACCGCTTCCATGGCTTCTTTGATTGTTCCACAC
CCACAAAAACAATTGTCCTACAACACCTCCAAAGCTGGTGTCGTTAAATT

GACCCAAACTTTGGGTACTGAATGGATTGATAGAGGTGTCCGTGTTAACT

-continued

GTATTTCTCCAGGTATCGTCGACACCCCTTTGATTCATTCTGAGTCCTTG

GAACCATTGGTCCAAAGATGGTTATCCGACATTCCAGCCGGTAGATTGGC
TCAAGTCACCGACTTGCAAGCCGCCGTCGTCTACTTGGCTTCCGACGCTT
CCGACTACATGACTGGTCATAATTTGGTCATTGAAGGTGGTCAATCTTTA
TGG

*S. cerevisiae*-optimized MT-Ox sequence #4

SEQ ID NO. 14

ATGCAAACTGCTAAAGTTTCTGATACTCCTGTCGAATTCATCGTCGAACA

TTTGTTAAAGGCTAAGGAAATCGCCGAAAACCACGCCTCTATCCCTGTTG

AATTAAGAGATAACTTGCAAAAGGCTTTGGATATTGCTTCTGGTTTGGAC

GAATACTTAGAACAAATGTCTTCTAAGGAATCTGAACCATTGACCGAATT

GTACCGTAAATCCGTTTCTCACGACTGGAACAAAGTCCATGCTGACGGTA

AAACCTTGTTTAGATTGCCAGTTACCTGTATCACTGGTCAAGTTGAAGGT

CAAGTCTTAAAAATGTTGGTTCACATGTCTAAGGCCAAGCGTGTCTTGGA

AATTGGTATGTTTACTGGTTATGGTGCTTTATCTATGGCTGAAGCTTTGC

CAGAAAACGGTCAATTGATTGCTTGTGAATTGGAACCTTACTTGAAGGAC

TTCGCTCAACCTATCTTCGACAAGTCCCCACACGGTAAAAAGATCACCGT

TAAGACTGGTCCAGCTATGGATACTTTGAAAGAATTAGCTGCTACTGGTG

AGCAATTCGACATGGTTTTCATCGATGCTGACAAACAAAACTACATCAAC

TATTACAAGTTTTTGTTGGACCATAACTTGTTGAGAATCGATGGTGTCAT

TTGTGTTGATAACACCTTATTCAAAGGTAGAGTCTACTTAAAAGACTCTG

TCGACGAAATGGGTAAGGCTTTAAGAGACTTCAACCAATTTGTTACTGCT

GACCCAAGAGTTGAACAAGTTATTATCCCATTGAGAGATGGTTTGACTAT

TATCCGTAGAGTTCCATACACTCCACAACCAAACTCTCAATCCGGTACCG

TTACTTATGATGAAGTCTTCCGTGGTGTCCAAGGTAAACCAGTCTTGGAC

AGATTGAGATTGGATGGTAAGGTCGCCTATGTTACCGGTGCTGGTCAAGG

TATCGGTAGAGCTTTCGCTCACGCCTTGGGTGAGGCCGGTGCCAAAGTTG

CTATTATTGATATGGACAGAGGTAAGGCTGAAGACGTTGCCCACGAATTG

ACCTTGAAGGGTATTTCTTCCATGGCCGTCGTTGCCGATATTTCTAAGCC

AGACGACGTTCAAAAGATGATTGACGATATCGTTACTAAATGGGGTACTT

TACACATCGCTTGTAACAATGCTGGTATTAATAAGAACTCTGCTTCCGAG

GAAACCTCTTTGGAAGAATGGGATCAAACTTTTAATGTCAATTTGAGAGG

TACCTTCATGTGTTGTCAAGCTGCTGGTAGAGTTATGTTGAAGCAAGGTT

ACGGTAAGATTATTAACACCGCTTCCATGGCTTCTTTGATCGTCCCTCAC

CCACAAAAGCAATTGTCTTACAACACCTCCAAGGCCGGTGTTGTCAAGTT

AACTCAAACTTTAGGTACTGAGTGGATCGACAGAGGTGTCAGAGTTAACT

GCATTTCTCCAGGTATTGTTGACACCCCATTGATCCATTCCGAATCCTTG

GAACCATTAGTCCAAAGATGGTTGTCCGACATTCCTGCCGGTAGATTGGC

TCAAGTCACTGACTTGCAAGCCGCTGTCGTTTATTTGGCCTCTGACGCTT

CCGATTATATGACCGGTCACAACTTGGTCATCGAAGGTGGTCAATCTTTA

TGG

*S. cerevisiae*-optimized MT-Ox sequence #5
SEQ ID NO. 15

ATGCAAACTGCTAAGGTCTCCGACACTCCTGTTGAATTTATCGTTGAACA
TTTGTTGAAGGCTAAAGAAATCGCCGAAAACCACGCTTCCATCCCAGTCG
AATTGAGAGATAATTTACAAAAGGCTTTAGATATTGCTTCTGGTTTGGAC
GAATACTTGGAACAAATGTCTTCCAAGGAATCTGAACCATTGACTGAGTT
GTACAGAAAGTCCGTTTCTCATGATTGGAACAAAGTTCACGCTGACGGTA
AGACCTTGTTCCGTTTGCCAGTTACTTGTATTACTGGTCAAGTTGAAGGT
CAAGTCTTGAAGATGTTGGTCCACATGTCTAAAGCTAAGAGAGTTTTGGA
AATCGGTATGTTTACCGGTTACGGTGCCTTGTCCATGGCCGAAGCTTTGC
CAGAAAACGGTCAATTGATTGCTTGTGAATTGGAACCATACTTAAAGGAT
TTTGCTCAACCAATTTTTGACAAATCCCCTCATGGTAAGAAGATCACTGT
TAAGACTGGTCCAGCTATGGATACCTTGAAGGAATTGGCTGCTACTGGTG
AACAATTCGACATGGTCTTCATTGATGCCGATAAGCAAACTACATTAAC
TACTACAAGTTTTTGTTGGATCATAACTTGTTAAGAATTGATGGTGTTAT
CTGTGTTGACAACACCTTGTTCAAAGGTAGAGTTTATTTGAAAGATTCCG
TCGATGAAATGGGTAAGGCTTTAAGAGACTTCAACCAATTTGTCACTGCT
GACCCAAGAGTTGAACAAGTCATTATCCCATTGCGTGATGGTTTGACTAT
CATCCGTAGAGTTCCTTACACTCCACAACCAAACTCTCAATCTGGTACTG
TTACTTACGACGAAGTCTTCAGAGGTGTTCAAGGTAAGCCAGTTTTGGAC
AGATTGAGATTGGACGGTAAGGTTGCTTACGTCACCGGTGCTGGTCAAGG
TATTGGTAGAGCTTTCGCTCACGCTTTGGGTGAAGCTGGTGCTAAGGTTG
CTATCATCGACATGGATAGAGGTAAGGCTGAAGATGTCGCTCACGAATTG
ACCTTGAAGGGTATTTCTTCTATGGCTGTTGTTGCTGATATTTCTAAGCC
AGACGATGTCCAAAAGATGATTGATGACATCGTCACTAAGTGGGGTACCT
TGCATATCGCCTGTAACAACGCTGGTATCAACAAGAATTCTGCTTCTGAA
GAAACTTCTTTGGAAGAATGGGACCAAACTTTCAACGTTAACTTGCGTGG
TACTTTCATGTGTTGTCAAGCTGCTGGTCGTGTCATGTTGAAGCAAGGTT
ACGGTAAGATTATTAACACTGCTTCTATGGCTTCCTTGATCGTTCCTCAC
CCACAAAAGCAATTGTCTTACAACACTTCTAAGGCTGGTGTCGTCAAGTT
GACTCAAACCTTGGGTACCGAATGGATCGATAGAGGTGTCCGTGTTAACT
GCATCTCCCCAGGTATCGTCGATACCCCATTGATTCACTCTGAGTCTTTG
GAGCCATTGGTTCAAAGATGGTTGTCTGACATTCCAGCCGGTAGATTAGC
TCAAGTTACTGATTTGCAAGCTGCCGTCGTCTACTTGGCTTCCGACGCCT
CTGATTACATGACTGGTCATAACTTGGTCATTGAAGGTGGTCAATCTTTA
TGG

*S. cerevisiae*-optimized MT-Ox sequence #6
SEQ ID NO. 16

ATGCAAACTGCTAAGGTTTCTGACACTCCAGTTGAATTCATCGTTGAACA
CTTGTTGAAGGCTAAGGAAATCGCTGAAAACCACGCTTCTATCCCAGTTG
AATTGAGAGACAACTTGCAAAAGGCTTTGGACATCGCTTCTGGTTTGGAC
GAATACTTGGAACAAATGTCTTCTAAGGAATCTGAACCATTGACTGAATT
GTACAGAAAGTCTGTTTCTCACGACTGGAACAAGGTTCACGCTGACGGTA
AGACTTTGTTCAGATTGCCAGTTACTTGTATCACTGGTCAAGTTGAAGGT
CAAGTTTTGAAGATGTTGGTTCACATGTCTAAGGCTAAGAGAGTTTTGGA
AATCGGTATGTTCACTGGTTACGGTGCTTTGTCTATGGCTGAAGCTTTGC
CAGAAAACGGTCAATTGATCGCTTGTGAATTGGAACCATACTTGAAGGAC
TTCGCTCAACCAATCTTCGACAAGTCTCCACACGGTAAGAAGATCACTGT
TAAGACTGGTCCAGCTATGGACACTTTGAAGGAATTGGCTGCTACTGGTG
AACAATTCGACATGGTTTTCATCGACGCTGACAAGCAAACTACATCAAC
TACTACAAGTTCTTGTTGGACCACAACTTGTTGAGAATCGACGGTGTTAT
CTGTGTTGACAACACTTTGTTCAAGGGTAGAGTTTACTTGAAGGACTCTG
TTGACGAAATGGGTAAGGCTTTGAGAGACTTCAACCAATTCGTTACTGCT
GACCCAAGAGTTGAACAAGTTATCATCCCATTGAGAGACGGTTTGACTAT
CATCAGAAGAGTTCCATACACTCCACAACCAAACTCTCAATCTGGTACTG
TTACTTACGACGAAGTTTTCAGAGGTGTTCAAGGTAAGCCAGTTTTGGAC
AGATTGAGATTGGACGGTAAGGTTGCTTACGTTACTGGTGCTGGTCAAGG
TATCGGTAGAGCTTTCGCTCACGCTTTGGGTGAAGCTGGTGCTAAGGTTG
CTATCATCGACATGGACAGAGGTAAGGCTGAAGACGTTGCTCACGAATTG
ACTTTGAAGGGTATCTCTTCTATGGCTGTTGTTGCTGACATCTCTAAGCC
AGACGACGTTAAAAGATGATCGACGACATCGTTACTAAGTGGGGTACTT
TGCACATCGCTTGTAACAACGCTGGTATCAACAAGAACTCTGCTTCTGAA
GAAACTTCTTTGGAAGAATGGGACCAAACTTTCAACGTTAACTTGAGAGG
TACTTTCATGTGTTGTCAAGCTGCTGGTAGAGTTATGTTGAAGCAAGGTT
ACGGTAAGATCATCAACACTGCTTCTATGGCTTCTTTGATCGTTCCACAC
CCACAAAAGCAATTGTCTTACAACACTTCTAAGGCTGGTGTTGTTAAGTT
GACTCAAACTTTGGGTACTGAATGGATCGACAGAGGTGTTAGAGTTAACT
GTATCTCTCCAGGTATCGTTGACACTCCATTGATCCACTCTGAATCTTTG
GAACCATTGGTTCAAAGATGGTTGTCTGACATCCCAGCTGGTAGATTGGC
TCAAGTTACTGACTTGCAAGCTGCTGTTGTTTACTTGGCTTCTGACGCTT
CTGACTACATGACTGGTCACAACTTGGTTATCGAAGGTGGTCAATCTTTG
TGG pUC57-Kan (Addgene)
SEQ ID NO. 17 tcgcgcgtttcggtgatgacggtgaaaacctctgacacatgcagctcccg
gagacggtcacagcttgtctgtaagcggatgccgggagcagacaagcccg
tcagggcgcgtcagcgggtgttggcgggtgtcggggctggcttaactatg
cggcatcagagcagattgtactgagagtgcaccatatgcggtgtgaaata
ccgcacagatgcgtaaggagaaaataccgcatcaggcgccattcgccatt
caggctgcgcaactgttgggaagggcgatcggtgcgggcctcttcgctat
tacgccagctggcgaaaggggggatgtgctgcaaggcgattaagttgggta
acgccagggttttcccagtcacgacgttgtaaaacgacggccagtgaatt
cgagctcggtacctcgcgaatgcatctagatatcggatcccgggcccgtc
gactgcagaggcctgcatgcaagcttggcgtaatcatggtcatagctgtt -continued tcctgtgtgaaattgttatccgctcacaattccacacaacatacgagccg gaagcataaagtgtaaagcctggggtgcctaatgagtgagctaactcaca ttaattgcgttgcgctcactgcccgctttccagtcgggaaacctgtcgtg ccagctgcattaatgaatcggccaacgcgcgggagaggcggtttgcgta ttgggcgctcttccgcttcctcgctcactgactcgctgcgctcggtcgtt cggctgcggcgagcggtatcagctcactcaaaggcggtaatacggttatc cacagaatcaggggataacgcaggaaagaacatgtgagcaaaaggccagc aaaaggccaggaaccgtaaaaaggccgcgttgctggcgttttttccatagg ctccgcccccctgacgagcatcacaaaaatcgacgctcaagtcagaggtg gcgaaacccgacaggactataaagataccaggcgtttccccctggaagct ccctcgtgcgctctcctgttccgaccctgccgcttaccggatacctgtcc gcctttctcccttcgggaagcgtggcgctttctcatagctcacgctgtag gtatctcagttcggtgtaggtcgttcgctccaagctgggctgtgtgcacg aaccccccgttcagcccgaccgctgcgccttatccggtaactatcgtctt gagtccaacccggtaagacacgacttatcgccactggcagcagccactgg taacaggattagcagagcgaggtatgtaggcggtgctacagagttcttga agtggtggcctaactacggctacactagaagaacagtatttggtatctgc gctctgctgaagccagttaccttcggaaaaagagttggtagctcttgatc cggcaaacaaaccaccgctggtagcggtggtttttttgtttgcaagcagc agattacgcgcagaaaaaaggatctcaagaagatcctttgatcttttct acggggtctgacgctcagtggaacgaaaactcacgttaagggattttggt catgagattatcaaaaaggatcttcacctagatccttttaaattaaaaat gaagttttaaatcaagcccaatctgaataatgttacaaccaattaaccaa ttctgattagaaaaactcatcgagcatcaaatgaaactgcaatttattca tatcaggattatcaataccatattttgaaaaagccgtttctgtaatgaa ggagaaaactcaccgaggcagttccataggatggcaagatcctggtatcg gtctgcgattccgactcgtccaacatcaatacaacctattaatttcccct cgtcaaaaataaggttatcaagtgagaaatcaccatgagtgacgactgaa tccggtgagaatggcaaaagtttatgcatttctttccagacttgttcaac aggccagccattacgctcgtcatcaaaatcactcgcatcaaccaaaccgt tattcattcgtgattgcgcctgagcgagacgaaatacgcgatcgctgtta aaaggacaattacaaacaggaatcgaatgcaaccggcgcaggaacactgc cagcgcatcaacaatattttcacctgaatcaggatattcttctaatacct ggaatgctgttttccggggatcgcagtggtgagtaaccatgcatcatca ggagtacggataaaatgcttgatggtcggaagaggcataaattccgtcag ccagtttagtctgaccatctcatctgtaacatcattggcaacgctaccgtt tgccatgtttcagaaacaactctggcgcatcgggcttcccatacaagcga tagattgtcgcacctgattgcccgacattatcgcgagcccatttataccc atataaatcagcatccatgttggaatttaatcgcggcctcgacgtttccc gttgaatatggctcataacaccccttgtattactgtttatgtaagcagac -continued agttttattgttcatgatgatatattttatcttgtgcaatgtaacatca gagattttgagacacgggccagagctgca pRSETB (see the world wide web; tools.lifetechnologies.com/content/sfs/vectors/prsetb_seq.txt)
>pRSETB

SEQ ID NO. 18

GATCTCGATCCCGCGAAATTAATACGACTCACTATAGGGAGACCACAACG

GTTTCCCTCTAGAAATAATTTTGTTTAACTTTAAGAAGGAGATATACATA

TGCGGGGTTCTCATCATCATCATCATCATGGTATGGCTAGCATGACTGGT

GGACAGCAAATGGGTCGGGATCTGTACGACGATGACGATAAGGATCCGAG

CTCGAGATCTGCAGCTGGTACCATGGAATTCGAAGCTTGATCCGGCTGCT

AACAAAGCCCGAAAGGAAGCTGAGTTGGCTGCTGCCACCGCTGAGCAATA

ACTAGCATAACCCCTTGGGGCCTCTAAACGGGTCTTGAGGGGTTTTTTGC

TGAAAGGAGGAACTATATCCGGATCTGGCGTAATAGCGAAGAGGCCCGCA

CCGATCGCCCTTCCCAACAGTTGCGCAGCCTGAATGGCGAATGGGACGCG

CCCTGTAGCGGCGCATTAAGCGCGGCGGGTGTGGTGGTTACGCGCAGCGT

GACCGCTACACTTGCCAGCGCCCTAGCGCCCGCTCCTTTCGCTTTCTTCC

CTTCCTTTCTCGCCACGTTCGCCGGCTTTCCCCGTCAAGCTCTAAATCGG

GGGCTCCCTTTAGGGTTCCGATTTAGTGCTTTACGGCACCTCGACCCCAA

AAAACTTGATTAGGGTGATGGTTCACGTAGTGGGCCATCGCCCTGATAGA

CGGTTTTTCGCCCTTTGACGTTGGAGTCCACGTTCTTTAATAGTGGACTC

TTGTTCCAAACTGGAACAACACTCAACCCTATCTCGGTCTATTCTTTTGA

TTTATAAGGGATTTTGCCGATTTCGGCCTATTGGTTAAAAAATGAGCTGA

TTTAACAAAAATTTAACGCGAATTTTAACAAAATATTAACGCTTACAATT

TAGGTGGCACTTTTCGGGGAAATGTGCGCGGAACCCCTATTTGTTTATTT

TTCTAAATACATTCAAATATGTATCCGCTCATGAGACAATAACCCTGATA

AATGCTTCAATAATATTGAAAAAGGAAGAGTATGAGTATTCAACATTTCC

GTGTCGCCCTTATTCCCTTTTTTGCGGCATTTTGCCTTCCTGTTTTTGCT

CACCCAGAAACGCTGGTGAAAGTAAAAGATGCTGAAGATCAGTTGGGTGC

ACGAGTGGGTTACATCGAACTGGATCTCAACAGCGGTAAGATCCTTGAGA

GTTTTCGCCCCGAAGAACGTTTTCCAATGATGAGCACTTTTAAAGTTCTG

CTATGTGGCGCGGTATTATCCCGTATTGACGCCGGGCAAGAGCAACTCGG

TCGCCGCATACACTATTCTCAGAATGACTTGGTTGAGTACTCACCAGTCA

CAGAAAAGCATCTTACGGATGGCATGACAGTAAGAGAATTATGCAGTGCT

GCCATAACCATGAGTGATAACACTGCGGCCAACTTACTTCTGACAACGAT

CGGAGGACCGAAGGAGCTAACCGCTTTTTTGCACAACATGGGGGATCATG

TAACTCGCCTTGATCGTTGGGAACCGGAGCTGAATGAAGCCATACCAAAC

GACGAGCGTGACACCACGATGCCTGTAGCAATGGCAACAACGTTGCGCAA

ACTATTAACTGGCGAACTACTTACTCTAGCTTCCCGGCAACAATTAATAG

ACTGGATGGAGGCGGATAAAGTTGCAGGACCACTTCTGCGCTCGGCCCTT

CCGGCTGGCTGGTTTATTGCTGATAAATCTGGAGCCGGTGAGCGTGGGTC

TCGCGGTATCATTGCAGCACTGGGGCCAGATGGTAAGCCCTCCCGTATCG

```
TAGTTATCTACACGACGGGGAGTCAGGCAACTATGGATGAACGAAATAGA
CAGATCGCTGAGATAGGTGCCTCACTGATTAAGCATTGGTAACTGTCAGA
CCAAGTTTACTCATATATACTTTAGATTGATTTAAAACTTCATTTTTAAT
TTAAAAGGATCTAGGTGAAGATCCTTTTTGATAATCTCATGACCAAAATC
CCTTAACGTGAGTTTTCGTTCCACTGAGCGTCAGACCCCGTAGAAAAGAT
CAAAGGATCTTCTTGAGATCCTTTTTTTCTGCGCGTAATCTGCTGCTTGC
AAACAAAAAAACCACCGCTACCAGCGGTGGTTTGTTTGCCGGATCAAGAG
CTACCAACTCTTTTTCCGAAGGTAACTGGCTTCAGCAGAGCGCAGATACC
AAATACTGTTCTTCTAGTGTAGCCGTAGTTAGGCCACCACTTCAAGAACT
CTGTAGCACCGCCTACATACCTCGCTCTGCTAATCCTGTTACCAGTGGCT
GCTGCCAGTGGCGATAAGTCGTGTCTTACCGGGTTGGACTCAAGACGATA
GTTACCGGATAAGGCGCAGCGGTCGGGCTGAACGGGGGGTTCGTGCACAC
AGCCCAGCTTGGAGCGAACGACCTACACCGAACTGAGATACCTACAGCGT
GAGCTATGAGAAAGCGCCACGCTTCCCGAAGGGAGAAAGGCGGACAGGTA
TCCGGTAAGCGGCAGGGTCGGAACAGGAGAGCGCACGAGGGAGCTTCCAG
GGGGAAACGCCTGGTATCTTTATAGTCCTGTCGGGTTTCGCCACCTCTGA
CTTGAGCGTCGATTTTTGTGATGCTCGTCAGGGGGGCGGAGCCTATGGAA
AAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGT
ATTACCGCCTTTGAGTGAGCTGATACCGCTCGCCGCAGCCGAACGACCGA
GCGCAGCGAGTCAGTGAGCGAGGAAGCGGAAGAGCGCCCAATACGCAAAC
CGCCTCTCCCCGCGCGTTGGCCGATTCATTAATGCAG
pXP416 (www.addgene.org/26842/sequences/)
>p416
                                                SEQ ID NO. 19
TCGCGCGTTTCGGTGATGACGGTGAAAACCTCTGACACATGCAGCTCCCG
GAGACGGTCACAGCTTGTCTGTAAGCGGATGCCGGGAGCAGACAAGCCCG
TCAGGGCGCGTCAGCGGGTGTTGGCGGGTGTCGGGGCTGGCTTAACTATG
CGGCATCAGAGCAGATTGTACTGAGAGTGCACCATATGCGGTGTGAAATA
CCGCACAGATGCGTAAGGAGAAAATACCGCATCAGGCGCCATTCGCCATT
CAGGCTGCGCAACTGTTGGGAAGGGCGATCGGTGCGGGCCTCTTCGCTAT
TACGCCAGCTGGCGAAAGGGGGATGTGCTGCAAGGCGATTAAGTTGGGTA
ACGCCAGGGTTTTCCCAGTCACGACGTTGTAAAACGACGGCCAGTGCCAA
GCTTGCATGCCTGCAGGTCGACTCTAGAGGATCCCCGGGATAACTTCGTA
TAGCATACATTATACGAAGTTATAACGACATTACTATATATATAATATAG
GAAGCATTTAATAGAACAGCATCGTAATATATGTGTACTTTGCAGTTATG
ACGCCAGATGGCAGTAGTGGAAGATATTCTTTATTGAAAAATAGCTTGTC
ACCTTACGTACAATCTTGATCCGGAGCTTTTCTTTTTTGCCGATTAAGA
ATTAATTCGGTCGAAAAAGAAAAGGAGAGGGCCAAGAGGGAGGCATTG
GTGACTATTGAGCACGTGAGTATACGTGATTAAGCACACAAAGGCAGCTT
GGAGTATGTCTGTTATTAATTTCACAGGTAGTTCTGGTCCATTGGTGAAA
GTTTGCGGCTTGCAGAGCACAGAGGCCGCAGAATGTGCTCTAGATTCCGA
TGCTGACTTGCTGGGTATTATATGTGTGCCCAATAGAAAGAGAACAATTG
ACCCGGTTATTGCAAGGAAAATTTCAAGTCTTGTAAAAGCATATAAAAAT
AGTTCAGGCACTCCGAAATACTTGGTTGGCGTGTTTCGTAATCAACCTAA
GGAGGATGTTTTGGCTCTGGTCAATGATTACGGCATTGATATCGTCCAAC
TGCATGGAGATGAGTCGTGGCAAGAATACCAAGAGTTCCTCGGTTTGCCA
GTTATTAAAGACTCGTATTTCCAAAAGACTGCAACATACTACTCAGTGC
AGCTTCACAGAAACCTCATTCGTTTATTCCCTTGTTTGATTCAGAAGCAG
GTGGGACAGGTGAACTTTTGGATTGGAACTCGATTTCTGACTGGGTTGGA
AGGCAAGAGAGCCCCGAAAGCTTACATTTTATGTTAGCTGGTGGACTGAC
GCCAGAAAATGTTGGTGATGCGCTTAGATTAAATGGCGTTATTGGTGTTG
ATGTAAGCGGAGGTGTGGAGACAAATGGTGTAAAAGACTCTAACAAATA
GCAAATTTCGTCAAAAATGCTAAGAAATAGGTTATTACTGAGTAGTATTT
ATTTAAGTATTGTTTGTGCACTTGCCTGATAACTTCGTATAGCATACATT
ATACGAAGTTATCCCGGGTACCGAGCTCGAATTCAACGAAGCATCTGTGC
TTCATTTTGTAGAACAAAAATGCAACGCGAGAGCGCTAATTTTTCAAACA
AGAATCTGAGCTGCATTTTTACAGAACAGAAATGCAACGCGAAAGCGCT
ATTTTACCAACGAAGAATCTGTGCTTCATTTTTGTAAAACAAAAATGCAA
CGCGAGAGCGCTAATTTTTCAAACAAAGAATCTGAGCTGCATTTTTACAG
AACAGAAATGCAACGCGAGAGCGCTATTTTACCAACAAAGAATCTATACT
TCTTTTTTGTTCTACAAAAATGCATCCCGAGAGCGCTATTTTTCTAACAA
AGCATCTTAGATTACTTTTTTCTCCTTTGTGCGCTCTATAATGCAGTCT
CTTGATAACTTTTTGCACTGTAGGTCCGTTAAGGTTAGAAGAAGGCTACT
TTGGTGTCTATTTTCTCTTCCATAAAAAAGCCTGACTCCACTTCCCGCG
TTTACTGATTACTAGCGAAGCTGCGGGTGCATTTTTTCAAGATAAAGGCA
TCCCCGATTATATTCTATACCGATGTGGATTGCGCATACTTTGTGAACAG
AAAGTGATAGCGTTGATGATTCTTCATTGGTCAGAAAATTATGAACGGTT
TCTTCTATTTTGTCTCTATATACTACGTATAGGAAATGTTTACATTTTCG
TATTGTTTTCGATTCACTCTATGAATAGTTCTTACTACAATTTTTTTGTC
TAAAGAGTAATACTAGAGATAAACATAAAAAATGTAGAGGTCGAGTTTAG
ATGCAAGTTCAAGGAGCGAAAGGTGGATGGGTAGGTTATATAGGGATATA
GCACAGAGATATATAGCAAAGAGATACTTTTGAGCAATGTTTGTGGAAGC
GGTATTCGCAATATTTTAGTAGCTCGTTACAGTCCGGTGCGTTTTTGGTT
TTTTGAAAGTGCGTCTTCAGAGCGCTTTTGGTTTTCAAAAGCGCTCTGAA
GTTCCTATACTTTCTAGAGAATAGGAACTTCGGAATAGGAACTTCAAAGC
GTTTCCGAAAACGAGCGCTTCCGAAAATGCAACGCGAGCTGCGCACATAC
AGCTCACTGTTCACGTCGCACCTATATCTGCGTGTTGCCTGTATATATAT
ATACATGAGAAGAACGGCATAGTGCGTGTTTATGCTTAAATGCGTACTTA
TATGCGTCTATTTATGTAGGATGAAAGGTAGTCTAGTACCTCCTGTGATA
TTATCCCATTCCATGCGGGGTATCGTATGCTTCCTTCAGCACTACCCTTT
AGCTGTTCTATATGCTGCCACTCCTCAATTGGATTAGTCTCATCCTTCAA
TGCTATCATTTCCTTTGATATTGGATCATACGAATTCGTAATCATGGTCA
```

-continued
```
TAGCTGTTTCCTGTGTGAAATTGTTATCCGCTCACAATTCCACACAACAT
ACGAGCCGGAAGCATAAAGTGTAAAGCCTGGGGTGCCTAATGAGTGAGCT
AACTCACATTAATTGCGTTGCGCTCACTGCCCGCTTTCCAGTCGGGAAAC
CTGTCGTGCCAGCTGCATTAATGAATCGGCCAACGCGCGGGGAGAGGCGG
TTTGCGTATTGGGCGCTCTTCCGCTTCCTCGCTCACTGACTCGCTGCGCT
CGGTCGTTCGGCTGCGGCGAGCGGTATCAGCTCACTCAAAGGCGGTAATA
CGGTTATCCACAGAATCAGGGGATAACGCAGGAAAGAACATGTGAGCAAA
AGGCCAGCAAAAGGCCAGGAACCGTAAAAAGGCCGCGTTGCTGGCGTTTT
TCCATAGGCTCCGCCCCCCTGACGAGCATCACAAAAATCGACGCTCAAGT
CAGAGGTGGCGAAACCCGACAGGACTATAAAGATACCAGGCGTTTCCCCC
TGGAAGCTCCCTCGTGCGCTCTCCTGTTCCGACCCTGCCGCTTACCGGAT
ACCTGTCCGCCTTTCTCCCTTCGGGAAGCGTGGCGCTTTCTCATAGCTCA
CGCTGTAGGTATCTCAGTTCGGTGTAGGTCGTTCGCTCCAAGCTGGGCTG
TGTGCACGAACCCCCCGTTCAGCCCGACCGCTGCGCCTTATCCGGTAACT
ATCGTCTTGAGTCCAACCCGGTAAGACACGACTTATCGCCACTGGCAGCA
GCCACTGGTAACAGGATTAGCAGAGCGAGGTATGTAGGCGGTGCTACAGA
GTTCTTGAAGTGGTGGCCTAACTACGGCTACACTAGAAGGACAGTATTTG
GTATCTGCGCTCTGCTGAAGCCAGTTACCTTCGGAAAAAGAGTTGGTAGC
TCTTGATCCGGCAAACAAACCACCGCTGGTAGCGGTGGTTTTTTTGTTTG
CAAGCAGCAGATTACGCGCAGAAAAAAAGGATCTCAAGAAGATCCTTTGA
TCTTTTCTACGGGGTCTGACGCTCAGTGGAACGAAAACTCACGTTAAGGG
ATTTTGGTCATGAGATTATCAAAAAGGATCTTCACCTAGATCCTTTTAAA
TTAAAAATGAAGTTTTAAATCAATCTAAAGTATATATGAGTAAACTTGGT
CTGACAGTTACCAATGCTTAATCAGTGAGGCACCTATCTCAGCGATCTGT
CTATTTCGTTCATCCATAGTTGCCTGACTCCCCGTCGTGTAGATAACTAC
GATACGGGAGGGCTTACCATCTGGCCCCAGTGCTGCAATGATACCGCGAG
ACCCACGCTCACCGGCTCCAGATTTATCAGCAATAAACCAGCCAGCCGGA
AGGGCCGAGCGCAGAAGTGGTCCTGCAACTTTATCCGCCTCCATCCAGTC
TATTAATTGTTGCCGGGAAGCTAGAGTAAGTAGTTCGCCAGTTAATAGTT
TGCGCAACGTTGTTGCCATTGCTACAGGCATCGTGGTGTCACGCTCGTCG
TTTGGTATGGCTTCATTCAGCTCCGGTTCCCAACGATCAAGGCGAGTTAC
ATGATCCCCCATGTTGTGCAAAAAAGCGGTTAGCTCCTTCGGTCCTCCGA
TCGTTGTCAGAAGTAAGTTGGCCGCAGTGTTATCACTCATGGTTATGGCA
GCACTGCATAATTCTCTTACTGTCATGCCATCCGTAAGATGCTTTTCTGT
GACTGGTGAGTACTCAACCAAGTCATTCTGAGAATAGTGTATGCGGCGAC
CGAGTTGCTCTTGCCCGGCGTCAATACGGGATAATACCGCGCCACATAGC
AGAACTTTAAAAGTGCTCATCATTGGAAAACGTTCTTCGGGGCGAAAACT
CTCAAGGATCTTACCGCTGTTGAGATCCAGTTCGATGTAACCCACTCGTG
CACCCAACTGATCTTCAGCATCTTTTACTTTCACCAGCGTTTCTGGGTGA
GCAAAAACAGGAAGGCAAAATGCCGCAAAAAAGGGAATAAGGGCGACACG
GAAATGTTGAATACTCATACTCTTCCTTTTTCAATATTACCGCGAATCCT
TACATCACACCCAATCCCCCACAAGTGATCCCCCACACACCATAGCTTCA
AAATGTTTCTACTCCTTTTTTACTCTTCCAGATTTTCTCGGACTCCGCGC
ATCGCCGTACCACTTCAAAACACCCAAGCACAGCATACTAAATTTCCCCT
CTTTCTTCCTCTAGGGTGTCGTTAATTACCCGTACTAAAGGTTTGGAAAA
GAAAAAGAGACCGCCTCGTTTCTTTTTCTTCGTCGAAAAAGGCAATAAA
AATTTTTATCACGTTTCTTTTTCTTGAAAATTTTTTTTTTGATTTTTTT
CTCTTTCGATGACCTCCCATTGATATTTAAGTTAATAAACGGTCTTCAAT
TTCTCAAGTTTCAGTTTCATTTTTCTTGTTCTATTACAACTTTTTTTACT
TCTTGCTCATTAGAAAGAAAGCATAGCAATCTAATCTAAGTTTTAATTAC
AAAACTAGTGATATCTGCGCACTCGAGTCATGTAATTAGTTATGTCACGC
TTACATTCACGCCCTCCCCCCACATCCGCTCTAACCGAAAAGGAAGGAGT
TAGACAACCTGAAGTCTAGGTCCCTATTTATTTTTTTATAGTTATGTTAG
TATTAAGAACGTTATTTATATTTCAAATTTTTCTTTTTTTTCTGTACAGA
CGCGTGTACGCATGTAACATTATACTGAAAACCTTGCTTGAGAAGGTTTT
GGGACGCTCGAAGGCTTTAATTTGCGGCCAATATTATTGAAGCATTTATC
AGGGTTATTGTCTCATGAGCGGATACATATTTGAATGTATTTAGAAAAAT
AAACAAATAGGGGTTCCGCGCACATTTCCCCGAAAAGTGCCACCTGACGT
CTAAGAAACCATTATTATCATGACATTAACCTATAAAAATAGGCGTATCA
CGAGGCCCTTTCGTC
``` pXP420 (www.addgene.org/26844/sequences/)
>pXP420

SEQ ID NO. 20
```
TCGCGCGTTTCGGTGATGACGGTGAAAACCTCTGACACATGCAGCTCCCG
GAGACGGTCACAGCTTGTCTGTAAGCGGATGCCGGGAGCAGACAAGCCCG
TCAGGGCGCGTCAGCGGGTGTTGGCGGGTGTCGGGGCTGGCTTAACTATG
CGGCATCAGAGCAGATTGTACTGAGAGTGCACCATATGCGGTGTGAAATA
CCGCACAGATGCGTAAGGAGAAAATACCGCATCAGGCGCCATTCGCCATT
CAGGCTGCGCAACTGTTGGGAAGGGCGATCGGTGCGGGCCTCTTCGCTAT
TACGCCAGCTGGCGAAAGGGGGATGTGCTGCAAGGCGATTAAGTTGGGTA
ACGCCAGGGTTTTCCCAGTCACGACGTTGTAAAACGACGGCCAGTGCCAA
GCTTGCATGCCTGCAGGTCGACTCTAGAGGATCCCCGGGTAACTTCGTA
TAGCATACATTATACGAAGTTATCGTTTAAGAGCTTGGTGAGCGCTAGG
AGTCACTGCCAGGTATCGTTTGAACACGGCATTAGTCAGGGAAGTCATAA
CACAGTCCTTTCCCGCAATTTTCTTTTTCTATTACTCTTGGCCTCCTCTA
GTACACTCTATATTTTTTATGCCTCGGTAATGATTTTCATTTTTTTTTT
TCCACCTAGCGGATGACTCTTTTTTTTTCTTAGCGATTGGCATTATCACA
TAATGAATTATACATTATATAAAGTAATGTGATTTCTTCGAAGAATATAC
TAAAAAATGAGCAGGCAAGATAAACGAAGGCAAAGATGACAGAGCAGAAA
GCCCTAGTAAAGCGTATTACAAATGAAACCAAGATTCAGATTGCGATCTC
TTTAAAGGGTGGTCCCCTAGCGATAGAGCACTCGATCTTCCCAGAAAAAG
AGGCAGAAGCAGTAGCAGAACAGGCCACACAATCGCAAGTGATTAACGTC
```

```
CACACAGGTATAGGGTTTCTGGACCATATGATACATGCTCTGGCCAAGCA
TTCCGGCTGGTCGCTAATCGTTGAGTGCATTGGTGACTTACACATAGACG
ACCATCACACCACTGAAGACTGCGGGATTGCTCTCGGTCAAGCTTTTAAA
GAGGCCCTAGGGGCCGTGCGTGGAGTAAAAAGGTTTGGATCAGGATTTGC
GCCTTTGGATGAGGCACTTTCCAGAGCGGTGGTAGATCTTTCGAACAGGC
CGTACGCAGTTGTCGAACTTGGTTTGCAAAGGGAGAAAGTAGGAGATCTC
TCTTGCGAGATGATCCCGCATTTTCTTGAAAGCTTTGCAGAGGCTAGCAG
AATTACCCTCCACGTTGATTGTCTGCGAGGCAAGAATGATCATCACCGTA
GTGAGAGTGCGTTCAAGGCTCTTGCGGTTGCCATAAGAGAAGCCACCTCG
CCCAATGGTACCAACGATGTTCCCTCCACCAAAGGTGTTCTTATGTAGTG
ACACCGATTATTTAAAGCTGCAGCATACGATATATATACATGTGTATATA
TGTATACCTATGAATGTCAGTAAGTATGTATACGAACAGTATGATACTGA
AGATGACAAGGTAATGCATCATTCTATACGTGTCATTCTGAACGAGGCGC
GCTTTCCTTTTTCTTTTGCTTTTTCTTTTTTTTCTCTTGAACTCGAA
TAACTTCGTATAGCATACATTATACGAAGTTATCCCGGGTACCGAGCTCG
AATTCGTATGATCCAATATCAAAGGAAATGATAGCATTGAAGGATGAGAC
TAATCCAATTGAGGAGTGGCAGCATATAGAACAGCTAAAGGGTAGTGCTG
AAGGAAGCATACGATACCCCGCATGGAATGGGATAATATCACAGGAGGTA
CTAGACTACCTTTCATCCTACATAAATAGACGCATATAAGTACGCATTTA
AGCATAAACACGCACTATGCCGTTCTTCTCATGTATATATATACAGGC
AACACGCAGATATAGGTGCGACGTGAACAGTGAGCTGTATGTGCGCAGCT
CGCGTTGCATTTTCGGAAGCGCTCGTTTTCGGAAACGCTTTGAAGTTCCT
ATTCCGAAGTTCCTATTCTCTAGAAAGTATAGGAACTTCAGAGCGCTTTT
GAAAACCAAAAGCGCTCTGAAGACGCACTTTCAAAAAACCAAAAACGCAC
CGGACTGTAACGAGCTACTAAAATATTGCGAATACCGCTTCCACAAACAT
TGCTCAAAAGTATCTCTTTGCTATATATCTCTGTGCTATATCCCTATATA
ACCTACCCATCCACCTTTCGCTCCTTGAACTTGCATCTAAACTCGACCTC
TACATTTTTATGTTTATCTCTAGTATTACTCTTTAGACAAAAAATTGT
AGTAAGAACTATTCATAGAGTGAATCGAAAACAATACGAAAATGTAAACA
TTTCCTATACGTAGTATATAGAGACAAAATAGAAGAAACCGTTCATAATT
TTCTGACCAATGAAGAATCATCAACGCTATCACTTTCTGTTCACAAAGTA
TGCGCAATCCACATCGGTATAGAATATAATCGGGGATGCCTTTATCTTGA
AAAAATGCACCCGCAGCTTCGCTAGTAATCAGTAAACGCGGGAAGTGGAG
TCAGGCTTTTTTATGGAAGAGAAAATAGACACCAAAGTAGCCTTCTTCT
AACCTTAACGGACCTACAGTGCAAAAAGTTATCAAGAGACTGCATTATAG
AGCGCACAAAGGAGAAAAAAGTAATCTAAGATGCTTTGTTAGAAAATA
GCGCTCTCGGGATGCATTTTTGTAGAACAAAAAGAAGTATAGATTCTTT
GTTGGTAAAATAGCGCTCTCGCGTTGCATTTCTGTTCTGTAAAAATGCAG
CTCAGATTCTTTGTTTGAAAAATTAGCGCTCTCGCGTTGCATTTTTGTTT
TACAAAAATGAAGCACAGATTCTTCGTTGGTAAAATAGCGCTTTCGCGTT
GCATTTCTGTTCTGTAAAAATGCAGCTCAGATTCTTTGTTTGAAAAATTA

GCGCTCTCGCGTTGCATTTTTGTTCTACAAAATGAAGCACAGATGCTTCG
TTGAATTCGTAATCATGGTCATAGCTGTTTCCTGTGTGAAATTGTTATCC
GCTCACAATTCCACACAACATACGAGCCGGAAGCATAAAGTGTAAAGCCT
GGGGTGCCTAATGAGTGAGCTAACTCACATTAATTGCGTTGCGCTCACTG
CCCGCTTTCCAGTCGGGAAACCTGTCGTGCCAGCTGCATTAATGAATCGG
CCAACGCGCGGGAGAGGCGGTTTGCGTATTGGGCGCTCTTCCGCTTCCT
CGCTCACTGACTCGCTGCGCTCGGTCGTTCGGCTGCGGCGAGCGGTATCA
GCTCACTCAAAGGCGGTAATACGGTTATCCACAGAATCAGGGGATAACGC
AGGAAAGAACATGTGAGCAAAAGGCCAGCAAAAGGCCAGGAACCGTAAAA
AGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATA
AAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGC
GTGGCGCTTTCTCATAGCTCACGCTGTAGGTATCTCAGTTCGGTGTAGGT
CGTTCGCTCCAAGCTGGGCTGTGTGCACGAACCCCCCGTTCAGCCCGACC
GCTGCGCCTTATCCGGTAACTATCGTCTTGAGTCCAACCCGGTAAGACAC
GACTTATCGCCACTGGCAGCAGCCACTGGTAACAGGATTAGCAGAGCGAG
GTATGTAGGCGGTGCTACAGAGTTCTTGAAGTGGTGGCCTAACTACGGCT
ACACTAGAAGGACAGTATTTGGTATCTGCGCTCTGCTGAAGCCAGTTACC
TTCGGAAAAAGAGTTGGTAGCTCTTGATCCGGCAAACAAACCACCGCTGG
TAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGG
AACGAAAACTCACGTTAAGGGATTTTGGTCATGAGATTATCAAAAAGGAT
CTTCACCTAGATCCTTTTAAATTAAAAATGAAGTTTTAAATCAATCTAAA
GTATATATGAGTAAACTTGGTCTGACAGTTACCAATGCTTAATCAGTGAG
GCACCTATCTCAGCGATCTGTCTATTTCGTTCATCCATAGTTGCCTGACT
CCCCGTCGTGTAGATAACTACGATACGGGAGGGCTTACCATCTGGCCCCA
GTGCTGCAATGATACCGCGAGACCCACGCTCACCGGCTCCAGATTTATCA
GCAATAAACCAGCCAGCCGGAAGGGCCGAGCGCAGAAGTGGTCCTGCAAC
TTTATCCGCCTCCATCCAGTCTATTAATTGTTGCCGGGAAGCTAGAGTAA
GTAGTTCGCCAGTTAATAGTTTGCGCAACGTTGTTGCCATTGCTACAGGC
ATCGTGGTGTCACGCTCGTCGTTTGGTATGGCTTCATTCAGCTCCGGTTC
CCAACGATCAAGGCGAGTTACATGATCCCCCATGTTGTGCAAAAAGCGG
TTAGCTCCTTCGGTCCTCCGATCGTTGTCAGAAGTAAGTTGGCCGCAGTG
TTATCACTCATGGTTATGGCAGCACTGCATAATTCTCTTACTGTCATGCC
ATCCGTAAGATGCTTTTCTGTGACTGGTGAGTACTCAACCAAGTCATTCT
GAGAATAGTGTATGCGGCGACCGAGTTGCTCTTGCCCGGCGTCAATACGG
GATAATACCGCGCCACATAGCAGAACTTTAAAAGTGCTCATCATTGGAAA
ACGTTCTTCGGGGCGAAAACTCTCAAGGATCTTACCGCTGTTGAGATCCA
GTTCGATGTAACCCACTCGTGCACCCAACTGATCTTCAGCATCTTTTACT
```

```
TTCACCAGCGTTTCTGGGTGAGCAAAAACAGGAAGGCAAAATGCCGCAAA
AAAGGGAATAAGGGCGACACGGAAATGTTGAATACTCATACTCTTCCTTT
TTCAATATTACCGCGAATCCTTACATCACACCCAATCCCCCACAAGTGAT
CCCCCACACACCATAGCTTCAAAATGTTTCTACTCCTTTTTTACTCTTCC
AGATTTTCTCGGACTCCGCGCATCGCCGTACCACTTCAAAACACCCAAGC
ACAGCATACTAAATTTCCCCTCTTTCTTCCTCTAGGGTGTCGTTAATTAC
CCGTACTAAAGGTTTGGAAAAGAAAAAAGAGACCGCCTCGTTTCTTTTTC
TTCGTCGAAAAAGGCAATAAAAATTTTTATCACGTTTCTTTTTCTTGAAA
ATTTTTTTTTTGATTTTTTTCTCTTTCGATGACCTCCCATTGATATTTA
AGTTAATAAACGGTCTTCAATTTCTCAAGTTTCAGTTTCATTTTTCTTGT
TCTATTACAACTTTTTTTACTTCTTGCTCATTAGAAAGAAAGCATAGCAA
TCTAATCTAAGTTTTAATTACAAAACTAGTGATATCTGCGCACTCGAGTC
ATGTAATTAGTTATGTCACGCTTACATTCACGCCCTCCCCCCACATCCGC
TCTAACCGAAAAGGAAGGAGTTAGACAACCTGAAGTCTAGGTCCCTATTT
ATTTTTTTATAGTTATGTTAGTATTAAGAACGTTATTTATATTTCAAATT
TTTCTTTTTTTTCTGTACAGACGCGTGTACGCATGTAACATTATACTGAA
AACCTTGCTGAGAAGGTTTTGGGACGCTCGAAGGCTTTAATTTGCGGCC
AATATTATTGAAGCATTTATCAGGGTTATTGTCTCATGAGCGGATACATA
TTTGAATGTATTTAGAAAAATAAACAAATAGGGGTTCCGCGCACATTTCC
CCGAAAAGTGCCACCTGACGTCTAAGAAACCATTATTATCATGACATTAA
CCTATAAAAATAGGCGTATCACGAGGCCCTTTCGTC
```

Exemplary EEVS Protein
SEQ ID NO. 21
MERPGETFTVSSPEEVRLPSVHRDNSTMENHNKQETVFSLVQVKGTWKRK
AGQNAKQGMKGRVSPAKIYESSSSSGTTWTVVTPITFTYTVTQTKNLLDP
SNDTLLLGHIIDTQQLEAVRSNTKPLKRFIVMDEVVYNIYGSQVTEYLEA
RNVLYRILPLPTTEENKSMDMALKILEEVHQFGIDRRTEPIIAIGGGVCL
DIVGLAASLYRRRTPYIRVPTTLLSYIDASVGAKTGVNFANCKNKLGTYI
APVAAFLDRSFIQSIPRRHIANGLAEMLKMALMKHRGLFELLEVHGQFLL
DSKFQSASVLENDRIDPASVSTRVAIETMLEELAPNLWEDDLDRLVDFGH
LISPQLEMKVLPALLHGEAVNIDMAYMVYVSCEIGLLTEEEKFRIICCMM
GLELPVWHQDFTFALVQKSLCDRLQHSGGLVRMPLPTGLGRAEIFNDTDE
GSLFRAYEKWCDELSTGSPQ Exemplary MT-Ox Protein
SEQ ID NO. 22
MQTAKVSDTPVEFIVEHLLKAKEIAENHASIPVELRDNLQKALDIASGLD
EYLEQMSSKESEPLTELYRKSVSHDWNKVHADGKTLFRLPVTCITGQVEG
QVLKMLVHMSKAKRVLEIGMFTGYGALSMAEALPENGQLIACELEPYLKD
FAQPIFDKSPHGKKITVKTGPAMDTLKELAATGEQFDMVFIDADKQNYIN
YYKFLLDHNLLRIDGVICVDNTLFKGRVYLKDSVDEMGKALRDFNQFVTA
DPRVEQVIIPLRDGLTIIRRVPYTPQPNSQSGTVTYDEVFRGVQGKPVLD
RLRLDGKVAYVTGAGQGIGRAFAHALGEAGAKVAIIDMDRGKAEDVAHEL
TLKGISSMAVVADISKPDDVQKMIDDIVTKWGTLHIACNNAGINKNSASE
ETSLEEWDQTFNVNLRGTFMCCQAAGRVMLKQGYGKIINTASMASLIVPH
PQKQLSYNTSKAGVVKLTQTLGTEWIDRGVRVNCISPGIVDTPLIHSESL
EPLVQRWLSDIPAGRLAQVTDLQAAVVYLASDASDYMTGHNLVIEGGQSL
W.

SHB17, sedoheptulose 1,7-bisphosphatase ORF from
S. cerevisiae
SEQ ID NO. 77
```
ATGCCTTCGCTAACCCCCAGATGTATCATTGTCAGACACGGTCAAACTGA
ATGGTCCAAGTCAGGCCAGTATACTGGTTTGACAGATCTACCGTTAACGC
CCTACGGTGAGGGCCAAATGTTGAGGACCGGTGAGAGTGTTTTCCGCAAT
AATCAGTTTTTGAATCCAGACAACATCACTTATATCTTCACCTCTCCACG
TTTGCGTGCCAGGCAAACTGTGGATTTGGTTTTGAAACCATTAAGCGACG
AGCAAGAGCTAAGATCCGTGTGGTGGTAGACGACGACTTGCGAGAGTGG
GAGTACGGTGACTACGAGGGAATGCTGACTCGAGAAATCATTGAATTGAG
AAAGTCACGCGGTTTGGACAAGGAGAGGCCATGGAATATCTGGAGAGATG
GGTGTGAGAACGGTGAGACTACTCAGCAAATTGGGTTGAGACTTTCCCGC
GCTATTGCCAGAATCCAGAACTTGCACCGCAAGCACCAGAGTGAGGGCAG
AGCATCAGACATCATGGTCTTTGCGCACGGACATGCATTGCGTTATTTG
CTGCTATTTGGTTTGGACTGGGTGTGCAAAAGAAGTGTGAGACGATTGAA
GAAATTCAAATGTCAAATCTTATGATGACGACAGTTCCATATGTGAA
ATTGGAATCTTACAGACATTTGGTAGACAATCCATGTTTCTTACTGGACG
CCGGTGGGATTGGTGTTTTGTCATACGCTCACCACAACATTGACGAACCT
GCATTGGAATTAGCAGGTCCATTTGTCTCACCACCAGAGGAGGAATCCCA
GCATGGCGATGTGTAA
```

ZWF1, glucose 6-P dehydrogenase ORF from
S. cerevisiae
SEQ ID NO. 78
```
ATGAGTGAAGGCCCCGTCAAATTCGAAAAAAATACCGTCATATCTGTCTT
TGGTGCGTCAGGTGATCTGGCAAAGAAGAAGACTTTTCCCGCCTTATTTG
GGCTTTTCAGAGAAGGTTACCTTGATCCATCTACCAAGATCTTCGGTTAT
GCCCGGTCCAAATTGTCCATGGAGGAGGACCTGAAGTCCCGTGTCCTACC
CCACTTGAAAAAACCTCACGGTGAAGCCGATGACTCTAAGGTCGAACAGT
TCTTCAAGATGGTCAGCTACATTTCGGGAAATTACGACACAGATGAAGGC
TTCGACGAATTAAGAACGCAGATCGAGAAATTCGAGAAAGTGCCAACGT
CGATGTCCCACACCGTCTCTTCTATCTGGCCTTGCCGCCAGCGTTTTTTT
GACGGTGGCCAAGCAGATCAAGAGTCGTGTGTACGCAGAGAATGGCATCA
CCCGTGTAATCGTAGAGAAACCTTTCGGCCACGACCTGGCCTCTGCCAGG
GAGCTGCAAAAAACCTGGGGCCCCTCTTTAAAGAAGAAGAGTTGTACAG
AATTGACCATTACTTGGGTAAAGAGTTGGTCAAGAATCTTTTAGTCTTGA
GGTTCGGTAACCAGTTTTTGAATGCCTCGTGGAATAGAGACAACATTCAA
AGCGTTCAGATTTCGTTTAAAGAGAGGTTCGGCACCGAAGGCCGTGGCGG
CTATTTCGACTCTATAGGCATAATCAGAGACGTGATGCAGAACCATCTGT
TACAAATCATGACTCTCTTGACTATGGAAAGACCGGTGTCTTTTGACCCG
```

```
GAATCTATTCGTGACGAAAAGGTTAAGGTTCTAAAGGCCGTGGCCCCCAT
CGACACGGACGACGTCCTCTTGGGCCAGTACGGTAAATCTGAGGACGGGT
CTAAGCCCGCCTACGTGGATGATGACACTGTAGACAAGGACTCTAAATGT
GTCACTTTTGCAGCAATGACTTTCAACATCGAAAACGAGCGTTGGGAGGG
CGTCCCCATCATGATGCGTGCCGGTAAGGCTTTGAATGAGTCCAAGGTGG
AGATCAGACTGCAGTACAAAGCGGTCGCATCGGGTGTCTTCAAAGACATT
CCAAATAACGAACTGGTCATCAGAGTGCAGCCCGATGCCGCTGTGTACCT
AAAGTTTAATGCTAAGACCCCTGGTCTGTCAAATGCTACCCAAGTCACAG
ATCTGAATCTAACTTACGCAAGCAGGTACCAAGACTTTTGGATTCCAGAG
GCTTACGAGGTGTTGATAAGAGACGCCCTACTGGGTGACCATTCCAACTT
TGTCAGAGATGACGAATTGGATATCAGTTGGGGCATATTCACCCCATTAC
TGAAGCACATAGAGCGTCCGGACGGTCCAACACCGGAAATTTACCCCTAC
GGATCAAGAGGTCCAAAGGGATTGAAGGAATATATGCAAAAACACAAGTA
TGTTATGCCCGAAAAGCACCCTTACGCTTGGCCCGTGACTAAGCCAGAAG
ATACGAAGGATAATTAG
Same as SEQ ID NO. 82 except that a 1,353 bp
EcoRI fragment containing the 2μ sequence has
been removed
pGH420-EEVS-MTOx-2μΔ
                                        SEQ ID NO. 79
ACTATATGTGAAGGCATGGCTATGGCACGGCAGACATTCCGCCAGATCAT
CAATAGGCACCTTCATTCAACGTTTCCCATTGTTTTTTTCTACTATTGCT
TTGCTGTGGGAAAAACTTATCGAAAGATGACGACTTTTTCTTAATTCTCG
TTTTAAGAGCTTGGTGAGCGCTAGGAGTCACTGCCAGGTATCGTTTGAAC
ACGGCATTAGTCAGGGAAGTCATAACACAGTCCTTTCCCGCAATTTTCTT
TTTCTATTACTCTTGGCCTCCTCTAGTACACTCTATATTTTTTATGCCT
CGGTAATGATTTTCATTTTTTTTTTTCCACCTAGCGGATGACTCTTTTTT
TTTCTTAGCGATTGGCATTATCACATAATGAATTATACATTATATAAAGT
AATGTGATTTCTTCGAAGAATATACTAAAAAATGAGCAGGCAAGATAAAC
GAAGGCAAAGATGACAGAGCAGAAAGCCCTAGTAAAGCGTATTACAAATG
AAACCAAGATTCAGATTGCGATCTCTTTAAAGGGTGGTCCCCTAGCGATA
GAGCACTCGATCTTCCCAGAAAAGAGGCAGAAGCAGTAGCAGAACAGGC
CACACAATCGCAAGTGATTAACGTCCACACAGGTATAGGGTTTCTGGACC
ATATGATACATGCTCTGGCCAAGCATTCCGGCTGGTCGCTAATCGTTGAG
TGCATTGGTGACTTACACATAGACGACCATCACACCACTGAAGACTGCGG
GATTGCTCTCGGTCAAGCTTTTAAAGAGGCCCTAGGGGCCGTGCGTGGAG
TAAAAAGGTTTGGATCAGGATTTGCGCCTTTGGATGAGGCACTTTCCAGA
GCGGTGGTAGATCTTTCGAACAGGCCGTACGCAGTTGTCGAACTTGGTTT
GCAAAGGGAGAAAGTAGGAGATCTCTCTTGCGAGATGATCCCGCATTTTC
TTGAAAGCTTTGCAGAGGCTAGCAGAATTACCCTCCACGTTGATTGTCTG
CGAGGCAAGAATGATCATCACCGTAGTGAGAGTGCGTTCAAGGCTCTTGC
GGTTGCCATAAGAGAAGCCACCTCGCCCAATGGTACCAACGATGTTCCCT
CCACCAAAGGTGTTCTTATGTAGTGACACCGATTATTTAAAGCTGCAGCA
```

```
TACGATATATATACATGTGTATATATGTATACCTATGAATGTCAGTAAGT
ATGTATACGAACAGTATGATACTGAAGATGACAAGGTAATGCATCACACC
TTTCGAGAGGACGATGCCCGTGTCTAAATGATTCGACCAGCCTAAGAATG
TTCAACCCTGACTTCAACTCAAGACGCACAGATATTATAACATCTGCATA
ATAGGCATTTGCAAGAATTACTCGTGAGTAAGGAAAGAGTGAGGAACTAT
CGCATACCTGCATTTAAAGATGCCGATTTGGGCGCGAATCCTTTATTTTG
GCTTCACCCTCATACTATTATCAGGGCCAGAAAAAGGAAGTGTTTCCCTC
CTTCTTGAATTGATGTTACCCTCATAAAGCACGTGGCCTCTTATCGAGAA
AGAAATTACCGTCGCTCGTGATTTGTTTGCAAAAAGAACAAAACTGAAAA
AACCCAGACACGCTCGACTTCCTGTCTTCCTATTGATTGCAGCTTCCAAT
TTCGTCACACAACAAGGTCCTAGCGACGGCTCACAGGTTTTGTAACAAGC
AATCGAAGGTTCTGGAATGGCGGGAAAGGGTTTAGTACCACATGCTATGA
TGCCCACTGTGATCTCCAGAGCAAAGTTCGTTCGATCGTACTGTTACTCT
CTCTCTTTCAAACAGAATTGTCCGAATCGTGTGACAACAACAGCCTGTTC
TCACACACTCTTTTCTTCTAACCAAGGGGGTGGTTTAGTTTAGTAGAACC
TCGTGAAACTTACATTTACATATATATAAACTTGCATAAATTGGTCAATG
CAAGAAATACATATTTGGTCTTTTCTAATTCGTAGTTTTTCAAGTTCTTA
GATGCTTTCTTTTTCTCTTTTTTACAGATCATCAAGGAAGTAATTATCTA
CTTTTTACAACAAATATAATGCAAACGGCAAAAGTCTCGGACACCCCGGT
TGAATTTATTGTGGAACATCTGCTGAAGGCTAAGGAAATCGCTGAAAATC
ACGCTTCCATTCCGGTGGAACTGCGCGATAACCTGCAGAAAGCTCTGGAT
ATCGCGAGCGGCCTGGACGAATATCTGGAACAAATGAGCTCTAAAGAATC
TGAACCGCTGACGGAACTGTACCGCAAGTCAGTCTCGCATGATTGGAATA
AAGTGCACGCGGACGGCAAGACCCTGTTTCGTCTGCCGGTGACCTGCATT
ACGGGCCAGGTCGAAGGTCAAGTGCTGAAAATGCTGGTTCACATGAGTAA
AGCGAAGCGTGTCCTGGAAATTGGCATGTTTACCGGCTATGGTGCCCTGT
CCATGGCAGAAGCTCTGCCGGAAAACGGTCAGCTGATCGCTTGTGAACTG
GAACCGTACCTGAAAGATTTTGCACAACCGATTTTCGACAAGAGTCCGCA
TGGCAAAAAGATCACCGTGAAAACGGGTCCGGCAATGGATACCCTGAAGG
AACTGGCGGCCACGGGCGAACAGTTTGACATGGTTTTCATTGATGCGGAC
AAGCAAAACTACATCAACTACTACAAGTTCCTGCTGGATACAAACCTGCT
GCGTATTGATGGCGTCATCTGCGTGGACAATACGCTGTTCAAAGGTCGCG
TGTACCTGAAGGATAGCGTTGACGAAATGGGTAAAGCCCTGCGTGATTTT
AACCAGTTCGTGACCGCAGACCCGCGTGTTGAACAAGTCATTATCCCGCT
GCGCGATGGCCTGACCATTATCCGTCGCGTCCCGTATACGCCGCAGCCGA
ATAGCCAATCTGGTACCGTGACGTACGATGAAGTTTTTCGCGGCGTCCAG
GGTAAACCGGTTCTGGATCGTCTGCGCCTGGACGGCAAAGTGGCTTATGT
TACCGGTGCCGGTCAGGGTATTGGTCGTGCATTCGCCCATGCACTGGGCG
AAGCTGGTGCGAAAGTTGCCATTATCGATATGGACCGTGGCAAGGCCGAA
GATGTCGCACACGAACTGACCCTGAAAGGTATTAGTTCCATGGCCGTGGT
TGCAGATATCAGCAAACCGGATGACGTGCAGAAGATGATTGATGACATCG
```

```
TTACCAAATGGGGCACGCTGCATATTGCTTGCAACAATGCGGGTATCAAC
AAAAATAGTGCGTCCGAAGAAACCTCTCTGGAAGAATGGGATCAGACGTT
TAACGTCAATCTGCGTGGCACCTTCATGTGCTGTCAGGCAGCTGGTCGCG
TTATGCTGAAACAAGGCTATGGCAAGATTATCAACACCGCTAGCATGGCG
TCTCTGATTGTGCCGCACCCGCAGAAACAACTGTCATACAATACGTCGAA
AGCCGGCGTCGTGAAGCTGACCCAGACGCTGGGCACCGAATGGATCGATC
GTGGTGTGCGCGTTAACTGTATTTCACCGGGTATCGTGGATACCCCGCTG
ATTCATTCAGAATCGCTGGAACCGCTGGTTCAGCGTTGGCTGTCGGATAT
CCCGGCAGGTCGTCTGGCACAGGTGACGGACCTGCAAGCGGCCGTTGTCT
ATCTGGCCAGTGATGCATCCGACTACATGACCGGTCACAATCTGGTTATT
GAAGGCGGTCAGTCTCTGTGGTGAATTGAATTGAATTGAAATCGATAGAT
CAATTTTTTTCTTTTCTCTTTCCCCATCCTTTACGCTAAAATAATAGTTT
ATTTTATTTTTTGAATATTTTTATTTATATACGTATATATAGACTATTA
TTTATCTTTTAATGATTATTAAGATTTTTATTAAAAAAAAAATTCGCTCCT
CTTTTAATGCCTTTATGCAGTTTTTTTTTCCCATTCGATATTTCTATGTT
CGGGTTCAGCGTATTTTAAGTTTAATAACTCGAAAATTCTGCGTTCGTTA
AAGCTTTCGAGAAGGATATTATTTCGAAATAAACCGTGTTGTGTAAGCTT
GAAGCCTTTTTGCGCTGCCAATATTCTTATCCATCTATTGTACTCTTTAG
ATCCAGTATAGTGTATTCTTCCTGCTCCAAGCTCATCCCACTTGCAACAA
AATATTCACGTAGACGGATAGGTATAGCCAGACATCAGCAGCATACTTCG
GGAACCGTAGGCGAATTCCATACGTTGAAACTACGGCAAAGGATTGGTCA
GATCGCTTCATACAGGGAAAGTTCGGCAaaaggcggtaatacggttatcc
acagaatcaggggataacgcaggaaagaacatgtgagcaaaaggccagca
aaaggccaggaaccgtaaaaaggccgcgttgctggcgttttttccataggc
tccgcccccctgacgagcatcacaaaaatcgacgctcaagtcagaggtgg
cgaaacccgacaggactataaagataccaggcgtttccccctggaagctc
cctcgtgcgctctcctgttccgaccctgccgcttaccggatacctgtccg
cctttctcccttcgggaagcgtggcgctttctcatagctcacgctgtagg
tatctcagttcggtgtaggtcgttcgctccaagctgggctgtgtgcacga
accccccgttcagcccgaccgctgcgccttatccggtaactatcgtcttg
agtccaacccggtaagacacgacttatcgccactggcagcagccactggt
aacaggattagcagagcgaggtatgtaggcggtgctacagagttcttgaa
gtggtggcctaactacggctacactagaaggacagtatttggtatctgcg
ctctgctgaagccagttaccttcggaaaaagagttggtagctcttgatcc
ggcaaacaaaccaccgctggtagcggtggtttttttgtttgcaagcagca
gattacgcgcagaaaaaaaggatctcaagaagatcctttgatcttttcta
cggggtctgacgctcagtggaacgaaaactcacgttaagggattttggtc
atgagattatcaaaaaggatcttcacctagatccttttaaattaaaaatg
aagttttaaatcaatctaaagtatatatgagtaaacttggtctgacagtt
accaatgcttaatcagtgaggcacctatctcagcgatctgtctatttcgt
```

```
tcatccatagttgcctgactcccccgtcgtgtagataactacgatacggga
gggcttaccatctggccccagtgctgcaatgataccgcgagacccacgct
caccggctccagatttatcagcaataaaccagccagccggaagggccgag
cgcagaagtggtcctgcaactttatccgcctccatccagtctattaattg
ttgccgggaagctagagtaagtagttcgccagttaatagtttgcgcaacg
ttgttgccattgctacaggcatcgtggtgtcacgctcgtcgtttggtatg
gcttcattcagctccggttcccaacgatcaaggcgagttacatgatcccc
catgttgtgcaaaaaagcggttagctccttcggtcctccgatcgttgtca
gaagtaagttggccgcagtgttatcactcatggttatggcagcactgcat
aattctcttactgtcatgccatccgtaagatgcttttctgtgactggtga
gtactcaaccaagtcattctgagaatagtgtatgcggcgaccgagttgct
cttgcccggcgtcaatacgggataataccgcgccacatagcagaacttta
aaagtgctcatcattggaaaacgttcttcggggcgaaaactctcaaggat
cttaccgctgttgagatccagttcgatgtaacccactcgtgcacccaact
gatcttcagcatcttttactttcaccagcgtttctgggtgagcaaaaaca
ggaaggcaaaatgccgcaaaaaagggaataagggcgacacggaaatgttg
aatactcatactcttcctttttcAGATTACTCTAACGCCTCAGCCATCAT
CGGTAATAGCTCGAATTGCTGAGAACCCGTGACACCGCGAATCCTTACAT
CACACCCAATCCCCCACAAGTGATCCCCCACACACCATAGCTTCAAATG
TTTCTACTCCTTTTTTTACTCTTCCAGATTTTCTCGGACTCCGCGCATCGC
CGTACCACTTCAAAACACCCAAGCACAGCATACTAAATTTCCCCTCTTTC
TTCCTCTAGGGTGTCGTTAATTACCCGTACTAAAGGTTTGGAAAAGAAAA
AAGAGACCGCCTCGTTTCTTTTTCTTCGTCGAAAAAGGCAATAAAAATTT
TTATCACGTTTCTTTTTCTTGAAAATTTTTTTTTTTGATTTTTTTCTCTT
TCGATGACCTCCCATTGATATTTAAGTTAATAAACGGTCTTCAATTTCTC
AAGTTTCAGTTTCATTTTTCTTGTTCTATTACAACTTTTTTTACTTCTTG
CTCATTAGAAAGAAAGCATAGCAATCTAATCTAAGTTTTAATTACAAAAC
TAGTATGGAACGTCCGGGCGAAACCTTTACCGTCAGCTCCCCGGAAGAAG
TGCGTCTGCCGTCTGTTCACCGCGATAACTCAACGATGGAAAACCATAAT
AAACAGGAAACGGTGTTTTCTCTGGTTCAAGTCAAGGGTACCTGGAAGCG
TAAGGCGGGCCAGAACGCCAAACAGGGTATGAAGGGCCGCGTTAGTCCGG
CCAAAATTTATGAAAGCTCTAGTTCCTCAGGTACCACGTGGACGGTGGTT
ACCCCGATCACCTTTACGTACACCGTGACGCAGACCAAAAACCTGCTGGA
CCCGTCGAACGACACGCTGCTGCTGGGCCATATTATCGATACCCAGCAAC
TGGAAGCTGTCCGCAGCAATACGAAACCGCTGAAGCGTTTCATTGTGATG
GACGAAGTCGTGTATAATATCTACGGTTCCCAAGTCACCGAATATCTGGA
AGCGCGACCGTGCTGTACCGTATTCTGCCGCTGCCGACCACGGAAGAAA
ATAAATCAATGGATATGGCTCTGAAGATTCTGGAAGAAGTGCACCAGTTT
GGTATCGACCGTCGCACCGAACCGATTATCGCGATTGGCGGTGGCGTTTG
CCTGGATATCGTCGGTCTGGCAGCCTCTCTGTATCGTCGCCGTACCCCGT
ACATTCGTGTGCCGACCACGCTGCTGTCTTATATCGACGCAAGTGTGGGT
```

```
GCTAAAACGGGCGTTAACTTTGCTAATTGTAAAAACAAGCTGGGTACCTA
CATTGCGCCGGTTGCAGCTTTTCTGGATCGTTCGTTCATTCAGAGCATCC
CGCGCCGTCACATCGCAAACGGTCTGGCCGAAATGCTGAAAATGGCCCTG
ATGAAGCATCGCGGTCTGTTCGAACTGCTGGAAGTTCACGGCCAGTTTCT
GCTGGATAGTAAATTCCAATCGGCAAGCGTCCTGGAAAACGATCGCATTG
ACCCGGCCTCTGTCAGTACGCGTGTGGCAATCGAAACCATGCTGGAAGAA
CTGGCCCCGAATCTGTGGGAAGATGACCTGGATCGTCTGGTGGACTTTGG
TCATCTGATTTCGCCGCAGCTGGAAATGAAAGTTCTGCCGGCACTGCTGC
ACGGCGAAGCTGTCAACATTGATATGGCGTATATGGTGTACGTTTCATGC
GAAATCGGTCTGCTGACCGAAGAAGAAAAATTCCGCATTATCTGCTGTAT
GATGGGCCTGGAACTGCCGGTGTGGCATCAGGATTTTACCTTCGCACTGG
TTCAAAAGTCCCTGTGTGACCGCCTGCAGCACTCAGGTGGCCTGGTTCGT
ATGCCGCTGCCGACGGGTCTGGGTCGTGCAGAATTTTTAATGATACCGA
CGAAGGTAGCCTGTTCCGCGCGTATGAAAAATGGTGCGATGAACTGTCCA
CCGGCTCACCGCAGTGACTCGAGTCATGTAATTAGTTATGTCACGCTTAC
ATTCACGCCCTCCCCCCACATCCGCTCTAACCGAAAAGGAAGGAGTTAGA
CAACCTGAAGTCTAGGTCCCTATTTATTTTTTTATAGTTATGTTAGTATT
AAGAACGTTATTTATATTTCAAATTTTTCTTTTTTTTCTGTACAGACGCG
TGTACGCATGTAACATTATACTGAAAACCTTGCTTGAGAAGGTTTTGGGA
CGCTCGAAGGCTTTAATTTGCGGCCAATATTATTGAAGCATTTATCAGGG
TTATTGTCTCATGAGCGGATACATATTTGAATGTATTTAGAAAAATAAAC
AAATAGGGGTTCCGCGCACATTTCCCCGAAAAGTGCCACCTGACGTCTAA
GAAACCATTATTATCATGACATTAACCTATAAAAATAGGCGTATCACGAG
GCCCTTTCGTCTCGCGCGTTTCGGTGATGACGGTGAAAACCTCTGACACA
TGCAGCTCCCGGAGACGGTCACAGCTTGTCTG
``` pXP416-SHB17-2μΔ

SEQ ID NO. 80

```
tcgcgcgtttcggtgatgacggtgaaaacctctgacacatgcagctcccg
agacggtcacagcttgtctgtaagcggatgccgggagcagacaagcccg
tcagggcgcgtcagcgggtgttggcgggtgtcggggctggcttaactatg
cggcatcagagcagattgtactgagagtgcaccatatgcggtgtgaaata
ccgcacagatgcgtaaggagaaaataccgcatcaggcgccattcgccatt
caggctgcgcaactgttgggaagggcgatcggtgcgggcctcttcgctat
tacgccagctggcgaaaggggggatgtgctgcaagcgattaagttgggta
acgccagggttttcccagtcacgacgttgtaaaacgacggccagtgccaa
gcttgcatgcctgcaggtcgactctagaggatcCCCGGGATAACTTCGTA
TAGCATACATTATACGAAGTTATAACGACATTACTATATATAATATAG
GAAGCATTTAATAGAACAGCATCGTAATATATGTGTACTTTGCAGTTATG
ACGCCAGATGGCAGTAGTGGAAGATATTCTTTATTGAAAAATAGCTTGTC
ACCTTACGTACAATCTTGATCGGAGCTTTTCTTTTTTTGCCGATTAAGA
ATTAATTCGGTCGAAAAAAGAAAGGAGAGGGCCAAGAGGGAGGGCATTG
GTGACTATTGAGCACGTGAGTATACGTGATTAAGCACACAAAGGCAGCTT
GGAGTATGTCTGTTATTAATTTCACAGGTAGTTCTGGTCCATTGGTGAAA
GTTTGCGGCTTGCAGAGCACAGAGGCCGCAGAATGTGCTCTAGATTCCGA
TGCTGACTTGCTGGGTATTATATGTGTGCCCAATAGAAAGAGAACAATTG
ACCCGGTTATTGCAAGGAAAATTTCAAGTCTTGTAAAAGCATATAAAAAT
AGTTCAGGCACTCCGAAATACTTGGTTGGCGTGTTTCGTAATCAACCTAA
GGAGGATGTTTTGGCTCTGGTCAATGATTACGGCATTGATATCGTCCAAC
TGCATGGAGATGAGTCGTGGCAAGAATACCAAGAGTTCCTCGGTTTGCCA
GTTATTAAAAGACTCGTATTTCCAAAAGACTGCAACATACTACTCAGTGC
AGCTTCACAGAAACCTCATTCGTTTATTCCCTTGTTTGATTCAGAAGCAG
GTGGGACAGGTGAACTTTTGGATTGGAACTCGATTTCTGACTGGGTTGGA
AGGCAAGAGAGCCCCGAAAGCTTACATTTTATGTTAGCTGGTGGACTGAC
GCCAGAAAATGTTGGTGATGCGCTTAGATTAAATGGCGTTATTGGTGTTG
ATGTAAGCGGAGGTGTGGAGACAAATGGTGTAAAAGACTCTAACAAAATA
GCAAATTTCGTCAAAAATGCTAAGAAATAGGTTATTACTGAGTAGTATTT
ATTTAAGTATTGTTTGTGCACTTGCCTGATAACTTCGTATAGCATACATT
ATACGAAGTTATCCCGGGtaccgagctcGAATTCgtaatcatggtcatag
ctgtttcctgtgtgaaattgttatccgctcacaattccacacaacatacg
agccggaagcataaagtgtaaagcctggggtgcctaatgagtgagctaac
tcacattaattgcgttgcgctcactgcccgctttccagtcgggaaacctg
tcgtgccagctgcattaatgaatcggccaacgcgcggggagaggcggttt
gcgtattgggcgctcttccgcttcctcgctcactgactcgctgcgctcgg
tcgttcggctgcggcgagcggtatcagctcactcaaaggcggtaatacgg
ttatccacagaatcaggggataacgcaggaaagaacatgtgagcaaaagg
ccagcaaaaggccaggaaccgtaaaaaggccgcgttgctggcgtttttcc
ataggctccgcccccctgacgagcatcacaaaaatcgacgctcaagtcag
aggtggcgaaacccgacaggactataaagataccaggcgtttccccctgg
aagctccctcgtgcgctctcctgttccgaccctgccgcttaccggatacc
tgtccgcctttctcccttcgggaagcgtggcgctttctcatagctcacgc
tgtaggtatctcagttcggtgtaggtcgttcgctccaagctgggctgtgt
gcacgaaccccccgttcagcccgaccgctgcgccttatccggtaactatc
gtcttgagtccaacccggtaagacacgacttatcgccactggcagcagcc
actggtaacaggattagcagagcgaggtatgtaggcggtgctacagagtt
cttgaagtggtggcctaactacggctacactagaaggacagtatttggta
tctgcgctctgctgaagccagttaccttcggaaaaagagttggtagctct
tgatccggcaaacaaaccaccgctggtagcggtggtttttttgtttgcaa
gcagcagattacgcgcagaaaaaaaggatctcaagaagatcctttgatct
tttctacggggtctgacgctcagtggaacgaaaactcacgttaagggatt
ttggtcatgagattatcaaaaaggatcttcacctagatccttttaaatta
aaaatgaagttttaaatcaatctaaagtatatatgagtaaacttggtctg
acagttaccaatgcttaatcagtgaggcacctatctcagcgatctgtcta
```

-continued tttcgttcatccatagttgcctgactccccgtcgtgtagataactacgat acgggagggcttaccatctggccccagtgctgcaatgataccgcgagacc cacgctcaccggctccagatttatcagcaataaaccagccagccggaagg gccgagcgcagaagtggtcctgcaactttatccgcctccatccagtctat taattgttgccgggaagctagagtaagtagttcgccagttaatagtttgc gcaacgttgttgccattgctacaggcatcgtggtgtcacgctcgtcgttt ggtatggcttcattcagctccggttcccaacgatcaaggcgagttacatg atccccatgttgtgcaaaaaagcggttagctccttcggtcctccgatcg ttgtcagaagtaagttggccgcagtgttatcactcatggttatggcagca ctgcataattctcttactgtcatgccatccgtaagatgcttttctgtgac tggtgagtactcaaccaagtcattctgagaatagtgtatgcggcgaccga gttgctcttgcccggcgtcaatacgggataataccgcgccacatagcaga actttaaaagtgctcatcattggaaaacgttcttcggggcgaaaactctc aaggatcttaccgctgttgagatccagttcgatgtaacccactcgtgcac ccaactgatcttcagcatcttttactttcaccagcgtttctgggtgagca aaaacaggaaggcaaaatgccgcaaaaaagggaataaggggcgacacggaa atgttgaatactcatactcttcctttttcAATATTACCGCGAATCCTTAC

ATCACACCCAATCCCCCACAAGTGATCCCCCACACACCATAGCTTCAAAA

TGTTTCTACTCCTTTTTTACTCTTCCAGATTTTCTCGGACTCCGCGCATC

GCCGTACCACTTCAAAACACCCAAGCACAGCATACTAAATTTCCCCTCTT

TCTTCCTCTAGGGTGTCGTTAATTACCCGTACTAAAGGTTTGGAAAAGAA

AAAAGAGACCGCCTCGTTTCTTTTTCTTCGTCGAAAAAGGCAATAAAAAT

TTTTATCACGTTTCTTTTTCTTGAAAATTTTTTTTTTGATTTTTTCTC

TTTCGATGACCTCCCATTGATATTTAAGTTAATAAACGGTCTTCAATTTC

TCAAGTTTCAGTTTCATTTTTCTTGTTCTATTACAACTTTTTTTACTTCT

TGCTCATTAGAAAGAAAGCATAGCAATCTAATCTAAGTTTTAATTACAAA

ACTAGTATGCCTTCGCTAACCCCCAGATGTATCATTGTCAGACACGGTCA

AACTGAATGGTCCAAGTCAGGCCAGTATACTGGTTTGACAGATCTACCGT

TAACGCCCTACGGTGAGGGCCAAATGTTGAGGACCGGTGAGAGTGTTTTC

CGCAATAATCAGTTTTTGAATCCAGACAACATCACTTATATCTTCACCTC

TCCACGTTTGCGTGCCAGGCAAACTGTGGATTTGGTTTTGAAACCATTAA

GCGACGAGCAAAGAGCTAAGATCCGTGTGGTGGTAGACGACGACTTGCGA

GAGTGGGAGTACGGTGACTACGAGGGAATGCTGACTCAGAAATCATTGA

ATTGAGAAAGTCACGCGGTTTGGACAAGGAGAGGCCATGGAATATCTGGA

GAGATGGGTGTGAGAACGGTGAGACTACTCAGCAAATTGGGTTGAGACTT

TCCCGCGCTATTGCCAGAATCCAGAACTTGCACCGCAAGCACCAGAGTGA

GGGCAGAGCATCAGACATCATGGTCTTTGCGCACGGACATGCATTGCGTT

ATTTTGCTGCTATTTGGTTTGGACTGGGTGTGCAAAAGAAGTGTGAGACG

ATTGAAGAAATTCAAAATGTCAAATCTTATGATGACGACACAGTTCCATA

TGTGAAATTGGAATCTTACAGACATTTGGTAGACAATCCATGTTTCTTAC

-continued

TGGACGCCGGTGGGATTGGTGTTTTGTCATACGCTCACCACAACATTGAC

GAACCTGCATTGGAATTAGCAGGTCCATTTGTCTCACCACCAGAGGAGGA

ATCCCAGCATGGCGATGTGTAACTCGAGTCATGTAATTAGTTATGTCACG

CTTACATTCACGCCCTCCCCCCACATCCGCTCTAACCGAAAAGGAAGGAG

TTAGACAACCTGAAGTCTAGGTCCCTATTTATTTTTTTATAGTTATGTTA

GTATTAAGAACGTTATTTATATTTCAAATTTTTCTTTTTTTTCTGTACAG

ACGCGTGTACGCATGTAACATTATACTGAAAACCTTGCTTGAGAAGGTTT

TGGGACGCTCGAAGGCTTTAATTTGCGGCCAATATTattgaagcatttat cagggttattgtctcatgagcggatacatatttgaatgtatttagaaaaa taaacaaatagggggttccgcgcacatttccccgaaaagtgccacctgacg tctaagaaaccattattatcatgacattaacctataaaaataggcgtatc acgaggccctttcgtc PHO13 = YDL236W SGDID: S000002395, chrIV:
32296..33234

SEQ ID NO. 81
ATGACTGCTCAACAAGGTGTACCAATAAAGATAACCAATAAGGAGATTGC

TCAAGAATTCTTGGACAAATATGACACGTTTCTGTTCGATTGTGATGGTG

TATTATGGTTAGGTTCTCAAGCATTACCATACACCCTGGAAATTCTAAAC

CTTTTGAAGCAATTGGGCAAACAACTGATCTTCGTTACGAATAACTCTAC

CAAGTCCCGTTTAGCATACACGAAAAAGTTTGCTTCGTTTGGTATTGATG

TCAAAGAAGAACAGATTTTCACCTCTGGTTATGCGTCAGCTGTTTATATT

CGTGACTTTCTGAAATTGCAGCCTGGCAAAGATAAGGTATGGGTATTTGG

AGAAAGCGGTATTGGTGAAGAATTGAAACTAATGGGGTACGAATCTCTAG

GAGGTGCCGATTCCAGATTGGATACGCCGTTCGATGCAGCTAAATCACCA

TTTTTGGTGAACGGCCTTGATAAGGATGTTAGTTGTGTTATTGCTGGGTT

AGACACGAAGGTAAATTACCACCGTTTGGCTGTTACACTGCAGTATTTGC

AGAAGGATTCTGTTCACTTTGTTGGTACAAATGTTGATTCTACTTTCCCG

CAAAAGGGTTATACATTTCCCGGTGCAGGCTCCATGATTGAATCATTGGC

ATTCTCATCTAATAGGAGGCCATCGTACTGTGGTAAGCCAAATCAAAATA

TGCTAAACAGCATTATATCGGCATTCAACCTGGATAGATCAAAGTGCTGT

ATGGTTGGTGACAGATTAAACACCGATATGAAATTCGGTGTTGAAGGTGG

GTTAGGTGGCACACTACTCGTTTTGAGTGGTATTGAAACCGAAGAGAGAG

CCTTGAAGATTTCGCACGATTATCCAAGACCTAAATTTTACATTGATAAA

CTTGGTGACATCTACACCTTAACCAATAATGAGTTATAG

Same as SEQ ID NO. 79 with the addition of a
1,353 bp EcoRI fragment containing the 2µ sequence
pGH420-EEVS-MTOx

SEQ ID NO. 82
ACTATATGTGAAGGCATGGCTATGGCACGGCAGACATTCCGCCAGATCAT

CAATAGGCACCTTCATTCAACGTTTCCCATTGTTTTTTTCTACTATTGCT

TTGCTGTGGGAAAAACTTATCGAAAGATGACGACTTTTTCTTAATTCTCG

TTTTAAGAGCTTGGTGAGCGCTAGGAGTCACTGCCAGGTATCGTTTGAAC

ACGGCATTAGTCAGGGAAGTCATAACACAGTCCTTTCCCGCAATTTTCTT

TTTCTATTACTCTTGGCCTCCTCTAGTACACTCTATATTTTTTATGCCT

-continued

CGGTAATGATTTTCATTTTTTTTTTTCCACCTAGCGGATGACTCTTTTTT
TTTCTTAGCGATTGGCATTATCACATAATGAATTATACATTATATAAAGT
AATGTGATTTCTTCGAAGAATATACTAAAAAATGAGCAGGCAAGATAAAC
GAAGGCAAAGATGACAGAGCAGAAAGCCCTAGTAAAGCGTATTACAAATG
AAACCAAGATTCAGATTGCGATCTCTTTAAAGGGTGGTCCCCTAGCGATA
GAGCACTCGATCTTCCCAGAAAAAGAGGCAGAAGCAGTAGCAGAACAGGC
CACACAATCGCAAGTGATTAACGTCCACACAGGTATAGGGTTTCTGGACC
ATATGATACATGCTCTGGCCAAGCATTCCGGCTGGTCGCTAATCGTTGAG
TGCATTGGTGACTTACACATAGACGACCATCACACCACTGAAGACTGCGG
GATTGCTCTCGGTCAAGCTTTTAAAGAGGCCCTAGGGGCCGTGCGTGGAG
TAAAAAGGTTTGGATCAGGATTTGCGCCTTTGGATGAGGCACTTTCCAGA
GCGGTGGTAGATCTTTCGAACAGGCCGTACGCAGTTGTCGAACTTGGTTT
GCAAAGGGAGAAAGTAGGAGATCTCTCTTGCGAGATGATCCCGCATTTTC
TTGAAAGCTTTGCAGAGGCTAGCAGAATTACCCTCCACGTTGATTGTCTG
CGAGGCAAGAATGATCATCACCGTAGTGAGAGTGCGTTCAAGGCTCTTGC
GGTTGCCATAAGAGAAGCCACCTCGCCCAATGGTACCAACGATGTTCCCT
CCACCAAAGGTGTTCTTATGTAGTGACACCGATTATTTAAAGCTGCAGCA
TACGATATATATACATGTGTATATATGTATACCTATGAATGTCAGTAAGT
ATGTATACGAACAGTATGATACTGAAGATGACAAGGTAATGCATCACACC
TTTCGAGAGGACGATGCCCGTGTCTAAATGATTCGACCAGCCTAAGAATG
TTCAACCCTGACTTCAACTCAAGACGCACAGATATTATAACATCTGCATA
ATAGGCATTTGCAAGAATTACTCGTGAGTAAGGAAAGAGTGAGGAACTAT
CGCATACCTGCATTTAAAGATGCCGATTTGGGCGCGAATCCTTTATTTTG
GCTTCACCCTCATACTATTATCAGGGCCAGAAAAAGGAAGTGTTTCCCTC
CTTCTTGAATTGATGTTACCCTCATAAAGCACGTGGCCTCTTATCGAGAA
AGAAATTACCGTCGCTCGTGATTTGTTTGCAAAAAGAACAAAACTGAAAA
AACCCAGACACGCTCGACTTCCTGTCTTCCTATTGATTGCAGCTTCCAAT
TTCGTCACACAACAAGGTCCTAGCGACGGCTCACAGGTTTTGTAACAAGC
AATCGAAGGTTCTGGAATGGCGGGAAAGGGTTTAGTACCACATGCTATGA
TGCCCACTGTGATCTCCAGAGCAAAGTTCGTTCGATCGTACTGTTACTCT
CTCTCTTTCAAACAGAATTGTCCGAATCGTGTGACAACAACAGCCTGTTC
TCACACACTCTTTTCTTCTAACCAAGGGGGTGGTTTAGTTTAGTAGAACC
TCGTGAAACTTACATTTACATATATATAAACTTGCATAAATTGGTCAATG
CAAGAAATACATATTTGGTCTTTTCTAATTCGTAGTTTTTCAAGTTCTTA
GATGCTTTCTTTTTCTCTTTTTACAGATCATCAAGGAAGTAATTATCTA
CTTTTTACAACAAATATAATGCAAACGGCAAAGTCTCGGACACCCCGGT
TGAATTTATTGTGGAACATCTGCTGAAGGCTAAGGAAATCGCTGAAAATC
ACGCTTCCATTCCGGTGGAACTGCGCGATAACCTGCAGAAAGCTCTGGAT
ATCGCGAGCGGCCTGGACGAATATCTGGAACAAATGAGCTCTAAAGAATC
TGAACCGCTGACGGAACTGTACCGCAAGTCAGTCTCGCATGATTGGAATA
AAGTGCACGCGGACGGCAAGACCCTGTTTCGTCTGCCGGTGACCTGCATT

ACGGGCCAGGTCGAAGGTCAAGTGCTGAAAATGCTGGTTCACATGAGTAA
AGCGAAGCGTGTCCTGGAAATTGGCATGTTTACCGGCTATGGTGCCCTGT
CCATGGCAGAAGCTCTGCCGGAAAACGGTCAGCTGATCGCTTGTGAACTG
GAACCGTACCTGAAAGATTTTGCACAACCGATTTTCGACAAGAGTCCGCA
TGGCAAAAAGATCACCGTGAAAACGGGTCCGGCAATGGATACCCTGAAGG
AACTGGCGGCCACGGGCGAACAGTTTGACATGGTTTTCATTGATGCGGAC
AAGCAAAACTACATCAACTACTACAAGTTCCTGCTGGATCACAACCTGCT
GCGTATTGATGGCGTCATCTGCGTGGACAATACGCTGTTCAAAGGTCGCG
TGTACCTGAAGGATAGCGTTGACGAAATGGGTAAAGCCCTGCGTGATTTT
AACCAGTTCGTGACCGCAGACCCGCGTGTTGAACAAGTCATTATCCCGCT
GCGCGATGGCCTGACCATTATCCGTCGCGTCCCGTATACGCCGCAGCCGA
ATAGCCAATCTGGTACCGTGACGTACGATGAAGTTTTTCGCGGCGTCCAG
GGTAAACCGGTTCTGGATCGTCTGCGCCTGGACGGCAAAGTGGCTTATGT
TACCGGTGCCGGTCAGGGTATTGGTCGTGCATTCGCCCATGCACTGGGCG
AAGCTGGTGCGAAAGTTGCCATTATCGATATGGACCGTGGCAAGGCCGAA
GATGTCGCACACGAACTGACCCTGAAAGGTATTAGTTCCATGGCCGTGGT
TGCAGATATCAGCAAACCGGATGACGTGCAGAAGATGATTGATGACATCG
TTACCAAATGGGGCACGCTGCATATTGCTTGCAACAATGCGGGTATCAAC
AAAAATAGTGCGTCCGAAGAAACCTCTCTGGAAGAATGGGATCAGACGTT
TAACGTCAATCTGCGTGGCACCTTCATGTGCTGTCAGGCAGCTGGTCGCG
TTATGCTGAAACAAGGCTATGGCAAGATTATCAACACCGCTAGCATGGCG
TCTCTGATTGTGCCGCACCCGCAGAAACAACTGTCATACAATACGTCGAA
AGCCGGCGTCGTGAAGCTGACCCAGACGCTGGGCACCGAATGGATCGATC
GTGGTGTGCGCGTTAACTGTATTTCACCGGGTATCGTGGATACCCCGCTG
ATTCATTCAGAATCGCTGGAACCGCTGGTTCAGCGTTGGCTGTCGGATAT
CCCGGCAGGTCGTCTGGCACAGGTGACGGACCTGCAAGCGGCCGTTGTCT
ATCTGGCCAGTGATGCATCCGACTACATGACCGGTCACAATCTGGTTATT
GAAGGCGGTCAGTCTCTGTGGTGAATTGAATTGAATTGAAATCGATAGAT
CAATTTTTTCTTTTCTCTTTCCCCATCCTTTACGCTAAAATAATAGTTT
ATTTTATTTTTTGAATATTTTTTATTTATATACGTATATATAGACTATTA
TTTATCTTTTAATGATTATTAAGATTTTTATTAAAAAAAAATTCGCTCCT
CTTTTAATGCCTTTATGCAGTTTTTTTTTCCCATTCGATATTTCTATGTT
CGGGTTCAGCGTATTTTAAGTTTAATAACTCGAAAATTCTGCGTTCGTTA
AAGCTTTCGAGAAGGATATTATTTCGAAATAAACCGTGTTGTGTAAGCTT
GAAGCCTTTTTGCGCTGCCAATATTCTTATCCATCTATTGTACTCTTTAG
ATCCAGTATAGTGTATTCTTCCTGCTCCAAGCTCATCCCACTTGCAACAA
AATATTCACGTAGACGGATAGGTATAGCCAGACATCAGCAGCATACTTCG
GGAACCGTAGGCGAATTCaacgaagcatctgtgcttcattttgtagaaca
aaaatgcaacgcgagagcgctaattttcaaacaaagaatctgagctgca
ttttttacagaacagaaatgcaacgcgaaagcgctattttaccaacgaaga -continued

```
atctgtgcttcattttttgtaaaacaaaaatgcaacgcgagagcgctaatt
tttcaaacaaagaatctgagctgcatttttacagaacagaaatgcaacgc
gagagcgctattttaccaacaaagaatctatacttctttttttgttctaca
aaaatgcatcccgagagcgctattttttctaacaaagcatcttagattact
ttttttctcctttgtgcgctctataatgcagtctcttgataacttttttgc
actgtaggtccgttaaggttagaagaaggctactttggtgtctattttct
cttccataaaaaaagcctgactccacttcccgcgtttactgattactagc
gaagctgcgggtgcattttttcaagataaaggcatcccccgattatattct
ataccgatgtggattgcgcatactttgtgaacagaaagtgatagcgttga
tgattcttcattggtcagaaaattatgaacggtttcttctattttgtctc
tatatactacgtataggaaatgtttacattttcgtattgttttcgattca
ctctatgaatagttcttactacaattttttttgtctaaagagtaatactag
agataaacataaaaaatgtagaggtcgagtttagatgcaagttcaaggag
cgaaaggtggatgggtaggttatatagggatatagcacagagatatatag
caaagagatactttgagcaatgtttgtggaagcggtattcgcaatattt
tagtagctcgttacagtccggtgcgttttggttttttgaaagtgcgtct
tcagagcgcttttggttttcaaaagcgctctgaagttcctatactttcta
gagaataggaacttcggaataggaacttcaaagcgtttccgaaaacgagc
gcttccgaaaatgcaacgcgagctgcgcacatacagctcactgttcacgt
cgcacctatatctgcgtgttgcctgtatatatatacatgagaagaacg
gcatagtgcgtgtttatgcttaaatgcgtacttatatgcgtctatttatg
taggatgaaaggtagtctagtacctcctgtgatattatcccattccatgc
ggggtatcgtatgcttccttcagcactacccctttagctgttctatatgct
gccactcctcaattggattagtctcatccttcaatgctatcatttcctt
gatattggatcatacGAATTCCATACGTTGAAACTACGGCAAAGGATTGG
TCAGATCGCTTCATACAGGGAAAGTTCGGCAaaaggcggtaatacggtta
tccacagaatcaggggataacgcaggaaagaacatgtgagcaaaaggcca
gcaaaaggccaggaaccgtaaaaaggccgcgttgctggcgtttttccata
ggctccgcccccctgacgagcatcacaaaaatcgacgctcaagtcagagg
tggcgaaacccgacaggactataaagataccaggcgtttccccctggaag
ctccctcgtgcgctctcctgttccgaccctgccgcttaccggatacctgt
ccgcctttctcccttcgggaagcgtggcgctttctcatagctcacgctgt
aggtatctcagttcggtgtaggtcgttcgctccaagctgggctgtgtgca
cgaaccccccgttcagcccgaccgctgcgccttatccggtaactatcgtc
ttgagtccaacccggtaagacacgacttatcgccactggcagcagccact
ggtaacaggattagcagagcgaggtatgtaggcggtgctacagagttctt
gaagtggtggcctaactacggctacactagaaggacagtatttggtatct
gcgctctgctgaagccagttaccttcggaaaaagagttggtagctcttga
tccggcaaacaaaccaccgctggtagcggtggtttttttgtttgcaagca
gcagattacgcgcagaaaaaaaggatctcaagaagatcctttgatctttt
ctacggggtctgacgctcagtggaacgaaaactcacgttaagggattttg
```

-continued

```
gtcatgagattatcaaaaaggatcttcacctagatccttttaaattaaaa
atgaagttttaaatcaatctaaagtatatatgagtaaacttggtctgaca
gttaccaatgcttaatcagtgaggcacctatctcagcgatctgtctattt
cgttcatccatagttgcctgactcccgtcgtgtagataactacgatacg
ggagggcttaccatctggccccagtgctgcaatgataccgcgagacccac
gctcaccggctccagatttatcagcaataaaccagccagccggaagggcc
gagcgcagaagtggtcctgcaactttatccgcctccatccagtctattaa
ttgttgccgggaagctagagtaagtagttcgccagttaatagtttgcgca
acgttgttgccattgctacaggcatcgtggtgtcacgctcgtcgtttggt
atggcttcattcagctccggttcccaacgatcaaggcgagttacatgatc
ccccatgttgtgcaaaaaagcggttagctccttcggtcctccgatcgttg
tcagaagtaagttggccgcagtgttatcactcatggttatggcagcactg
cataattctcttactgtcatgccatccgtaagatgcttttctgtgactgg
tgagtactcaaccaagtcattctgagaatagtgtatgcggcgaccgagtt
gctcttgcccggcgtcaatacgggataataccgcgccacatagcagaact
ttaaaagtgctcatcattggaaaacgttcttcggggcgaaaactctcaag
gatcttaccgctgttgagatccagttcgatgtaacccactcgtgcaccca
actgatcttcagcatcttttactttcaccagcgtttctgggtgagcaaaa
acaggaaggcaaaatgccgcaaaaaagggaataagggcgacacggaaatg
ttgaatactcatactcttccttttcAGATTACTCTAACGCCTCAGCCAT
CATCGGTAATAGCTCGAATTGCTGAGAACCCGTGACACCGCGAATCCTTA
CATCACACCCAATCCCCCACAAGTGATCCCCACACACCATAGCTTCAAA
ATGTTTCTACTCCTTTTTTACTCTTCCAGATTTTCTCGGACTCCGCGCAT
CGCCGTACCACTTCAAAACACCCAAGCACAGCATACTAAATTTCCCCTCT
TTCTTCCTCTAGGGTGTCGTTAATTACCCGTACTAAAGGTTTGGAAAAGA
AAAAGAGACCGCCTCGTTTCTTTTTCTTCGTCGAAAAAGGCAATAAAAA
TTTTTATCACGTTTCTTTTTCTTGAAAATTTTTTTTTTTGATTTTTTTCT
CTTTCGATGACCTCCCATTGATATTTAAGTTAATAAACGGTCTTCAATTT
CTCAAGTTTCAGTTTCATTTTTCTTGTTCTATTACAACTTTTTTTACTTC
TTGCTCATTAGAAAGAAAGCATAGCAATCTAATCTAAGTTTTAATTACAA
AACTAGTATGGAACGTCCGGGCGAAACCTTTACCGTCAGCTCCCCGGAAG
AAGTGCGTCTGCCGTCTGTTCACCGCGATAACTCAACGATGGAAAACCAT
AATAAACAGGAAACGGTGTTTTCTCTGGTTCAAGTCAAGGGTACCTGGAA
GCGTAAGGCGGGCCAGAACGCCAAACAGGGTATGAAGGGCCGCGTTAGTC
CGGCCAAAATTTATGAAAGCTCTAGTTCCTCAGGTACCACGTGGACGGTG
GTTACCCCGATCACCTTTACGTACACCGTGACGCAGACCAAAAACCTGCT
GGACCCGTCGAACGACACGCTGCTGCTGGGCCATATTATCGATACCCAGC
AACTGGAAGCTGTCCGCAGCAATACGAAACCGCTGAAGCGTTTCATTGTG
ATGGACGAAGTCGTGTATAATATCTACGGTTCCCAAGTCACCGAATATCT
GGAAGCGCGCAACGTGCTGTACCGTATTCTGCCGCTGCCGACCACGGAAG
```

```
AAAATAAATCAATGGATATGGCTCTGAAGATTCTGGAAGAAGTGCACCAG
TTTGGTATCGACCGTCGCACCGAACCGATTATCGCGATTGGCGGTGGCGT
TTGCCTGGATATCGTCGGTCTGGCAGCCTCTCTGTATCGTCGCCGTACCC
CGTACATTCGTGTGCCGACCACGCTGCTGTCTTATATCGACGCAAGTGTG
GGTGCTAAAACGGGCGTTAACTTTGCTAATTGTAAAAACAAGCTGGGTAC
CTACATTGCGCCGGTTGCAGCTTTTCTGGATCGTTCGTTCATTCAGAGCA
TCCCGCGCCGTCACATCGCAAACGGTCTGGCCGAAATGCTGAAAATGGCC
CTGATGAAGCATCGCGGTCTGTTCGAACTGCTGGAAGTTCACGGCCAGTT
TCTGCTGGATAGTAAATTCCAATCGGCAAGCGTCCTGGAAAACGATCGCA
TTGACCCGGCCTCTGTCAGTACGCGTGTGGCAATCGAAACCATGCTGGAA
GAACTGGCCCCGAATCTGTGGGAAGATGACCTGGATCGTCTGGTGGACTT
TGGTCATCTGATTTCGCCGCAGCTGGAAATGAAAGTTCTGCCGGCACTGC
TGCACGGCGAAGCTGTCAACATTGATATGGCGTATATGGTGTACGTTTCA
TGCGAAATCGGTCTGCTGACCGAAGAAGAAAAATTCCGCATTATCTGCTG
TATGATGGGCCTGGAACTGCCGGTGTGGCATCAGGATTTTACCTTCGCAC
TGGTTCAAAAGTCCCTGTGTGACCGCCTGCAGCACTCAGGTGGCCTGGTT
CGTATGCCGCTGCCGACGGGTCTGGGTCGTGCAGAAATTTTTAATGATAC
CGACGAAGGTAGCCTGTTCCGCGCGTATGAAAAATGGTGCGATGAACTGT
CCACCGGCTCACCGCAGTGACTCGAGTCATGTAATTAGTTATGTCACGCT
TACATTCACGCCCTCCCCCCACATCCGCTCTAACCGAAAAGGAAGGAGTT
AGACAACCTGAAGTCTAGGTCCCTATTTATTTTTTTATAGTTATGTTAGT
ATTAAGAACGTTATTTATATTTCAAATTTTTCTTTTTTTTCTGTACAGAC
GCGTGTACGCATGTAACATTATACTGAAAACCTTGCTTGAGAAGGTTTTG
GGACGCTCGAAGGCTTTAATTTGCGGCCAATATTATTGAAGCATTTATCA
GGGTTATTGTCTCATGAGCGGATACATATTTGAATGTATTTAGAAAAATA
AACAAATAGGGGTTCCGCGCACATTTCCCCGAAAAGTGCCACCTGACGTC
TAAGAAACCATTATTATCATGACATTAACCTATAAAAATAGGCGTATCAC
GAGGCCCTTTCGTCTCGCGCGTTTCGGTGATGACGGTGAAAACCTCTGAC
ACATGCAGCTCCCGGAGACGGTCACAGCTTGTCTG
```
Amplicon 1: A-HIS3-B
SEQ ID NO. 83
```
ACTATATGTGAAGGCATGGCTATGGCACGGCAGACATTCCGCCAGATCAT
CAATAGGCACCTTCATTCAACGTTTCCCATTGTTTTTTTCTACTATTGCT
TTGCTGTGGGAAAAACTTATCGAAAGATGACGACTTTTTCTTAATTCTCG
TTTTAAGAGCTTGGTGAGCGCTAGGAGTCACTGCCAGGTATCGTTTGAAC
ACGGCATTAGTCAGGGAAGTCATAACACAGTCCTTTCCCGCAATTTTCTT
TTTCTATTACTCTTGGCCTCCTCTAGTACACTCTATATTTTTTATGCCT
CGGTAATGATTTTCATTTTTTTTTTCCACCTAGCGGATGACTCTTTTTTT
TTTCTTAGCGATTGGCATTATCACATAATGAATTATACATTATATAAGT
AATGTGATTTCTTCGAAGAATATACTAAAAAATGAGCAGGCAAGATAAAC
GAAGGCAAAGATGACAGAGCAGAAAGCCCTAGTAAAGCGTATTACAAATG
AAACCAAGATTCAGATTGCGATCTCTTTAAAGGGTGGTCCCCTAGCGATA
GAGCACTCGATCTTCCCAGAAAAAGAGGCAGAAGCAGTAGCAGAACAGGC
CACACAATCGCAAGTGATTAACGTCCACACAGGTATAGGGTTTCTGGACC
ATATGATACATGCTCTGGCCAAGCATTCCGGCTGGTCGCTAATCGTTGAG
TGCATTGGTGACTTACACATAGACGACCATCACACCACTGAAGACTGCGG
GATTGCTCTCGGTCAAGCTTTTAAAGAGGCCCTAGGGGCCGTGCGTGGAG
TAAAAAGGTTTGGATCAGGATTTGCGCCTTTGGATGAGGCACTTTCCAGA
GCGGTGGTAGATCTTTCGAACAGGCCGTACGCAGTTGTCGAACTTGGTTT
GCAAAGGGAGAAAGTAGGAGATCTCTCTTGCGAGATGATCCCGCATTTTC
TTGAAAGCTTTGCAGAGGCTAGCAGAATTACCCTCCACGTTGATTGTCTG
CGAGGCAAGAATGATCATCACCGTAGTGAGAGTGCGTTCAAGGCTCTTGC
GGTTGCCATAAGAGAAGCCACCTCGCCCAATGGTACCAACGATGTTCCCT
CCACCAAAGGTGTTCTTATGTAGTGACACCGATTATTTAAAGCTGCAGCA
TACGATATATATACATGTGTATATATGTATACCTATGAATGTCAGTAAGT
ATGTATACGAACAGTATGATACTGAAGATGACAAGGTAATGCATCACACC
TTTCGAGAGGACGATGCCCGTGTCTAAATGATTCGACCAGCCTAAGAATG
TTCAAC
```
Amplicon 2: B-P$_{PGK1}$-MT
SEQ ID NO. 84
```
ACCTTTCGAGAGGACGATGCCCGTGTCTAAATGATTCGACCAGCCTAAGA
ATGTTCAACCCTGACTTCAACTCAAGACGCACAGATATTATAACATCTGC
ATAATAGGCATTTGCAAGAATTACTCGTGAGTAAGGAAAGAGTGAGGAAC
TATCGCATACCTGCATTTAAAGATGCCGATTTGGGCGCGAATCCTTTATT
TTGGCTTCACCCTCATACTATTATCAGGGCCAGAAAAGGAAGTGTTTCC
CTCCTTCTTGAATTGATGTTACCCTCATAAAGCACGTGGCCTCTTATCGA
GAAAGAAATTACCGTCGCTCGTGATTTGTTTGCAAAAAGAACAAAACTGA
AAAAACCCAGACACGCTCGACTTCCTGTCTTCCTATTGATTGCAGCTTCC
AATTTCGTCACACAACAAGGTCCTAGCGACGGCTCACAGGTTTTGTAACA
AGCAATCGAAGGTTCTGGAATGGCGGGAAAGGGTTTAGTACCACATGCTA
TGATGCCCACTGTGATCTCCAGAGCAAAGTTCGTTCGATCGTACTGTTAC
TCTCTCTCTTTCAAACAGAATTGTCCGAATCGTGTGACAACAACAGCCTG
TTCTCACACACTCTTTTCTTCTAACCAAGGGGGTGGTTTAGTTTAGTAGA
ACCTCGTGAAACTTACATTTACATATATATAAACTTGCATAAATTGGTCA
ATGCAAGAAATACATATTTGGTCTTTTCTAATTCGTAGTTTTTCAAGTTC
TTAGATGCTTTCTTTTTCTCTTTTTTACAGATCATCAAGGAAGTAATTAT
CTACTTTTTACAACAAATATAATGCAAACGGCAAAAGTCTCGGACACCCC
GGTTGAATTATTGTGGAACATCTGCTG
```
Amplicon 7: E-P$_{TEF1}$-EEVS-T$_{CYC1}$-A
SEQ ID NO. 85
```
AGATTACTCTAACGCCTCAGCCATCATCGGTAATAGCTCGAATTGCTGAG
AACCCGTGACACCGCGAATCCTTACATCACACCCAATCCCCCACAAGTGA
TCCCCCACACACCATAGCTTCAAAATGTTTCTACTCCTTTTTTACTCTTC
CAGATTTTCTCGGACTCCGCGCATCGCCGTACCACTTCAAAACACCCAAG
```

```
CACAGCATACTAAATTTCCCCTCTTTCTTCCTCTAGGGTGTCGTTAATTA
CCCGTACTAAAGGTTTGGAAAAGAAAAAAGAGACCGCCTCGTTTCTTTTT
CTTCGTCGAAAAAGGCAATAAAAATTTTTATCACGTTTCTTTTTCTTGAA
AATTTTTTTTTTGATTTTTTTCTCTTTCGATGACCTCCCATTGATATTT
AAGTTAATAAACGGTCTTCAATTTCTCAAGTTTCAGTTTCATTTTTCTTG
TTCTATTACAACTTTTTTTACTTCTTGCTCATTAGAAAGAAAGCATAGCA
ATCTAATCTAAGTTTTAATTACAAAACTAGTATGGAACGTCCGGGCGAAA
CCTTTACCGTCAGCTCCCCGGAAGAAGTGCGTCTGCCGTCTGTTCACCGC
GATAACTCAACGATGGAAAACCATAATAAACAGGAAACGGTGTTTTCTCT
GGTTCAAGTCAAGGGTACCTGGAAGCGTAAGGCGGGCCAGAACGCCAAAC
AGGGTATGAAGGGCCGCGTTAGTCCGGCCAAAATTTATGAAAGCTCTAGT
TCCTCAGGTACCACGTGGACGGTGGTTACCCCGATCACCTTTACGTACAC
CGTGACGCAGACCAAAAACCTGCTGGACCCGTCGAACGACACGCTGCTGC
TGGGCCATATTATCGATACCCAGCAACTGGAAGCTGTCCGCAGCAATACG
AAACCGCTGAAGCGTTTCATTGTGATGGACGAAGTCGTGTATAATATCTA
CGGTTCCCAAGTCACCGAATATCTGGAAGCGCGCAACGTGCTGTACCGTA
TTCTGCCGCTGCCGACCACGGAAGAAAATAAATCAATGGATATGGCTCTG
AAGATTCTGGAAGAAGTGCACCAGTTTGGTATCGACCGTCGCACCGAACC
GATTATCGCGATTGGCGGTGGCGTTTGCCTGGATATCGTCGGTCTGGCAG
CCTCTCTGTATCGTCGCCGTACCCCGTACATTCGTGTGCCGACCACGCTG
CTGTCTTATATCGACGCAAGTGTGGGTGCTAAAACGGGCGTTAACTTTGC
TAATTGTAAAAACAAGCTGGGTACCTACATTGCGCCGGTTGCAGCTTTTC
TGGATCGTTCGTTCATTCAGAGCATCCCGCGCCGTCACATCGCAAACGGT
CTGGCCGAAATGCTGAAAATGGCCCTGATGAAGCATCGCGGTCTGTTCGA
ACTGCTGGAAGTTCACGGCCAGTTTCTGCTGGATAGTAAATTCCAATCGG
CAAGCGTCCTGGAAAACGATCGCATTGACCCGGCCTCTGTCAGTACGCGT
GTGGCAATCGAAACCATGCTGGAAGAACTGGCCCCGAATCTGTGGGAAGA
TGACCTGGATCGTCTGGTGGACTTTGGTCATCTGATTTCGCCGCAGCTGG
AAATGAAAGTTCTGCCGGCACTGCTGCACGGCGAAGCTGTCAACATTGAT
ATGGCGTATATGGTGTACGTTTCATGCGAAATCGGTCTGCTGACCGAAGA
AGAAAAATTCCGCATTATCTGCTGTATGATGGGCCTGGAACTGCCGGTGT
GGCATCAGGATTTTACCTTCGCACTGGTTCAAAAGTCCCTGTGTGACCGC
CTGCAGCACTCAGGTGGCCTGGTTCGTATGCCGCTGCCGACGGGTCTGGG
TCGTGCAGAAATTTTTAATGATACCGACGAAGGTAGCCTGTTCCGCGCGT
ATGAAAAATGGTGCGATGAACTGTCCACCGGCTCACCGCAGTGACTCGAG
TCATGTAATTAGTTATGTCACGCTTACATTCACGCCCTCCCCCCACATCC
GCTCTAACCGAAAAGGAAGGAGTTAGACAACCTGAAGTCTAGGTCCCTAT
TTATTTTTTATAGTTATGTTAGTATTAAGAACGTTATTTATATTTCAAA
TTTTTCTTTTTTTCTGTACAGACGCGTGTACGCATGTAACATTATACTG
AAAACCTTGCTTGAGAAGGTTTTGGGACGCTCGAAGGCTTTAATTTGCGG
CCAATATTATTGAAGCATTTATCAGGGTTATTGTCTCATGAGCGGATACA
TATTTGAATGTATTTAGAAAAATAAACAAATAGGGGTTCCGCGCACATTT
CCCCGAAAAGTGCCACCTGACGTCTAAGAAACCATTATTATCATGACATT
AACCTATAAAAATAGGCGTATCACGAGGCCCTTTCGTCTCGCGCGTTTCG
GTGATGACGGTGAAAACCTCTGACACATGCAGCTCCCGGAGACGGTCACA
GCTTGTCTGACTATATGTGAAGGCATGGCTATGGCACGGCAGACATTCCG
CCAGATCATCAATAGGCAC
```

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

We claim:

1. A transgenic yeast cell, comprising:
   a first nucleotide sequence integrated in a chromosome of the transgenic yeast cell, the first nucleotide sequence capable of expressing 2-epi-5-valione synthase (EEVS) protein; and
   a second nucleotide sequence integrated in the chromosome of the transgenic yeast cell, the second nucleotide capable of expressing methyltransferase/oxidoreductase (MT-Ox) protein.

2. The transgenic yeast cell of claim 1, wherein the yeast cell comprises one or more disrupted transaldolase genes of the transgenic yeast cell, wherein the disruption results in a reduction of transaldolase activity in the transgenic yeast cell as compared to a wild-type yeast cell.

3. The transgenic yeast cell of claim 2, wherein the one or more disrupted transaldolase genes comprises TAL1.

4. The transgenic yeast cell of claim 2, wherein the one or more disrupted transaldolase genes comprises NQM1.

5. The transgenic yeast cell of claim 2, wherein the one or more disrupted transaldolase genes comprises both TAL1 and NQM1.

6. The transgenic yeast cell of claim 1, wherein the yeast cell is engineered to over express ZWF1.

7. The transgenic yeast cell of claim 1, wherein at least one of the first nucleotide sequence capable of expressing EEVS protein and the second nucleotide sequence capable of expressing MT-Ox protein are codon optimized for expression in yeast.

8. The transgenic yeast cell of claim 1, wherein the yeast cell comprises a Saccharomyces cerevisiae yeast cell.

9. The transgenic yeast cell of claim 1, wherein the first nucleotide sequence capable of expressing EEVS protein comprises a yeast promoter operably connected to a nucleic acid sequence encoding a EEVS protein.

10. The transgenic yeast cell of claim 9, wherein the nucleic acid sequence encoding the EEVS protein comprises a nucleic acid sequence that encodes a protein having an amino acid sequence at least 95% identical to SEQ ID NO: 21.

11. The transgenic yeast cell of claim 9, wherein the nucleic acid sequence encoding the EEVS protein comprises a nucleic acid sequence at least 95% identical to any one of SEQ ID NOs: 1-8.

12. The transgenic yeast cell of claim 9, wherein the yeast promoter is a yeast TEF1 promoter.

13. The transgenic yeast cell of claim 1, wherein the second nucleotide sequence capable of expressing MT-Ox protein comprises a yeast promoter operably connected to a nucleic acid sequence encoding a MT-Ox protein.

14. The transgenic yeast cell of claim 13, wherein the nucleic acid sequence encoding the MT-Ox protein comprises a nucleic acid sequence that encodes a protein having an amino acid sequence at least 95% identical to SEQ ID NO: 22.

15. The transgenic yeast cell of claim 13, wherein the nucleic acid sequence encoding the MT-Ox protein comprises a nucleic acid sequence at least 95% identical to any one of SEQ ID NOs: 9-16.

16. The transgenic yeast cell of claim 13, wherein the yeast promoter is a yeast PGK1 promoter.

17. The transgenic yeast cell of claim 1, wherein the first nucleotide sequence capable of expressing EEVS and the second nucleotide sequence capable of expressing MT-Ox are integrated at chromosome 15 at the his3Δ1 locus.

18. The transgenic yeast cell of claim 1, wherein the first nucleotide sequence capable of expressing EEVS and the second nucleotide sequence capable of expressing MT-Ox are stably integrated.

19. The transgenic yeast cell of claim 18, wherein the first nucleotide sequence capable of expressing EEVS and the second nucleotide sequence capable of expressing MT-Ox are stably integrated for at least 20 generations.

20. A bioreactor comprising a population of the transgenic yeast cell of claim 1.

21. A method for producing gadusol, the method comprising:
    culturing a transgenic yeast cell of claim 1 in growth media, wherein at least a portion of the gadusol is secreted into the growth media; and
    isolating the secreted gadusol from the growth media.

22. A transgenic yeast cell, comprising:
    a nucleotide sequence capable of expressing 2-epi-5-valione synthase (EEVS) protein integrated in a genome of the transgenic yeast cell;
    a nucleotide sequence capable of expressing methyltransferase/oxidoreductase (MT-Ox) protein integrated in the genome of the transgenic yeast cell;
    wherein the transgenic yeast cell comprises one or more disrupted transaldolase genes of the transgenic yeast cell, wherein the disruption results in a reduction of transaldolase activity in the transgenic yeast cell as compared to a wild-type yeast cell; and
    wherein the one or more disrupted transaldolase genes comprises NQM1.

23. The transgenic yeast cell of claim 22, wherein the one or more disrupted transaldolase genes comprises both TAL1 and NQM1.

24. A transgenic yeast cell, comprising:
    a nucleotide sequence capable of expressing 2-epi-5-valione synthase (EEVS) protein integrated in a genome of the transgenic yeast cell;
    a nucleotide sequence capable of expressing methyltransferase/oxidoreductase (MT-Ox) protein integrated in the genome of the transgenic yeast cell; and
    wherein the yeast cell is engineered to over express ZWF1.

25. A transgenic yeast cell, comprising:
    a nucleotide sequence capable of expressing 2-epi-5-valione synthase (EEVS) protein integrated in a genome of the transgenic yeast cell;
    a nucleotide sequence capable of expressing methyltransferase/oxidoreductase (MT-Ox) protein integrated in the genome of the transgenic yeast cell; and
    wherein at least one of the nucleotide sequence capable of expressing EEVS protein and the nucleotide sequence capable of expressing MT-Ox protein are codon optimized for expression in yeast.

26. A transgenic yeast cell, comprising:
- a first nucleotide sequence chromosomally integrated in a genome of the transgenic yeast cell, the first nucleotide sequence capable of expressing 2-epi-5-valione synthase (EEVS) protein; and
- a second nucleotide sequence chromosomally integrated in the genome of the transgenic yeast cell, the second nucleotide capable of expressing methyltransferase/oxidoreductase (MT-Ox) protein.

* * * * *